US012588354B2

(12) United States Patent
Kim et al.

(10) Patent No.: US 12,588,354 B2
(45) Date of Patent: Mar. 24, 2026

(54) LIGHT-EMITTING DEVICE INCLUDING FUSED CYCLIC COMPOUND, ELECTRONIC APPARATUS INCLUDING THE LIGHT-EMITTING DEVICE, AND THE FUSED CYCLIC COMPOUND

(71) Applicant: Samsung Display Co., Ltd., Yongin-si (KR)

(72) Inventors: Seran Kim, Yongin-si (KR); Hoilim Kim, Yongin-si (KR); Dongsun Yoo, Yongin-si (KR); Saena Yun, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 1021 days.

(21) Appl. No.: 17/674,849

(22) Filed: Feb. 18, 2022

(65) Prior Publication Data

US 2022/0278295 A1 Sep. 1, 2022

(30) Foreign Application Priority Data

Feb. 19, 2021 (KR) ........................ 10-2021-0022599

(51) Int. Cl.

| | |
|---|---|
| ***H01L 51/54*** | (2006.01) |
| ***C07D 209/82*** | (2006.01) |
| ***C07D 213/74*** | (2006.01) |
| ***C07D 307/91*** | (2006.01) |
| ***C07D 333/76*** | (2006.01) |
| ***C07D 403/10*** | (2006.01) |
| ***C07D 403/14*** | (2006.01) |
| ***C07D 405/12*** | (2006.01) |
| ***C07D 409/12*** | (2006.01) |
| ***C07D 487/04*** | (2006.01) |
| ***C07D 487/14*** | (2006.01) |
| ***C07D 493/04*** | (2006.01) |
| ***C07D 495/04*** | (2006.01) |
| ***C07D 513/22*** | (2006.01) |
| ***C07F 5/02*** | (2006.01) |
| ***H10K 50/12*** | (2023.01) |
| ***H10K 50/125*** | (2023.01) |
| ***H10K 85/60*** | (2023.01) |

(52) U.S. Cl.

CPC ........... *H10K 50/12* (2023.02); *C07D 209/82* (2013.01); *C07D 213/74* (2013.01); *C07D 307/91* (2013.01); *C07D 333/76* (2013.01); *C07D 403/10* (2013.01); *C07D 403/14* (2013.01); *C07D 405/12* (2013.01); *C07D 409/12* (2013.01); *C07D 487/04* (2013.01); *C07D 487/14* (2013.01); *C07D 493/04* (2013.01); *C07D 495/04* (2013.01); *C07D 513/22* (2013.01); *C07F 5/027* (2013.01); *H10K 50/125* (2023.02); *H10K 85/657* (2023.02); *H10K 85/6572* (2023.02)

(58) Field of Classification Search

None

See application file for complete search history.

(56) References Cited

U.S. PATENT DOCUMENTS

| | | | | |
|---|---|---|---|---|
| 10,981,938 B2 | 4/2021 | Joo et al. | |
| 11,877,506 B2 | 1/2024 | Hatakeyama et al. | |
| 12,284,905 B2 | 4/2025 | Park et al. | |
| 2015/0303379 A1* | 10/2015 | Lee ...................... | H10K 85/636 548/440 |
| 2019/0013478 A1* | 1/2019 | Iijima .................. | H10K 85/342 |
| 2020/0119289 A1 | 4/2020 | Lin et al. | |
| 2020/0190115 A1* | 6/2020 | Hatakeyama ........ | H10K 85/322 |

FOREIGN PATENT DOCUMENTS

| | | |
|---|---|---|
| JP | 2019119680 | 7/2019 |
| KR | 10-2020-0006965 | 1/2020 |
| KR | 10-2094830 B9 | 3/2020 |
| KR | 10-2020-0140744 A | 12/2020 |
| KR | 10-2021-0009912 A | 1/2021 |
| KR | 10-2022-0046465 A | 4/2022 |

(Continued)

OTHER PUBLICATIONS

Machine translation of WO2020040298A1 (Year: 2020).*

(Continued)

*Primary Examiner* — Andrew K Bohaty

(74) *Attorney, Agent, or Firm* — Womble Bond Dickinson (US) LLP

(57) ABSTRACT

A light-emitting device having a fused cyclic compound includes: a first electrode; a second electrode facing the first electrode; an interlayer between the first electrode and the second electrode and including an emission layer; and a fused cyclic compound of Formula 1:

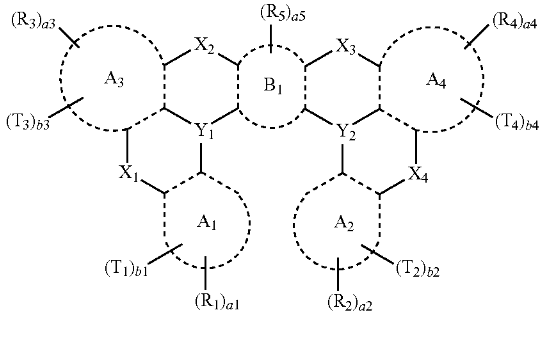

wherein, in Formula 1, the variables are as defined herein.

19 Claims, 3 Drawing Sheets

(56) References Cited

FOREIGN PATENT DOCUMENTS

| | | | | | |
|---|---|---|---|---|---|
| WO | 2018212169 | | 11/2018 | | |
| WO | WO-2020040298 | A1 * | 2/2020 | ............. | C09K 11/06 |
| WO | 2020/162600 | A1 | 8/2020 | | |

OTHER PUBLICATIONS

Hatakeyama, Takuji, et al. "Ultrapure Blue Thermally Activated Delayed Fluorescence Molecules: Efficient HOMO-LUMO Separation by the Multiple Resonance Effect." Advanced Materials, vol. 28, No. 14, 2016, pp. 2777-2781.

* cited by examiner

LIGHT-EMITTING DEVICE INCLUDING FUSED CYCLIC COMPOUND, ELECTRONIC APPARATUS INCLUDING THE LIGHT-EMITTING DEVICE, AND THE FUSED CYCLIC COMPOUND

CROSS-REFERENCE TO RELATED APPLICATION

This application claims priority from and the benefit of Korean Patent Application No. 10-2021-0022599, filed on Feb. 19, 2021, which is hereby incorporated by reference for all purposes as if fully set forth herein.

BACKGROUND

Field

Embodiments of the invention relate generally to display devices and, more particularly, to a light-emitting device including a fused cyclic compound, an electronic apparatus including the light-emitting device, and a fused cyclic compound.

Discussion of the Background

Organic light-emitting devices (OLEDs) are self-emissive devices that, as compared with devices in the art, have wide viewing angles, high contrast ratios, short response times, and excellent characteristics in terms of luminance, driving voltage, and response speed, and produce full-color images.

OLEDs may include a first electrode located on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state to thereby generate light.

The above information disclosed in this Background section is only for understanding of the background of the inventive concepts, and, therefore, it may contain information that does not constitute prior art.

SUMMARY

Light-emitting devices and electronic apparatuses constructed according to principles and illustrative implementations include a fused cyclic compound represented by one or more formulas disclosed herein have a particular structure that provide the light-emitting device with excellent emission efficiency and a long lifespan, and may be used to manufacture high-quality electronic apparatuses.

Additional features of the inventive concepts will be set forth in the description which follows, and in part will be apparent from the description, or may be learned by practice of the inventive concepts.

According to one aspect of the invention, a light-emitting device includes: a first electrode; a second electrode facing the first electrode; an first layer between the first electrode and the second electrode and including a second layer; and a fused cyclic compound of Formula 1.

Formula 1

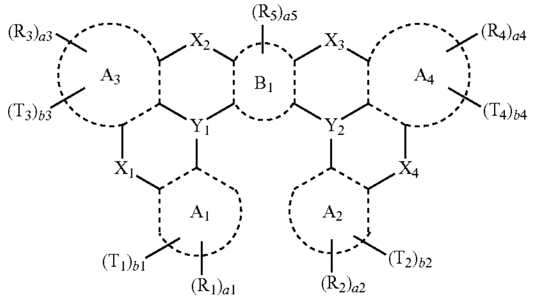

where the variables are defined herein.

The first electrode may include an anode, the second electrode may include a cathode, the first layer may be an interlayer that may further include a hole transport region between the first electrode and the second layer that may be an emission layer, and an electron transport region between the second layer that may be the emission layer and the second electrode, the hole transport region may include a hole injection layer, a hole transport layer, an emission auxiliary layer, an electron blocking layer, or any combination thereof, and the electron transport region may include a hole blocking layer, an electron transport layer, an electron injection layer, or any combination thereof.

The second layer may be an emission layer that includes the fused cyclic compound of Formula 1.

The fused cyclic compound included in the emission layer may be a condensed cyclic compound including a delayed fluorescence emitter, and the emission layer may be configured to emit delayed fluorescence.

The emission layer may be configured to emit blue light.

The emission layer may further include a host, and the fused cyclic compound included in the emission layer may be a dopant, and the amount of the host included in the emission layer may be greater than the amount of the fused cyclic compound included in the emission layer.

The light-emitting device may further include a capping layer located outside the first electrode or outside the second electrode, wherein the capping layer may include the fused cyclic compound of Formula 1.

An electronic apparatus may include the organic light-emitting device as defined above.

The electronic apparatus may further include a thin-film transistor, wherein the thin-film transistor may include a source electrode and a drain electrode, and the first electrode of the organic light-emitting device may be electronically connected to the source electrode or the drain electrode.

According to another aspect of the invention, a fused cyclic compound of Formula 1:

Formula 1

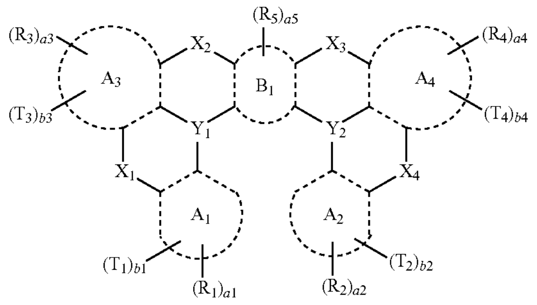

where the variables are defined herein.

The rings $A_1$ to $A_4$ may be each, independently from one another, a benzene group, a naphthalene group, an anthracene group, a fluoranthene group, a triphenylene group, a pyrene group, a chrysene group, or a perylene group, and ring $B_1$ is a benzene group.

The variables $Y_1$ and $Y_2$ may be identical to each other.

The variable may be $R_{22}$ may be a hydroxyl group, a $C_1$-$C_{20}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_1$-$C_{60}$ aryl group unsubstituted or substituted with at least one $R_{10a}$, or —$N(Q_1)(Q_2)$, and the variables $R_{10a}$, $Q_1$, and $Q_2$ have, independently from one another, the same meaning as described above.

A group of *-$(L_{21})_{d21}$-$R_{22}$ in Formula 2 may be a group of one of Formulae 3-1 to 3-5, as defined herein.

The variables $T_1$ to $T_4$ may be each, independently from one another, of —$N(Q_{1a})(Q_{2a})$, the variables $Q_{1a}$ and $Q_{2a}$ may be each, independently from one another: a group of Formula 2; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and at least one of the variables $Q_{1a}$ and $Q_{2a}$ may be a group of Formula 2.

A group in Formula 1 may be a group of one of Formulae 4-1 to 4-3, as defined herein.

A group in Formula 1 may be a group of one of Formulae 5-1 to 5-3, as defined herein.

A group in Formula 1 may be a group of one of Formulae 6-1 to 6-4, as defined herein.

A group in Formula 1 may be a group of one of Formulae 7-1 to 7-4, as defined herein.

The fused cyclic compound may satisfy one or more of the five categories of Conditions 1 to 5, as defined herein.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
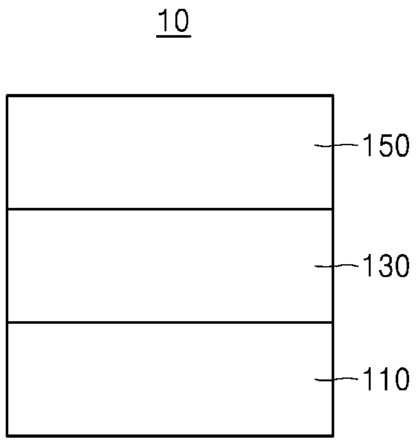
FIG. 1 is a schematic cross-sectional view of an embodiment of a light-emitting device constructed according to the principles of the invention.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be per formed substantially at the same time or performed in an order opposite to the described or der. Also, like reference numerals denote like elements, and redundant explanations are omit ted to avoid redundancy.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

The light-emitting device (for example, an organic light-emitting device) may include a first electrode, a second electrode facing the first electrode, a first layer in the form of an interlayer between the first electrode and the second electrode and including a second layer in the form of an emission layer, and a condensed cyclic compound represented by Formula 1. Hereinafter, the condensed cyclic compound will be described in more detail. The condensed cyclic compound may be represented by Formula 1.

Formula 1

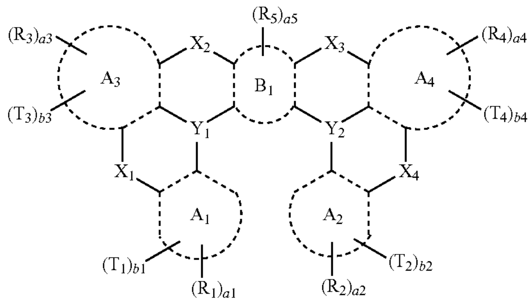

The variable $Y_1$ in Formula 1 may be B, P(=O), or P(=S), and in an embodiment, $Y_1$ may be B. The variable $Y_2$ in Formula 1 may be B, P(=O), or P(=S), and in an embodiment, $Y_1$ may be B. In an embodiment, $Y_1$ and $Y_2$ in Formula 1 may be identical to each other. For example, $Y_1$ and $Y_2$ may each be B. $X_1$ in Formula 1 may be $N(Ar_1)$, $N(Z_1)$, O, S, or Se. For example, $X_1$ may be $N(Ar_1)$, $N(Z_1)$, O, or S. The variable $X_2$ in Formula 1 may be $N(Ar_2)$, $N(Z_2)$, O, S, or Se. For example, $X_2$ may be $N(Ar_2)$, $N(Z_2)$, O, or S. The variable $X_3$ in Formula 1 may be $N(Ar_3)$, $N(Z_3)$, O, S, or Se. For example, $X_3$ may be $N(Ar_3)$, $N(Z_3)$, O, or S. The variable $X_4$ in Formula 1 may be $N(Ar_4)$, $N(Z_4)$, O, S, or Se. For example, $X_4$ may be $N(Ar_4)$, $N(Z_4)$, O, or S.

The variables $Z_1$ to $Z_4$ may each independently be a group represented by Formula 2:

Formula 2

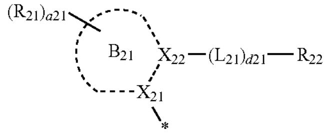

Formula 2 is the same as described herein.

Ring $A_1$ to $A_4$, $B_1$, and $B_{21}$ in Formula 1 and 2 may each independently be a $C_5$-$C_{60}$ carbocyclic group or a $C_1$-$C_{60}$ heterocyclic group. For example, rings $A_1$ to $A_4$, $B_1$, and $B_{21}$ may each independently be a benzene group, a naphthalene group, an anthracene group, a fluoranthene group, a phenanthrene group, a triphenylene group, a pyrene group, a chrysene group, a perylene group, cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group.

In an embodiment, rings $A_1$ to $A_4$ in Formula 1 may each independently be a benzene group, a naphthalene group, an anthracene group, a fluoranthene group, a triphenylene group, a pyrene group, a chrysene group, or a perylene group. Ring $B_1$ may be a benzene group.

In an embodiment, $B_{21}$ in Formula 2 may be a benzene group or a naphthalene group. The variables $X_{21}$ and $X_{22}$ in Formula 2 may each independently be a carbon or a heteroatom, and $X_{21}$ and $X_{22}$ may be linked to each other by a chemical bond. In an embodiment, when ring $B_{21}$ is a benzene group or a naphthalene group, $X_{21}$ and $X_{22}$ may each be a carbon.

The variables $Ar_1$ to $Ar_4$, $R_1$ to $R_5$, $T_1$ to $T_4$, and $R_{21}$ in Formulae 1 and 2 may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$.

The variables $R_{10a}$ and $Q_1$ to $Q_3$ are the same as described herein. In an embodiment, $Ar_1$ to $Ar_4$ may each independently be selected from: a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphtho silolyl group, an indeno carbazolyl group, an indolocarbazolyl group, a benzofuranoa carbazolyl group, a benzothienocarbazolyl group, a benzosilolocarbazolyl group, an imidazopyridinyl group, an imidazopyrimidinyl group, an azafluorenyl group, an azacarbazolyl group, an azadibenzofuranyl group, an azadibenzothiophenyl group, or an azadibenzosilolyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, naphthobenzosilolyl group, a dibenzofluorenyl group, a dibenzocarbazolyl group, a dinaphthofuranyl group, a dinaphthothiophenyl group, a dinaphtho silolyl group, an indeno carbazolyl group, an indolocarbazolyl group, a benzofuranoa carbazolyl group, a benzothienocarbazolyl group, a benzosilolocarbazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), —P(═O)($Q_{31}$)($Q_{32}$), or any combination thereof.

In one or more embodiments, $Ar_1$ to $Ar_4$ may each independently be a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, or a benzosilolocarbazolyl group, each unsubstituted or substituted with deuterium, —F, —Cl, —Br, —I, —$CD_3$, —$CD_2H$, —$CDH_2$, —$CF_3$, —$CF_2H$, —$CFH_2$, a cyano group, a $C_1$-$C_{20}$ alkyl group, a $C_1$-$C_{20}$ alkoxy group, a phenyl group, a biphenyl group, a terphenyl group, a $C_1$-$C_{20}$ alkylphenyl group, a naphthyl group, a fluorenyl group, a phenanthrenyl group, an anthracenyl group, a thiophenyl group, a furanyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, or any combination thereof.

For example, $Ar_1$ to $Ar_4$ may each independently be a phenyl group, a biphenyl group, a terphenyl group, or a naphthyl group. In an embodiment, $R_1$ to $R_5$ and $R_{21}$ may each independently be:

hydrogen, deuterium, —F, —Cl, —Br, —I, a hydroxyl group, a cyano group, a nitro group, an amidino group, a hydrazine group, a hydrazone group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, and an azadibenzosilolyl group, each unsubstituted or substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(═O)($Q_{31}$), —S(═O)$_2$($Q_{31}$), and —P(═O)($Q_{31}$)($Q_{32}$); and —Si($Q_1$)($Q_2$)($Q_3$), —N($Q_1$)($Q_2$), —B($Q_1$)($Q_2$), —C(═O)($Q_1$), —S(═O)$_2$($Q_1$), and —P(═O)($Q_1$)($Q_2$), wherein $Q_1$ to $Q_3$ and $Q_{31}$ to $Q_{33}$ may each independently be:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and—$CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, and a triazinyl group, each unsubstituted or substituted with at least one selected from deuterium, a $C_1$-$C_{10}$ alkyl group, a phenyl group, a biphenyl group, a pyridinyl group, a pyrimidinyl group, a pyridazinyl group, a pyrazinyl group, and a triazinyl group.

For example, $R_1$ to $R_5$ may each independently be hydrogen or deuterium.

The variables $T_1$ to $T_4$ in Formula 1 may each independently comprise a group represented by Formula 2.

In an embodiment, $T_1$ to $T_4$ may each independently be represented by —$N(Q_{1a})(Q_{2a})$, $Q_{1a}$ and $Q_{2a}$ may each independently be: a group represented by Formula 2; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and at least one of $Q_{1a}$ and $Q_{2a}$ may be a group represented by Formula 2.

In one or more embodiments, $Q_{1a}$ and $Q_{2a}$ may each independently be: a group represented by Formula 2; a phenyl group; a biphenyl group; a naphthyl group; a phenyl group, a biphenyl group, or a naphthyl group, each substituted with a cyano group, a $C_1$-$C_{20}$ alkyl group, a $C_1$-$C_{10}$ alkoxy group, or any combination thereof, and at least one of $Q_{1a}$ and $Q_{2a}$ may be a group represented by Formula 2. For example, $T_1$ to $T_4$ may each independently be represented by —$N(Q_{1a})(Q_{2a})$, and at least one of $Q_{1a}$ and $Q_{2a}$ may be a group represented by Formula 2 and the other one thereof may be a phenyl group.

For example, $Q_{1a}$ and $Q_{2a}$ may each independently be a group represented by Formula 2. The variables a1 to a5, b1 to b4, and a21 in Formulae 1 and 2 may each independently be an integer from 0 to 10. The variable $L_{21}$ in Formula 2 may be a single bond, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, and d21 may be an integer from 1 to 3.

In an embodiment, $L_{21}$ may be a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-a fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$.

The variable $R_{10a}$ is the same as described herein. In one or more embodiments, $L_{21}$ may be a benzene group or a naphthalene group, each substituted or unsubstituted with at least one $R_{10a}$, and d21 may be 1.

For example, $L_{21}$ may be a benzene group, and d21 may be 1. The variable $R_{22}$ in Formula 2 may be an electron donating group. Herein, the electron donating group refers to a group in a molecule that tends to give electrons based on hydrogen. For example, $R_{22}$ may be a hydroxyl group, a $C_1$-$C_{20}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_1$-$C_{60}$ aryl group unsubstituted or substituted with at least one $R_{10a}$, or —$N(Q_1)(Q_2)$, and $R_{10a}$, $Q_1$, and $Q_2$ are each the same as described herein.

For example, $R_{22}$ may be a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a 2-methylbutyl group, a 2-2 dimethylpropyl group, 1-ethylpropyl, or 1,2-dimethylpropyl. The symbol * in Formula 2 indicates a binding site to a neighboring atom.

Formula 2 may be represented by Formula 2-1 or 2-2.

Formula 2-1

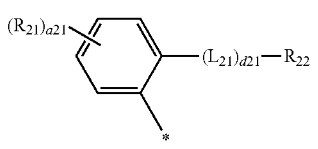

Formula 2-2

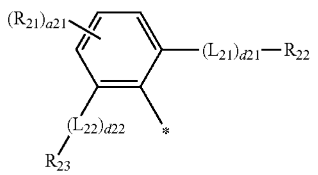

The variables $R_{21}$, $L_{21}$, d21, and $R_{22}$ in Formulae 2-1 and 2-2 are each the same as described herein. The variable $L_{22}$ in Formula 2-2 may be a single bond, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, d22 may be an integer from 1 to 3, and a22 may be an integer selected from 1 to 3.

For example, $L_{22}$ may be a benzene group or a naphthalene group, each unsubstituted or substituted with at least one $R_{10a}$, and d21 may be 1. For example, $L_{22}$ may be a benzene group, and d21 may be 1. In an embodiment, $L_{21}$ and $L_{22}$ in Formula 2 may be identical to each other. In one or more embodiments, $L_{21}$ and $L_{22}$ in Formula 2 may be different from each other. The variable $R_{23}$ in Formula 2-2 may be an electron donating group.

For example, $R_{23}$ may be a hydroxyl group, a $C_1$-$C_{20}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_1$-$C_{60}$ aryl group is unsubstituted or substituted with at least one $R_{10a}$, or —N($Q_1$)($Q_2$). For example, $R_{23}$ may be a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a 2-methylbutyl group, a 2-2 dimethylpropyl group, 1-ethylpropyl, or 1,2-dimethylpropyl.

In an embodiment, $R_{22}$ and $R_{23}$ in Formula 2 may be identical to each other. In one or more embodiments, $R_{22}$ and $R_{23}$ in Formula 2 may be different from each other. A group represented by *-$(L_{21})_{d21}$-$R_{22}$ in Formulae 2 and 2-1 may be a group represented by one of Formulae 3-1 to 3-5.

3-1

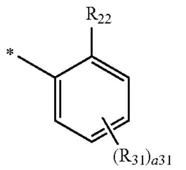

3-2

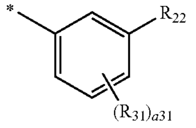

3-3

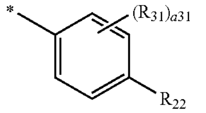

3-4

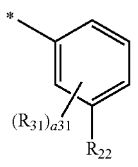

3-5

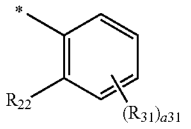

A group represented by *-$(L_{22})_{d22}$-$R_{23}$ in Formula 2-2 may be a group represented by one of Formulae 3-6 to 3-10.

3-6

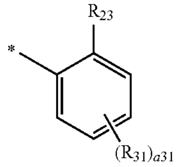

3-7

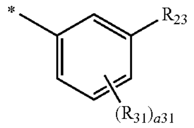

3-8

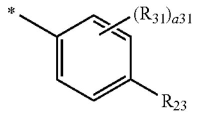

3-9

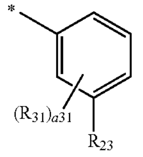

3-10

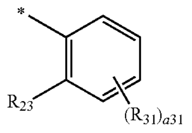

In Formulae 3-1 to 3-10, $R_{31}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), a31 may be an integer from 0 to 4, $R_{22}$ and $R_{23}$ are each the same as described herein, and indicates a binding site to a neighboring atom.

For example, $R_{31}$ may be hydrogen or deuterium. For example, $R_{22}$ and $R_{23}$ may each be a tert-butyl group. The condensed cyclic compound may satisfy at least one of Conditions 1 to 5.

Condition 1 $X_1$ is N($Z_1$).

Condition 2 $X_2$ is N($Z_2$).

Condition 3 $X_3$ is N($Z_3$).

Condition 4 $X_4$ is N($Z_4$).

Condition 5 The sum of b1 to b4 is 1 or more.

In an embodiment, the condensed cyclic compound may satisfy one of Conditions 1 to 5. In one or more embodiments, the condensed cyclic compound may satisfy: Conditions 1 and 5; Conditions 2 and 5; Conditions 3 and 5; or Conditions 4 and 5. In one or more embodiments, the condensed cyclic compound may satisfy: Conditions 1, 4, and 5; Conditions 1, 3, and 5; Conditions 2, 4, and 5; or Conditions 3, 4, and 5. In one or more embodiments, the condensed cyclic compound may satisfy: Conditions 1 to 3 and 5; Conditions 1 and 3 to 5; or Conditions 2 to 5. In one or more embodiments, the condensed cyclic compound may satisfy Conditions 1 to 5. In an embodiment, when the condensed cyclic compound satisfies Condition 5, the sum of b1 to b4 may be 1, 2, 3, or 4. For example, when the condensed cyclic compound satisfies Condition 5, b3 may be 1, and b1, b2, and b4 may each be 0. For example, when the condensed cyclic compound satisfies Condition 5, b4 may be 1, and b1, b2, and b3 may each be 0. For example, when the condensed cyclic compound satisfies Condition 5, b3 and b4 may each be 1, and b1 and b2 may each be 0.

A group represented by

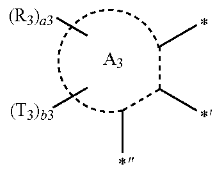

in Formula 1 may be a group represented by one of Formulae 4-1 to 4-3.

4-1

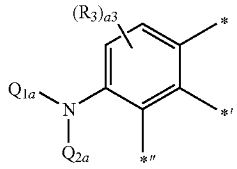

4-2

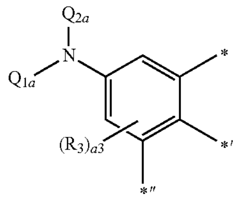

4-3

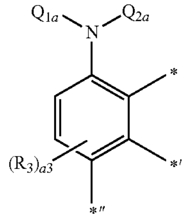

In Formulae 4-1 to 4-3, $Q_{1a}$ and $Q_{2a}$ may each independently be: a group represented by Formula 2; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and at least one of $Q_{1a}$ and $Q_{2a}$ may be a group represented by Formula 2, $R_3$ is the same as described herein, a3 may be an integer from 0 to 2, and

*, *', and *" each indicate a condensation site to a neighboring ring in Formula 1.

A group represented by

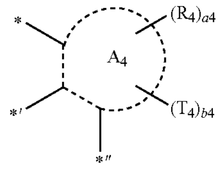

in Formula 1 may be a group represented by one of Formulae 5-1 to 5-3.

5-1

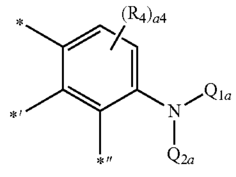

5-2

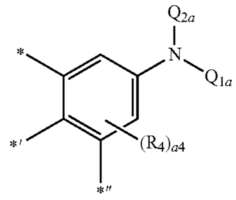

5-3

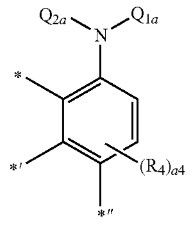

In Formulae 5-1 to 5-3, $Q_{1a}$ and $Q_{2a}$ may each independently be: a group represented by Formula 2; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and at least one of $Q_{1a}$ and $Q_{2a}$ may be a group represented by Formula 2, $R_4$ is the same as described herein, a4 may be an integer from 0 to 2, and

*, *', and *" each indicate a condensation site to a neighboring ring in Formula 1.

A group represented by

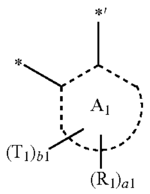

in Formula 1 may be a group represented by one of Formulae 6-1 to 6-4.

6-1

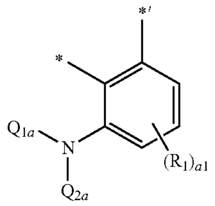

6-2

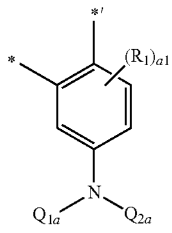

6-3

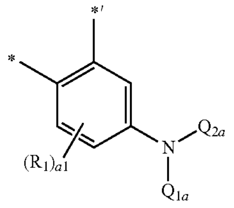

6-4

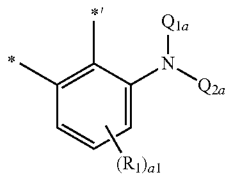

In Formulae 6-1 to 6-4, $Q_{1a}$ and $Q_{2a}$ may each independently be: a group represented by Formula 2; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and at least one of $Q_{1a}$ and $Q_{2a}$ may be a group represented by Formula 2, $R_1$ is the same as described herein, a1 may be an integer from 0 to 3, and

* and *' each indicate a condensation site to a neighboring ring in Formula 1.

A group represented by

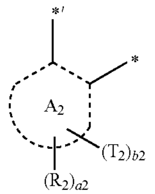

in Formula 1 may be a group represented by one of Formulae 7-1 to 7-4.

7-1

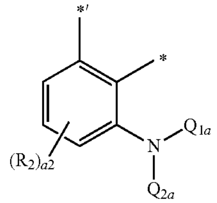

7-2

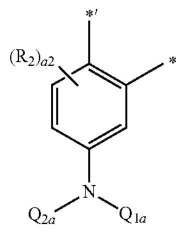

7-3

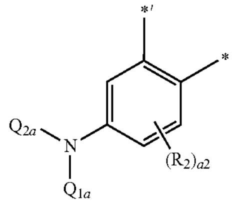

7-4

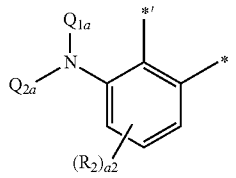

In Formulae 7-1 to 7-4, $Q_{1a}$ and $Q_{2a}$ may each independently be: a group represented by Formula 2; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and at least one of $Q_{1a}$ and $Q_{2a}$ may be a group represented by Formula 2, $R_2$ is the same as described herein, a2 may be an integer from 0 to 3, and

*, and *' each indicate a condensation site to a neighboring ring in Formula 1.

In an embodiment, the condensed cyclic compound represented by Formula 1 may be one of Compounds 1 to 105.

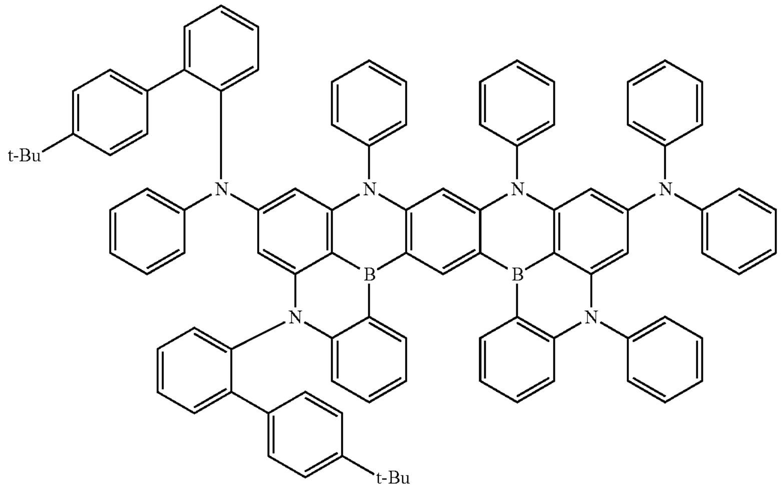
1
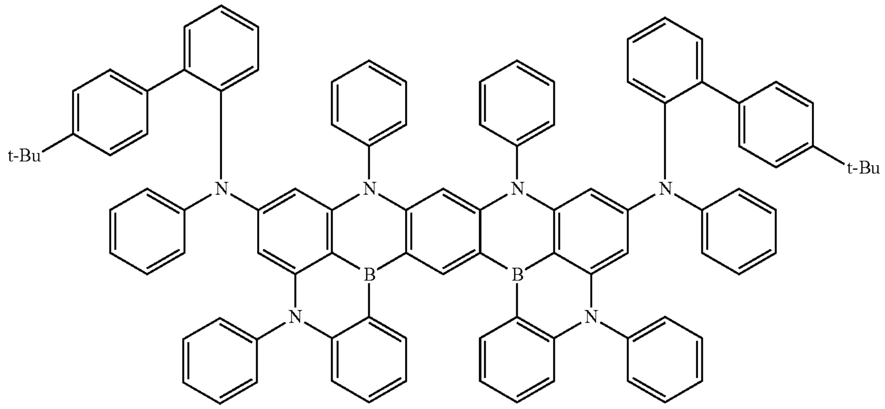
2
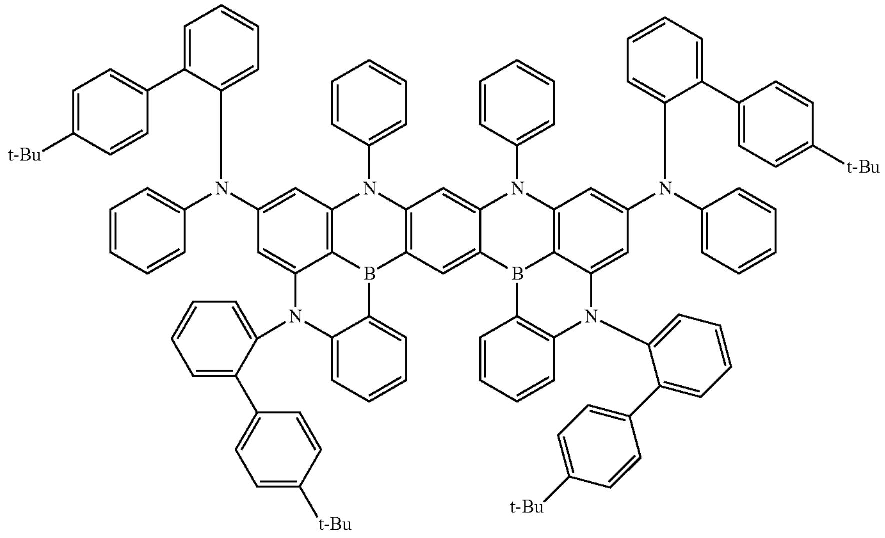
3

-continued
4
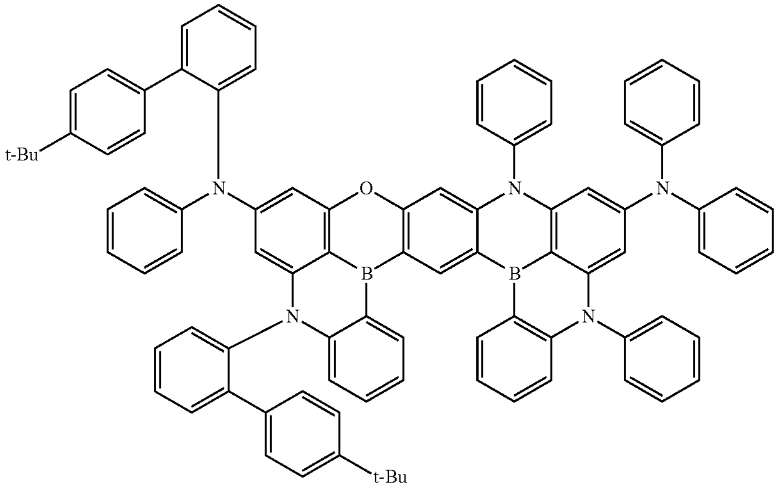
5
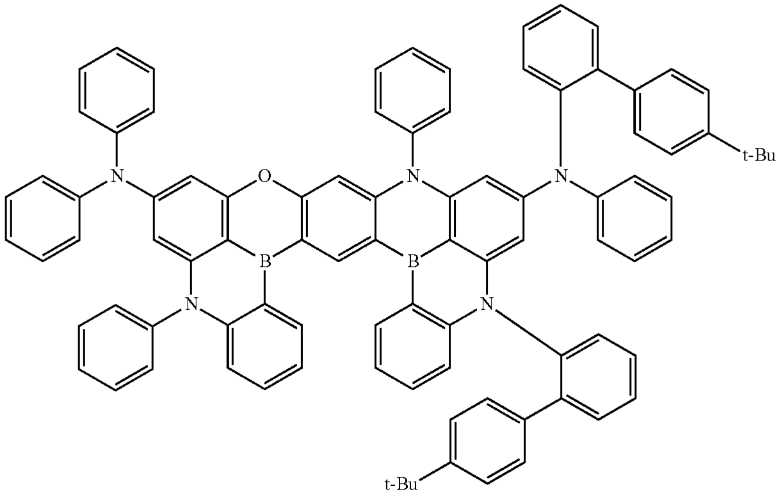
6
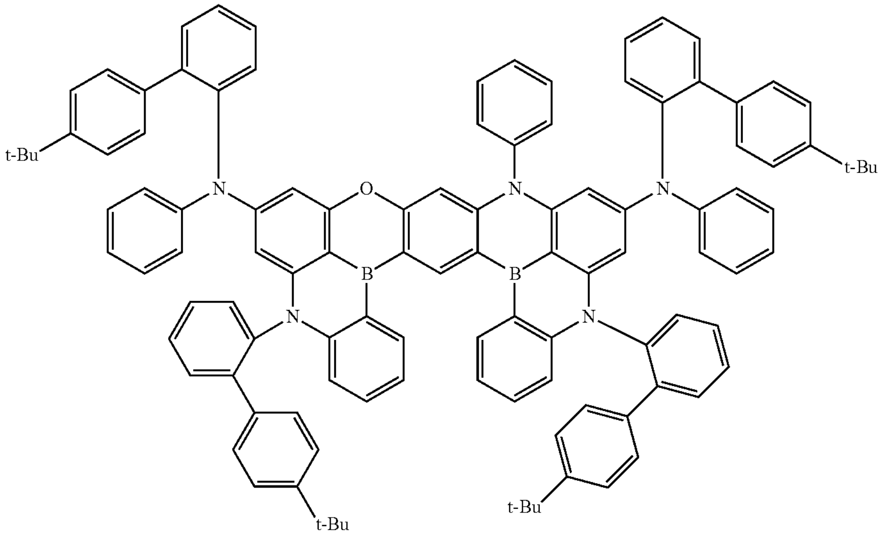

-continued
7
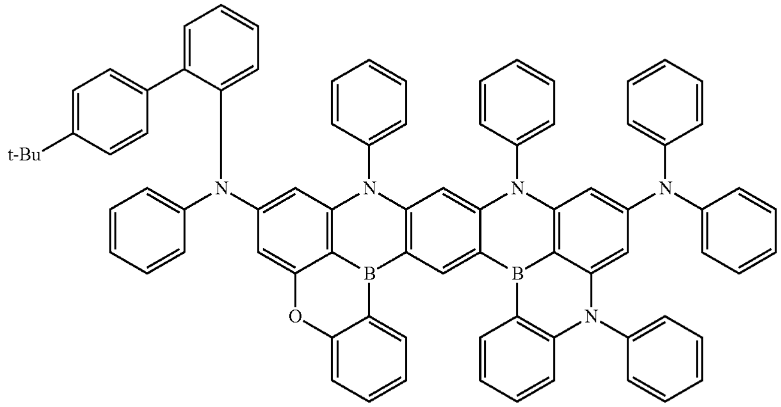
8
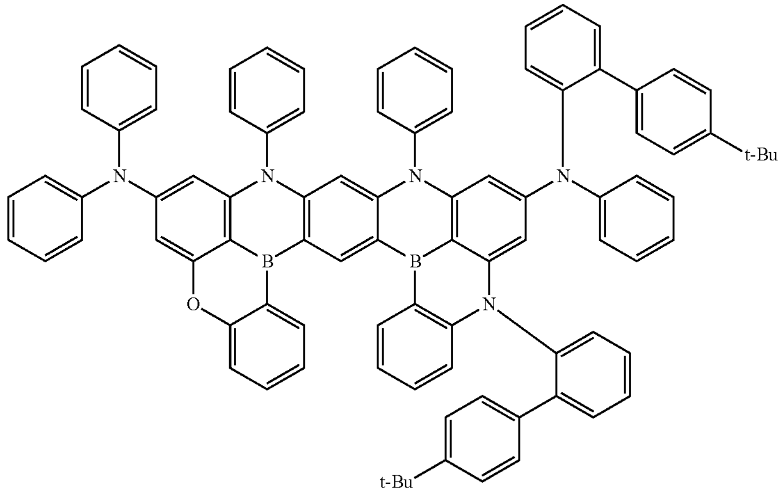
9
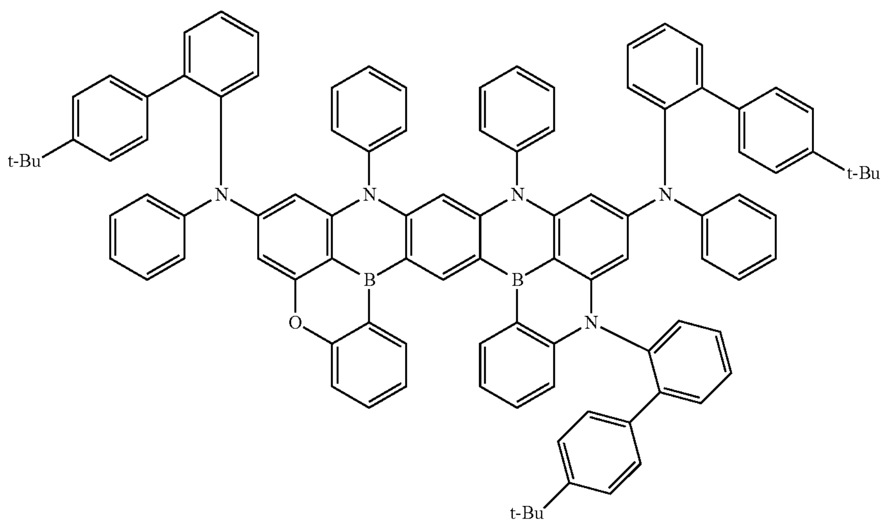

-continued
10
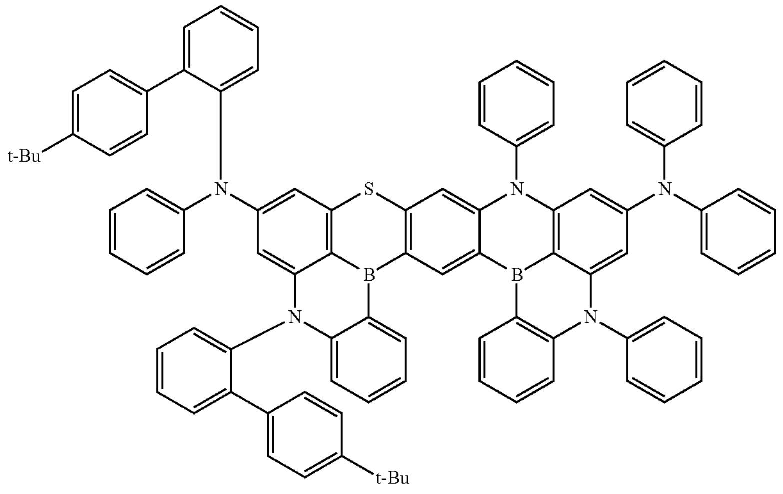
11
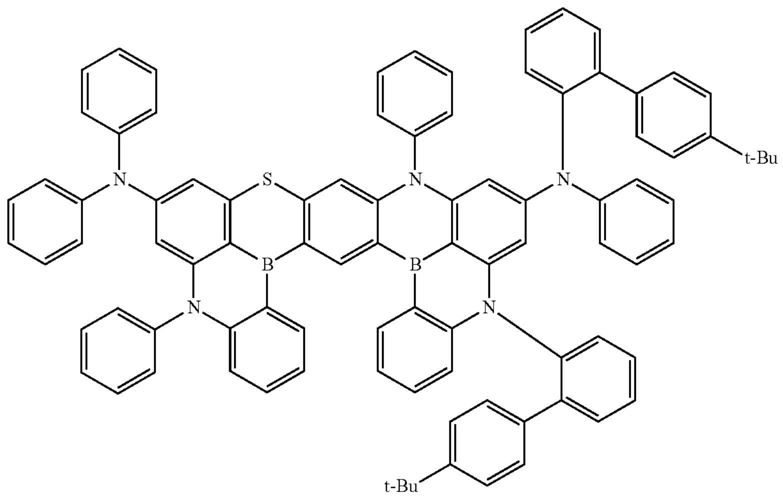
12
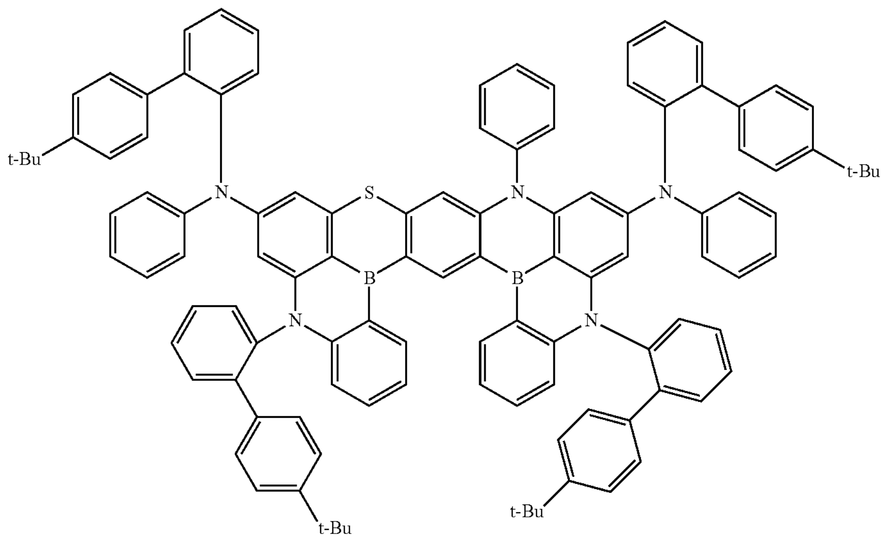

-continued
13
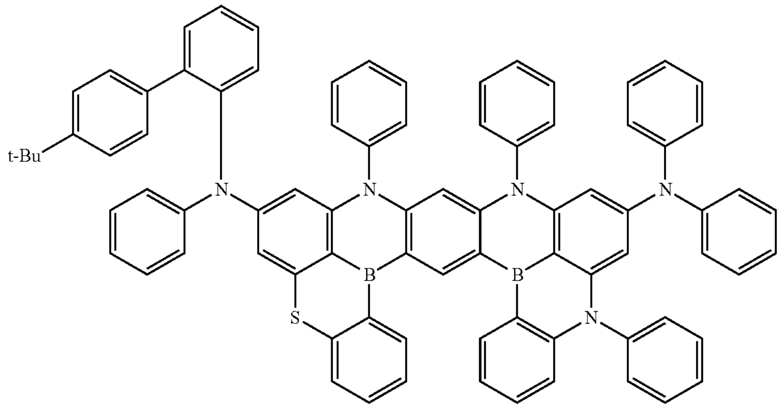
14
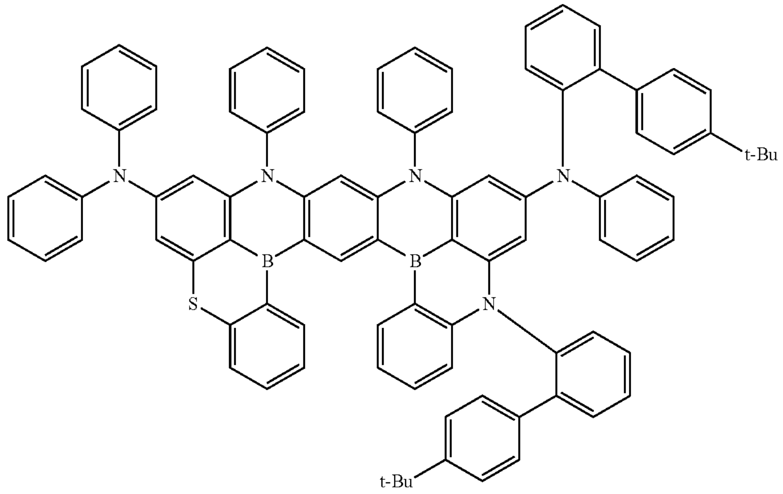
15
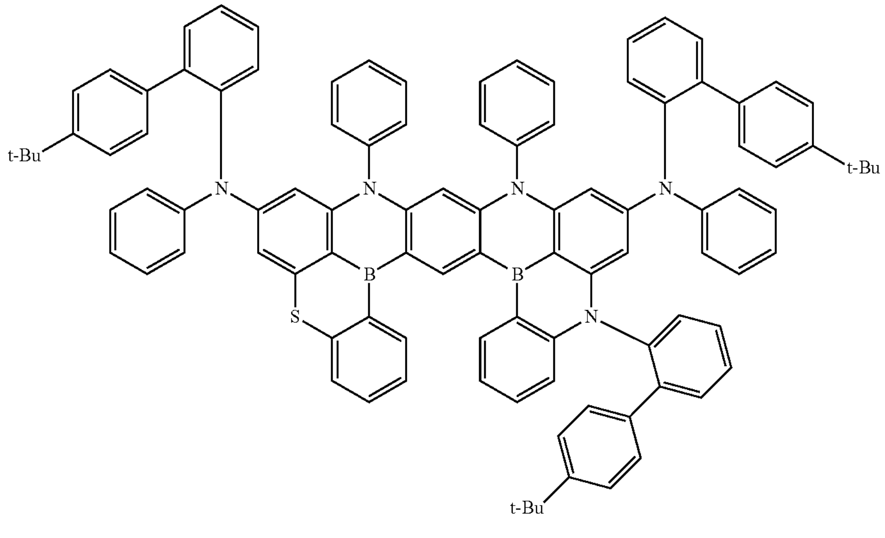

-continued
16
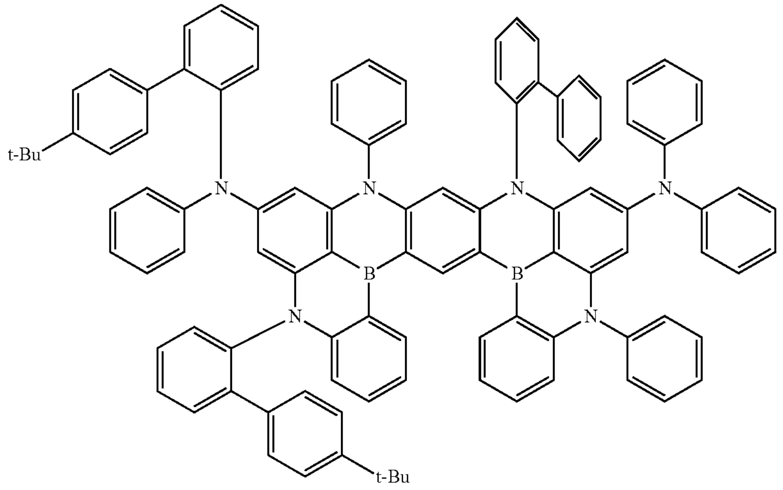
17
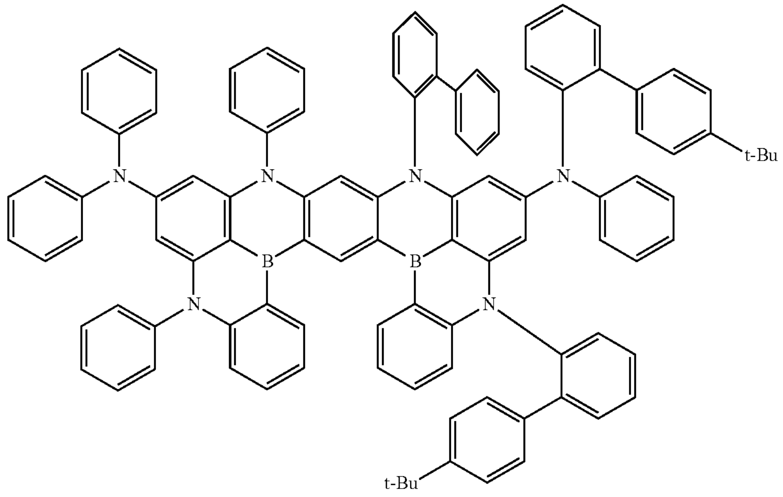
18
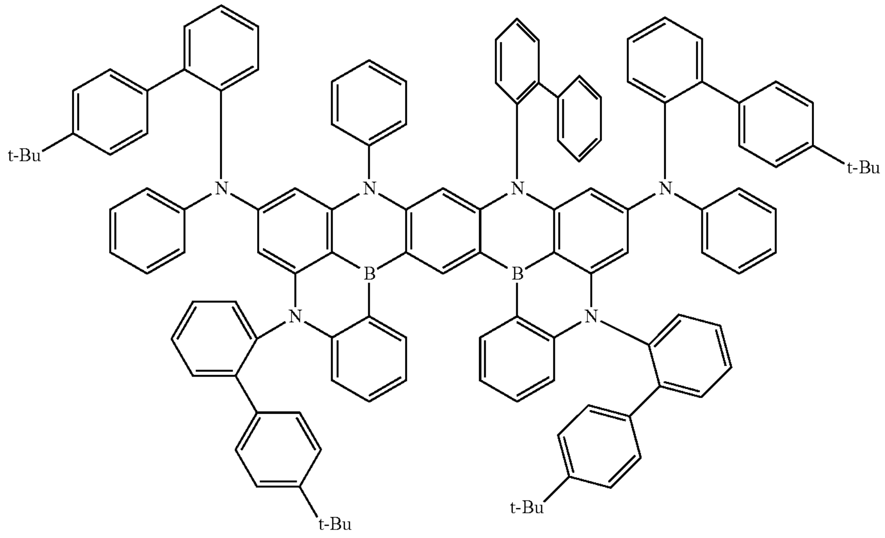

-continued
19
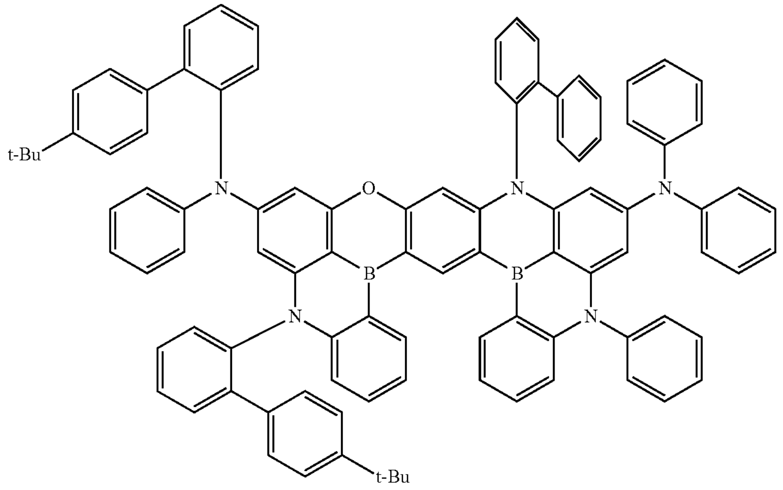
20
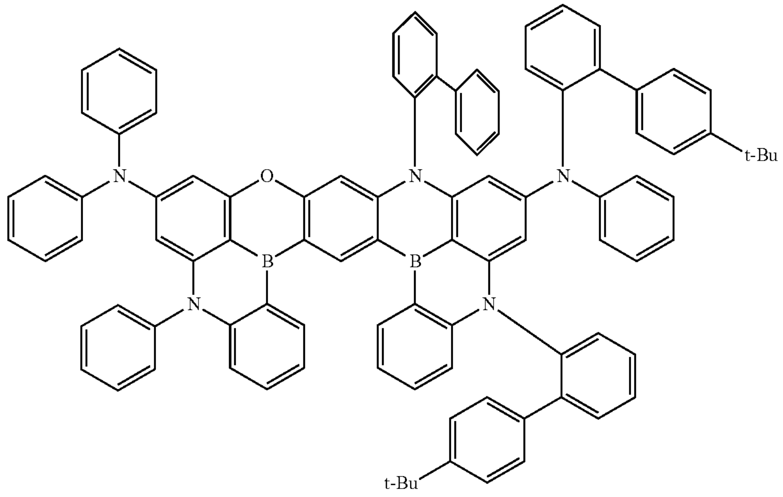
21
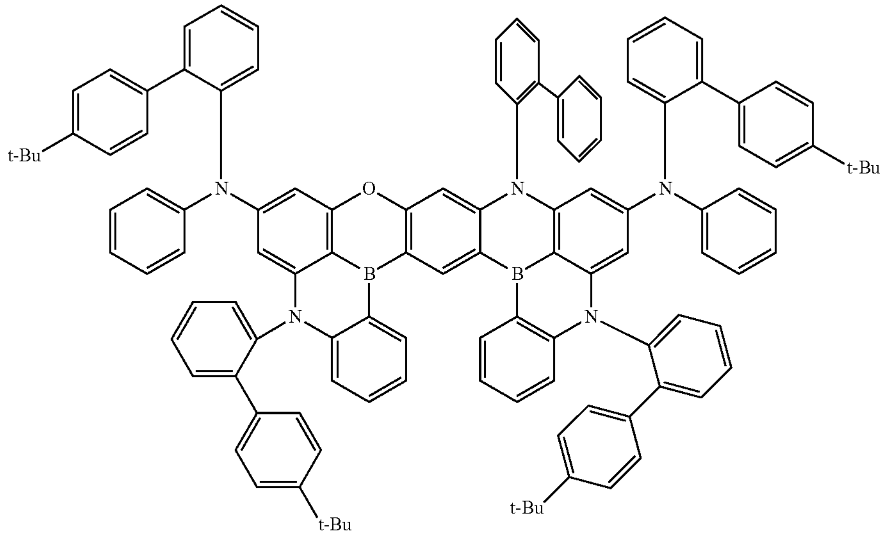

-continued
22
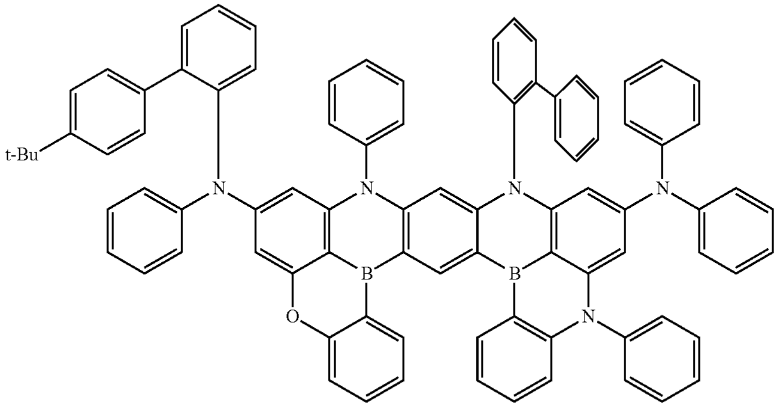
23
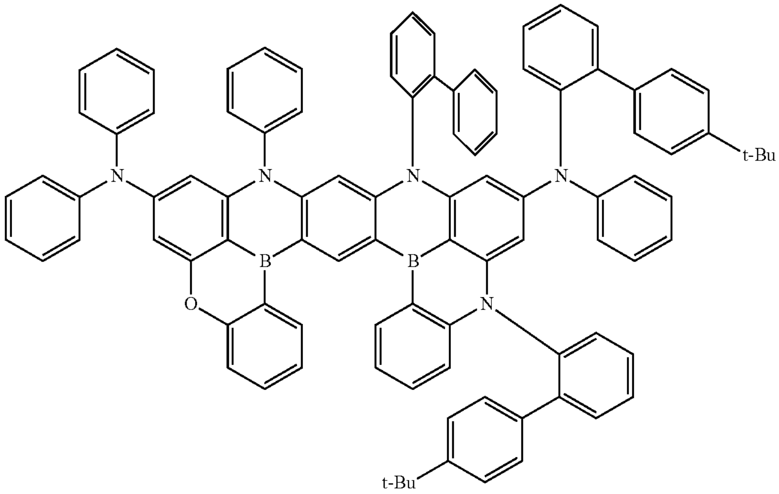
24
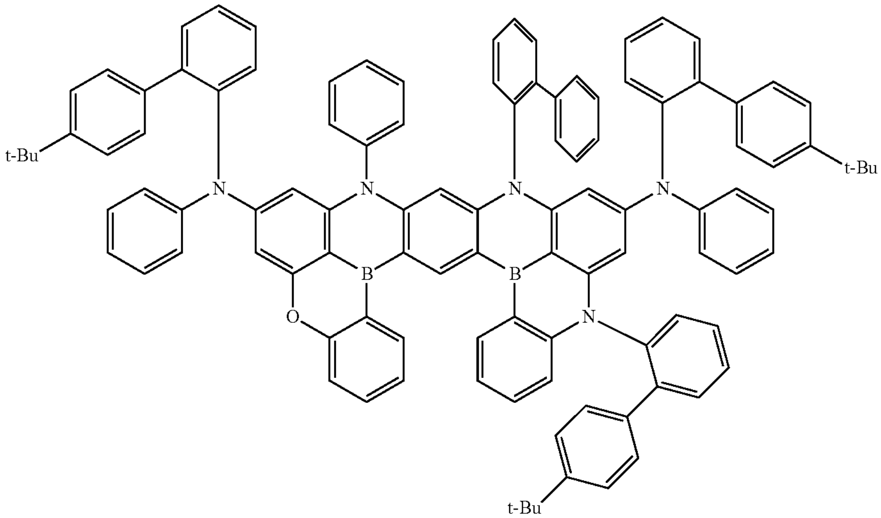

-continued
25
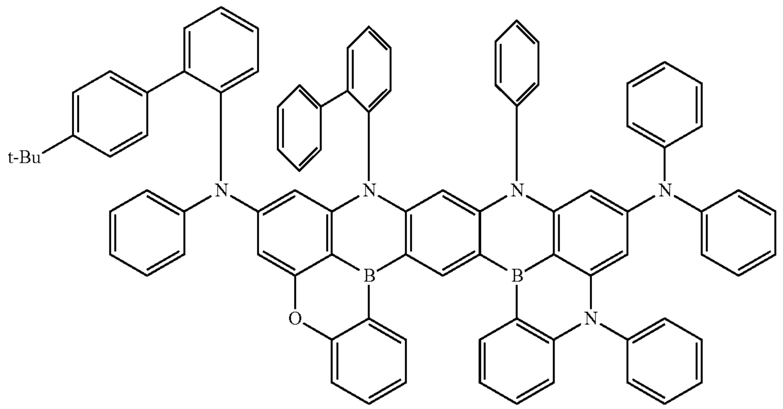
26
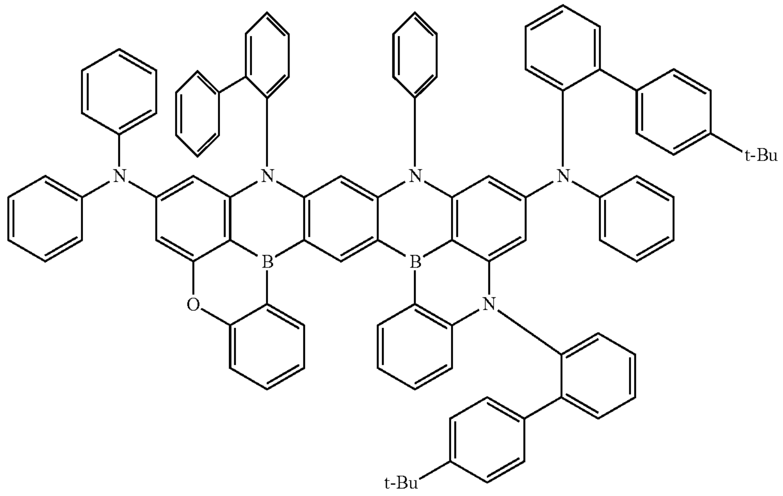
27
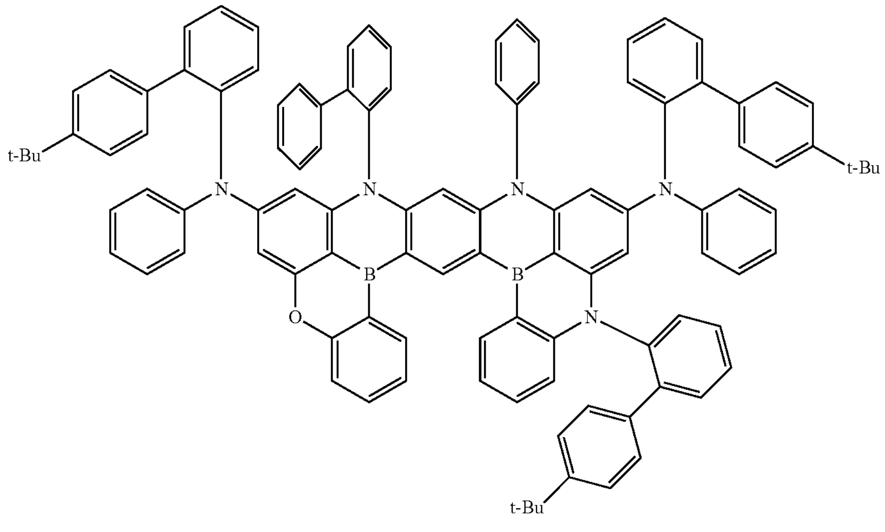

-continued
28
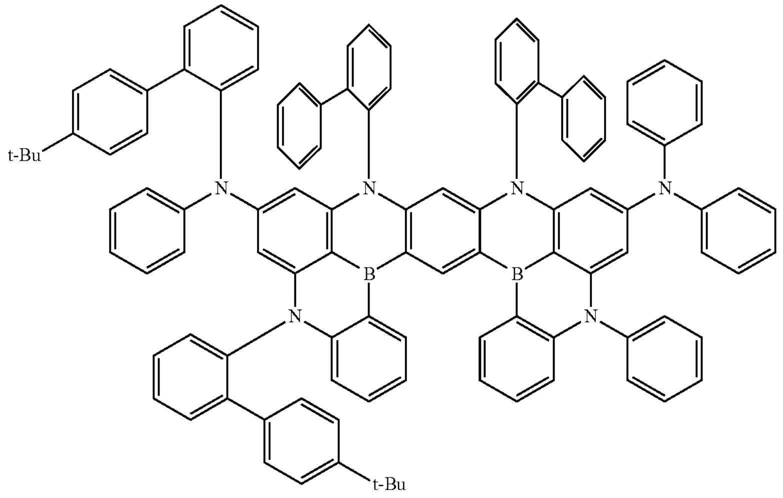
29
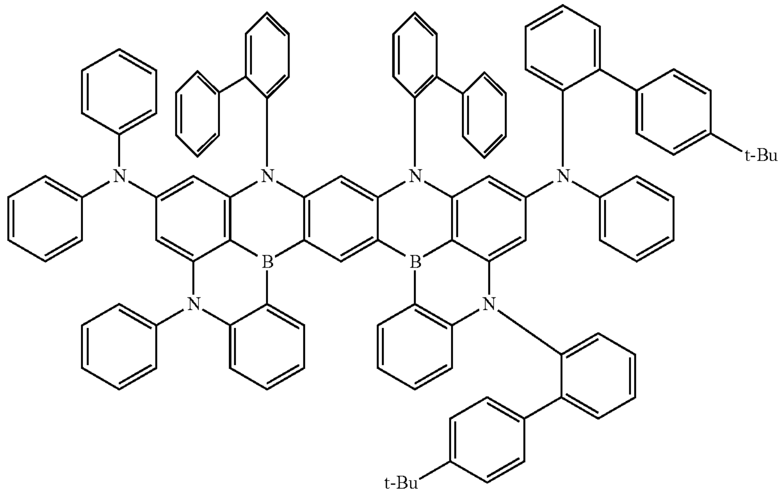
30
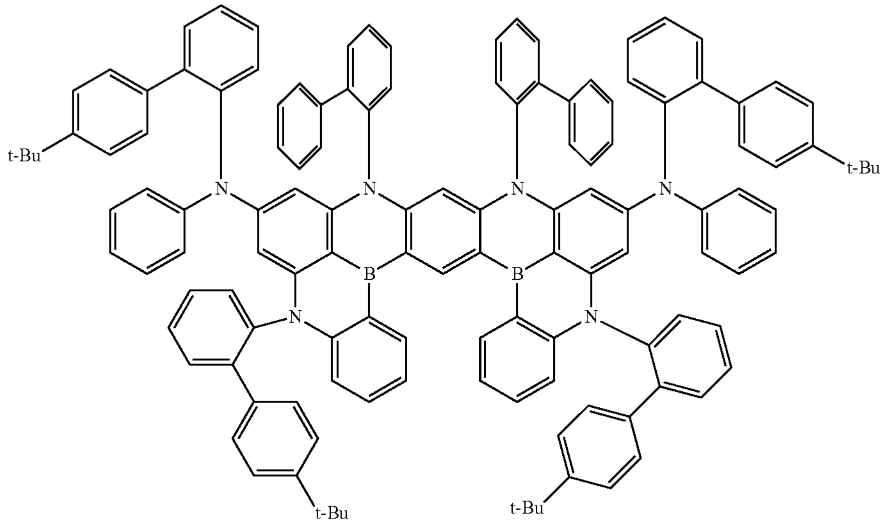

-continued
31
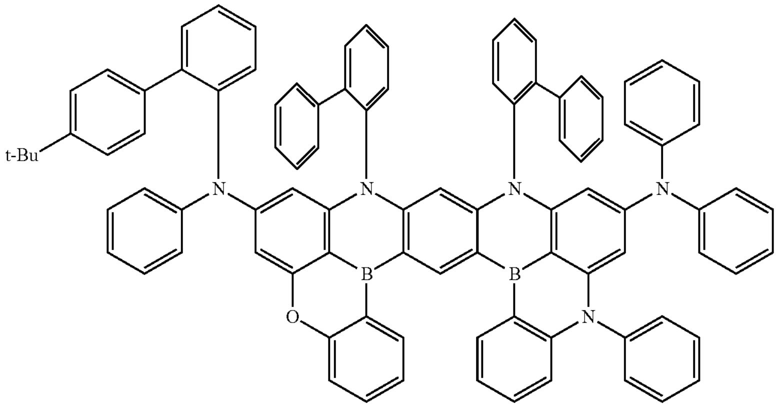
32
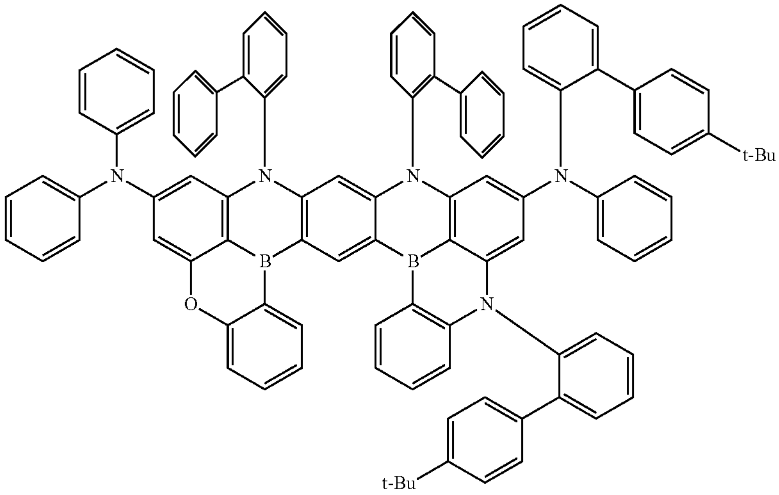
33
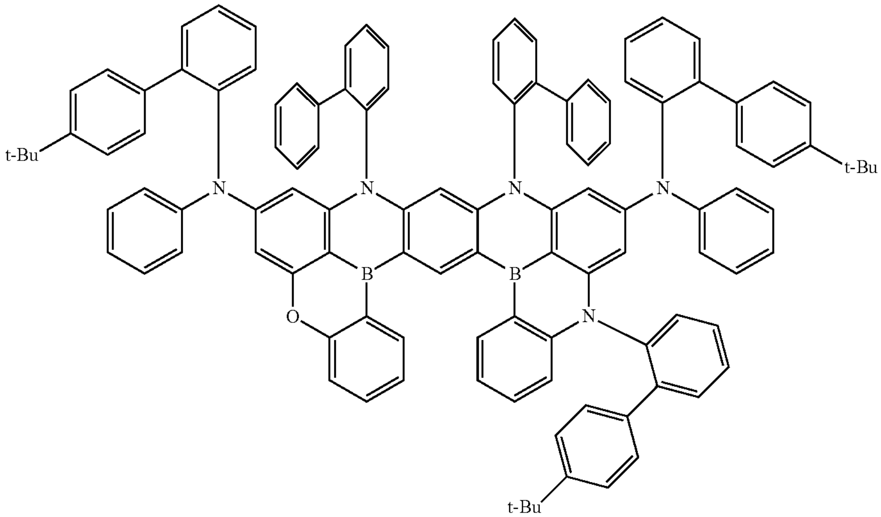

-continued
34
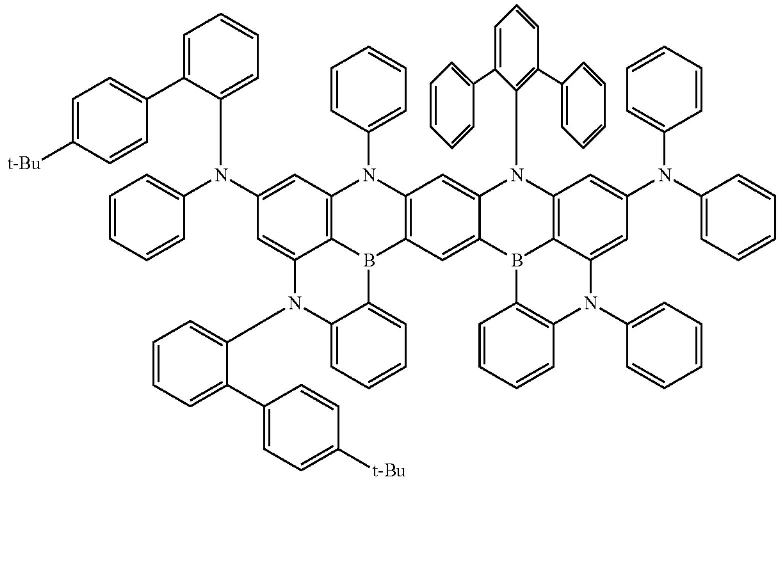
35
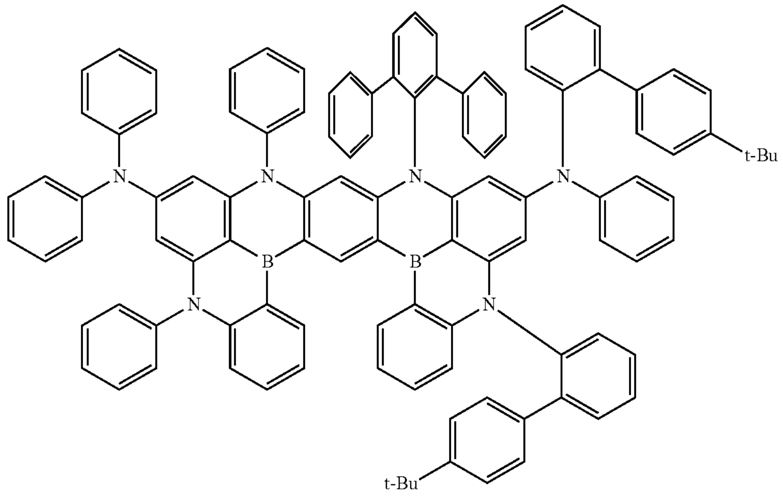
36
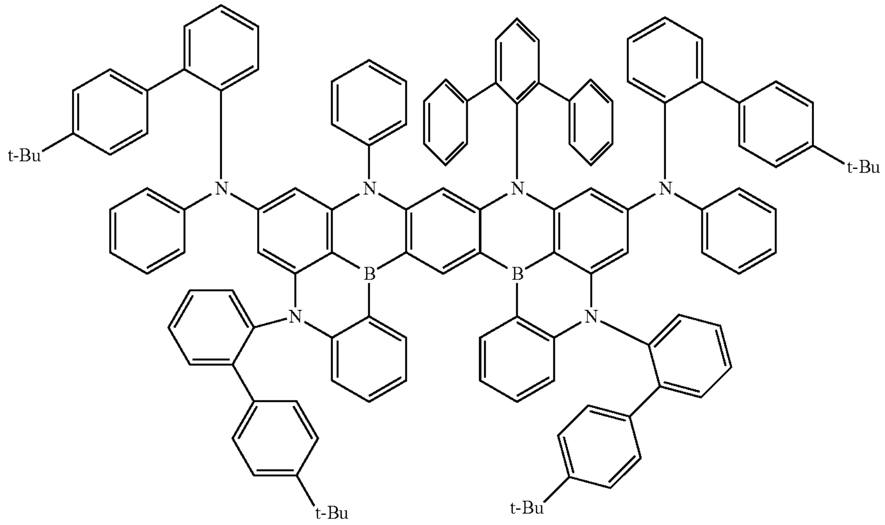

-continued
37
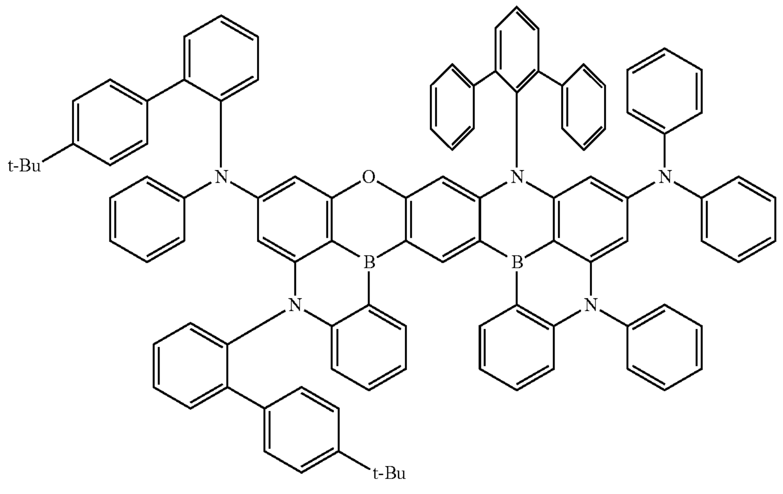
38
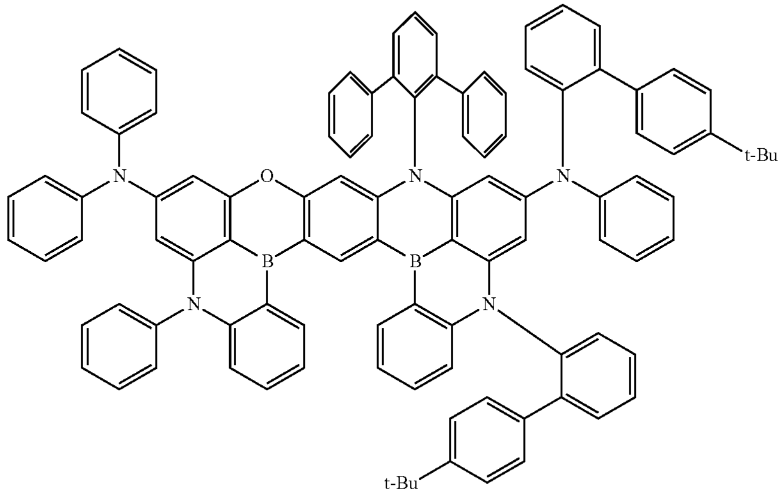
39
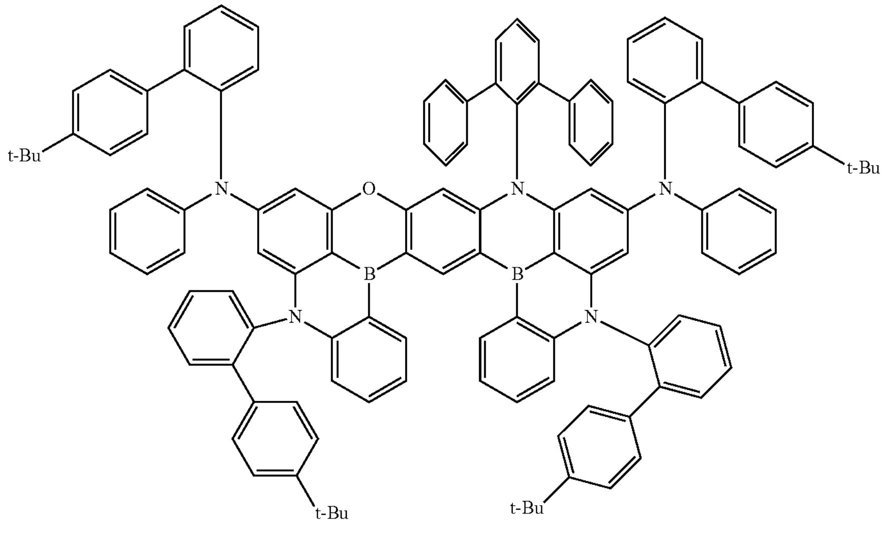

-continued
40
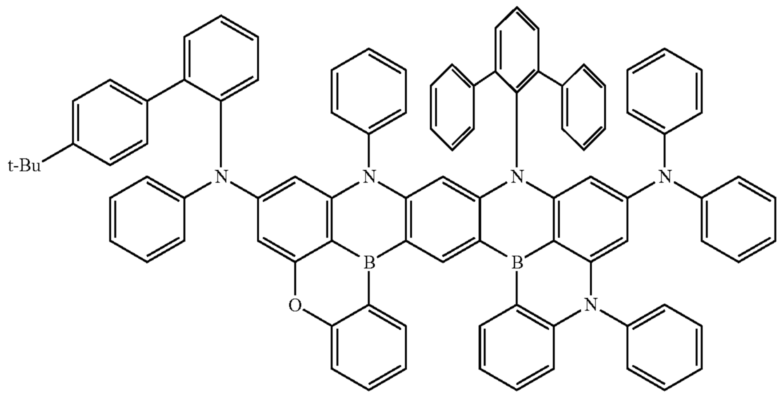
41
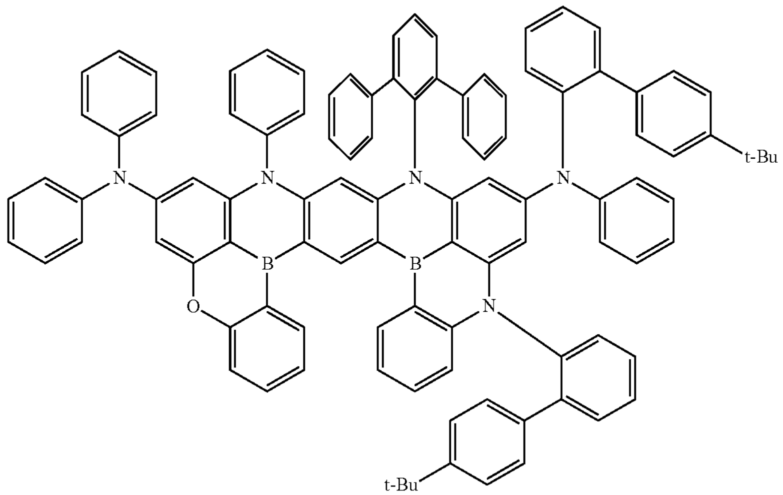
42
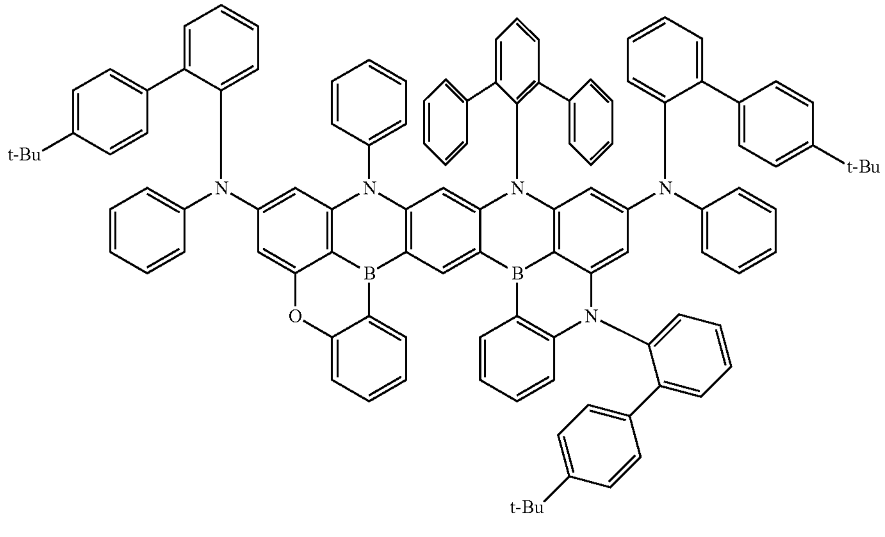

-continued
43
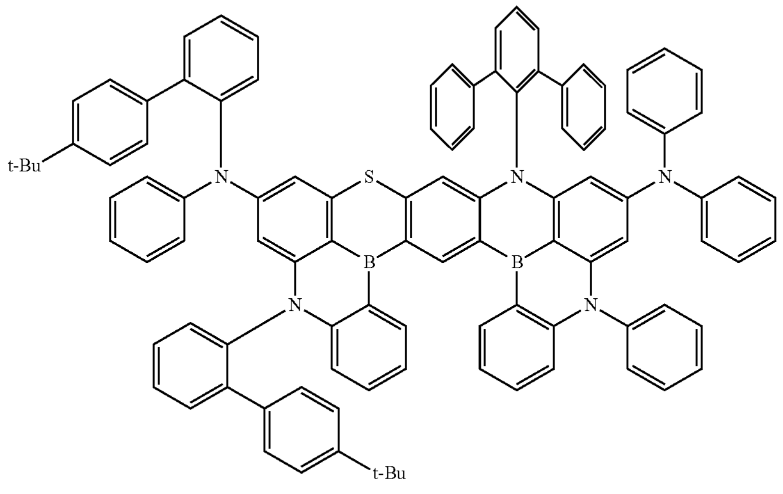
44
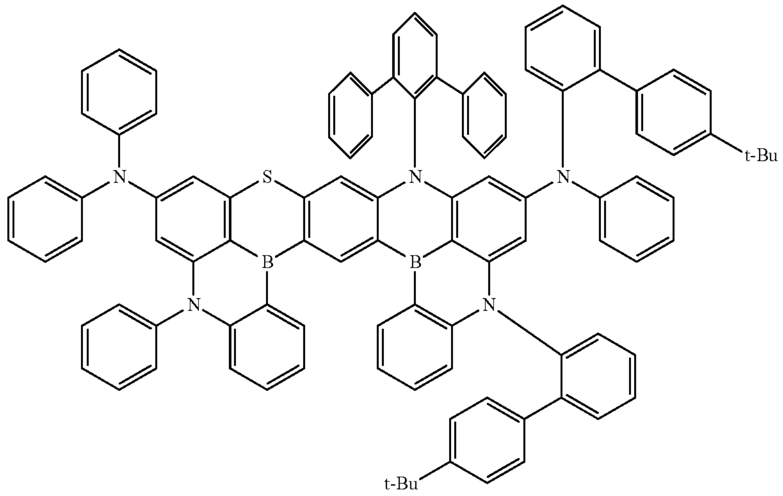
45
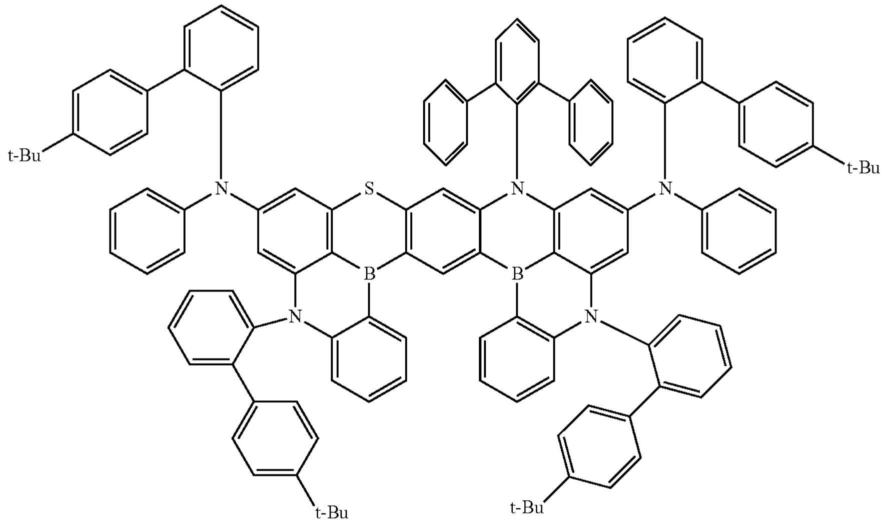

-continued
46
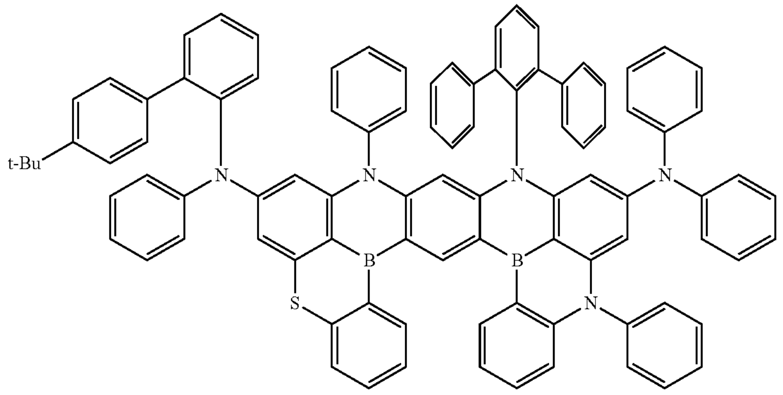
47
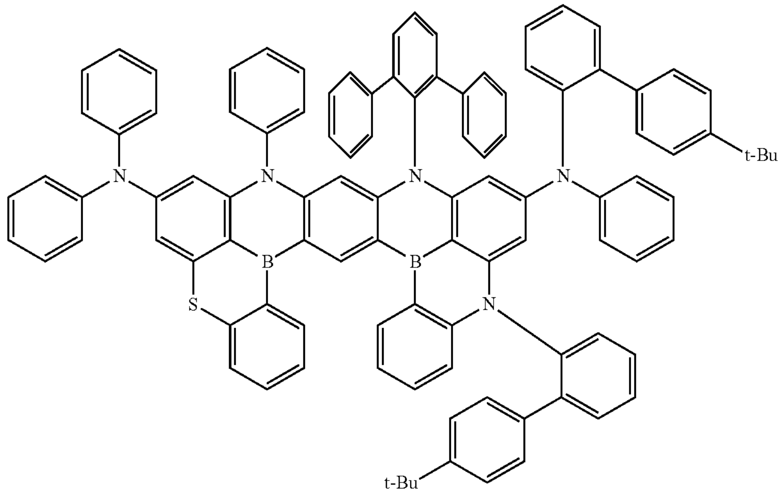
48
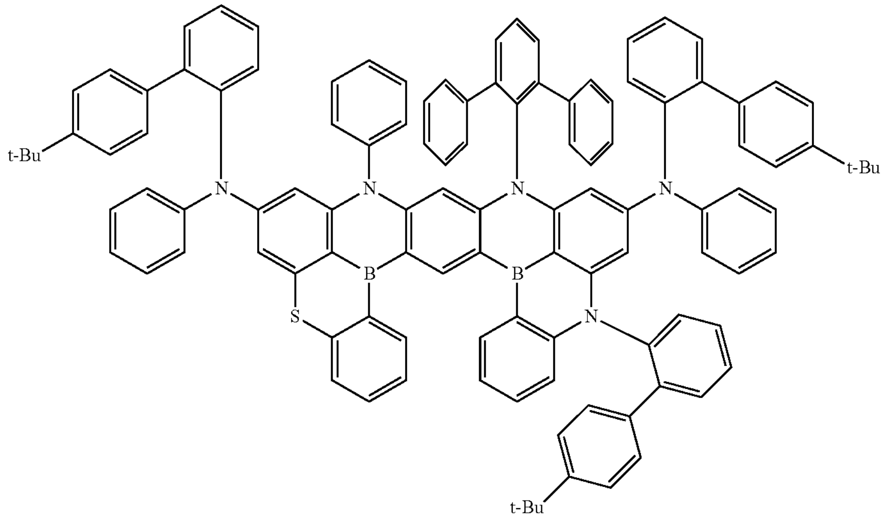

-continued
49
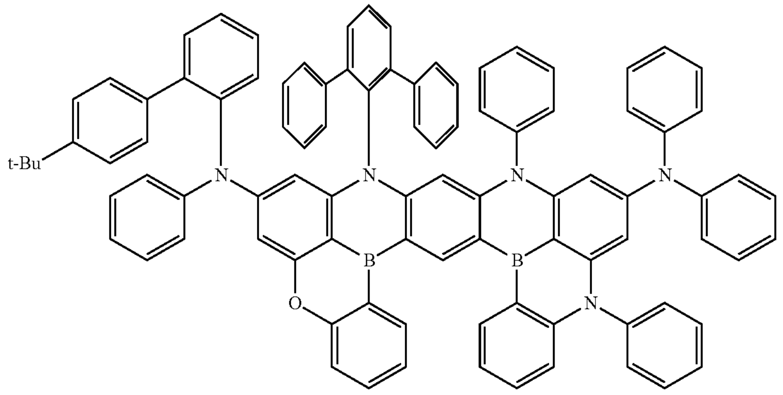
50
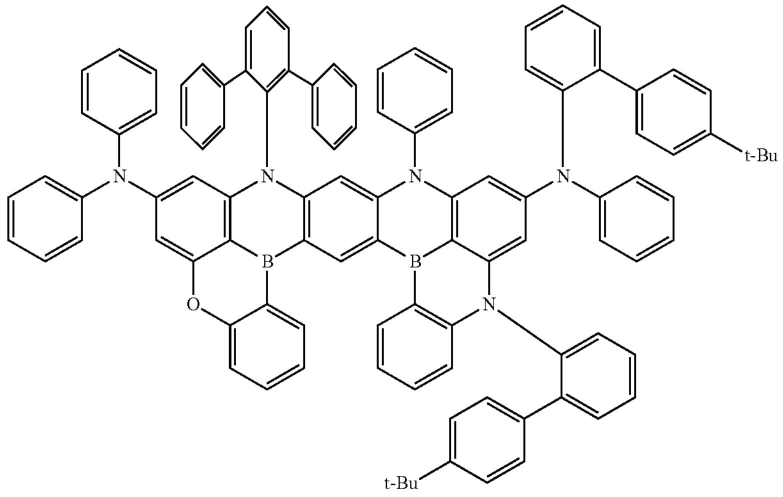
51
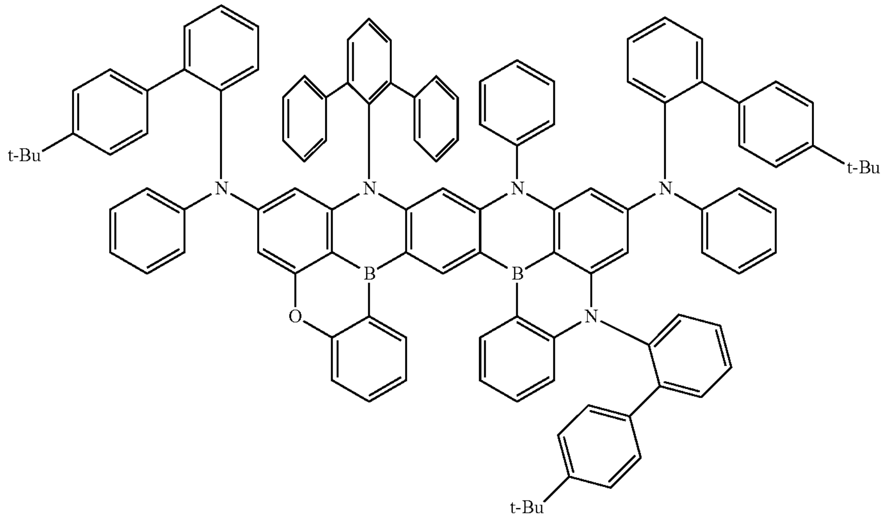

-continued
52
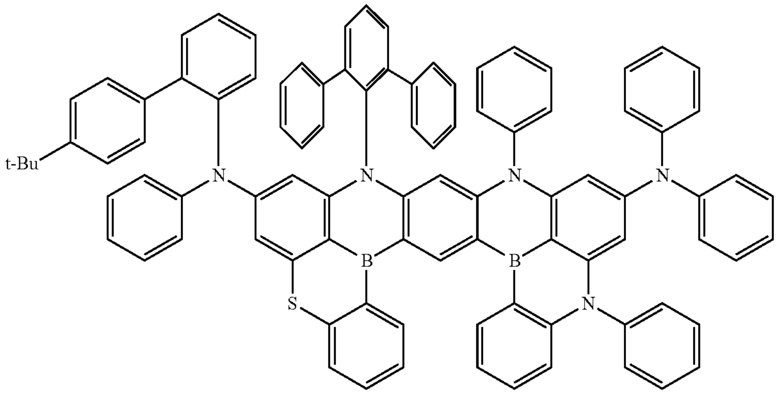
53
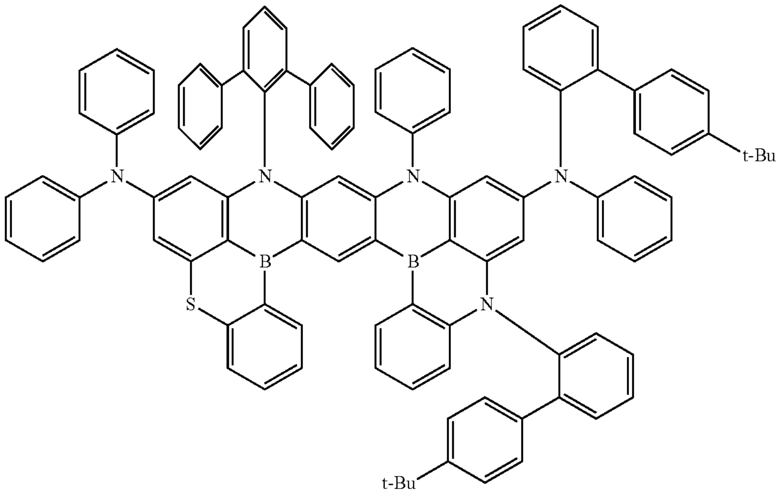
54
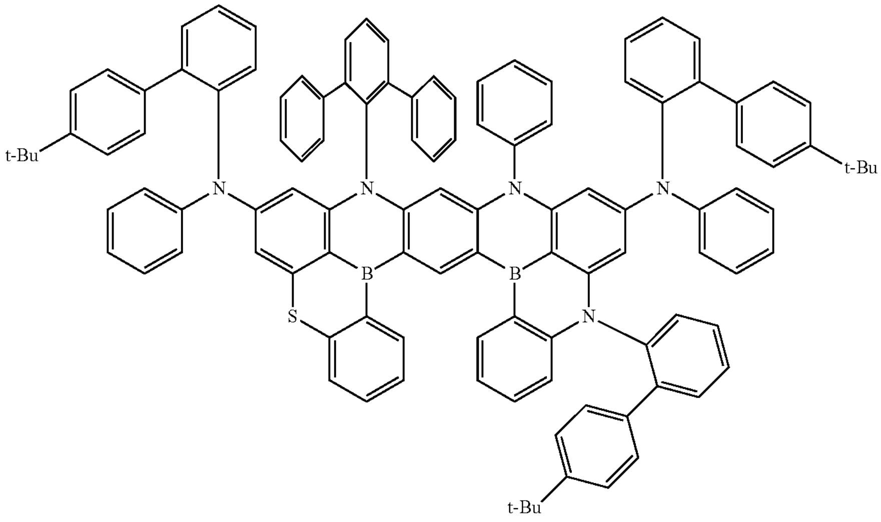

-continued
55
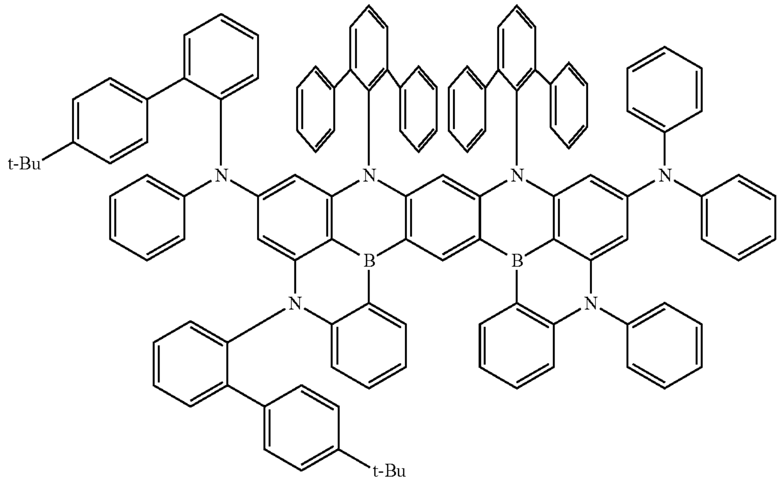
56
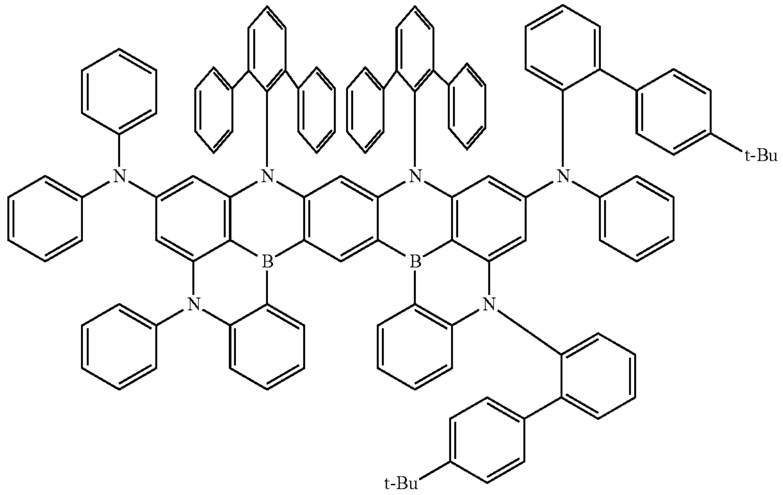
57
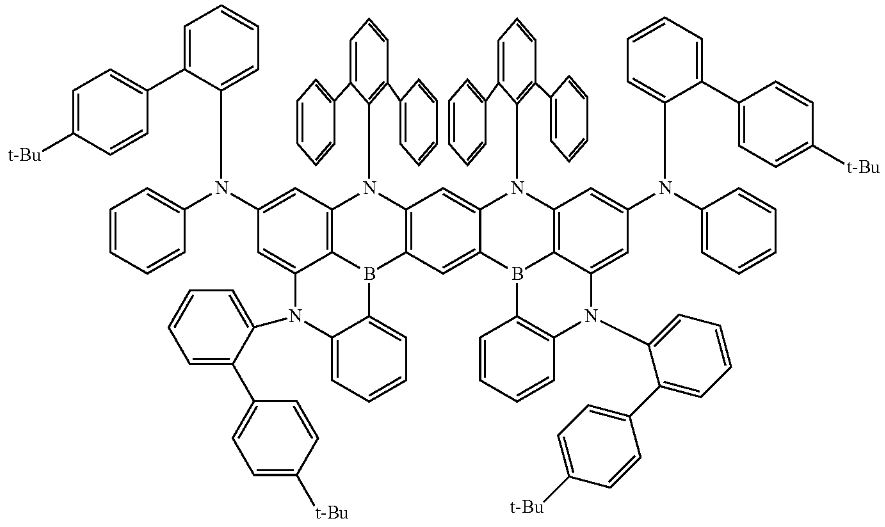

-continued
58
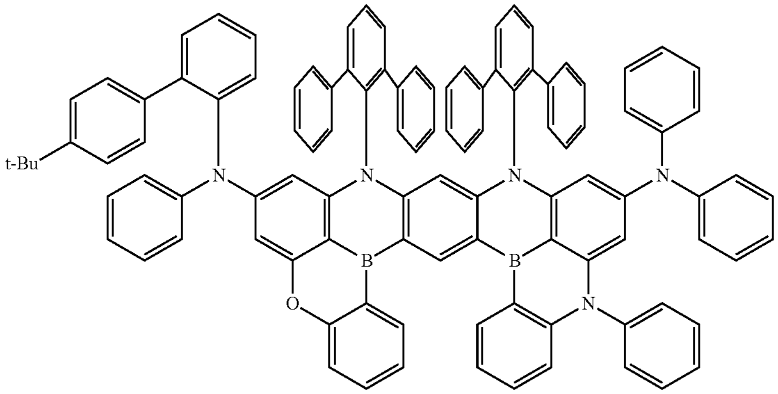
59
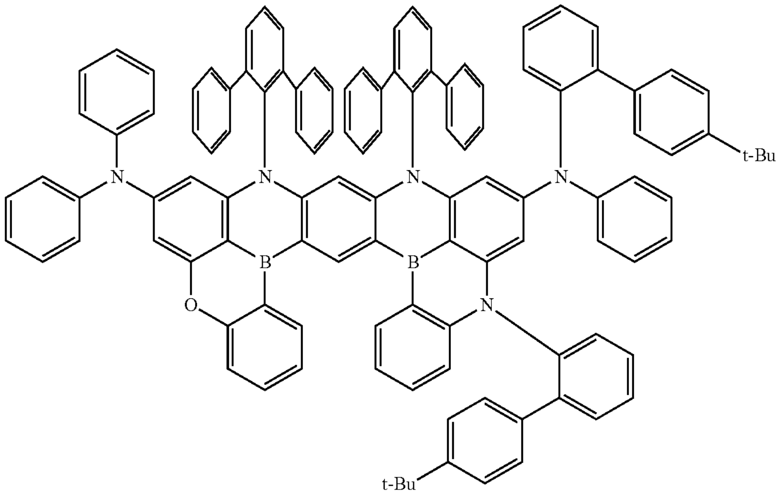
60
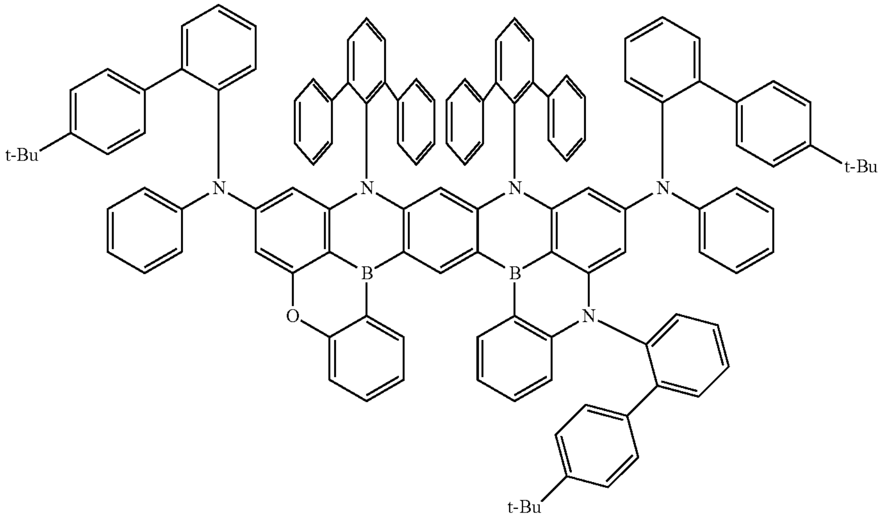

-continued
61
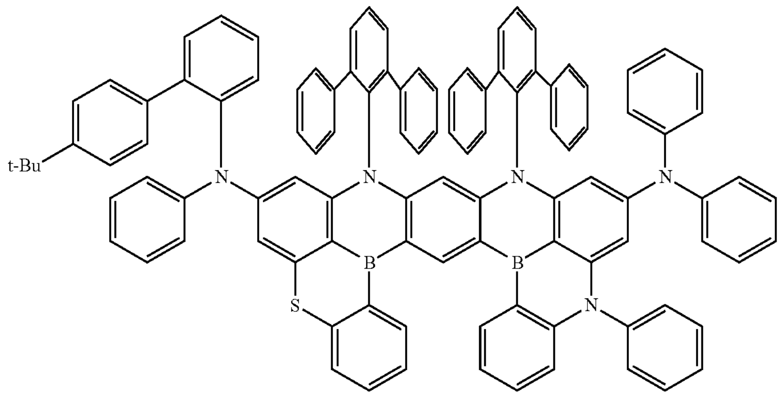
62
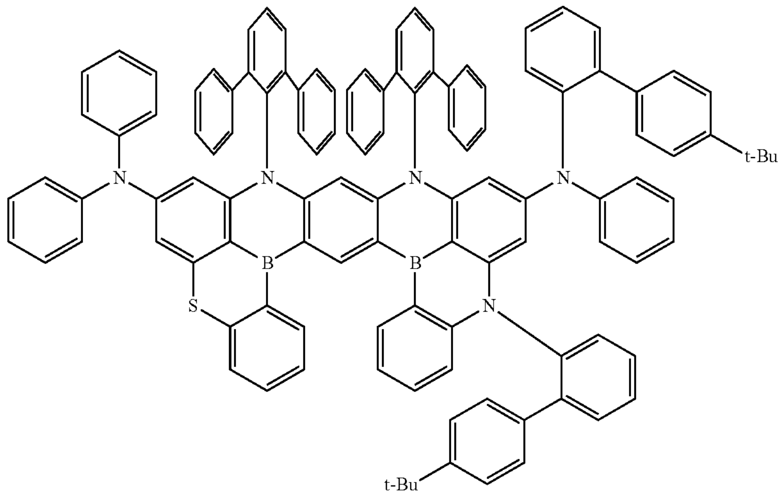
63
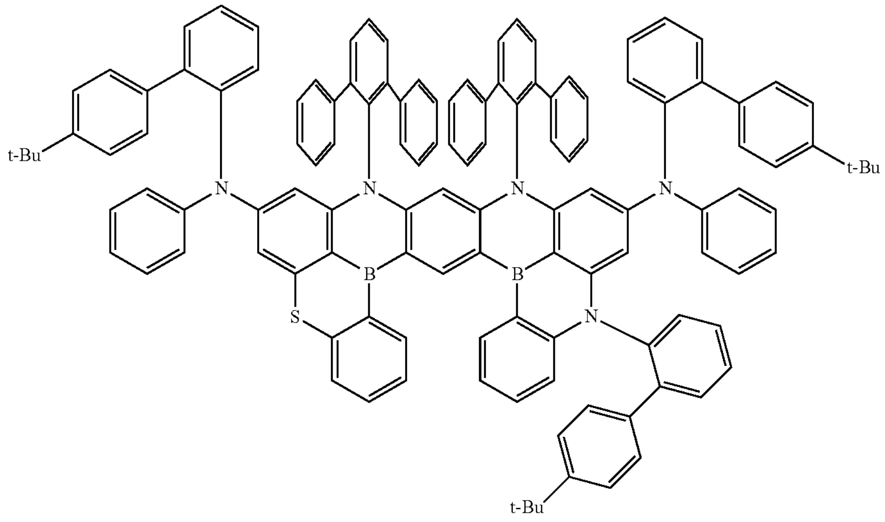

-continued
64
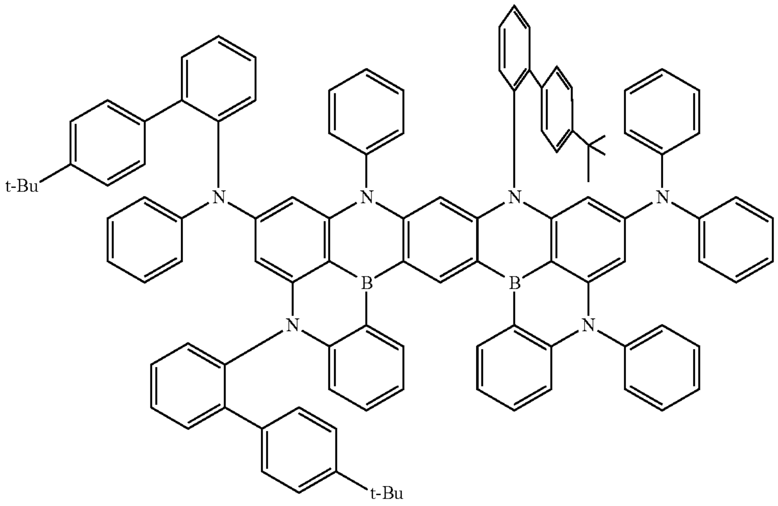
65
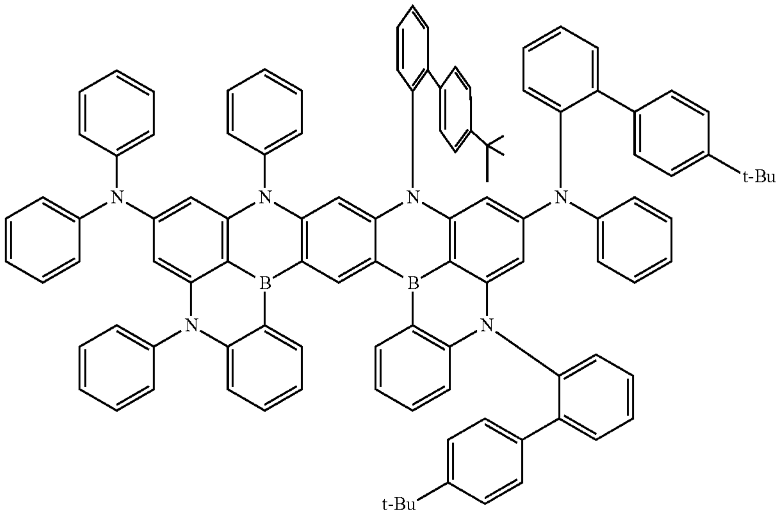
66
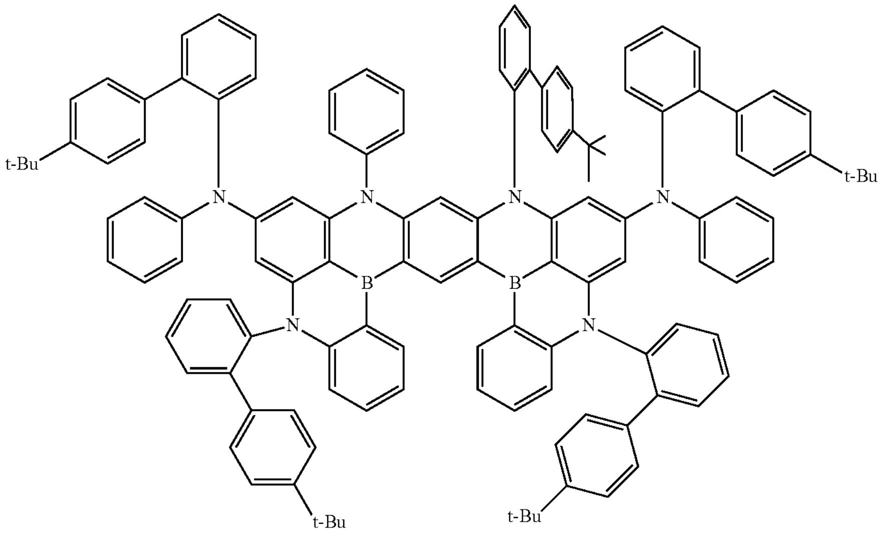

-continued
67
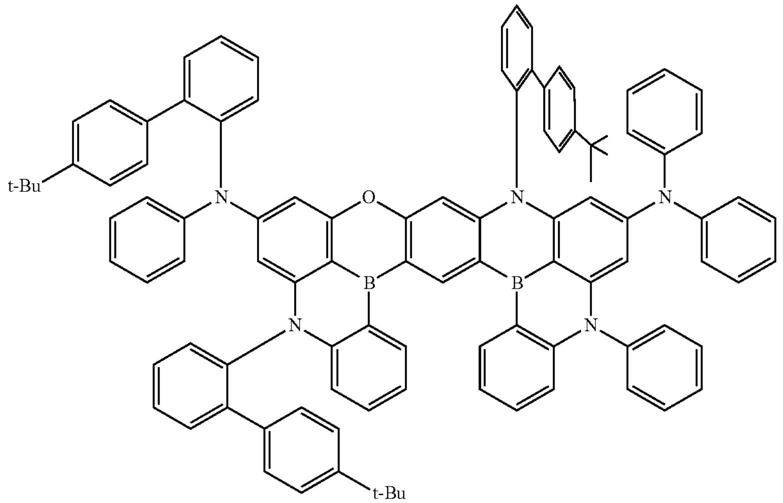
68
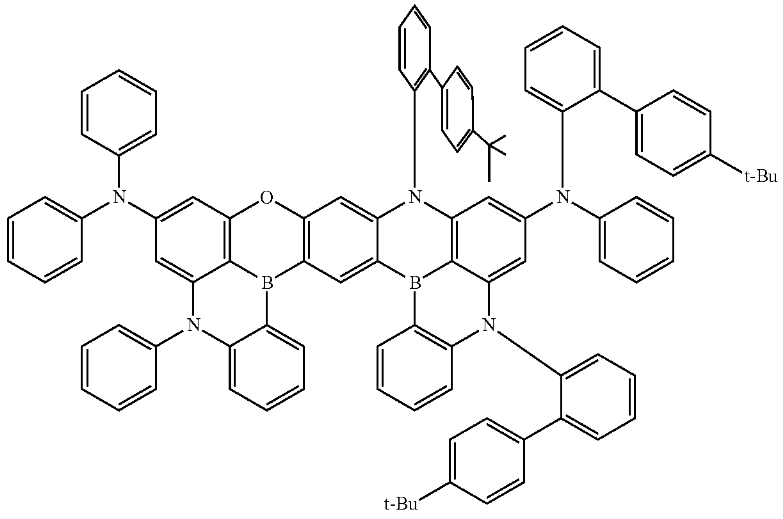
69
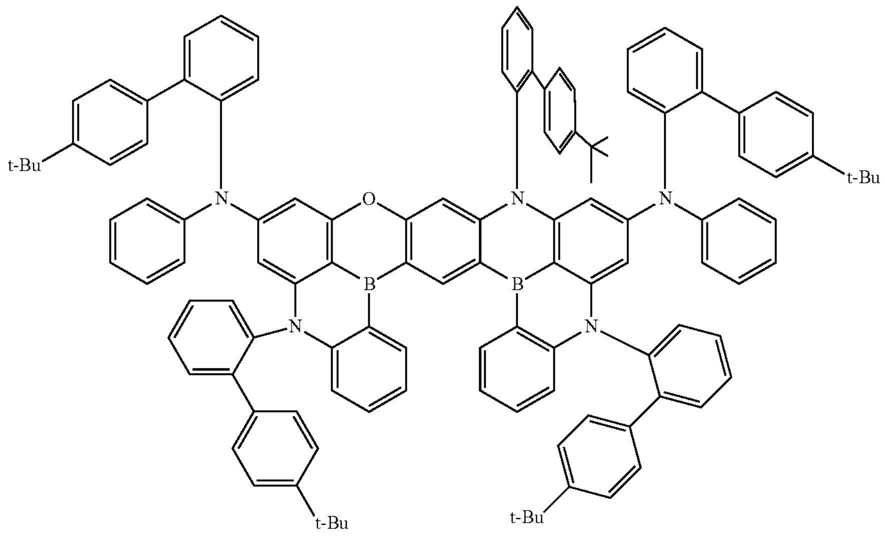

-continued
70
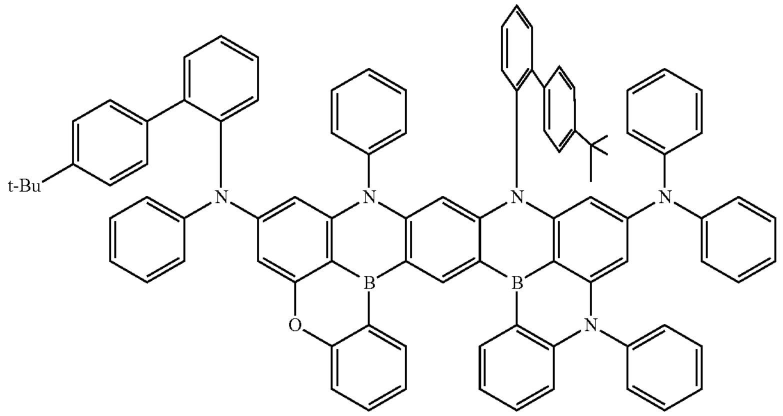
71
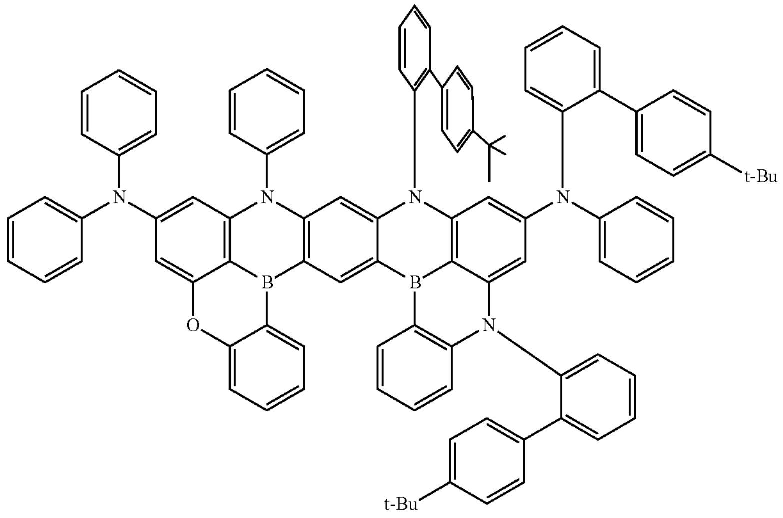
72
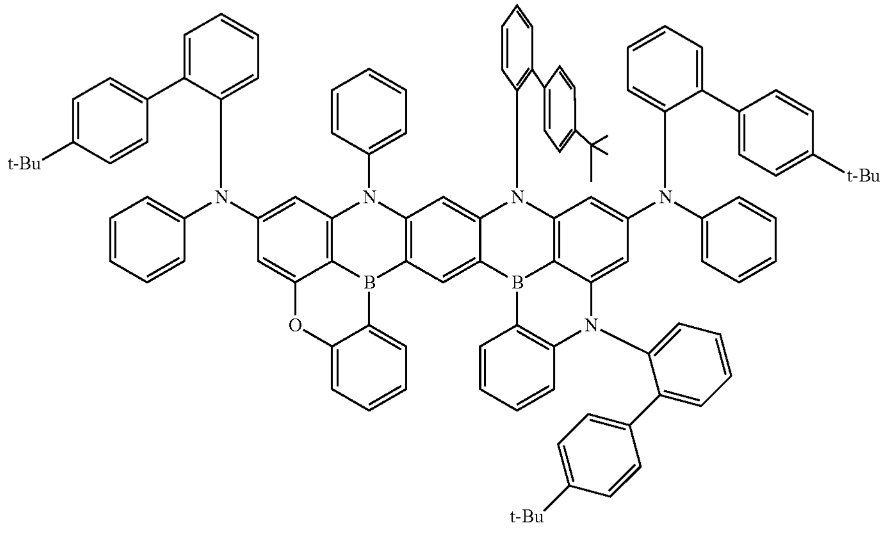

-continued
73
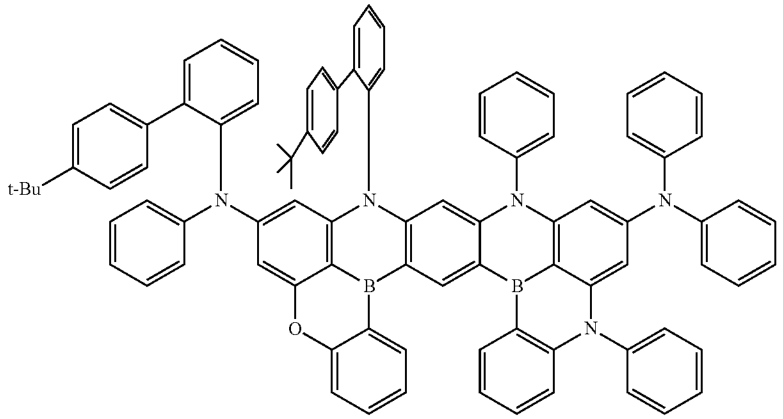
74
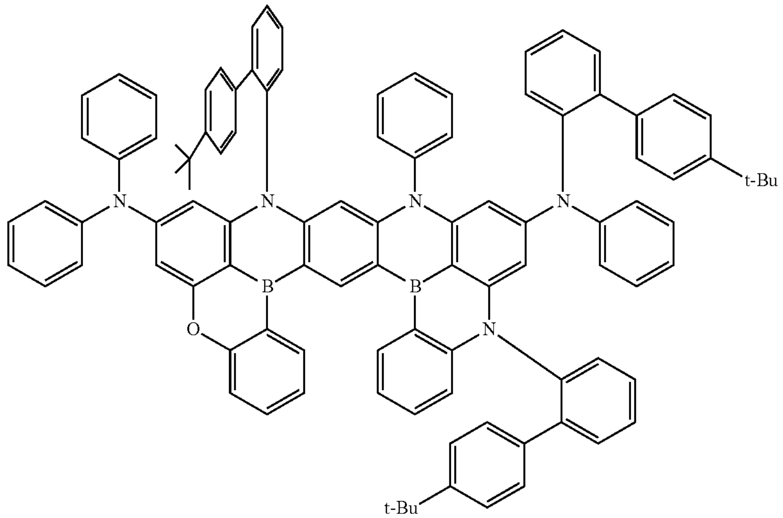
75
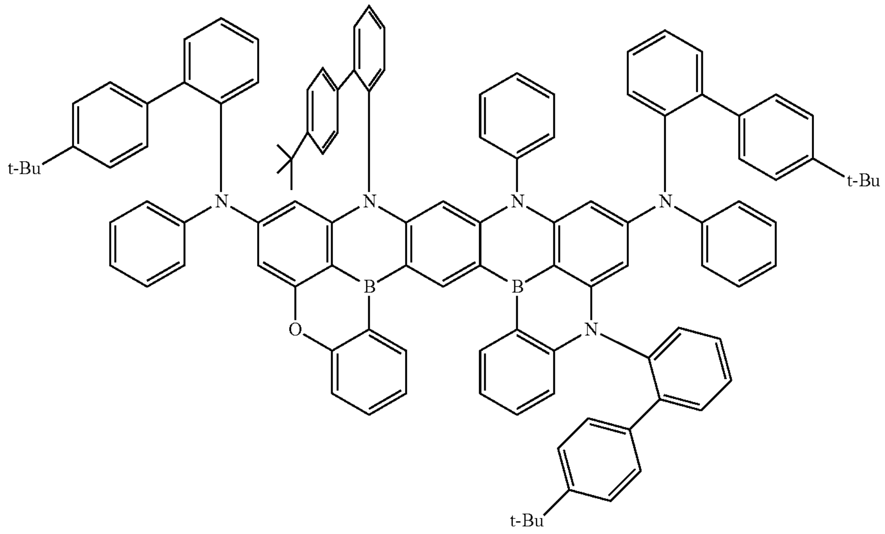

-continued
76
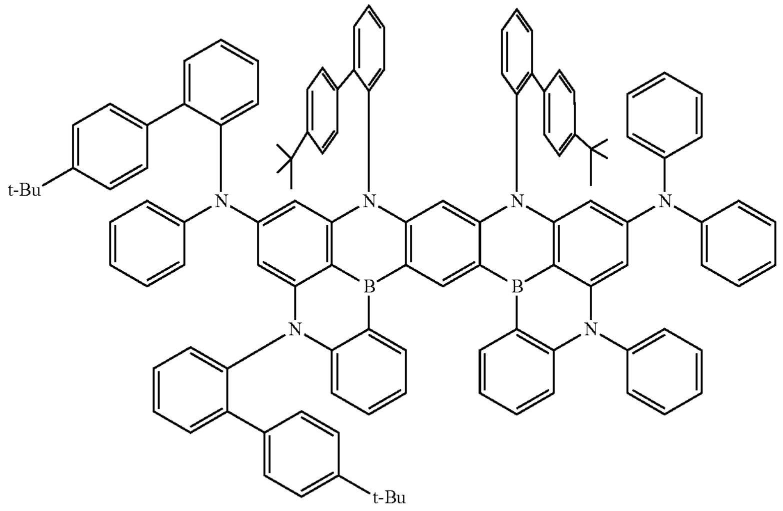
77
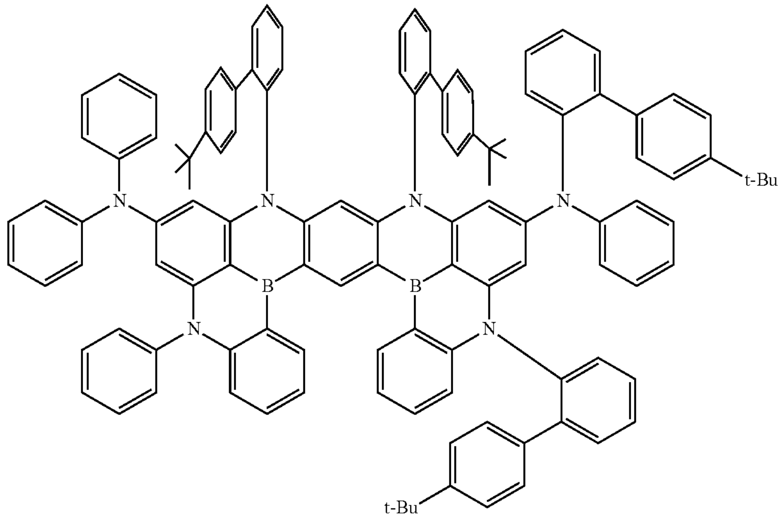
78
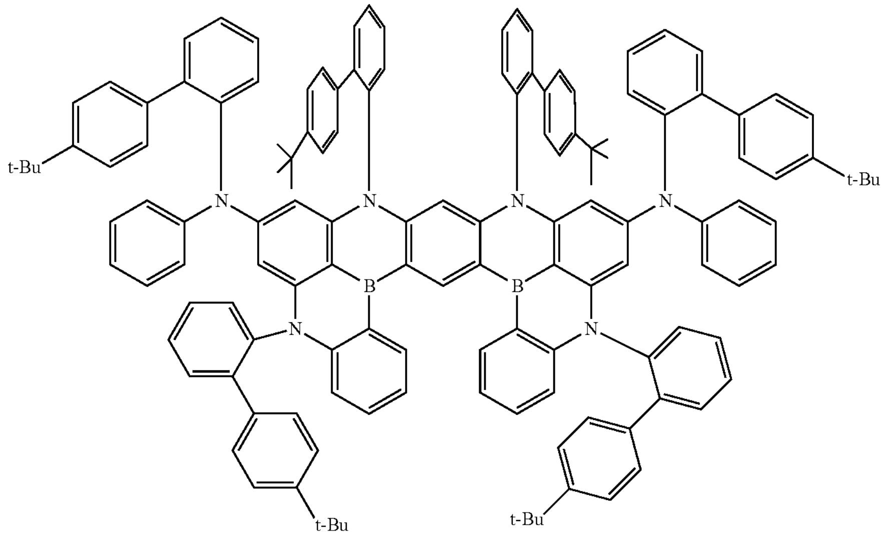

-continued
79
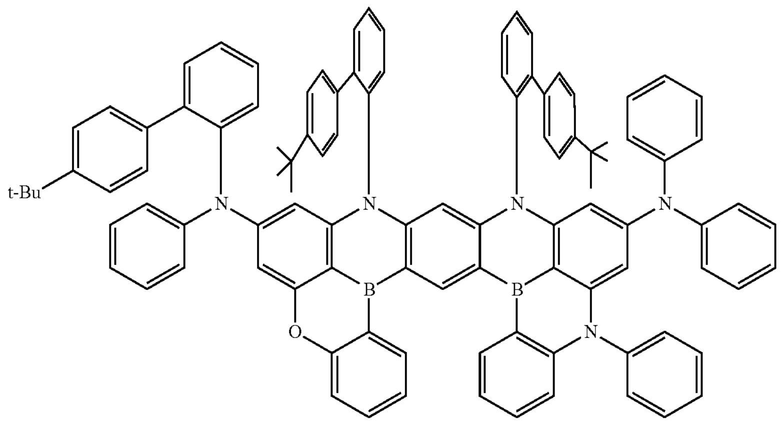
80
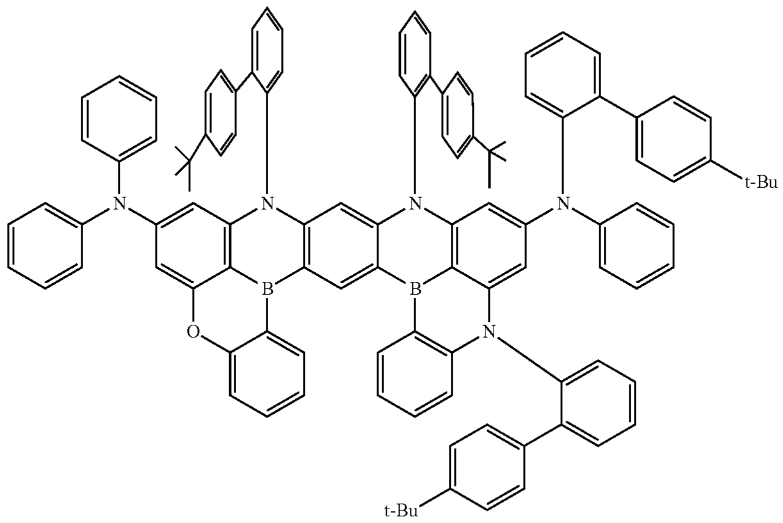
81
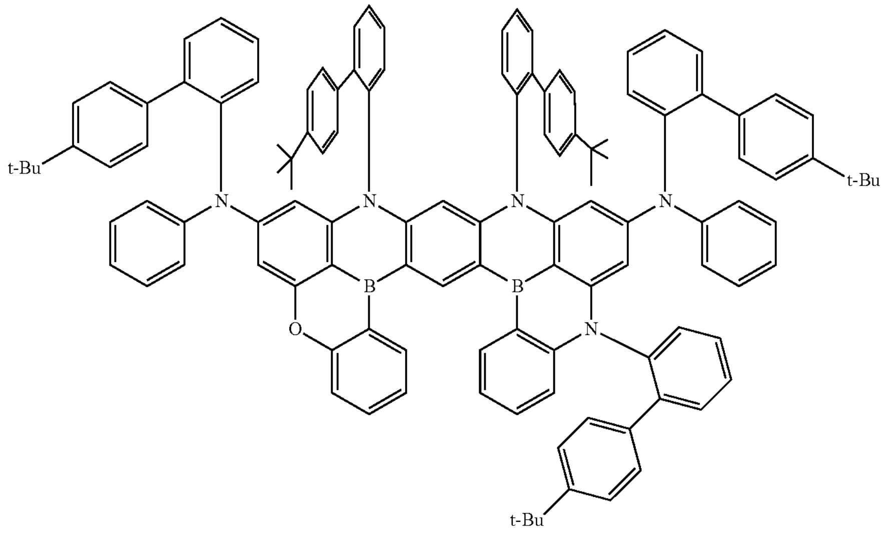

-continued
82
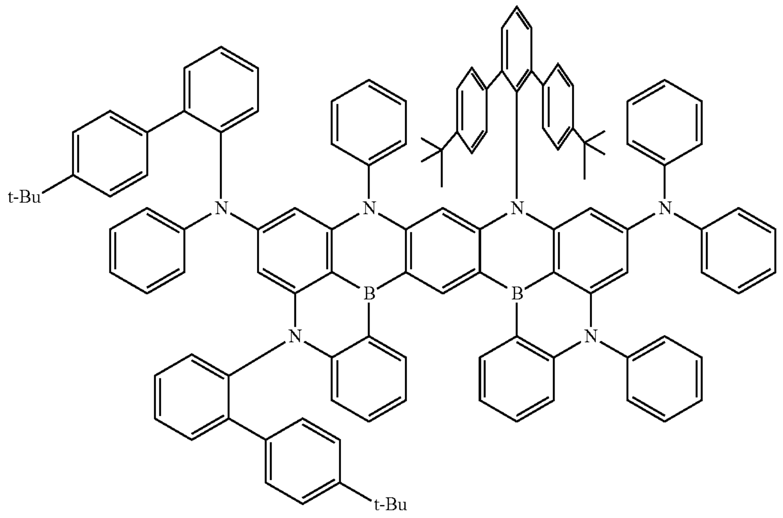
83
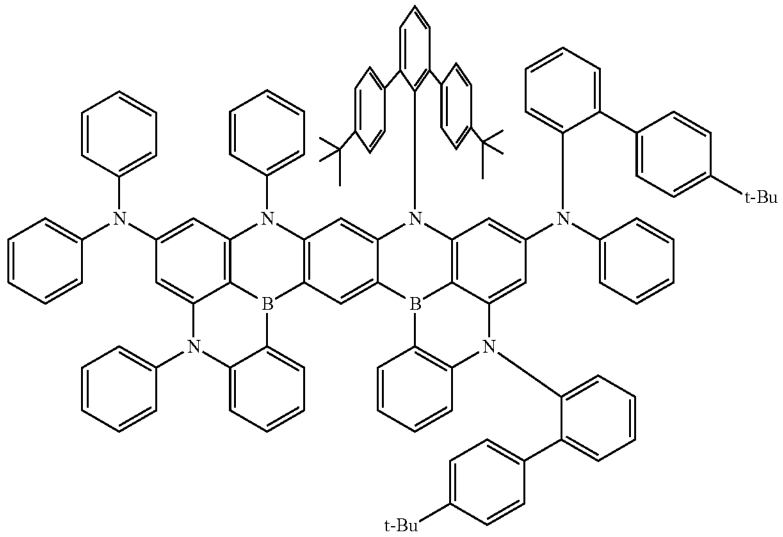
84
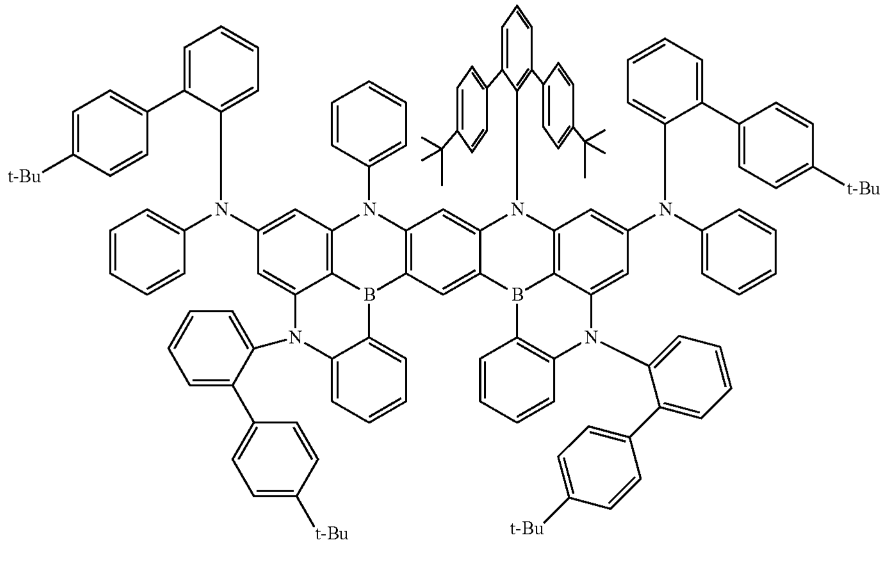

-continued
85
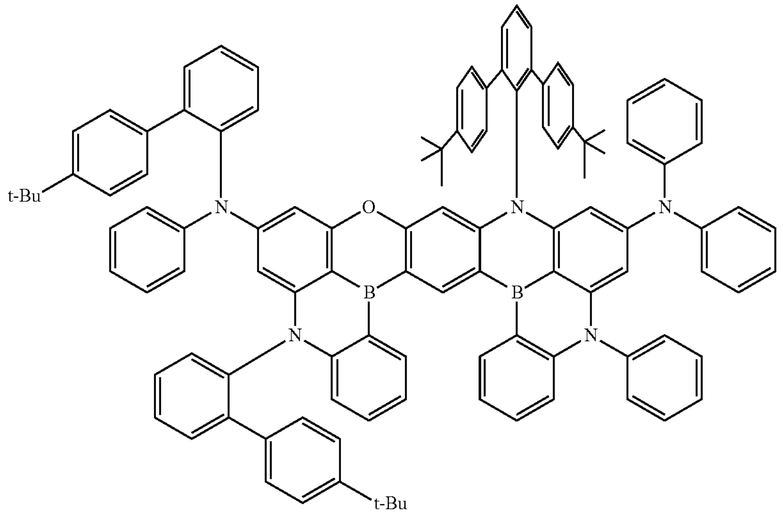
86
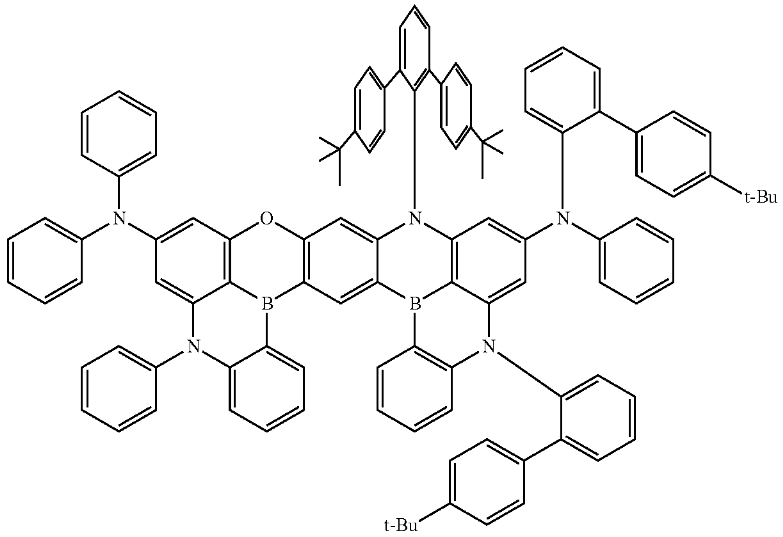
87
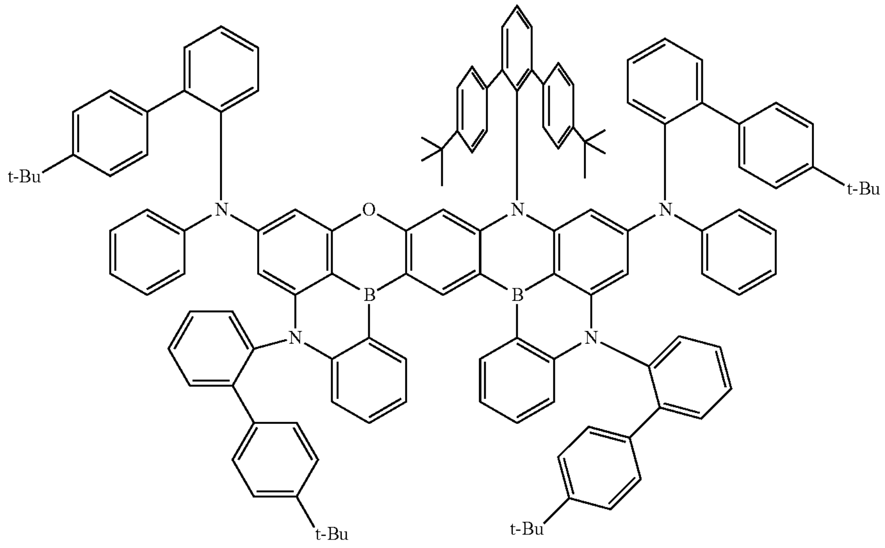

-continued
88
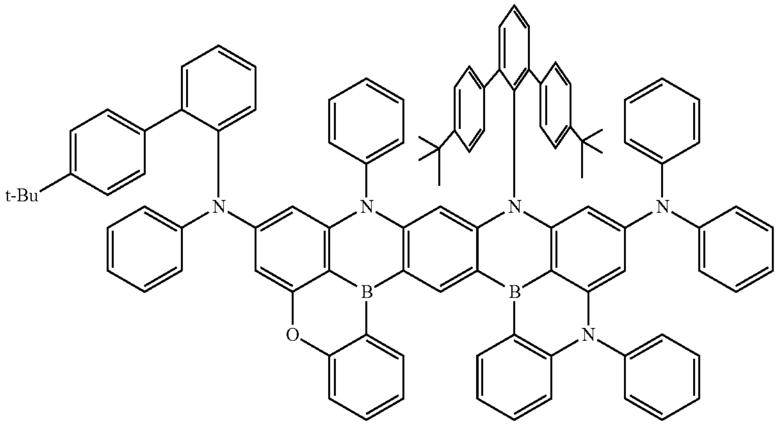
89
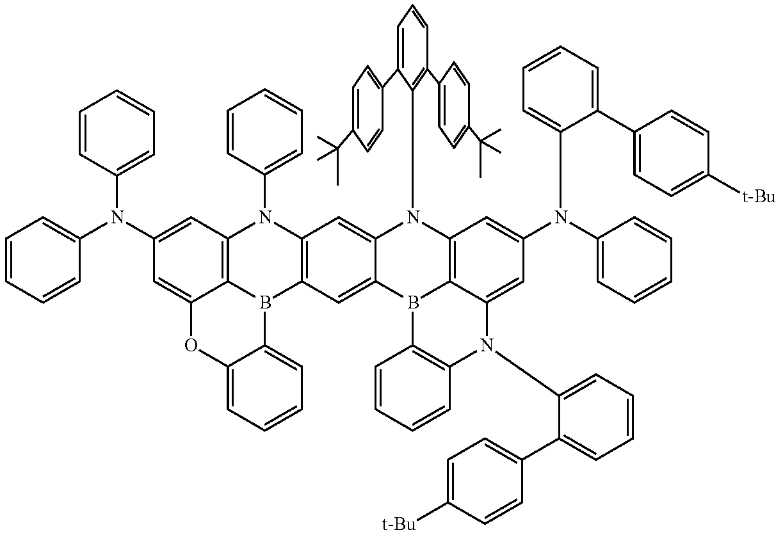
90
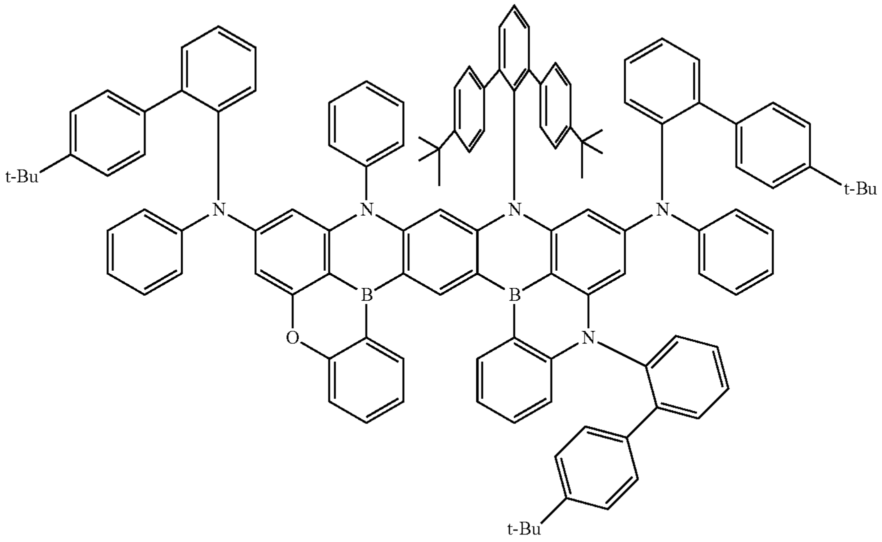

-continued
91
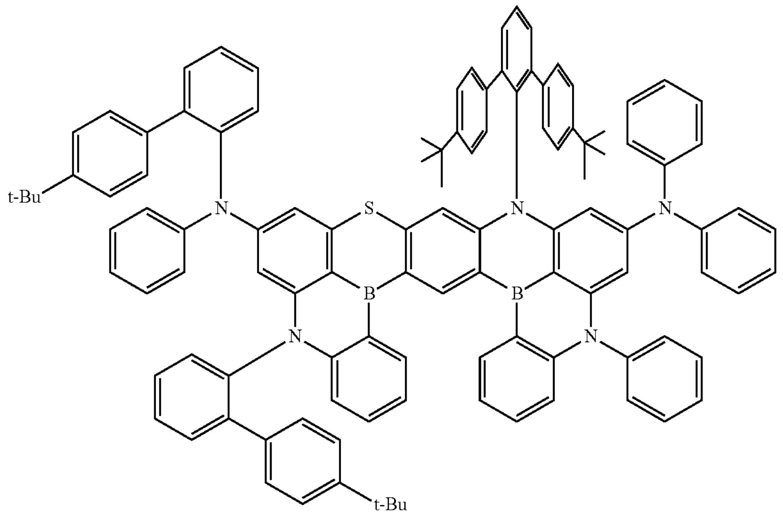
92
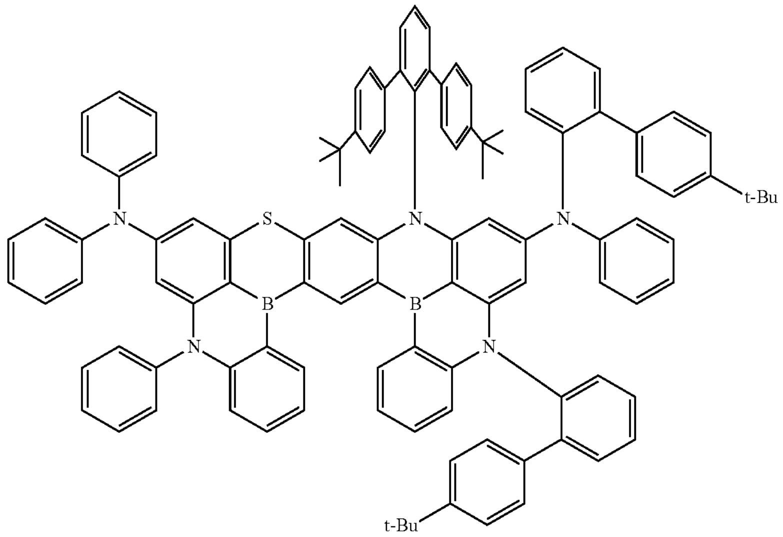
93
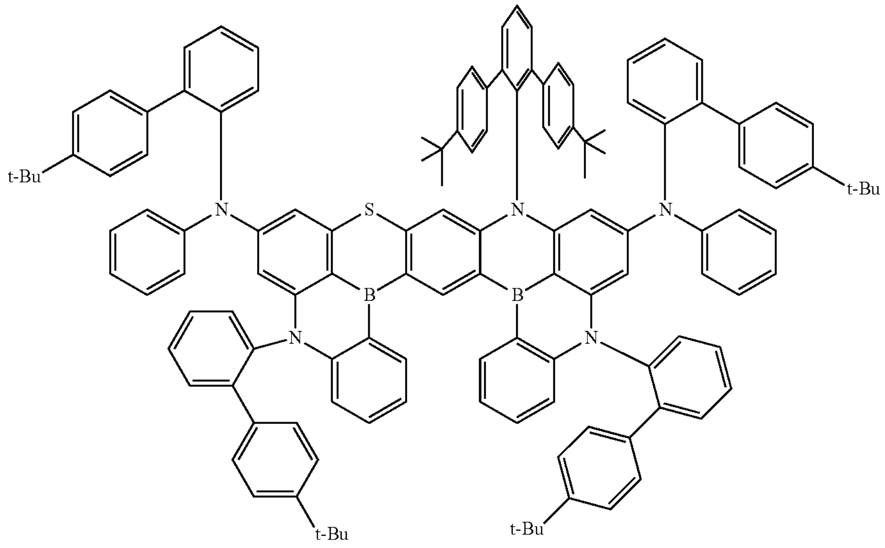

-continued
94
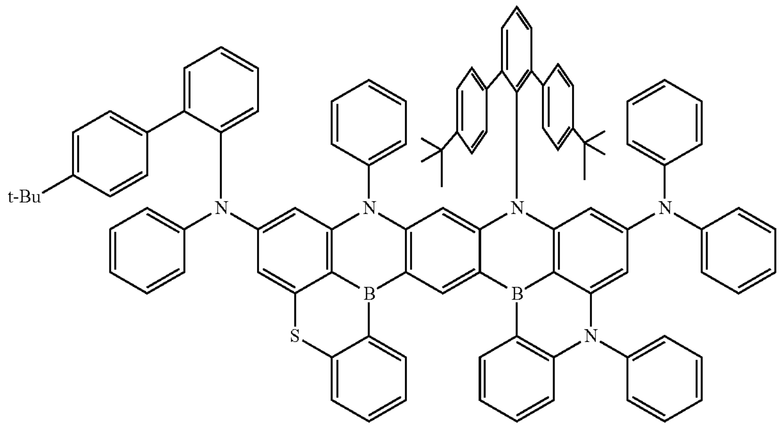
95
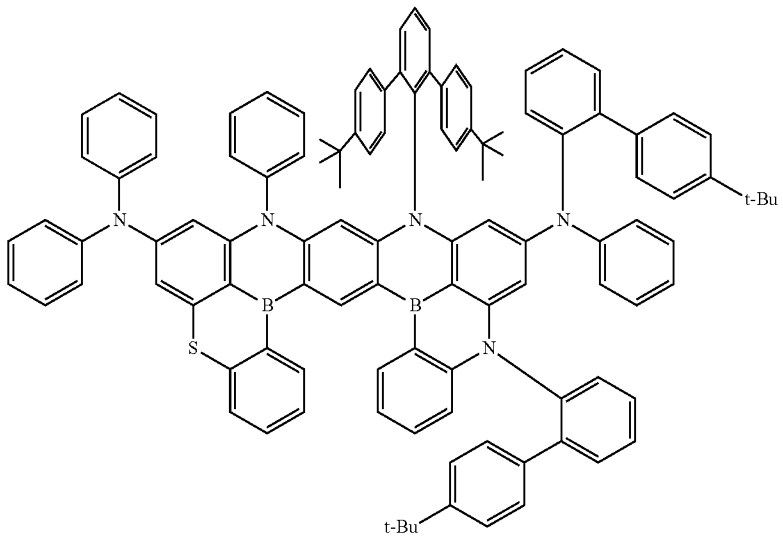
96
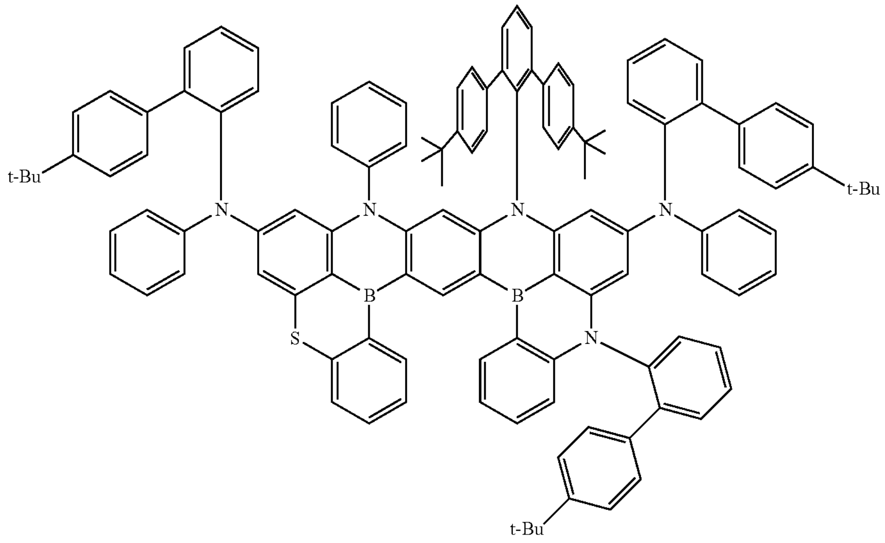

-continued
97
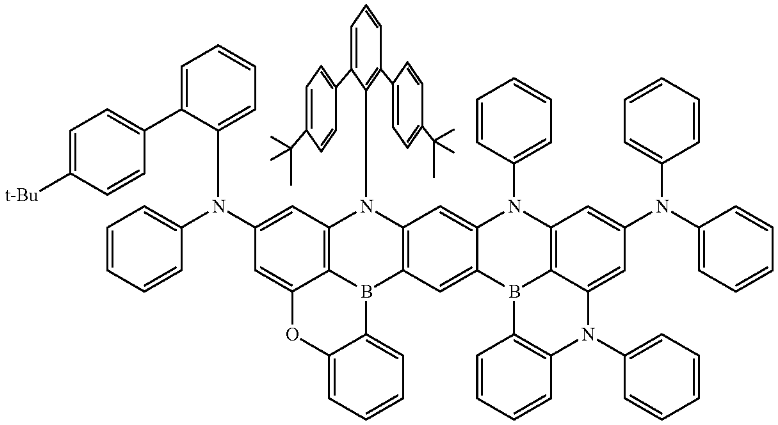
98
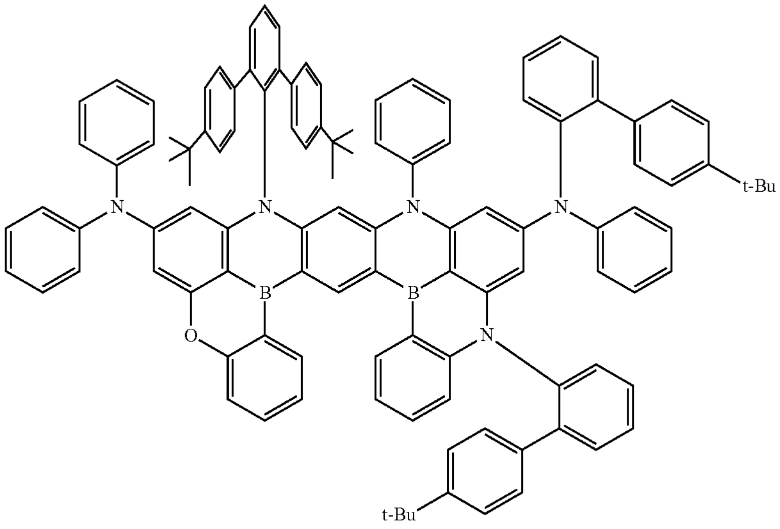
99
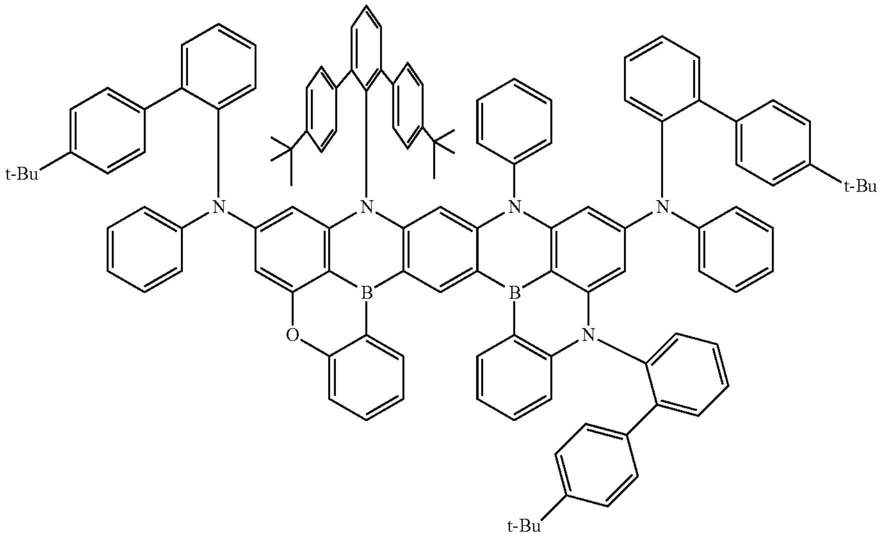

-continued
100
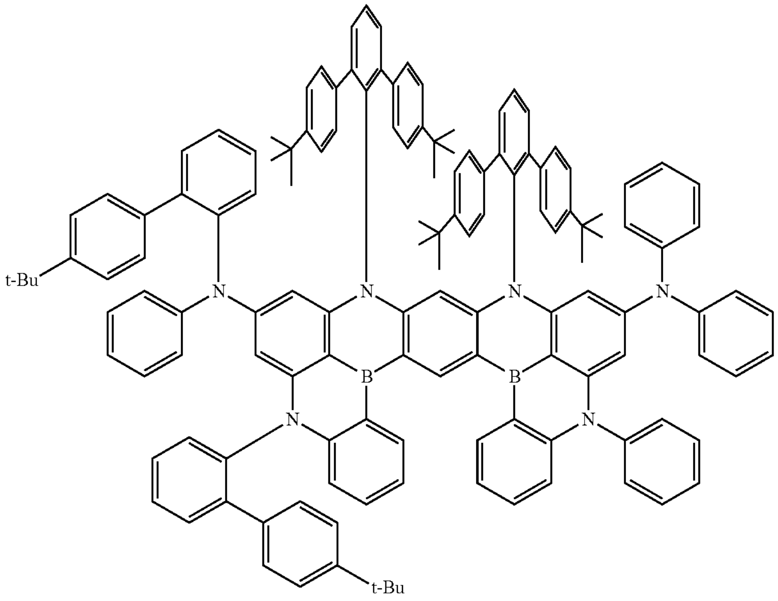
101
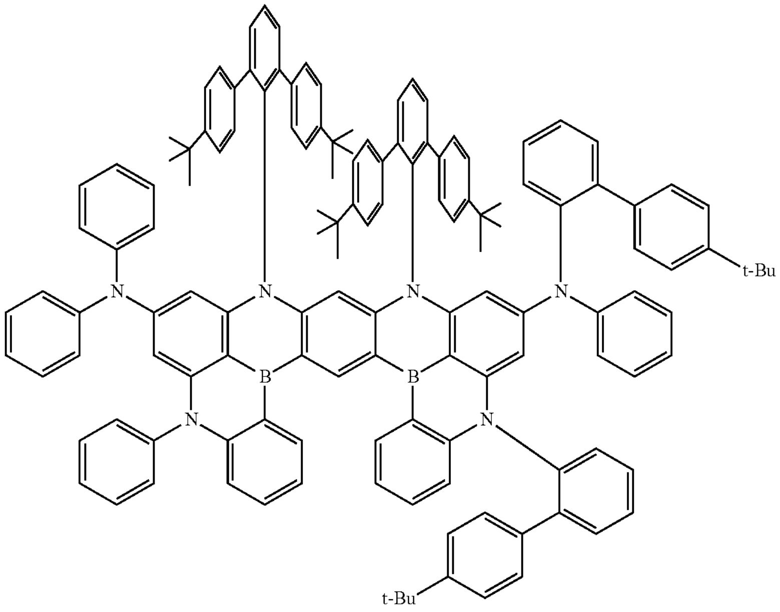

-continued
102
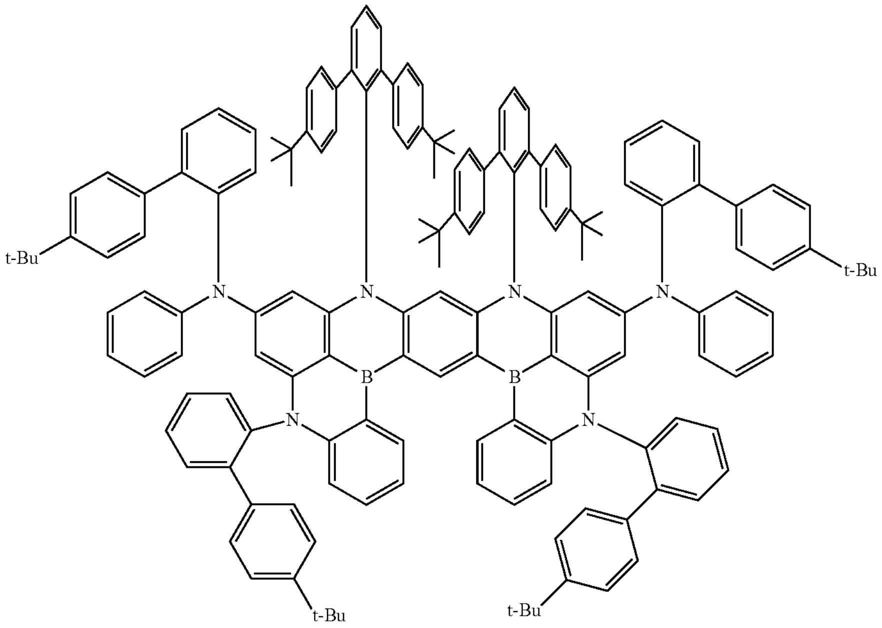
103
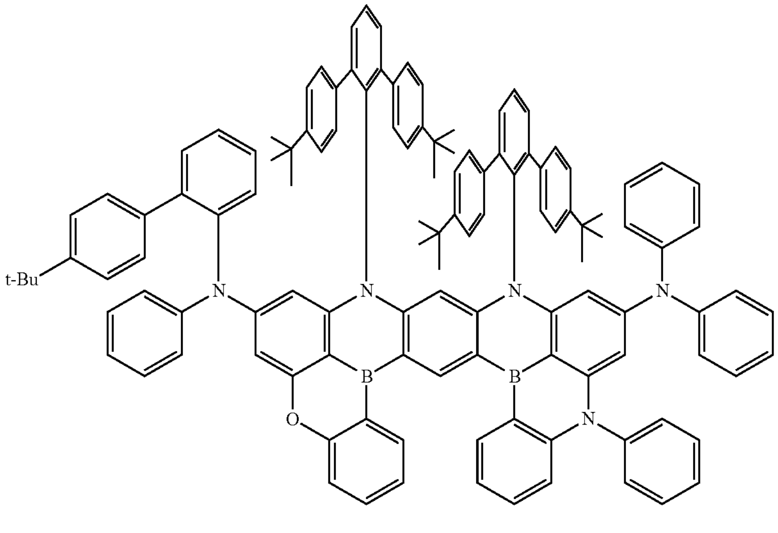

-continued

104

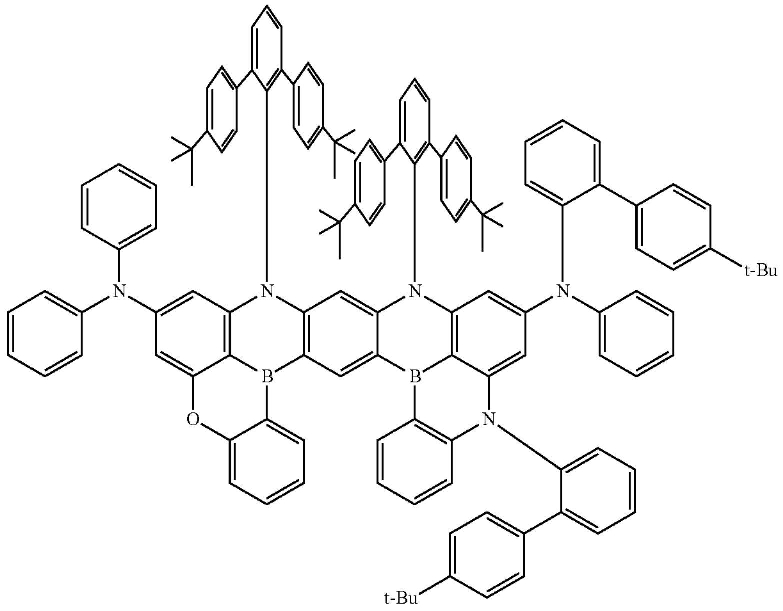

105

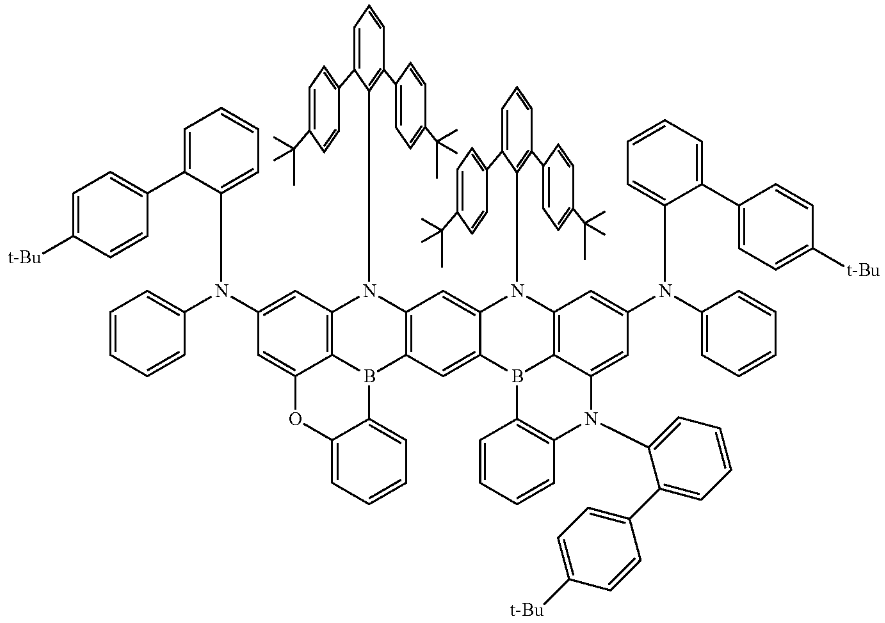

The condensed cyclic compound represented by Formula 1 may have a large planar structure. Although not wanting to be bound by theory, the condensed cyclic compound introduces a group represented by Formula 2 on the outside of the planar structure, wherein i) Formula 2 includes an electron donating group $R_{22}$, and thus may impart an electron injection effect that may cause multiple resonance inside a core, and simultaneously, ii) by introducing a substituent to the ortho position based on the position where the group represented by Formula 2 is substituted in the condensed cyclic compound represented by Formula 1, a physical orbital blocking effect on the injected electron may occur, and thus, Oscillator strength (f) may be improved.

In the condensed cyclic compound, iii) when a tert-butyl group is used as an electron donating group, as the vibration of the tert-butyl group increases the coupling strength between the different energy levels in the triplet excited state, Reverse InterSystem Crossing rate (kRISC) may be improved, and the characteristic of thermally activated delayed fluorescence (TADF) material, which is Reverse InterSystem Crossing (RISC), may occur more rapidly.

In addition, iv) because the group represented by Formula 2 extends lengthwise in an ortho direction, boron (B), etc. having high chemical reactivity may be obscured, thereby improving molecular stability, and improving molecular bonding dissociation energy (BDE).

Accordingly, a light-emitting device including a condensed cyclic compound represented by Formula 1, for example, an organic light-emitting device may have high emission efficiency and long lifespan. Synthesis methods of the condensed cyclic compound represented by Formula 1 may be recognizable by one of ordinary skill in the art by referring to Synthesis Examples and/or Examples provided below.

At least one condensed cyclic compound represented by Formula 1 may be used in a light-emitting device (for example, an organic light-emitting device). Accordingly, provided is a light-emitting device including: a first electrode; a second electrode facing the first electrode; and an interlayer located between the first electrode and the second electrode and including an emission layer, wherein the interlayer includes the heterocyclic compound represented by Formula 1.

In some embodiments, the first electrode of the light-emitting device may be an anode, the second electrode of the light-emitting device may be a cathode, the interlayer further includes a hole transport region located between the first electrode and the emission layer and an electron transport region located between the emission layer and the second electrode, the hole transport region includes a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof. In one or more embodiments, the condensed cyclic compound may be included between the first electrode and second electrode. Accordingly, the condensed cyclic compound may be included in the interlayer of the light-emitting device, for example, in the emission layer of the interlayer.

For example, the condensed cyclic compound included in the emission layer may be a delayed fluorescence emitter, and the emission layer may emit delayed fluorescence. The emission layer may emit red light, green light, blue light, and/or white light. For example, the emission layer may emit blue light. The blue light may have a maximum emission wavelength of, for example, about 400 nm to about 490 nm. The emission layer may further include a host, and the amount of the host may be greater than the amount of the condensed cyclic compound represented by Formula 1.

In one or more embodiments, the light-emitting device may include a capping layer located on the outside of the first or the second electrode. For example, the light-emitting device may include at least one of a first capping layer located on the outside of the first electrode and a second capping layer located on the outside of the second electrode, and a condensed cyclic compound represented by Formula 1 may be included in at least one of the first capping layer and the second capping layer. More details for the first capping layer and/or the second capping layer are the same as described herein.

In an embodiment, the light-emitting device may further include: a first capping layer located outside the first electrode and containing an organometallic compound represented by Formula 1; a second capping layer located outside the second electrode and containing the organometallic compound represented by Formula 1; or the first capping layer and the second capping layer.

The wording "(an interlayer and/or capping layer) includes a condensed cyclic compound" as used herein may include a case in which "(an interlayer and/or capping layer) includes identical condensed cyclic compounds represented by Formula 1" and a case in which "(an interlayer and/or capping layer) includes two or more different condensed cyclic compounds represented by Formula 1." For example, the interlayer and/or capping layer may include, as the condensed cyclic compound, Compound 1 only. In this regard, Compound 1 may be present in the emission layer of the light-emitting device. In one or more embodiments, the interlayer may include, as the condensed cyclic compound, Compound 1 and Compound 2. In this regard, Compound 1 and Compound 2 may be present in an identical layer (for example, Compound 1 and Compound 2 may all be present in an emission layer), or different layers (for example, Compound 1 may be present in an emission layer and Compound 2 may be present in an electron transport region).

Another aspect provides an electronic apparatus including the light-emitting device. The electronic apparatus may further include a thin-film transistor. For example, the electronic apparatus may further include a thin-film transistor including a source electrode and a drain electrode, and the first electrode of the light-emitting device may be electrically connected to the source electrode or the drain electrode. In an embodiment, the electronic apparatus may further include a color filter, a color conversion layer, a touch screen layer, a polarizing layer, or any combination thereof. More details on the electronic apparatus are described herein.

Description of FIG. 1

FIG. 1 is a schematic cross-sectional view of an embodiment of a light-emitting device constructed according to the principles of the invention.

The light-emitting device 10 includes a first electrode 110, an interlayer 130, and a second electrode 150. Hereinafter, the structure of the light-emitting device 10 according to an embodiment and a method of manufacturing the light-emitting device 10 will be described in connection with FIG. 1.

First Electrode 110

In FIG. 1, a substrate may be additionally located under the first electrode 110 or above the second electrode 150. As the substrate, a glass substrate or a plastic substrate may be used. In one or more embodiments, the substrate may be a flexible substrate, and may include plastics with excellent heat resistance and durability, such as a polyimide, a polyethylene terephthalate (PET), a polycarbonate, a polyethylene naphthalate, a polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high work function material that facilitates injection of holes.

The first electrode 110 may be a reflective electrode, a semi-transmissive electrode, or a transmissive electrode. When the first electrode 110 is a transmissive electrode, a material for forming the first electrode 110 may include an indium tin oxide (ITO), an indium zinc oxide (IZO), a tin oxide ($SnO_2$), a zinc oxide (ZnO), or any combinations thereof. In one or more embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be used as a material for forming a first electrode.

The first electrode 110 may have a single layer consisting of a single-layered structure or a multilayer structure including a plurality of layers. For example, the first electrode 110 may have a three-layered structure of an ITO/Ag/ITO.

Interlayer 130

The interlayer 130 may be located on the first electrode 110. The interlayer 130 may include an emission layer. The interlayer 130 may further include a hole transport region located between the first electrode 110 and the emission layer and an electron transport region located between the emission layer and the second electrode 150. The interlayer 130 may further include, in addition to various organic materials, metal-containing compounds such as organometallic compounds, inorganic materials such as quantum dots, and the like.

In one or more embodiments, the interlayer 130 may include, i) two or more light-emitting units sequentially stacked between the first electrode 110 and the second electrode 150 and ii) a charge generation layer located between the two emitting units. When the interlayer 130 includes the emitting unit and the charge generation layer as described above, the light-emitting device 10 may be a tandem light-emitting device.

Hole Transport Region in Interlayer 130

The hole transport region may have: i) a single-layered structure consisting of a single layer consisting of a single material, ii) a single-layered structure consisting of a single layer consisting of a plurality of different materials, or iii) a multi-layered structure including a plurality of layers including different materials. The hole transport region may include a hole injection layer, a hole transport layer, an emission auxiliary layer, an electron blocking layer, or any combination thereof.

For example, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, layers are stacked sequentially from the first electrode 110.

The hole transport region may include a compound represented by Formula 201, a compound represented by Formula 202, or any combination thereof:

Formula 201

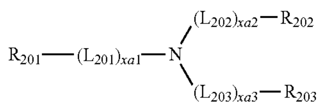

Formula 202

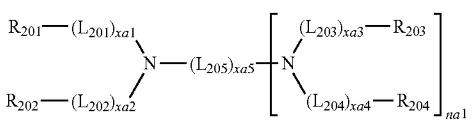

wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16), $R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

For example, each of Formulae 201 and 202 may include at least one of groups represented by Formulae CY201 to CY217.

CY201

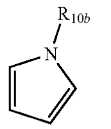

CY202

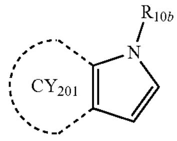

CY203

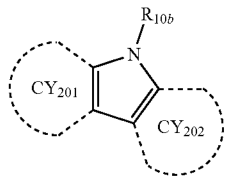

CY204

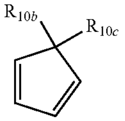

CY205

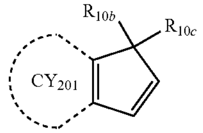

CY206

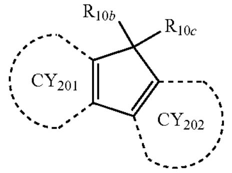

-continued

CY207

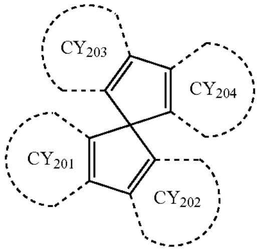

CY208

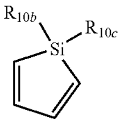

CY209

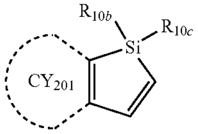

CY210

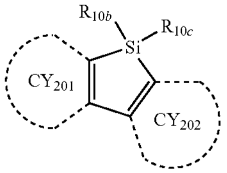

CY211

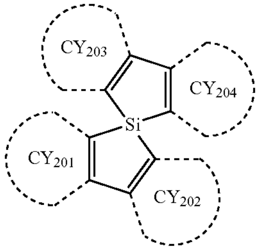

CY212

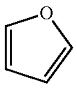

CY213

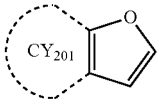

CY214

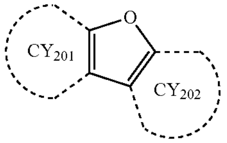

CY215

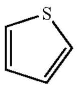

CY216

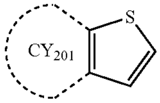

-continued

CY217

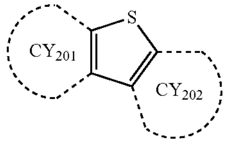

The variables $R_{10b}$ and $R_{10c}$ in Formulae CY201 to CY217 are the same as described in connection with $R_{10a}$, rings $CY_{201}$ to $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In an embodiment, ring $CY_{201}$ to ring $CY_{204}$ in Formulae CY201 to CY217 may each independently be a benzene group, a naphthalene group, a phenanthrene group, or an anthracene group. In one or more embodiments, each of Formulae 201 and 202 may include at least one of groups represented by Formulae CY201 to CY203. In one or more embodiments, Formula 201 may include at least one of groups represented by Formulae CY201 to CY203 and at least one of groups represented by Formulae CY204 to CY217.

In one or more embodiments, xa1 in Formula 201 may be 1, $R_{201}$ may be a group represented by one of Formulae CY201 to CY203, xa2 may be 0, and $R_{202}$ may be a group represented by one of Formulae CY204 to CY207. In one or more embodiments, each of Formulae 201 and 202 may not include a group represented by one of Formulae CY201 to CY203. In one or more embodiments, each of Formulae 201 and 202 may not include a group represented by one of Formulae CY201 to CY203, and may include at least one of groups represented by Formulae CY204 to CY217.

In one or more embodiments, each of Formulae 201 and 202 may not include a group represented by one of Formulae CY201 to CY217. For example, the hole transport region may include one of Compounds HT1 to HT46, 4,4',4"-tris[phenyl(m-tolyl)amino]triphenylamine (m-MTDATA), 1-N,1-N-bis[4-(diphenylamino)phenyl]-4-N,4-N-diphenylbenzene-1,4-diamine (TDATA), 4,4',4"-tris[2-naphthyl(phenyl)amino]triphenylamine (2-TNATA), bis(naphthalen-1-yl)-N,N'-bis(phenyl)benzidine (NPB or NPD), N4,N4'-di(naphthalen-2-yl)-N4,N4'-diphenyl-[1,1'-biphenyl]-4,4'-diamine (β-NPB), N,N'-bis(3-methylphenyl)-N,N'-diphenylbenzidine (TPD), N,N'-bis(3-methylphenyl)-N,N'-diphenyl-9,9-spirobifluorene-2,7-diamine (Spiro-TPD), N2,N7-di-1-naphthalenyl-N2,N7-diphenyl-9,9'-spirobi[9H-fluorene]-2,7-diamine (Spiro-NPB), N,N'-di(1-naphthyl)-N,N'-diphenyl-2,2'-dimethyl-(1,1'-biphenyl)-4,4'-diamine (methylated NPB), 4,4'-cyclohexylidenebis[N,N-bis(4-methylphenyl)benzenamine] (TAPC), N,N,N',N'-tetrakis(3-methylphenyl)-3,3'-dimethylbenzidine (HMTPD), 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

-continued
HT1
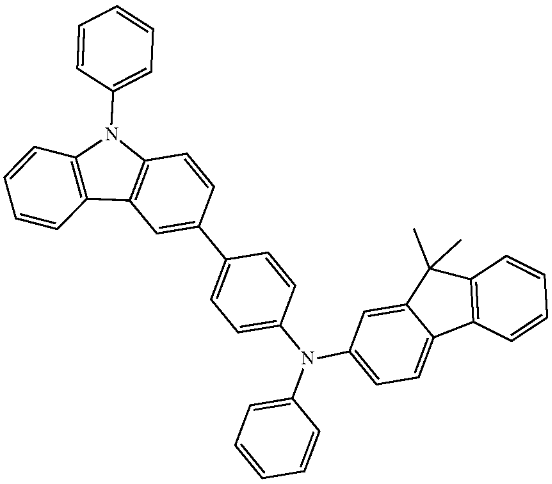
HT3
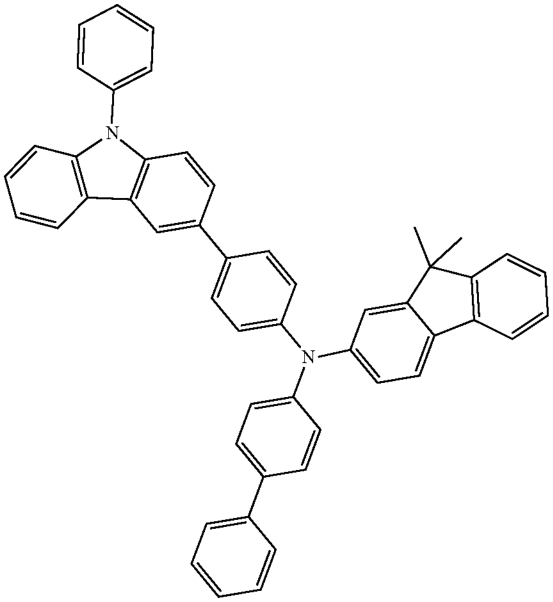
HT2
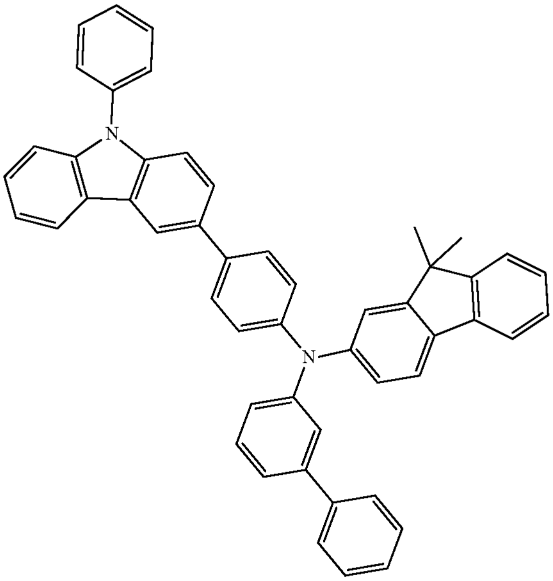
HT4
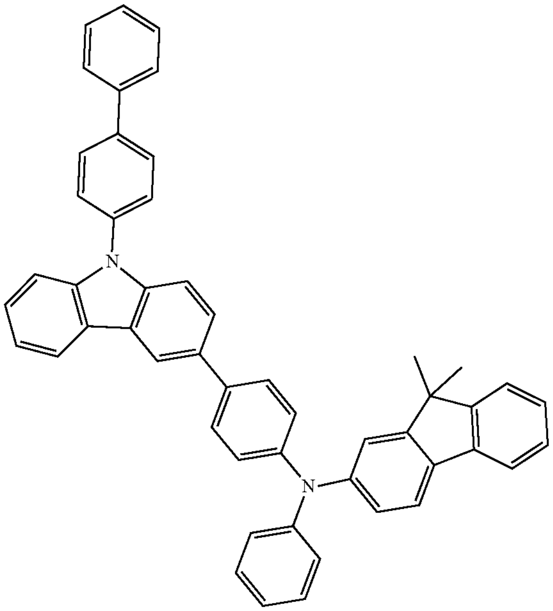

-continued
HT5
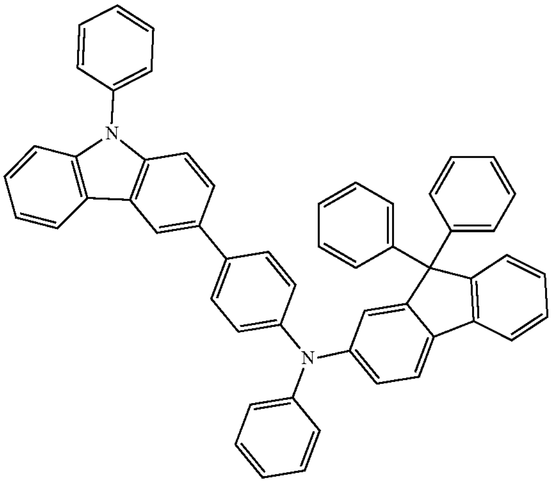
HT6
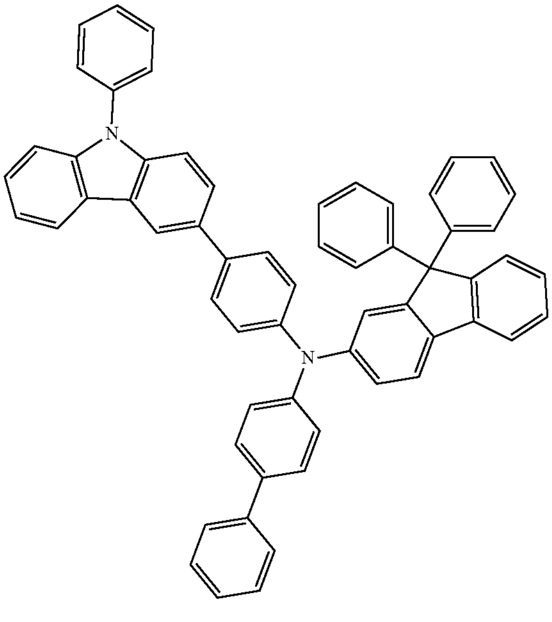
-continued
HT7
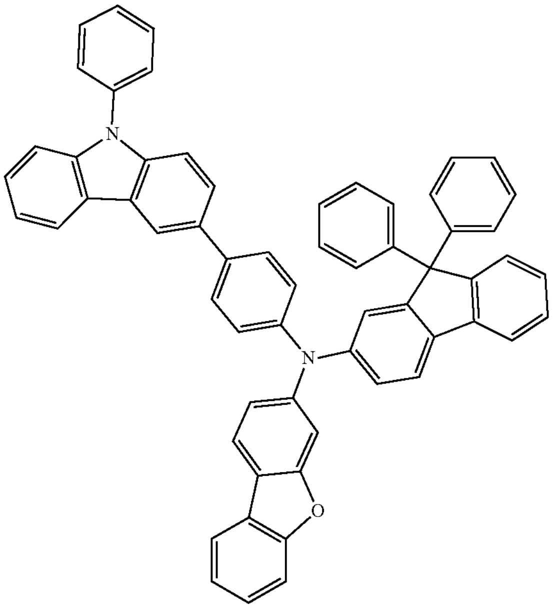
HT8
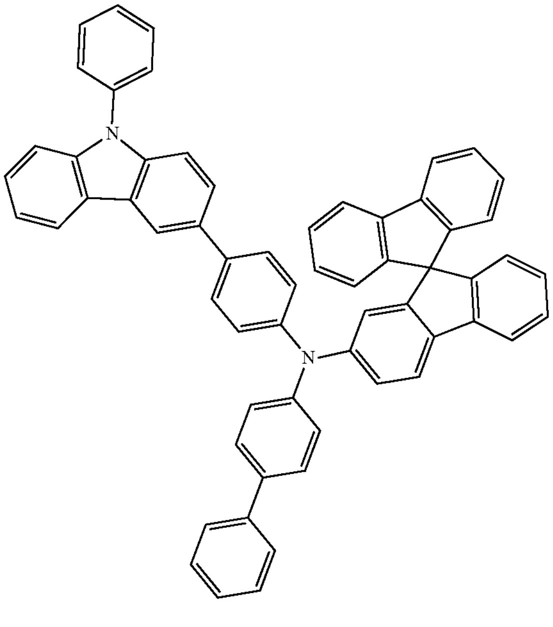

-continued
HT9
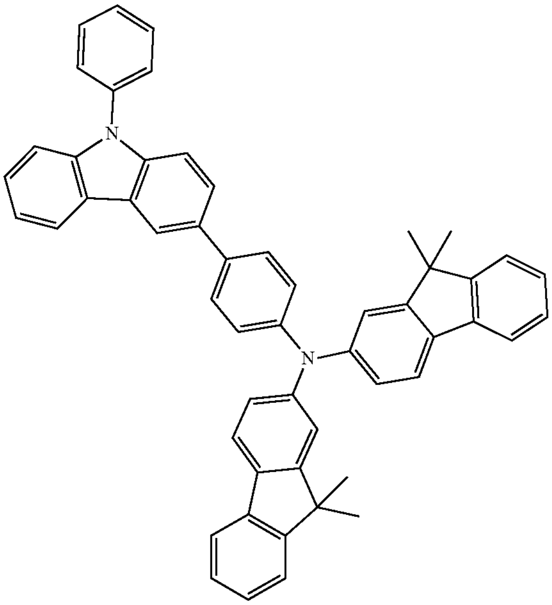
HT10
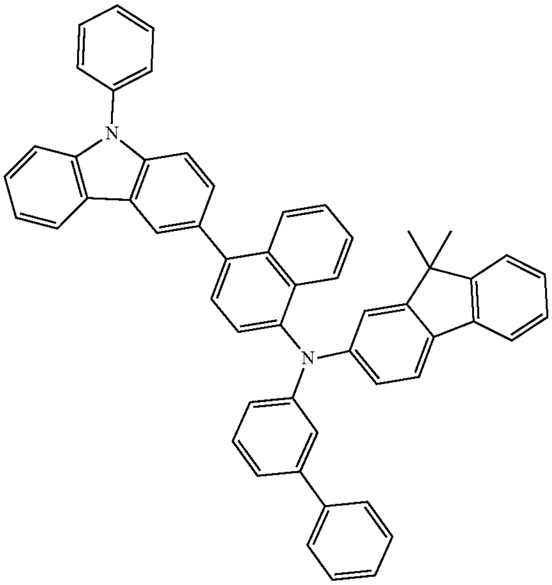
-continued
HT11
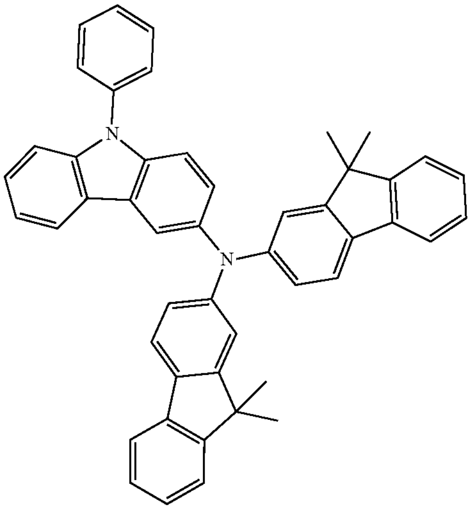
HT12
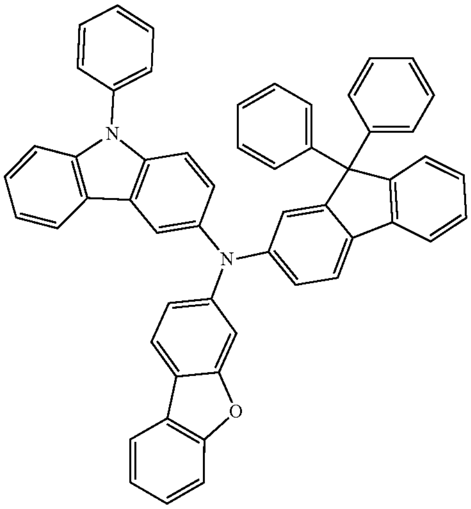
HT13
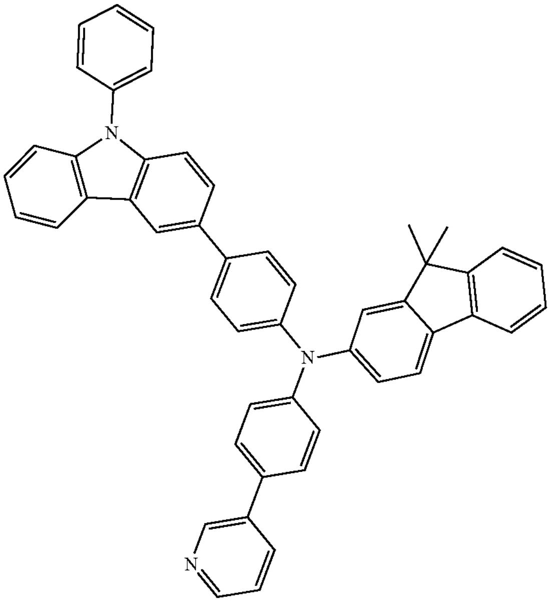

HT14
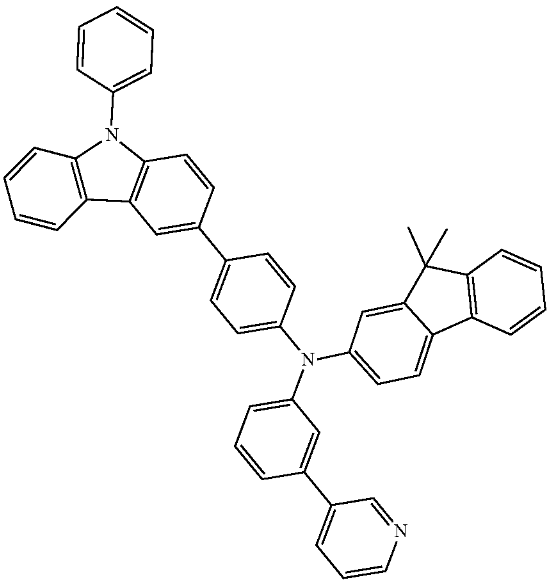
HT15
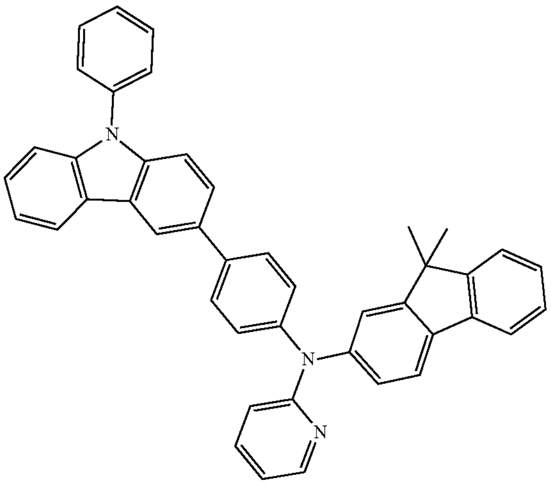
HT16
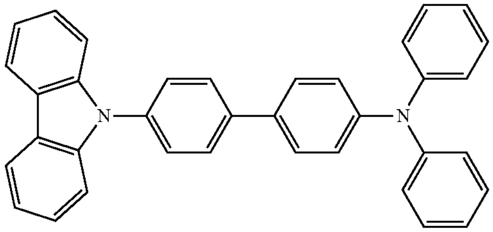
HT17
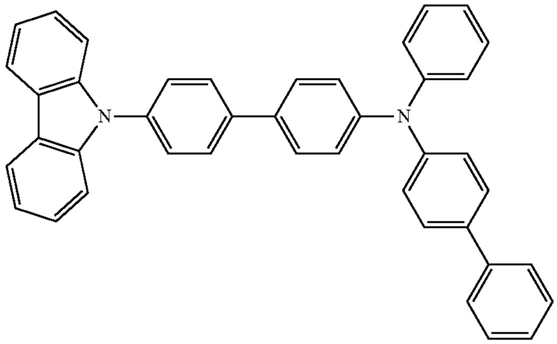
HT18
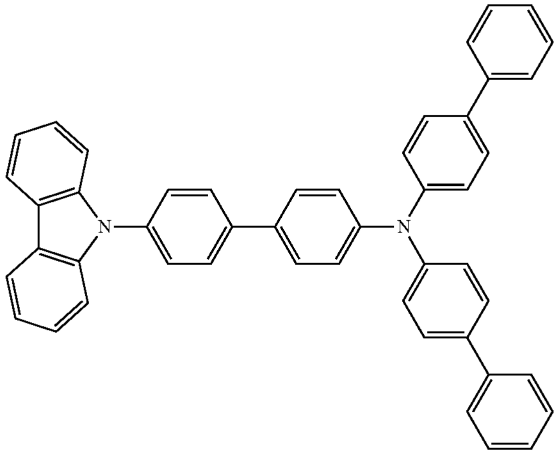
HT19
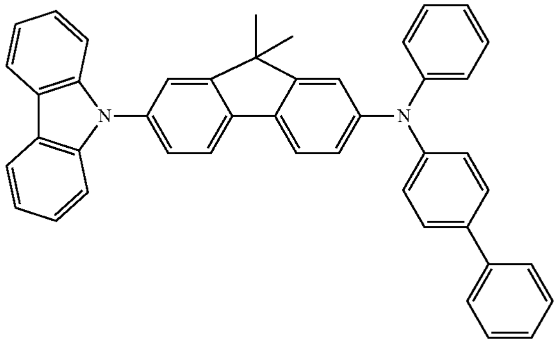

-continued
HT20
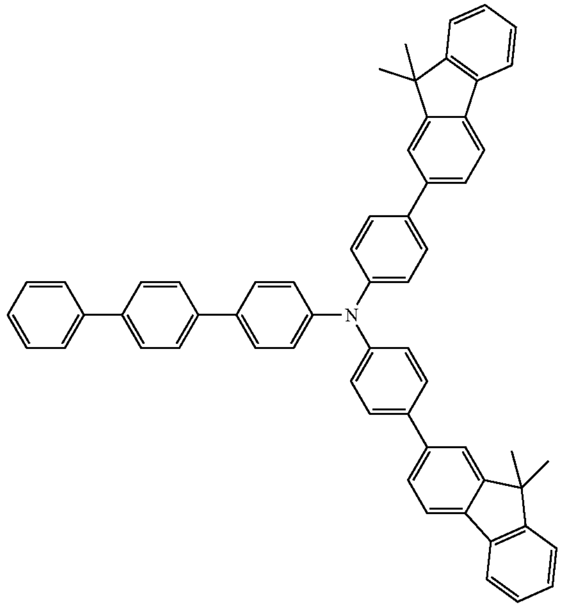
HT21
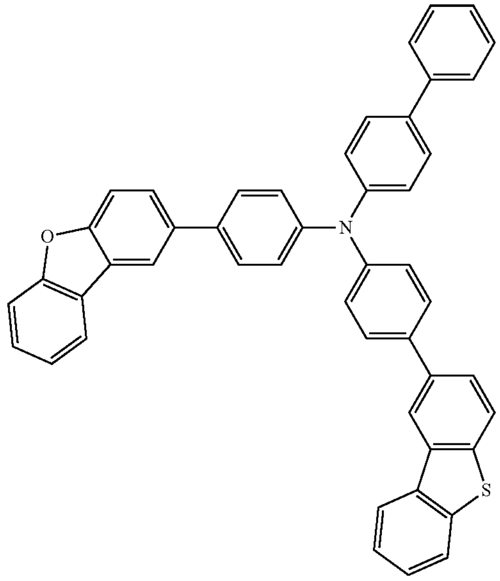
HT22
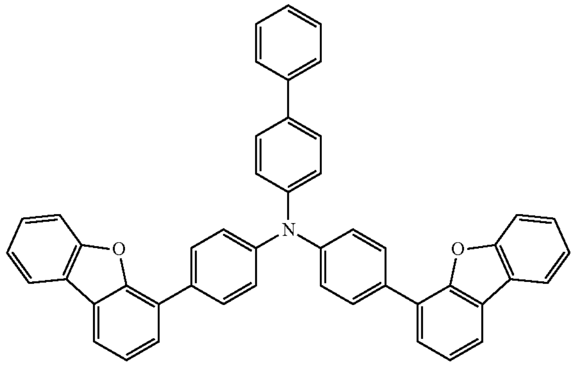
-continued
HT23
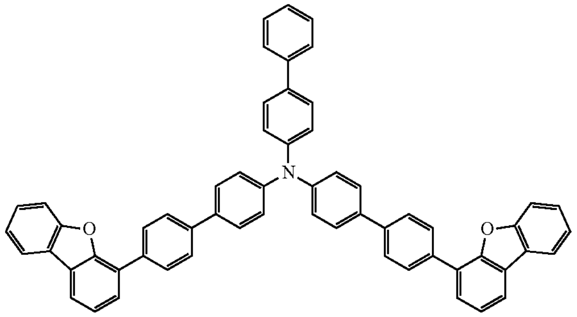
HT24
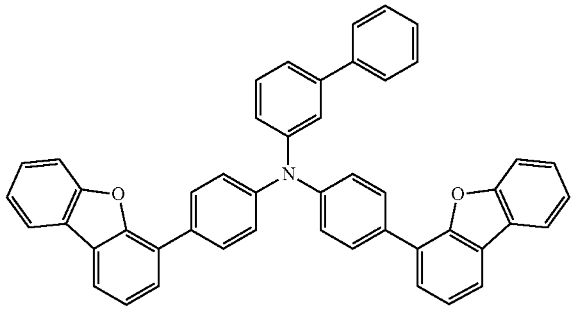
HT25
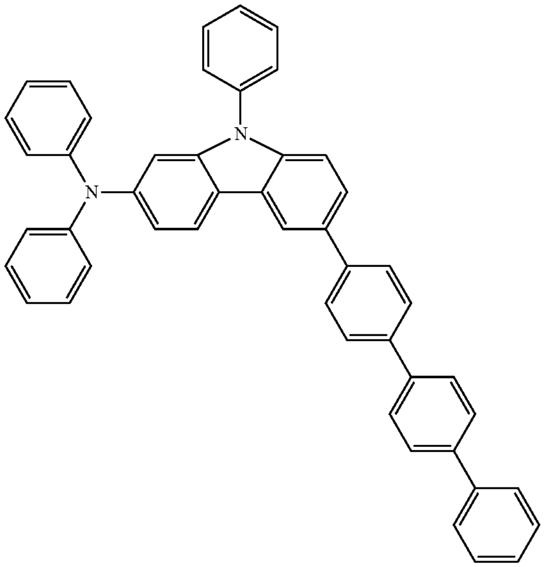

-continued
HT26
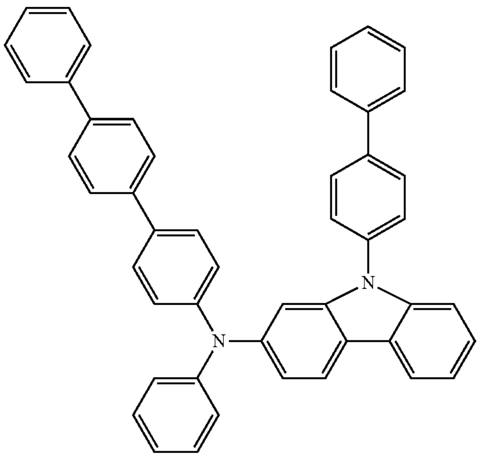
HT27
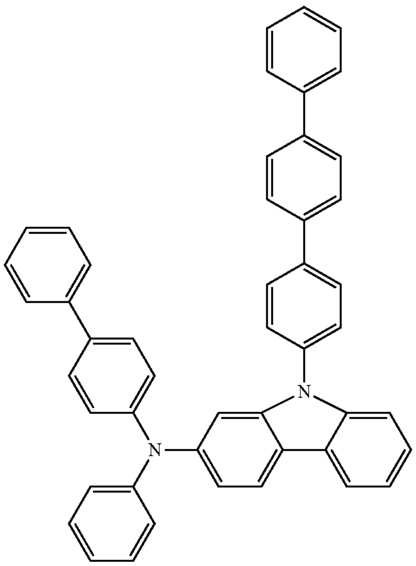
HT28
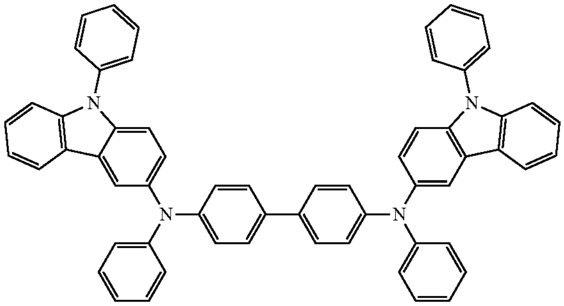
-continued
HT29
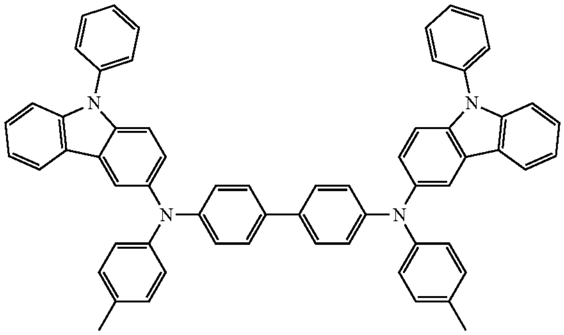
HT30
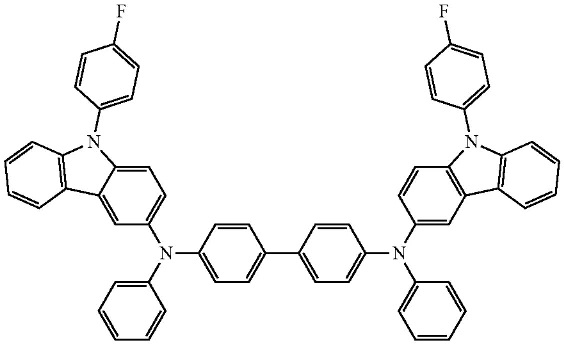
HT31
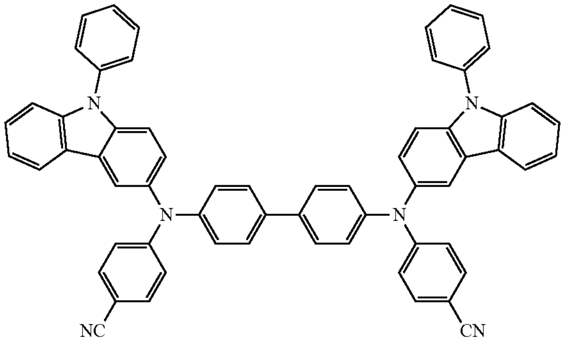
HT32
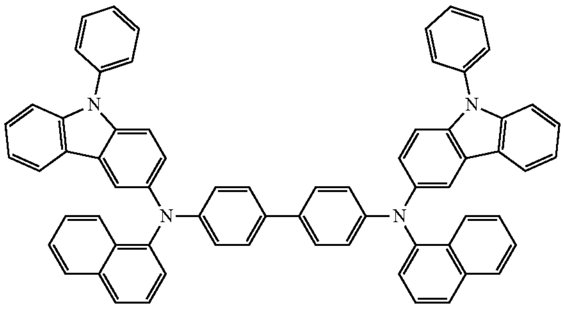

-continued
HT33
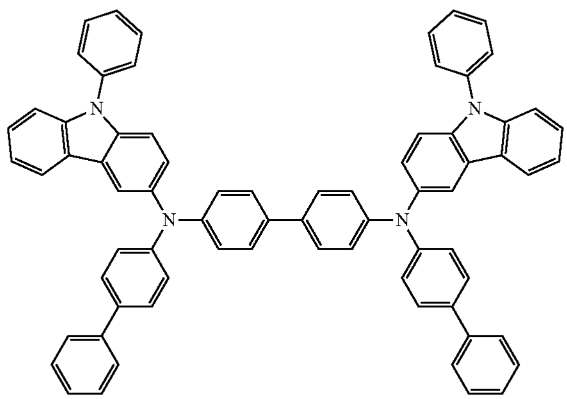
HT34
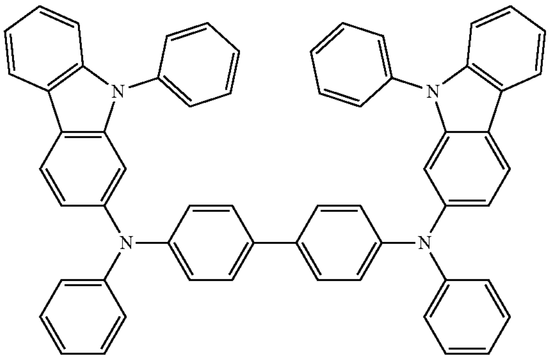
HT35
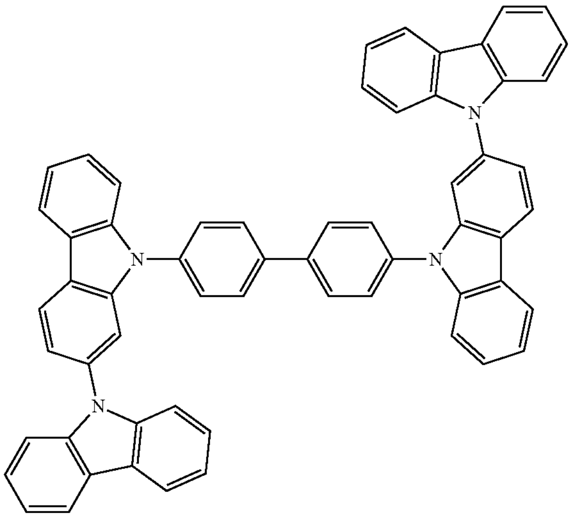
-continued
HT36
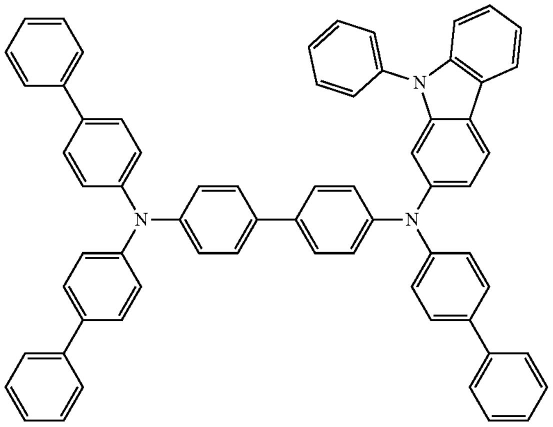
HT37
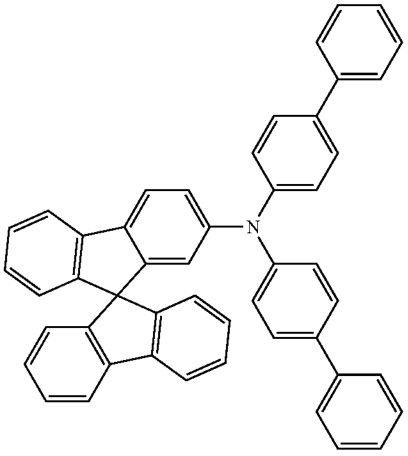
HT38
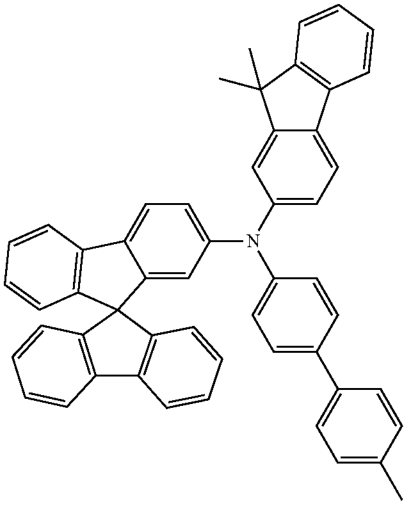

-continued
HT39
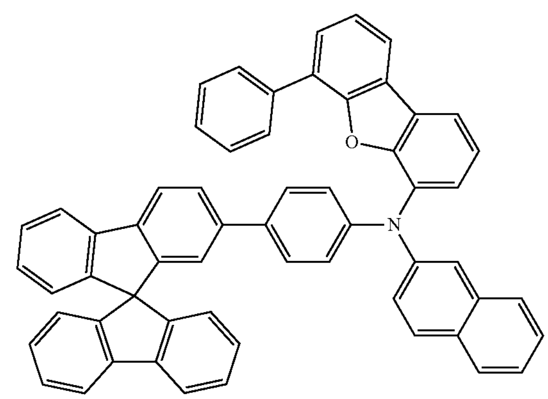
HT40
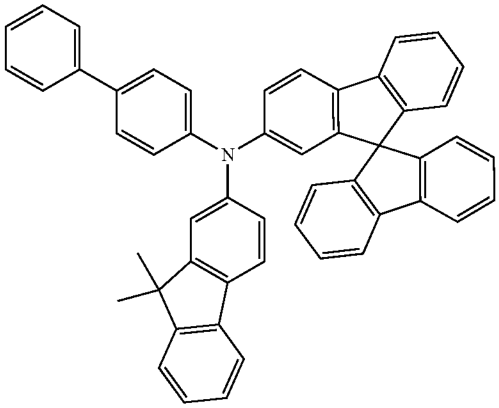
HT41
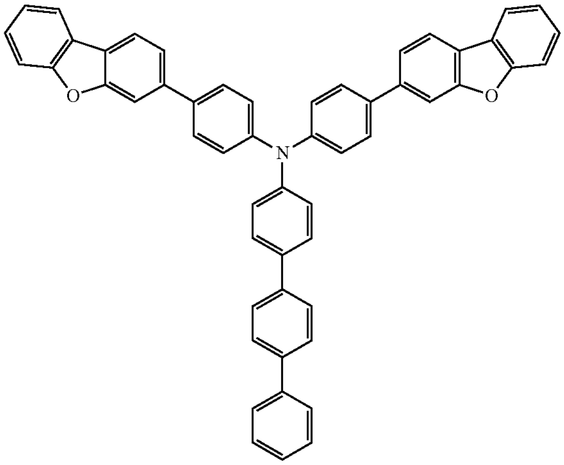
HT42
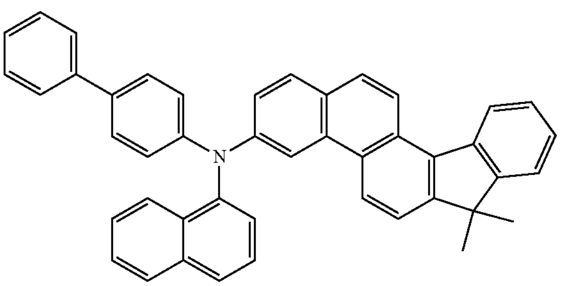
-continued
HT43
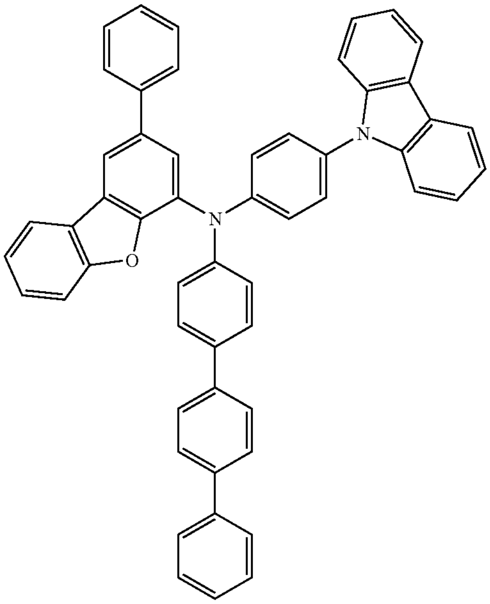
HT44
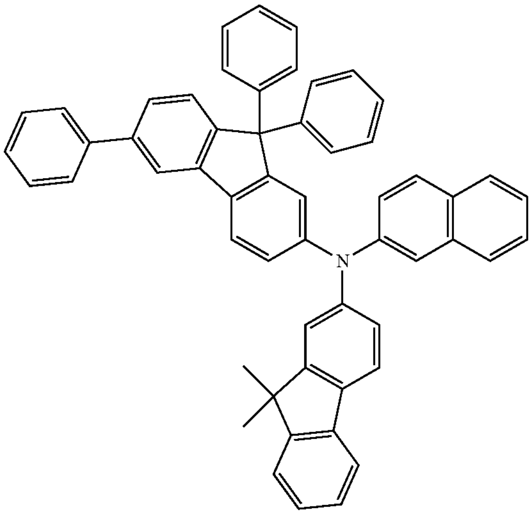
HT45
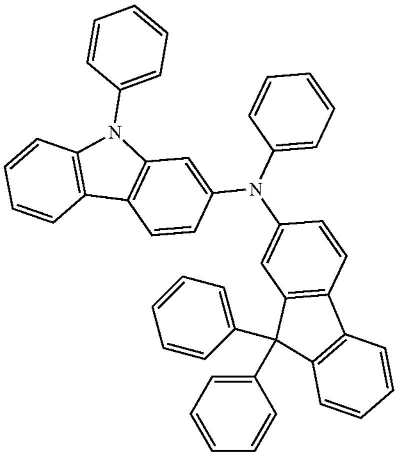

-continued
HT46
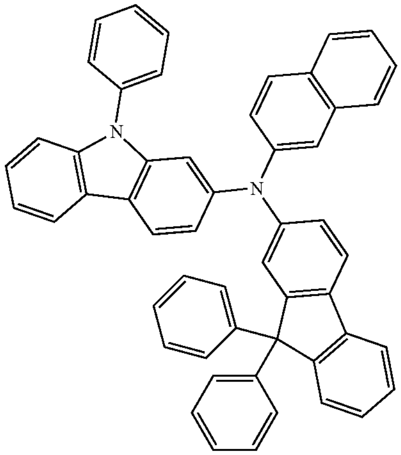
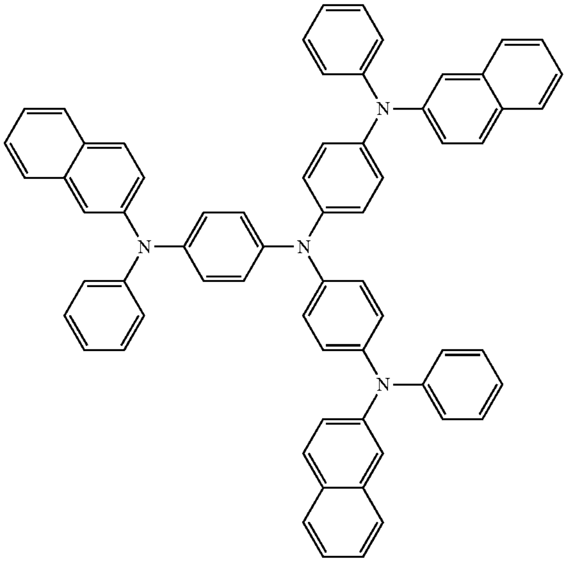
2-TNATA
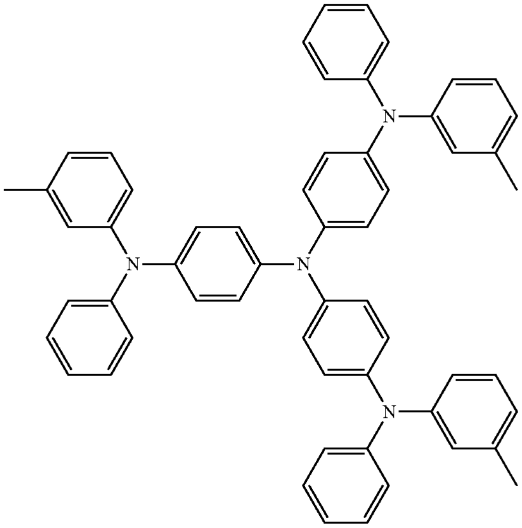
m-MTDATA
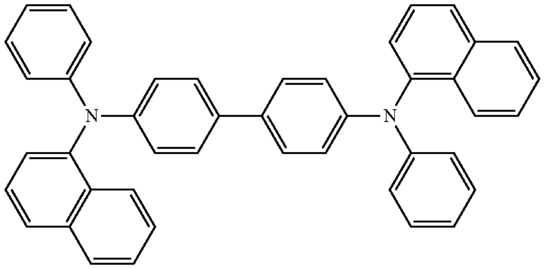
NPB
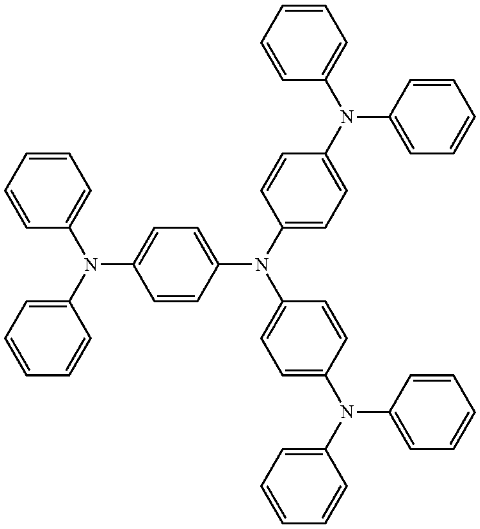
TDATA
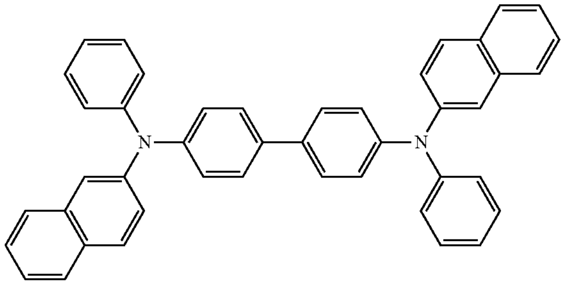
β-NPB
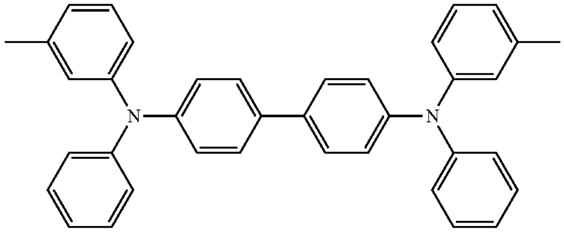
TPD -continued

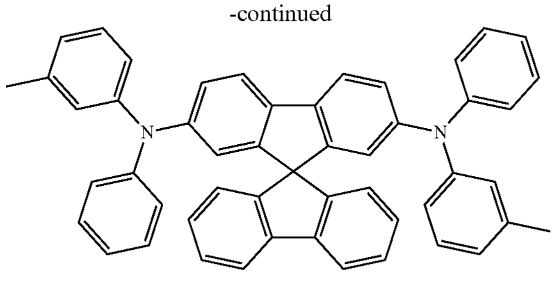

Spiro-TPD

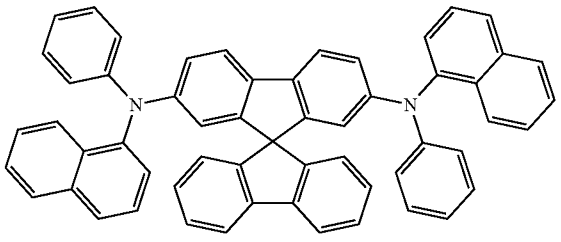

Spiro-NPB

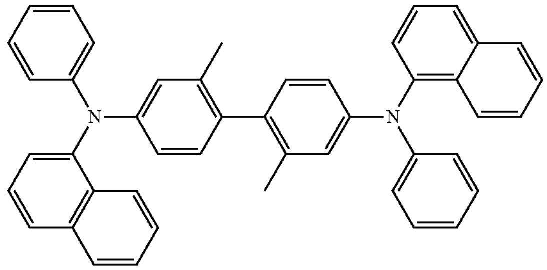

methylated-NPB

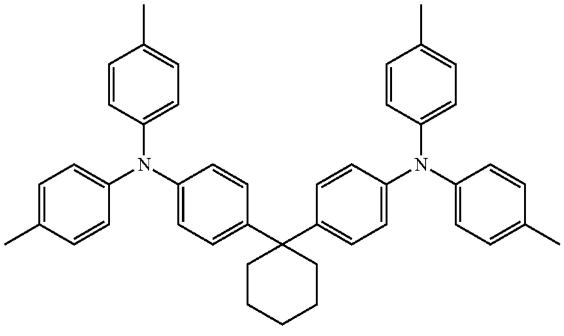

TAPC

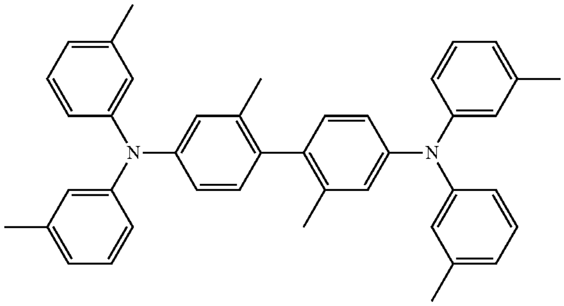

HMTPD

The thickness of the hole transport region may be in a range of about 50 Å to about 10,000 Å, for example, about 100 Å to about 4,000 Å. When the hole transport region includes a hole injection layer, a hole transport layer, or any combination thereof, the thickness of the hole injection layer may be in a range of about 100 Å to about 9,000 Å, for example, about 100 Å to about 1,000 Å, and the thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light emission efficiency by compensating for an optical resonance distance according to the wavelength of light emitted by the emission layer, and the electron blocking layer may block the leakage of electrons from the emission layer to the hole transport region. Materials that may be included in the hole transport region may be included in the emission auxiliary layer and the electron blocking layer.

p-Dopant

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material). The charge-generation material may be, for example, a p-dopant. In one or more embodiments, the lowest unoccupied molecular orbital (LUMO) energy level of the p-dopant may be about −3.5 eV or less In an embodiment, the p-dopant may include a quinone derivative, a cyano group-containing compound, a compound containing element EL1 and element EL2, or any combination thereof.

Examples of the quinone derivative include tetracyanoquinodimethane (TCNQ) and 2,3,5,6-tetrafluoro-7,7,8,8-tetracyanoquinodimethane (F4-TCNQ).

Examples of the cyano group-containing compound include 1,4,5,8,9,11-hexaazatriphenylene-hexacarbonitrile (HAT-CN) and a compound represented by Formula 221.

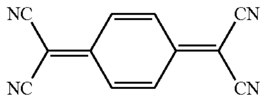

TCNQ

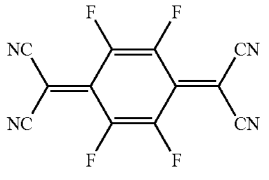

F4-TCNQ

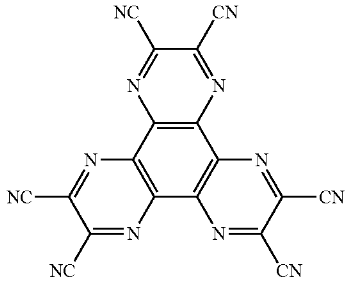

HAT-CN

-continued

Formula 221

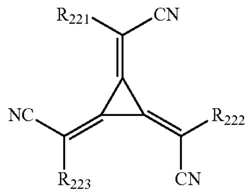

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof, or any combination thereof.

In the compound containing element EL1 and element EL2, element EL1 may be a metal, a metalloid, or any combination thereof, and element EL2 may be a non-metal, a metalloid, or any combination thereof. Examples of the metal are an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid are silicon (Si), antimony (Sb), and tellurium (Te). Examples of the non-metal are oxygen (O) and a halogen (for example, F, Cl, Br, I, etc.). In one or more embodiments, examples of the compound containing element EL1 and element EL2 are a metal oxide, a metal halide (for example, a metal fluoride, a metal chloride, a metal bromide, or a metal iodide), a metalloid halide (for example, a metalloid fluoride, a metalloid chloride, a metalloid bromide, or a metalloid iodide), a metal telluride, or any combination thereof.

Examples of the metal oxide are a tungsten oxide (for example, WO, $W_2O_3$, $WO_2$, $WO_3$, $W_2O_5$, etc.), a vanadium oxide (for example, VO, $V_2O_3$, $VO_2$, $V_2O_5$, etc.), a molybdenum oxide (MoO, $Mo_2O_3$, $MoO_2$, $MoO_3$, $Mo_2O_5$, etc.), and a rhenium oxide (for example, $ReO_3$, etc.). Examples of the metal halide are an alkali metal halide, an alkaline earth metal halide, a transition metal halide, a post-transition metal halide, and a lanthanide metal halide.

Examples of the alkali metal halide are LiF, NaF, KF, RbF, CsF, LiCl, NaCl, KCl, RbCl, CsCl, LiBr, NaBr, KBr, RbBr, CsBr, LiI, NaI, KI, RbI, and CsI. Examples of the alkaline earth metal halide are $BeF_2$, $MgF_2$, $CaF_2$, $SrF_2$, $BaF_2$, $BeCl_2$, $MgCl_2$, $CaCl_2$), $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$. Examples of the transition metal halide are a titanium halide (for example, $TiF_4$, $TiCl_4$, $TiBr_4$, $TiI_4$, etc.), a zirconium halide (for example, $ZrF_4$, $ZrCl_4$, $ZrBr_4$, $ZrI_4$, etc.), a hafnium halide (for example, $HfF_4$, $HfCl_4$, $HfBr_4$, $HfI_4$, etc.), a vanadium halide (for example, $VF_3$, $VCl_3$, $VBr_3$, $VI_3$, etc.), a niobium halide (for example, $NbF_3$, $NbCl_3$, $NbBr_3$, $NbI_3$, etc.), a tantalum halide (for example, $TaF_3$, $TaCl_3$, $TaBr_3$, $TaI_3$, etc.), a chromium halide (for example, $CrF_3$, $CrCl_3$, $CrBr_3$, $CrI_3$, etc.), a molybdenum halide (for example, $MoF_3$, $MoCl_3$, $MoBr_3$, $MoI_3$, etc.), a tungsten halide (for example, $WF_3$, $WCl_3$, $WBr_3$, $WI_3$, etc.), a manganese halide (for example, $MnF_2$, $MnCl_2$, $MnBr_2$, $MnI_2$, etc.), a technetium halide (for example, $TcF_2$, $TcCl_2$, $TcBr_2$, $TcI_2$, etc.), a rhenium halide (for example, $ReF_2$, $ReCl_2$, $ReBr_2$, $ReI_2$, etc.), an iron halide (for example, $FeF_2$, $FeCl_2$, $FeBr_2$, $FeI_2$, etc.), a ruthenium halide (for example, $RuF_2$, $RuCl_2$, $RuBr_2$, $RuI_2$, etc.), an osmium halide (for example, $OsF_2$, $OsCl_2$, $OsBr_2$, $OsI_2$, etc.), a cobalt halide (for example, $CoF_2$, $CoCl_2$, $CoBr_2$, $CoI_2$, etc.), a rhodium halide (for example, $RhF_2$, $RhCl_2$, $RhBr_2$, $RhJ_2$, etc.), an iridium halide (for example, $IrF_2$, $IrCl_2$, $IrBr_2$, $IrI_2$, etc.), a nickel halide (for example, $NiF_2$, $NiCl_2$, $NiBr_2$, $NiI_2$, etc.), a palladium halide (for example, $PdF_2$, $PdCl_2$, $PdBr_2$, $PdI_2$, etc.), a platinum halide (for example, $PtF_2$, $PtCl_2$, $PtBr_2$, $PtI_2$, etc.), a copper halide (for example, CuF, CuCl, CuBr, CuI, etc.), a silver halide (for example, AgF, AgCl, AgBr, AgI, etc.), and a gold halide (for example, AuF, AuCl, AuBr, AuI, etc.).

Examples of the post-transition metal halide are a zinc halide (for example, $ZnF_2$, $ZnCl_2$, $ZnBr_2$, $ZnI_2$, etc.), an indium halide (for example, $InI_3$, etc.), and a tin halide (for example, $SnI_2$, etc.). Examples of the lanthanide metal halide are YbF, $YbF_2$, $YbF_3$, $SmF_3$, YbCl, $YbCl_2$, $YbC_{13}$, $SmCl_3$, YbBr, $YbBr_2$, $YbBr_3$ $SmBr_3$, YbI, $YbI_2$, $YbI_3$, and $SmI_3$.

An example of the metalloid halide is an antimony halide (for example, SbCls, etc.). Examples of the metal telluride are an alkali metal telluride (for example, $Li_2Te$, $Na_2Te$, $K_2Te$, $Rb_2Te$, $Cs_2Te$, etc.), an alkaline earth metal telluride (for example, BeTe, MgTe, CaTe, SrTe, BaTe, etc.), a transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), a post-transition metal telluride (for example, ZnTe, etc.), and a lanthanide metal telluride (for example, LaTe, CeTe, PrTe, NdTe, PmTe, EuTe, GdTe, TbTe, DyTe, HoTe, ErTe, TmTe, YbTe, LuTe, etc.).

Emission Layer in Interlayer 130

When the light-emitting device 10 is a full-color light-emitting device, the emission layer may be patterned into a red emission layer, a green emission layer, and/or a blue emission layer, according to a sub-pixel. In one or more embodiments, the emission layer may have a stacked structure of two or more layers of a red emission layer, a green emission layer, and a blue emission layer, in which the two or more layers contact each other or are separated from each other. In one or more embodiments, the emission layer may include two or more materials of a red light-emitting material, a green light-emitting material, and a blue light-emitting material, in which the two or more materials are mixed with each other in a single layer to emit white light. For example, the emission layer may emit blue light.

In an embodiment, the emission layer may include the condensed cyclic compound represented by Formula 1 as described herein. The emission layer may include a host and a dopant.

In an embodiment, the dopant may include the condensed cyclic compound represented by Formula 1 as described herein. Herein, the dopant may further include, in addition to the condensed cyclic compound represented by Formula 1, a phosphorescence dopant, a fluorescence dopant, or any combination thereof. In addition to the condensed cyclic compound represented by Formula 1, the phosphorescence dopant and fluorescence dopant that may be included in the emission layer may be understood by referring to the description below.

The amount of the dopant in the emission layer may be from about 0.01 to about parts by weight based on 100 parts by weight of the host. In one or more embodiments, the emission layer may include a quantum dot. The emission layer may include a delayed fluorescence material. The delayed fluorescence material may act as a host or a dopant in the emission layer.

The thickness of the emission layer may be in a range of about 100 Å to about 1,000 Å, for example, about 200 Å to about 600 Å. When the thickness of the emission layer is within these ranges, excellent light-emission characteristics may be obtained without a substantial increase in driving voltage.

Host

In one or more embodiments, the host may include a compound represented by Formula 301 below:

$$[Ar_{301}]_{xb11}\text{-}[(L_{301})_{xb1}\text{-}R_{301}]_{xb21}$$ Formula 301

In Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{301})(Q_{302})(Q_{303})$, —$N(Q_{301})(Q_{302})$, —$B(Q_{301})(Q_{302})$, —$C(=O)(Q_{301})$, —$S(=O)_2(Q_{301})$, or —$P(=O)(Q_{301})(Q_{302})$, xb21 may be an integer from 1 to 5, and $Q_{301}$ to $Q_{303}$ are the same as described in connection with $Q_1$.

For example, when xb11 in Formula 301 is 2 or more, two or more of $Ar_{301}$(s) may be linked to each other via a single bond.

In one or more embodiments, the host may include a compound represented by Formula 301-1, a compound represented by Formula 301-2, or any combination thereof.

Formula 301-1

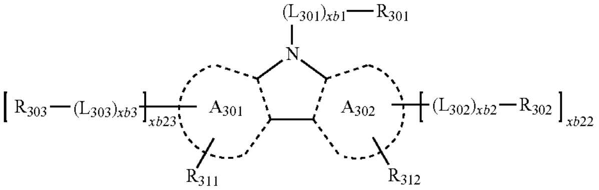

Formula 301-2

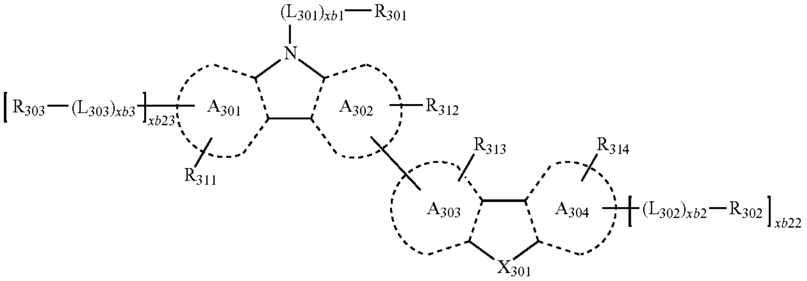

wherein, in Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-$[(L_{304})_{xb4}$-$R_{304}]$, $C(R_{304})(R_{305})$, or $Si(R_{304})(R_{305})$, xb22 and xb23 may each independently be 0, 1, or 2, $L_{301}$, xb1, and $R_{301}$ are the same as described herein, $L_{302}$ to $L_{304}$ may each independently be the same as described in connection with $L_{301}$, xb2 to xb4 may each independently be the same as described in connection with xb1, and $R_{302}$ to $R_{305}$ and $R_{311}$ to $R_{314}$ are the same as described in connection with $R_{301}$.

In one or more embodiments, the host may include an alkali earth metal complex, a post-transition metal complex, or any combination thereof. In one or more embodiments, the host may include a Be complex (for example, Compound H55), an Mg complex, a Zn complex, or any combination thereof.

In an embodiment, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di(carbazole-9-yl)benzene (mCP), 1,3,5-tri(carbazol-9-yl)benzene (TCP), or any combination thereof:

-continued
H1
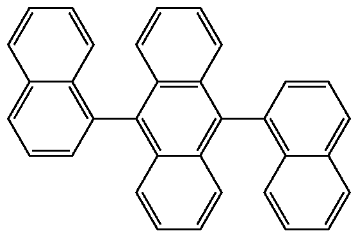
H2
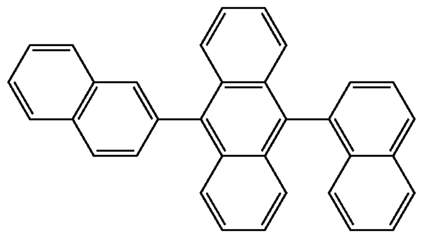
H3
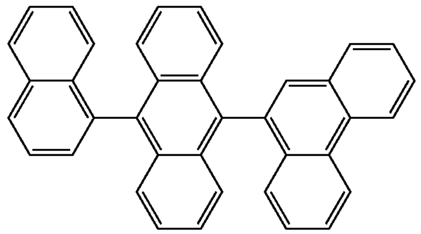
H4
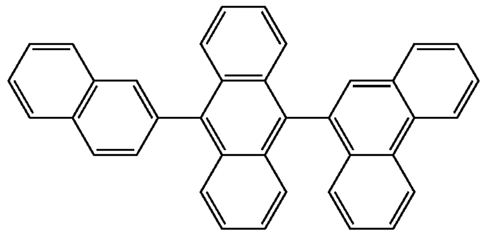
H5
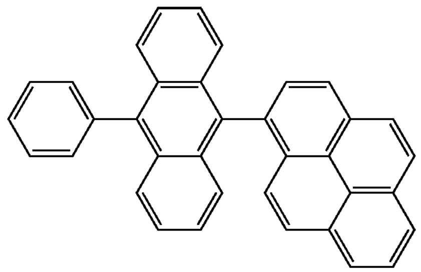
H6
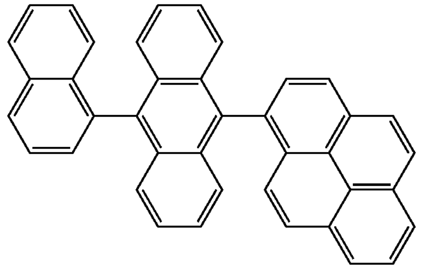
H7
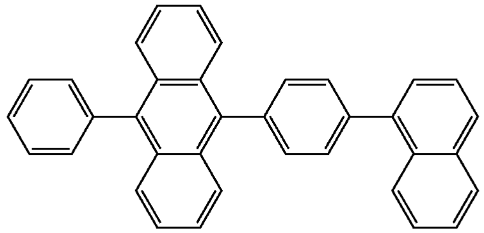
H8
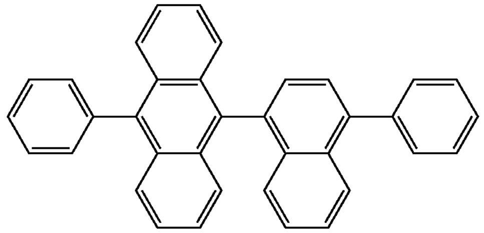
H9
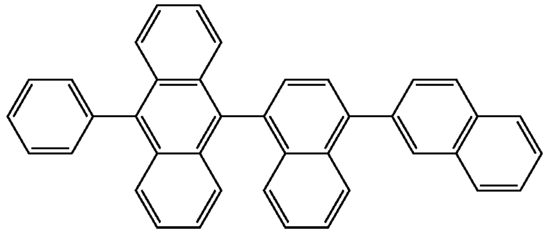
H10
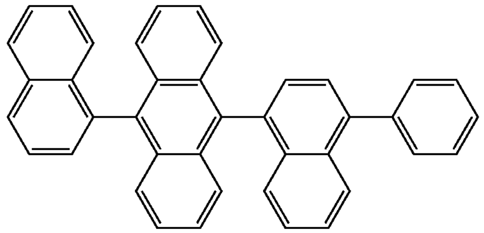
H11
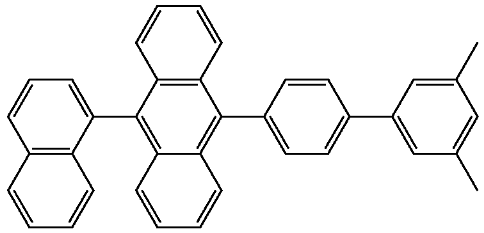
H12
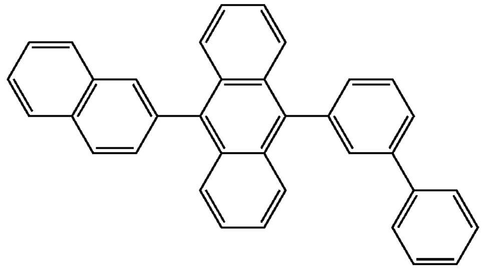

-continued
H13
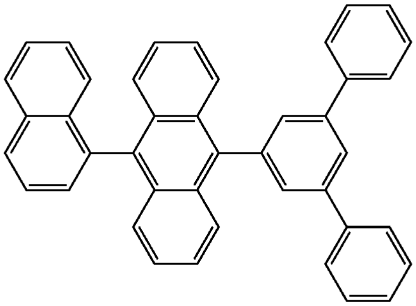
H14
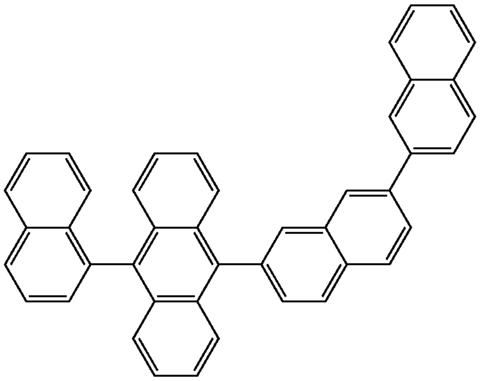
H15
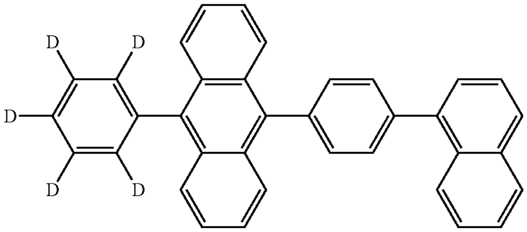
H16
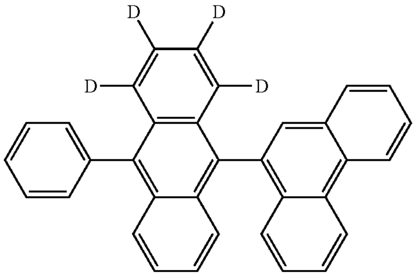
H17
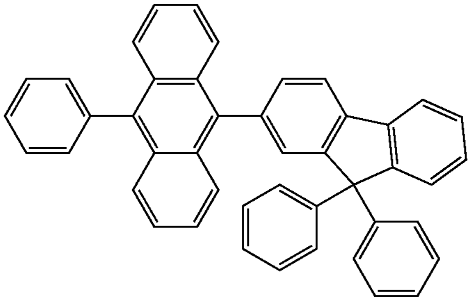
-continued
H18
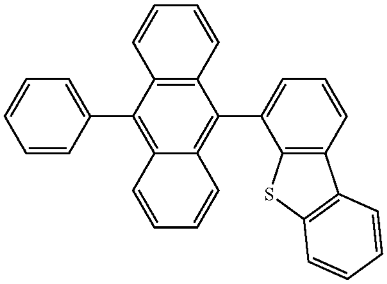
H19
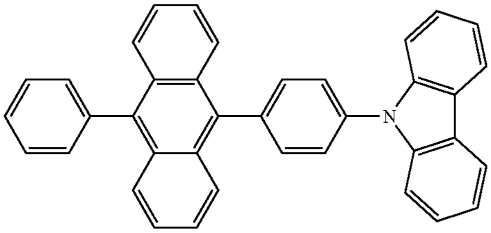
H20
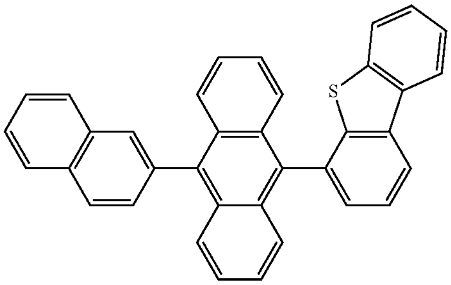
H21
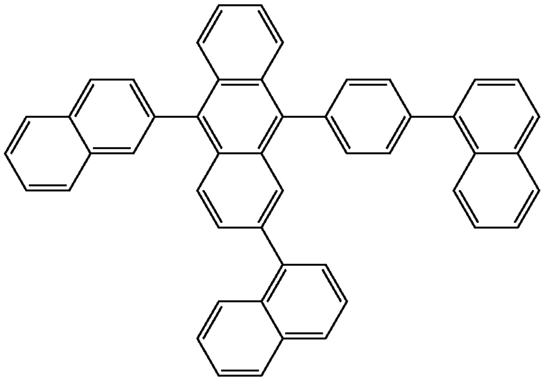
H22
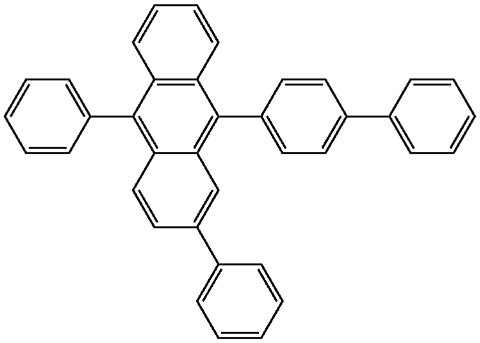

-continued
H23
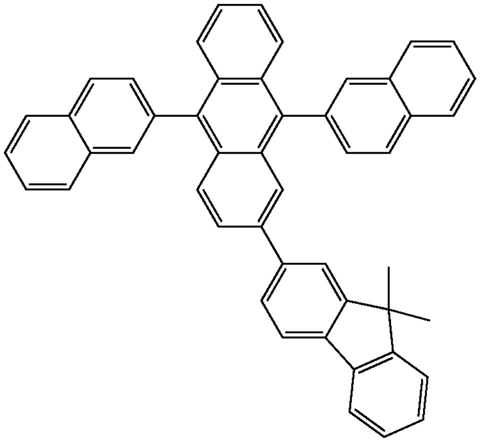
H24
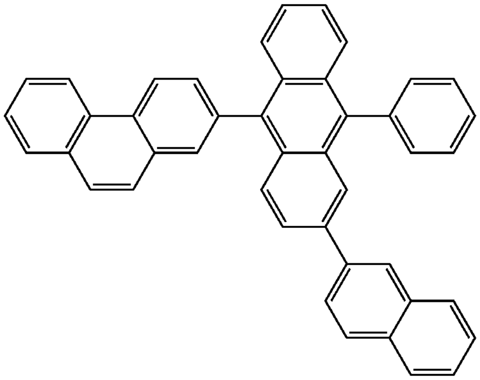
H25
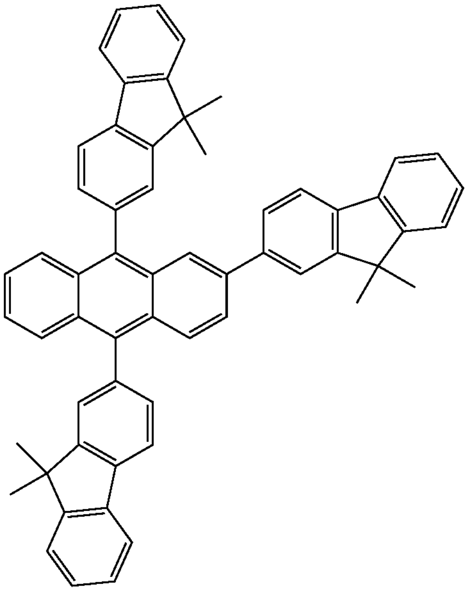
-continued
H26
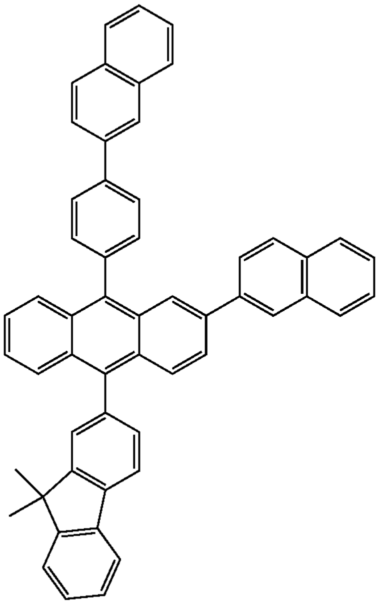
H27
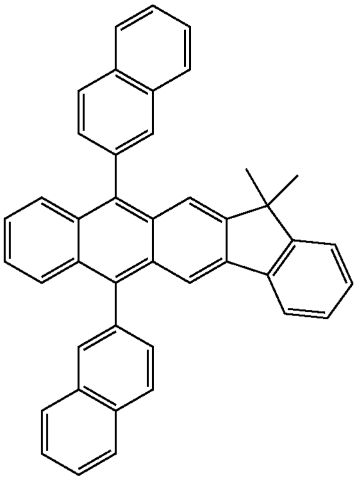
H28
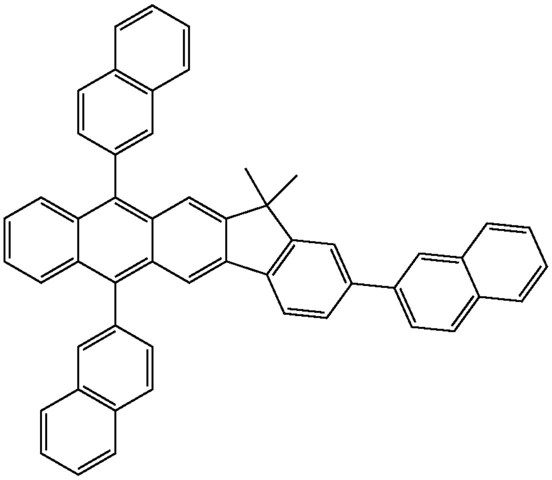

-continued
H29
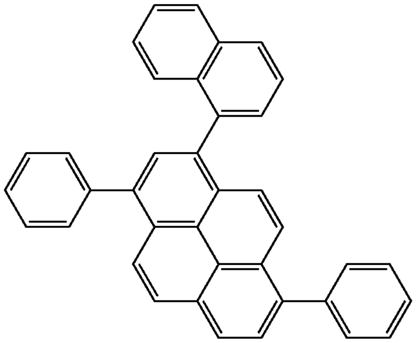
H30
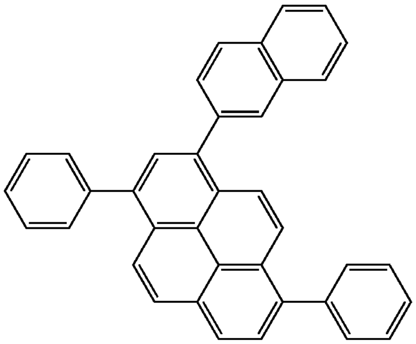
H31
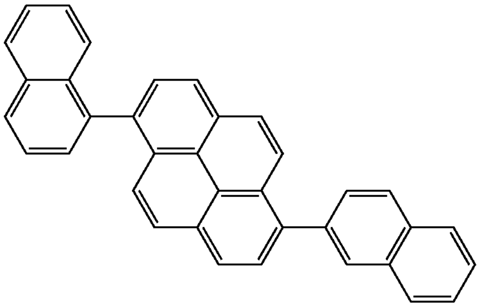
H32
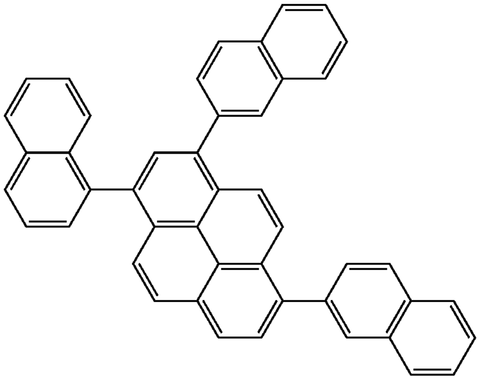
H33
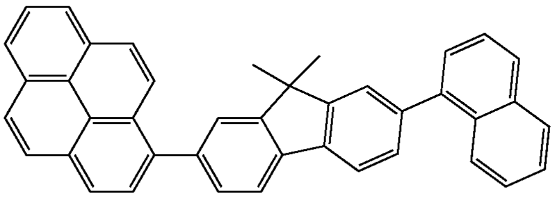
-continued
H34
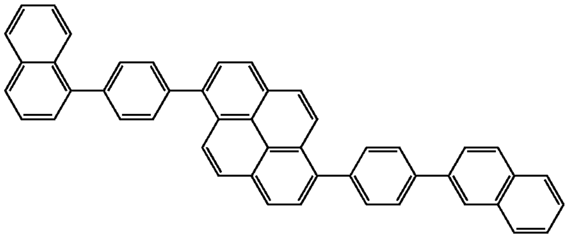
H35
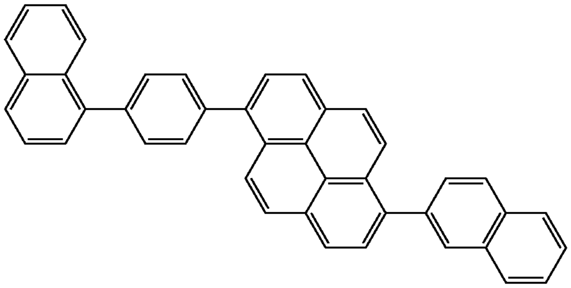
H36
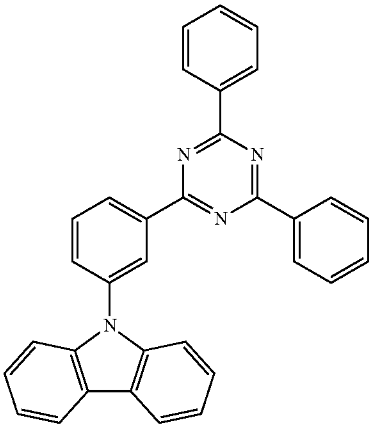
H37
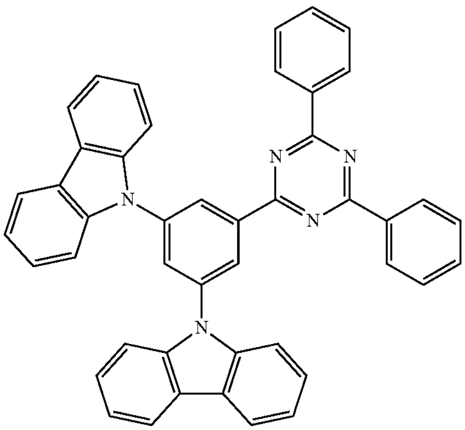

-continued
H38
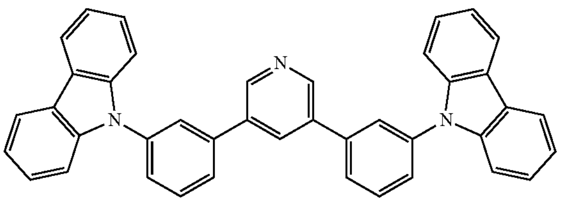
H39
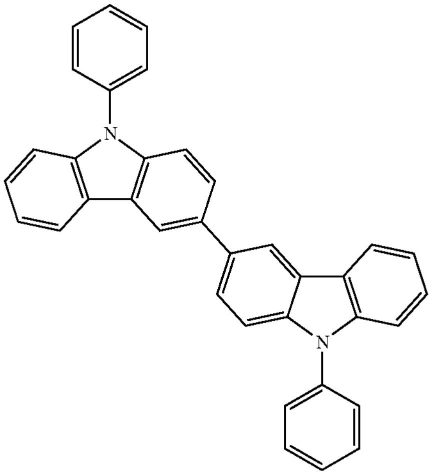
H40
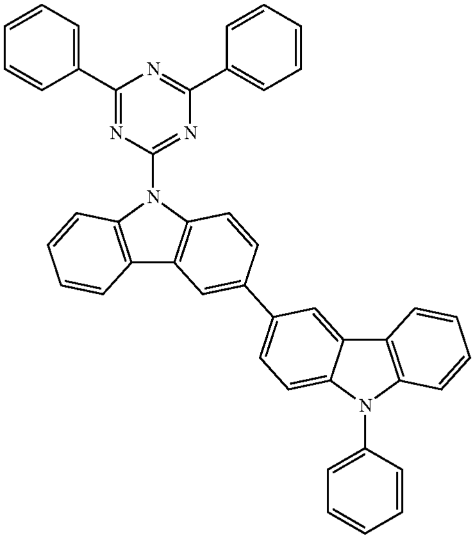
-continued
H41
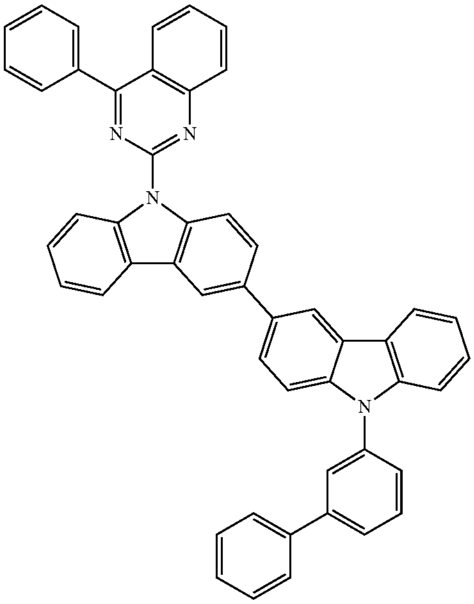
H42
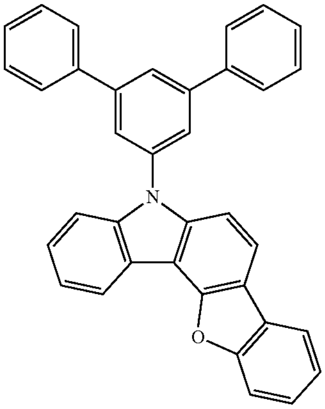
H43
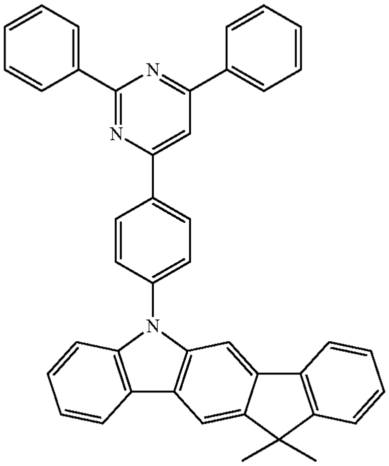

-continued
H44
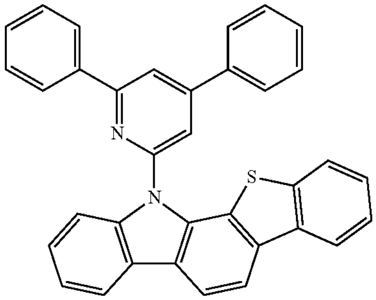
H45
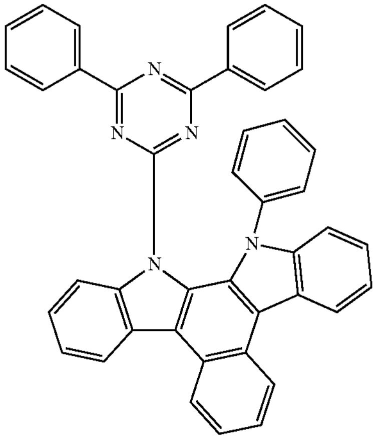
H46
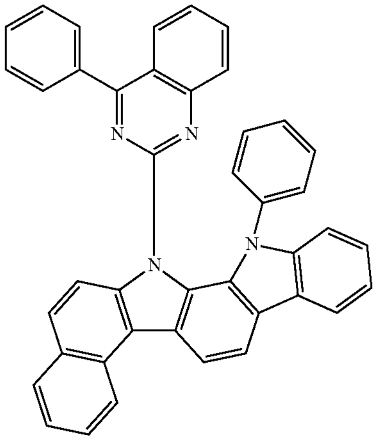
H47
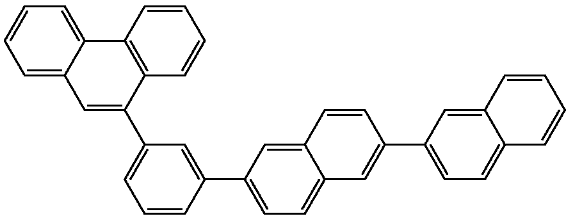
-continued
H48
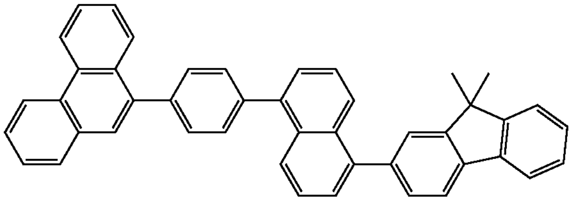
H49
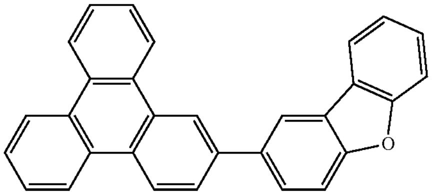
H50
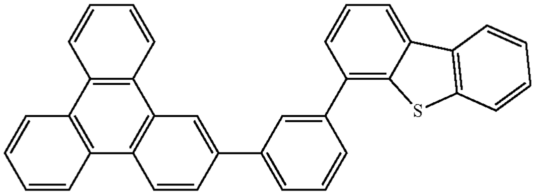
H51
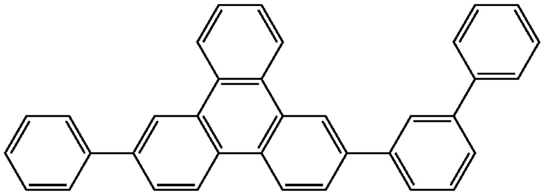
H52
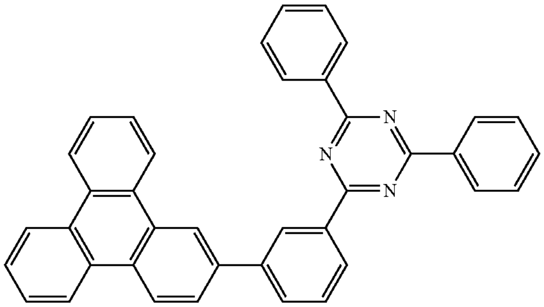
H53
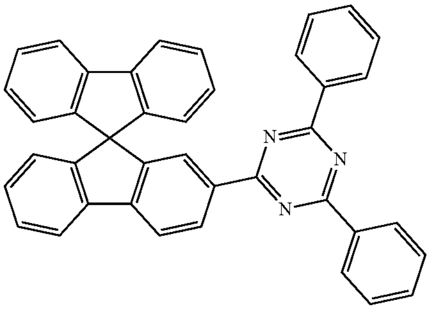

-continued
H54
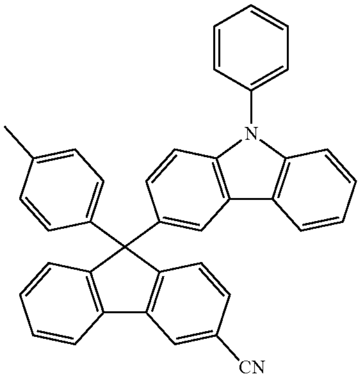
H55
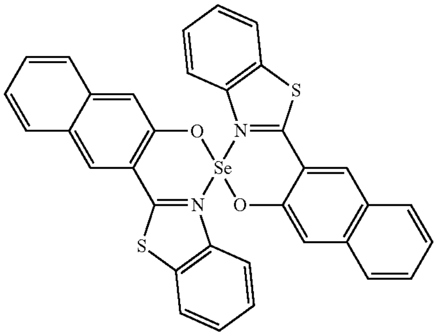
H56
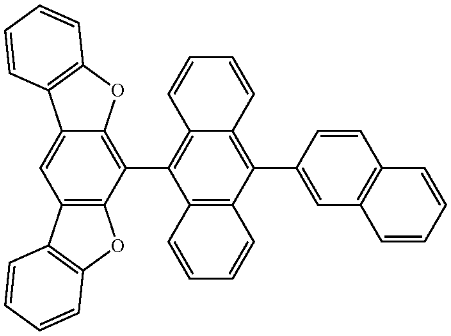
H57
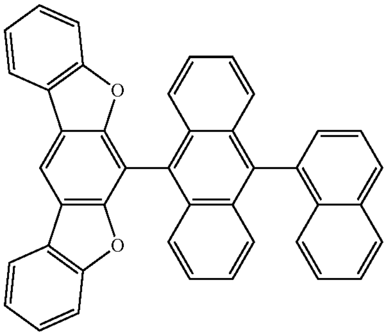
-continued
H58
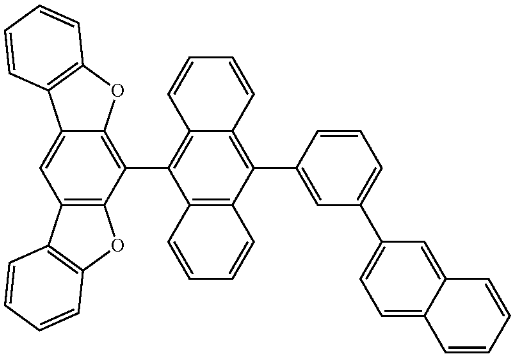
H59
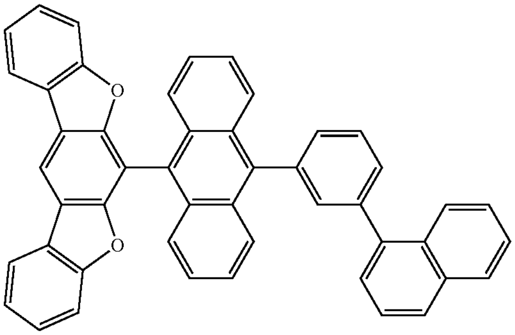
H60
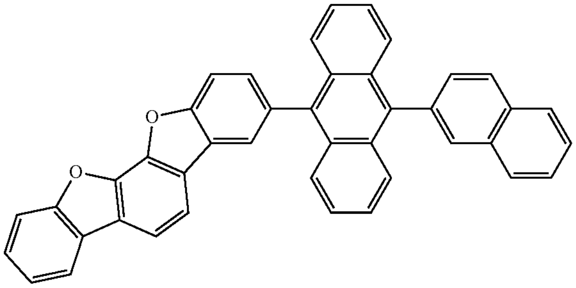
H61
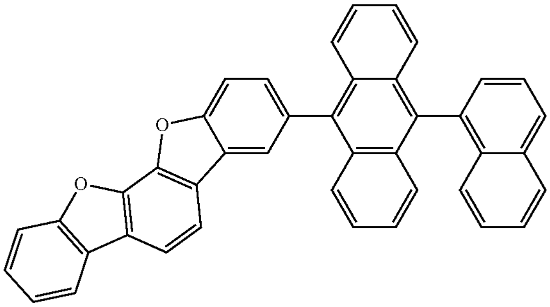

-continued
H62
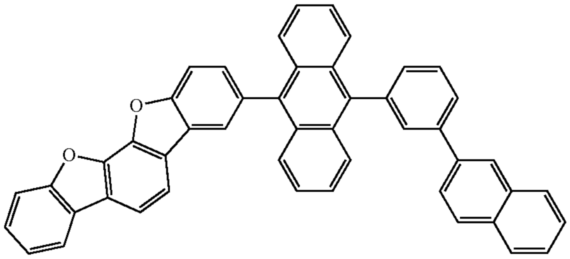
H63
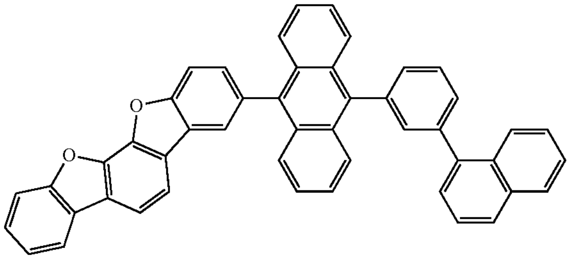
H64
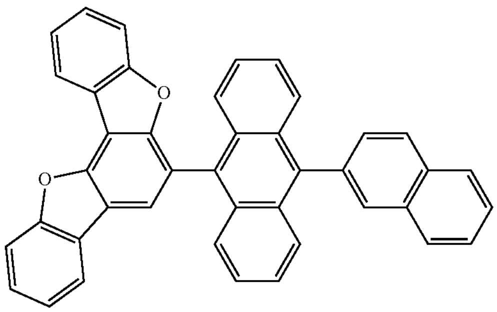
H65
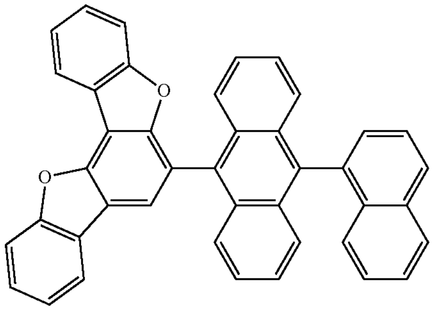
H66
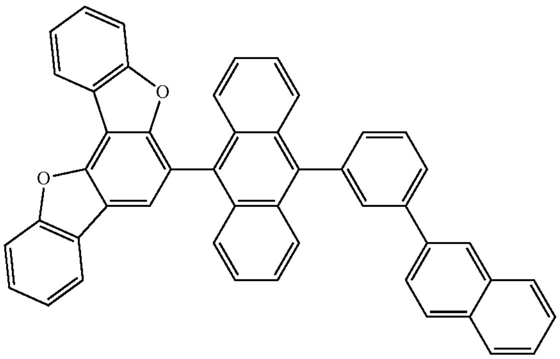
-continued
H67
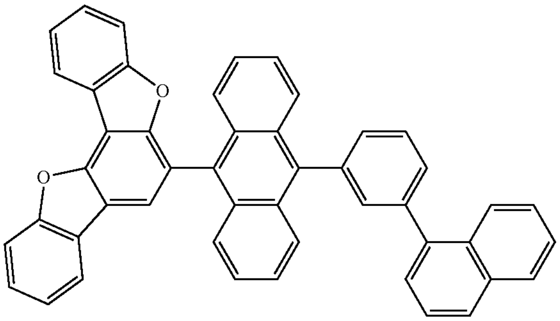
H68
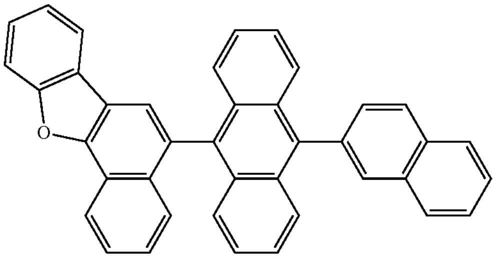
H69
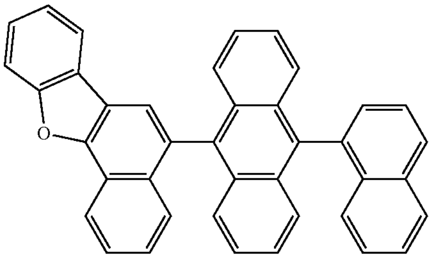
H70
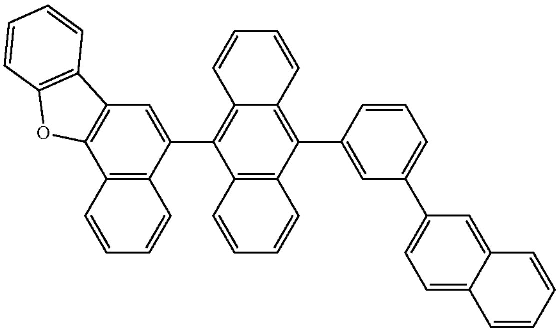
H71
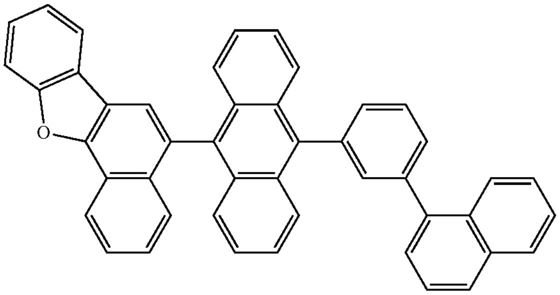

-continued
H72
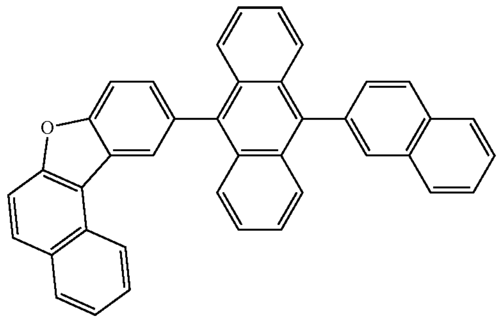
H73
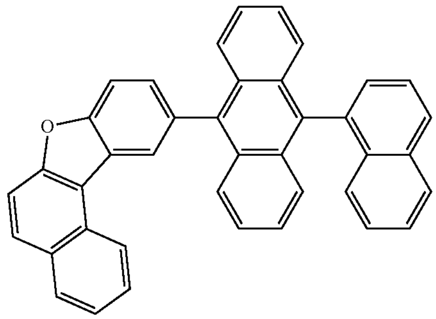
H74
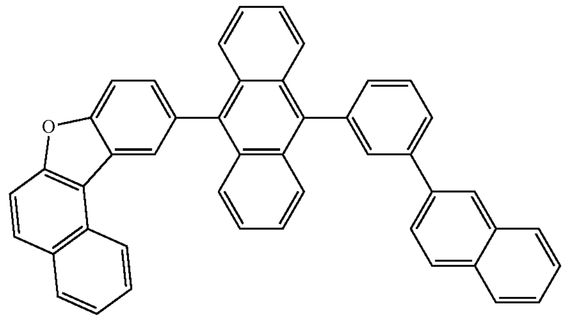
H75
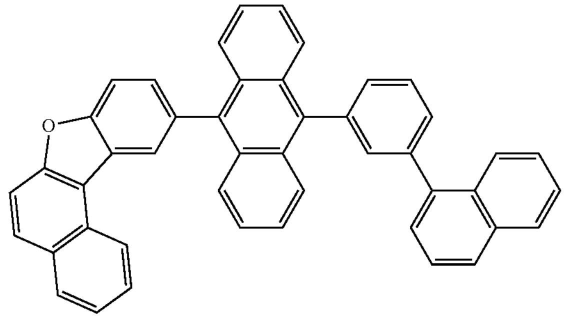
H76
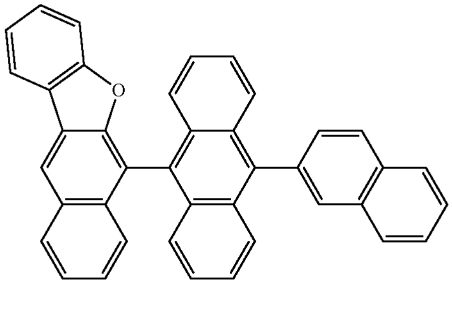
-continued
H77
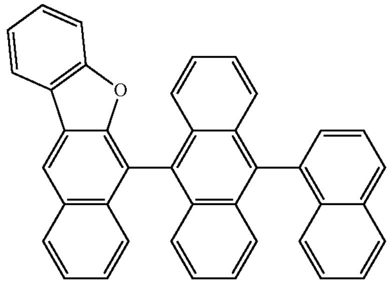
H78
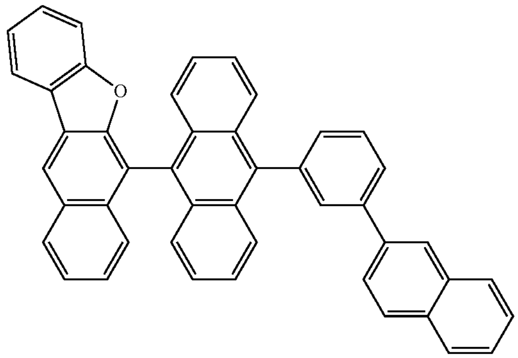
H79
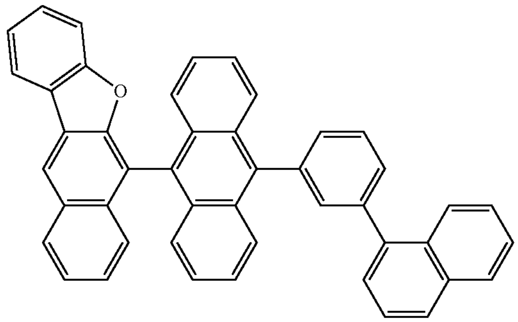
H80
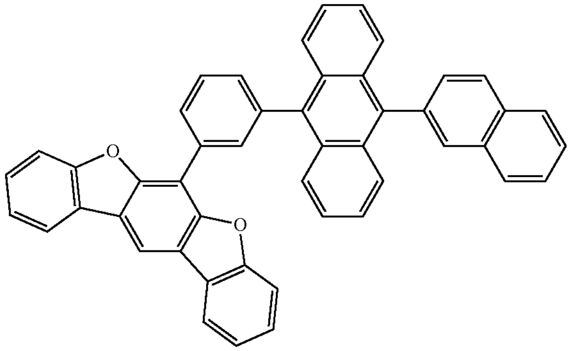

-continued
H81
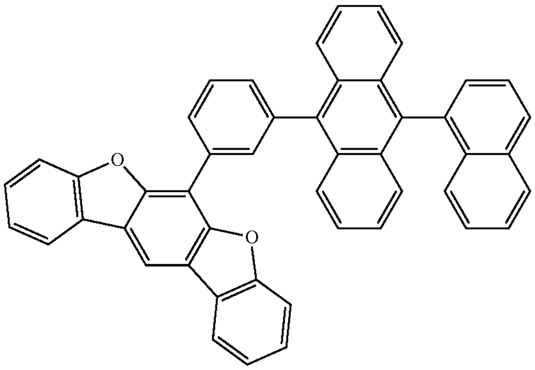
H82
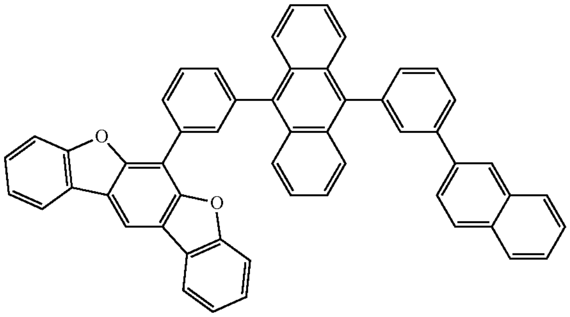
H83
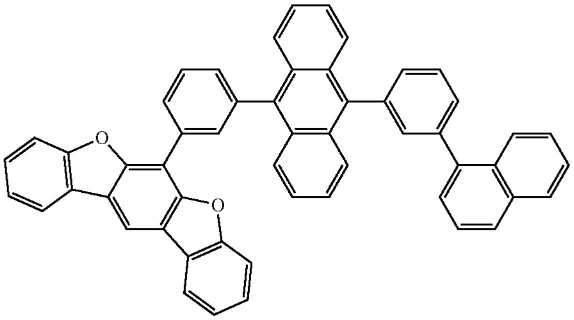
H84
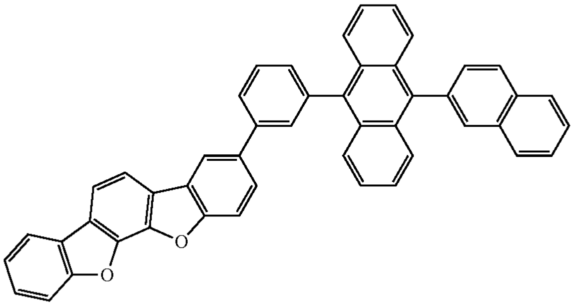
-continued
H85
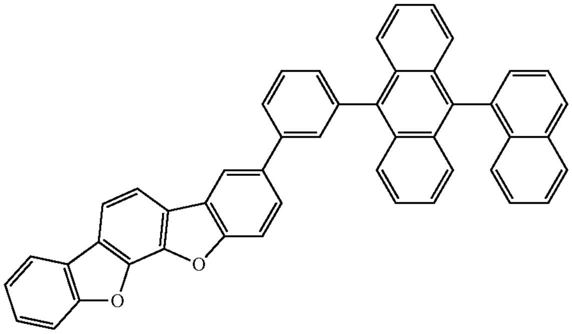
H86
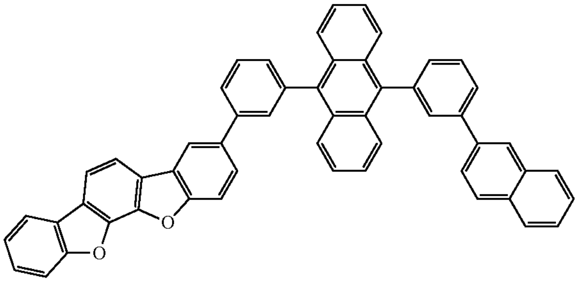
H87
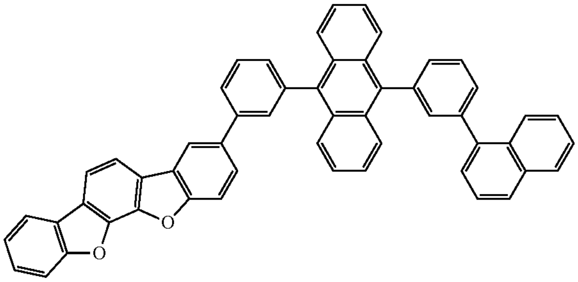
H88
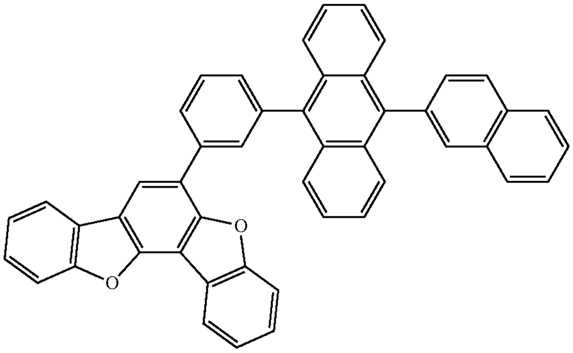

-continued
H89
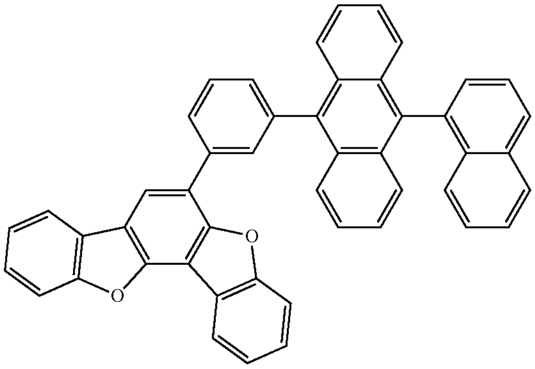
H90
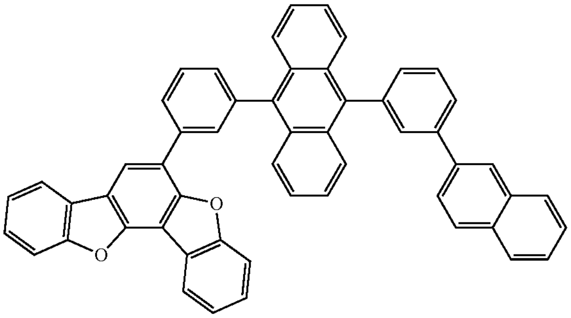
H91
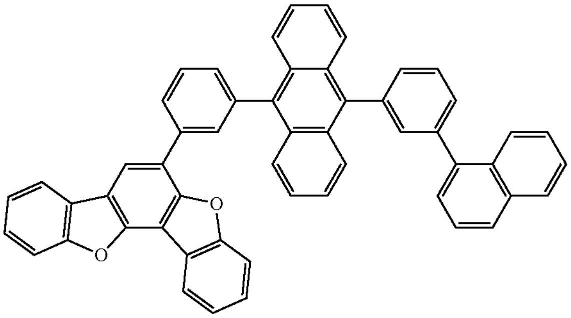
H92
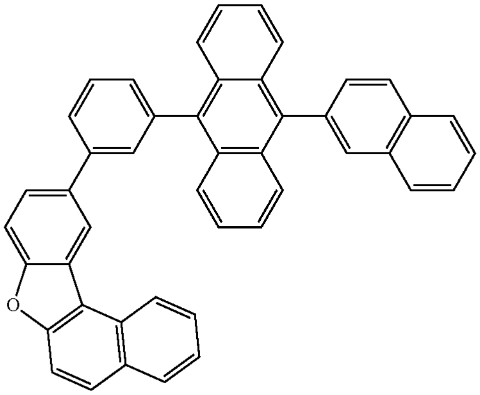
-continued
H93
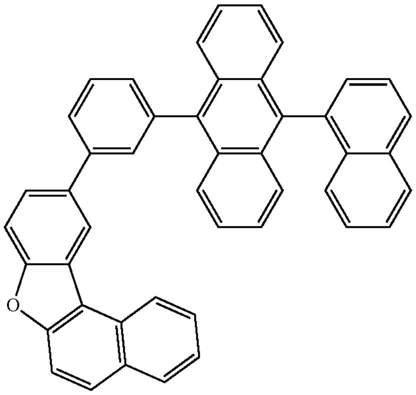
H94
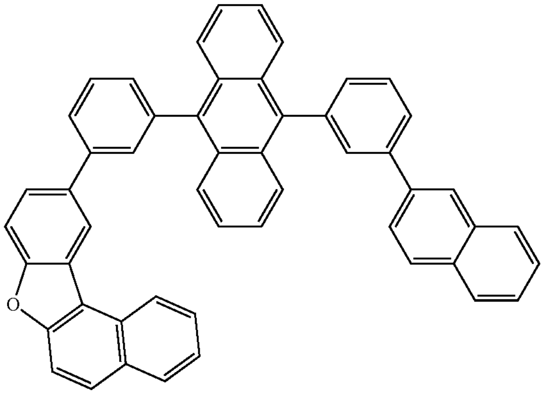
H95
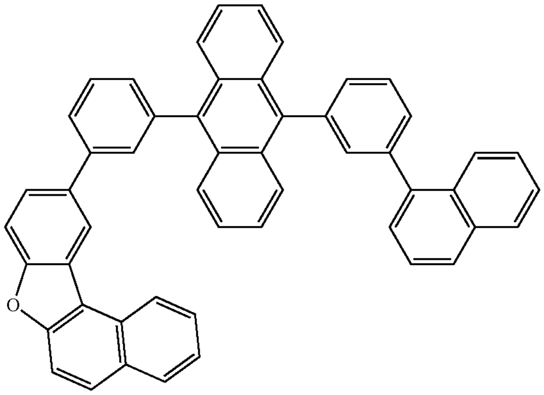
H96
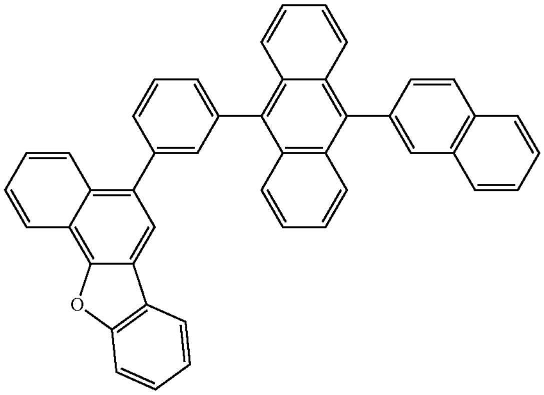

-continued
H97
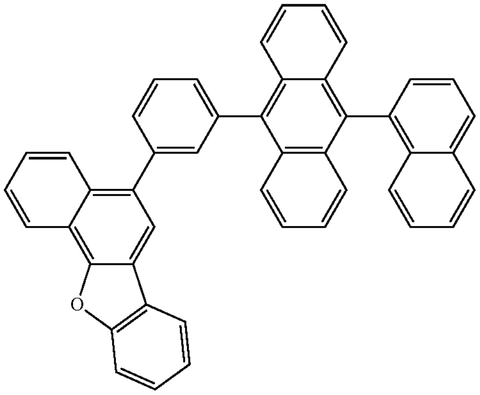
H98
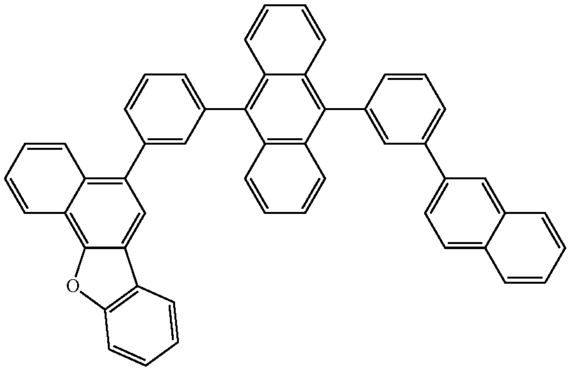
H99
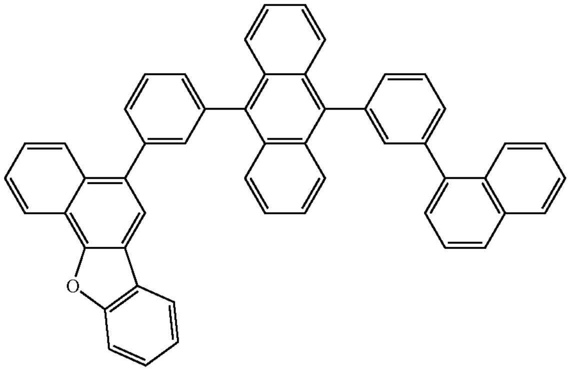
H100
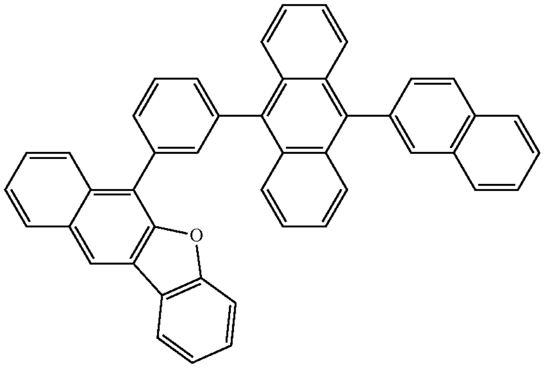
-continued
H101
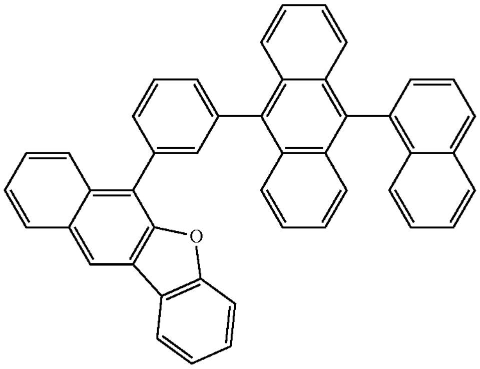
H102
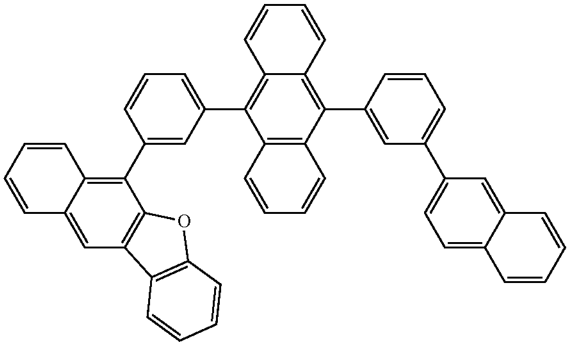
H103
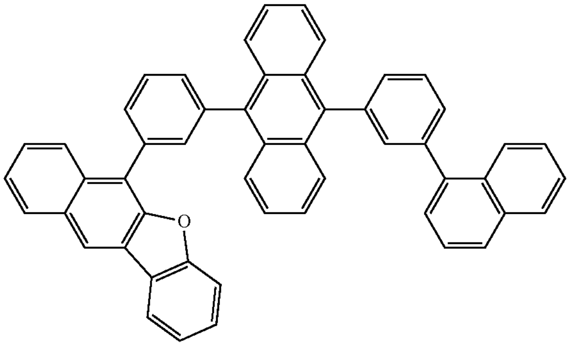
H104
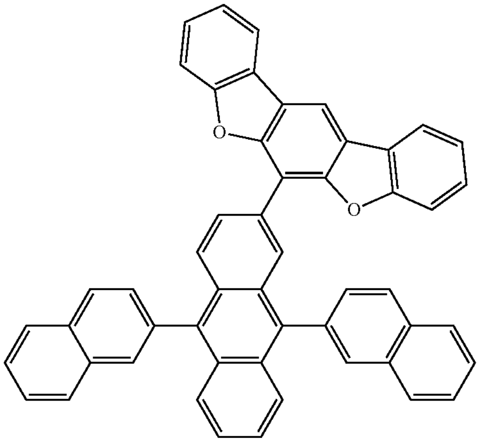

-continued
H105
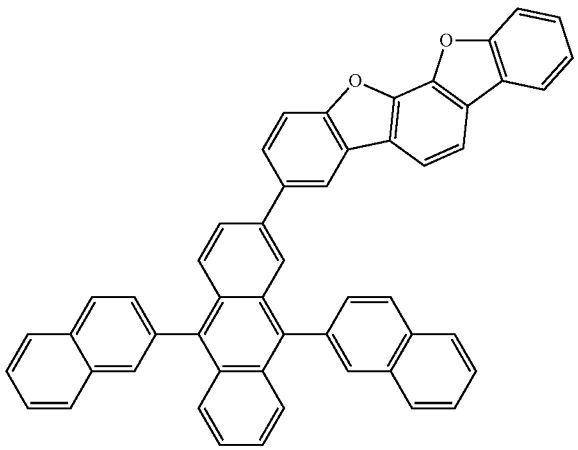
H106
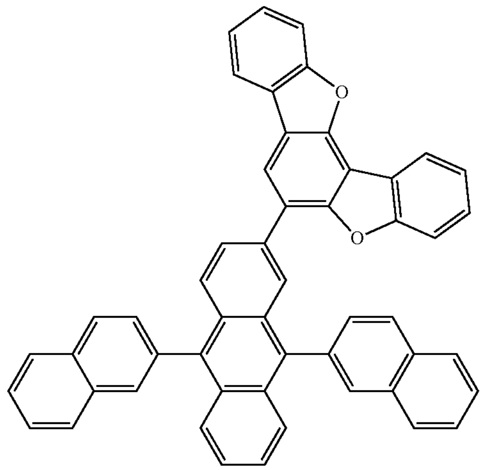
H107
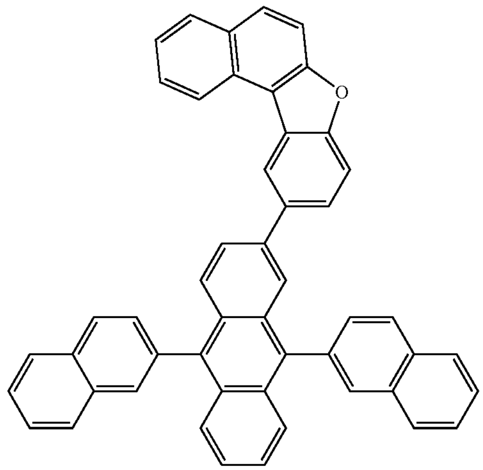
-continued
H108
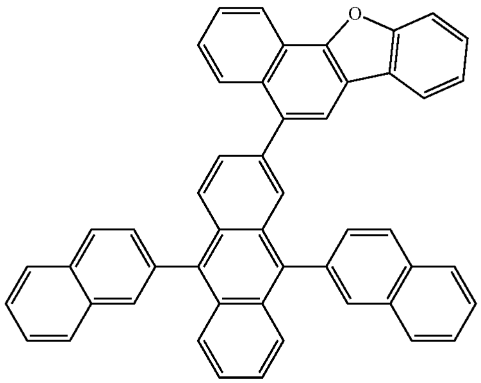
H109
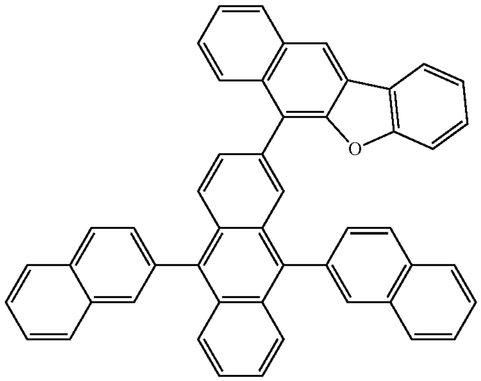
H110
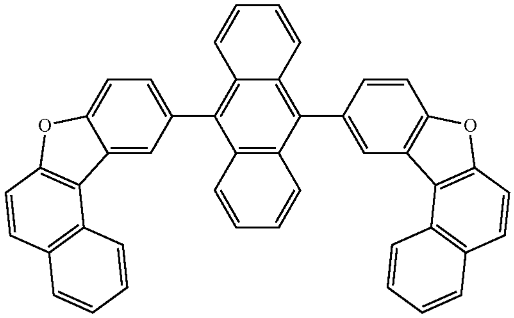
H111
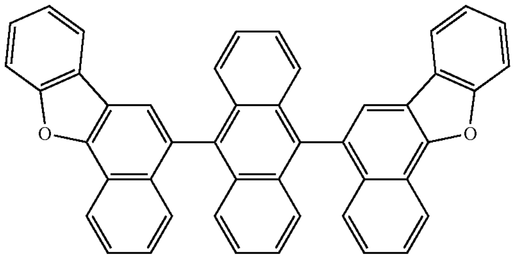

-continued
H112
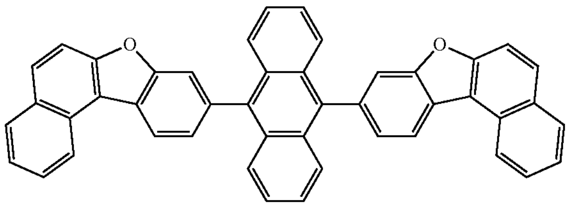
H113
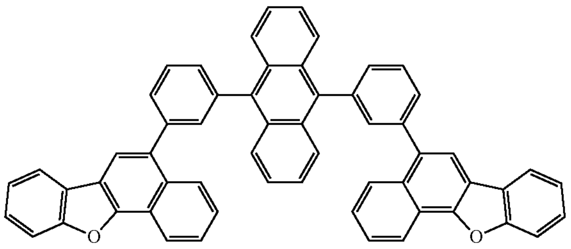
H114
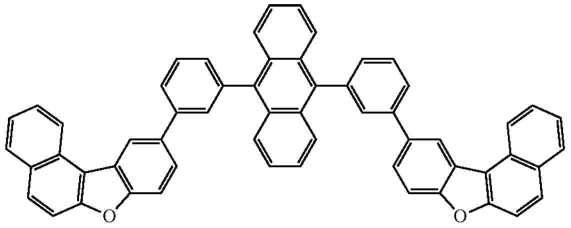
H115
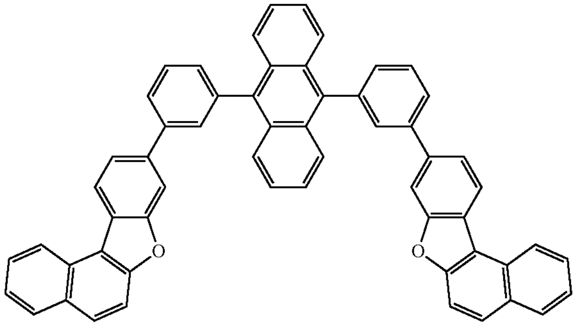
H116
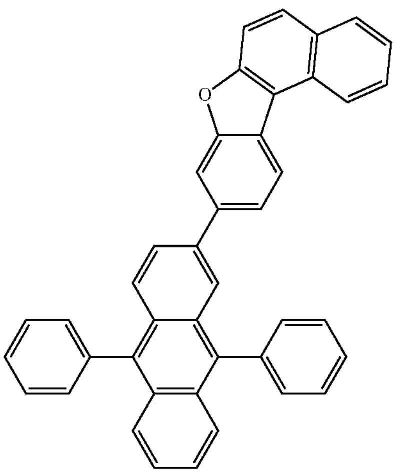
-continued
H117
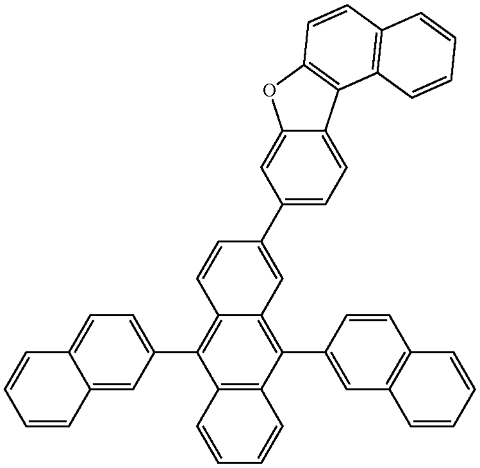
H118
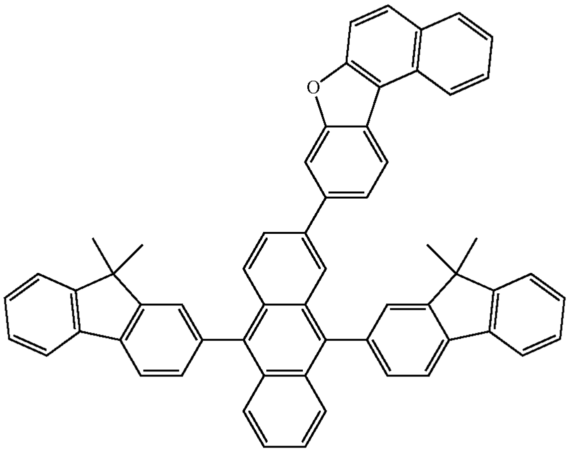
H119
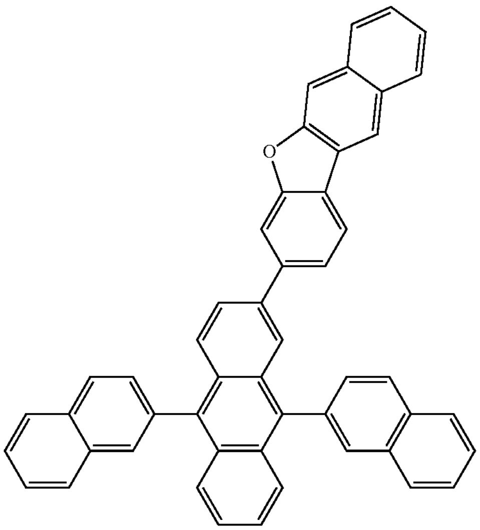

-continued

H120

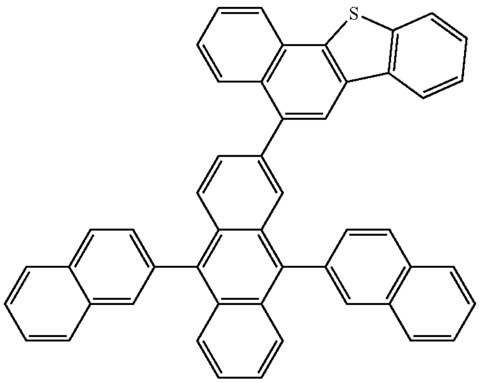

H121

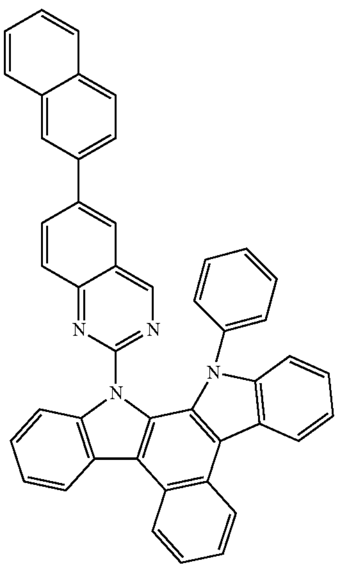

H122

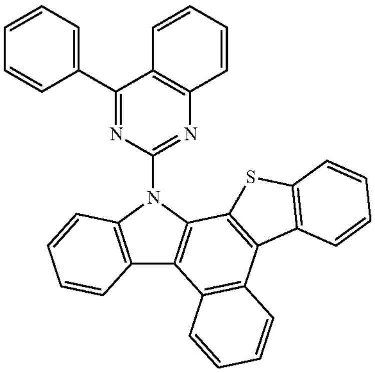

-continued

H123

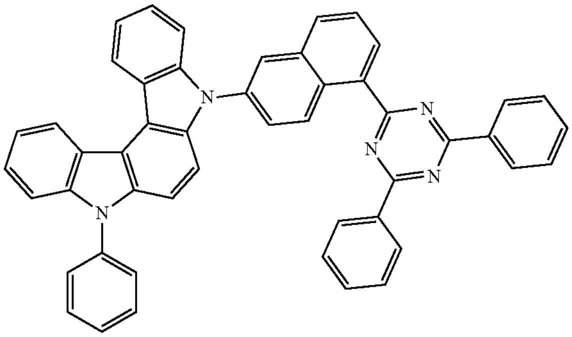

H124

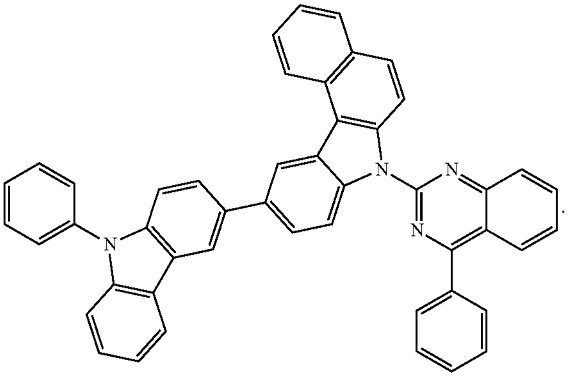

Phosphorescence Dopant

In one or more embodiments, the phosphorescence dopant may include at least one transition metal as a central metal. The phosphorescence dopant may include a monodentate ligand, a bidentate ligand, a tridentate ligand, a tetradentate ligand, a pentadentate ligand, a hexadentate ligand, or any combination thereof. The phosphorescence dopant may be electrically neutral.

For example, the phosphorescence dopant may include an organometallic compound represented by Formula 401.

Formula 401

$$M(L_{401})_{xc1}(L_{402})_{xc2}$$

Formula 402

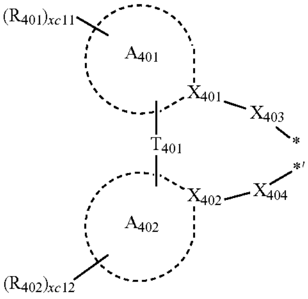

wherein, in Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein when xc1 is two or more, two or more of $L_{401}$(s) may be identical to or different from each other, $L_{402}$ may be an organic ligand, and xc2 may be 0, 1, 2, 3, or 4, and when xc2 is 2 or more, two or more of $L_{402}$(s) may be identical to or different from each other, $X_{401}$ and $X_4O_2$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (for example, a covalent bond or a coordination bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ are the same as described in connection with $Q_1$, xc11 and xc12 may each independently be an integer from 0 to 10, and

* and *' in Formula 402 each indicate a binding site to M in Formula 401.

For example, in Formula 402, i) $X_{401}$ is nitrogen, and $X_{402}$ is carbon, or ii) each of $X_{401}$ and $X_4O_2$ is nitrogen.

In one or more embodiments, when xc1 in Formula 402 is 2 or more, two ring $A_{401}$ in two or more of $L_{401}$(s) may be optionally linked to each other via $T_{402}$, which is a linking group, and two ring $A_{402}$ are optionally linked to each other via $T_{403}$, which is a linking group (see Compounds PD1 to PD4 and PD7). The variables $T_{402}$ and $T_{403}$ are the same as described in connection with $T_{401}$.

The variable $L_{402}$ in Formula 401 may be an organic ligand. For example, $L_{402}$ may include a halogen group, a diketone group (for example, an acetylacetonate group), a carboxylic acid group (for example, a picolinate group), a —C(=O) group, an isonitrile group, a —CN group, a phosphorus group (for example, a phosphine group, a phosphite group, etc.), or any combination thereof.

The phosphorescence dopant may include, for example, one of compounds PD1 to PD25, or any combination thereof:

PD1

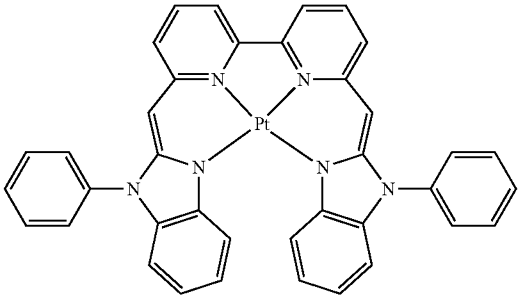

PD2

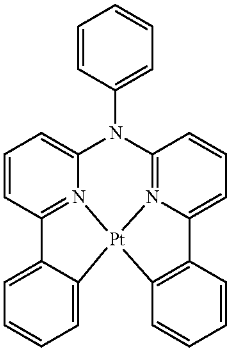

PD3

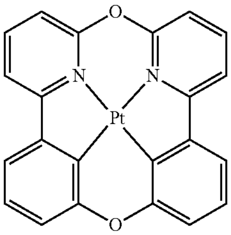

PD4

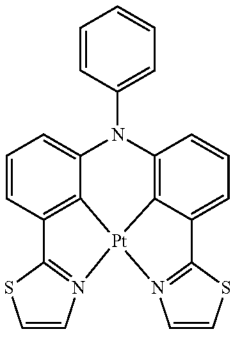

PD5

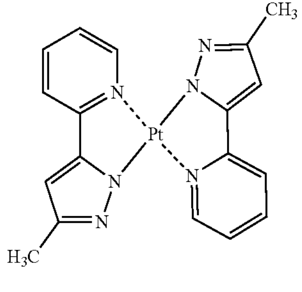

-continued
PD6
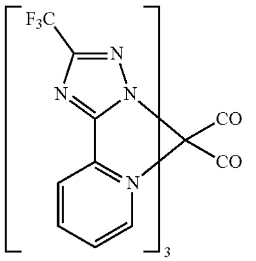
PD7
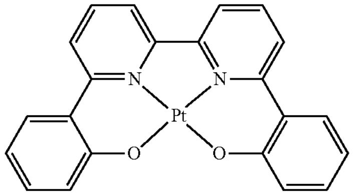
PD8
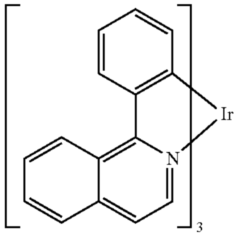
PD9
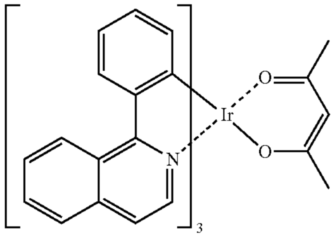
PD10
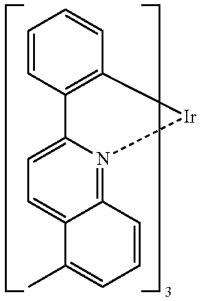
PD11
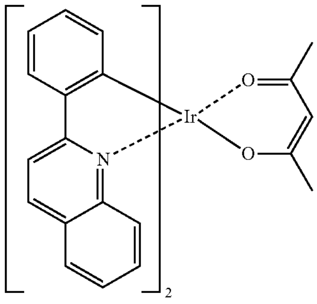
-continued
PD12
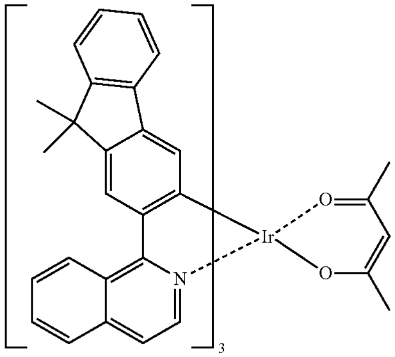
PD13
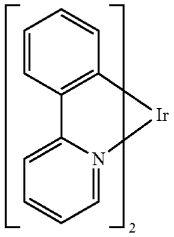
PD14
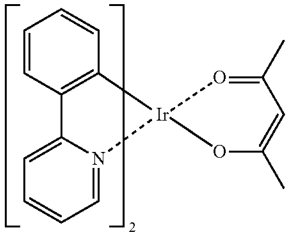
PD15
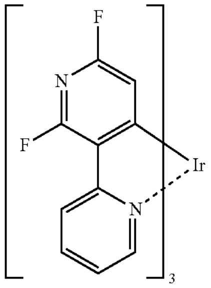
PD16
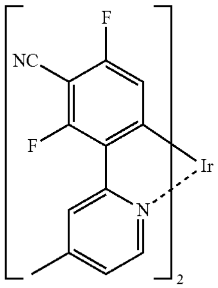

-continued
PD17
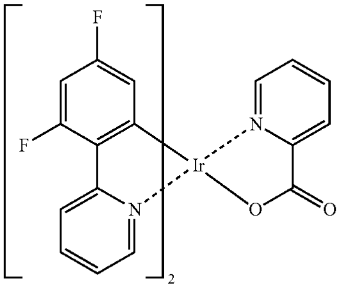
PD18
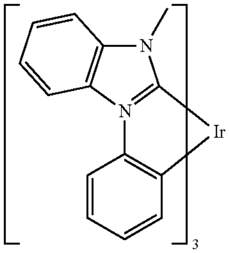
PD19
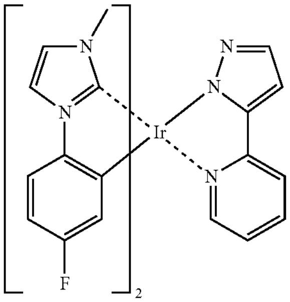
PD20
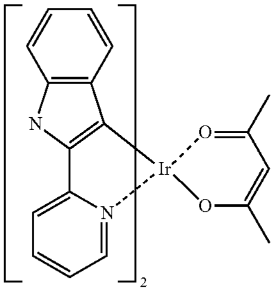
PD21
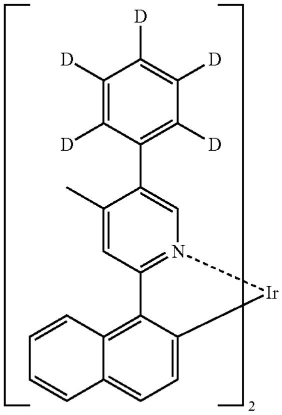
-continued
PD22
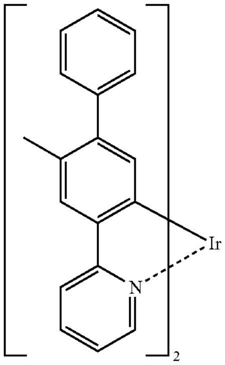
PD23
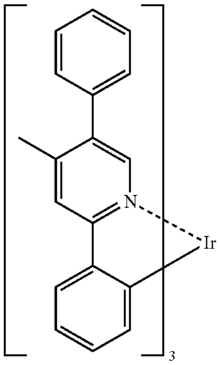
PD24
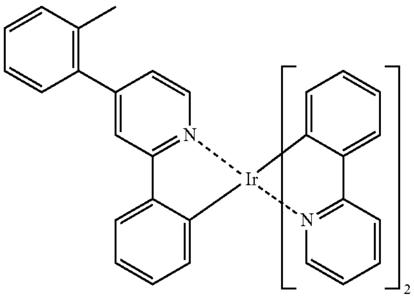
PD25
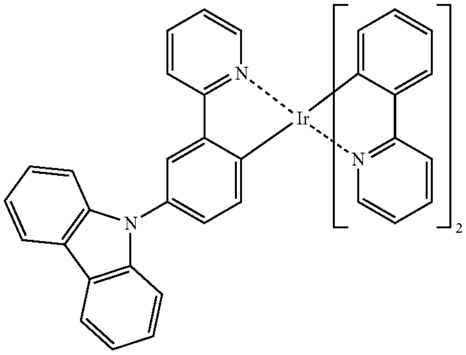
Fluorescence Dopant
The fluorescence dopant may include an amine group-containing compound, a styryl group-containing compound, or any combination thereof. In one or more embodiments, the fluorescence dopant may include a compound represented by Formula 501:

Formula 501

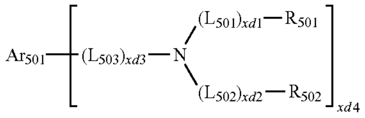

wherein, in Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In one or more embodiments, $Ar_{501}$ in Formula 501 may be a condensed cyclic group (for example, an anthracene group, a chrysene group, or a pyrene group) in which three or more monocyclic groups are condensed together. In one or more embodiments, xd4 in Formula 501 may be 2.

In one or more embodiments, the fluorescence dopant may include: one of Compounds FD1 to FD36; DPVBi; DPAVBi; or any combination thereof:

FD1

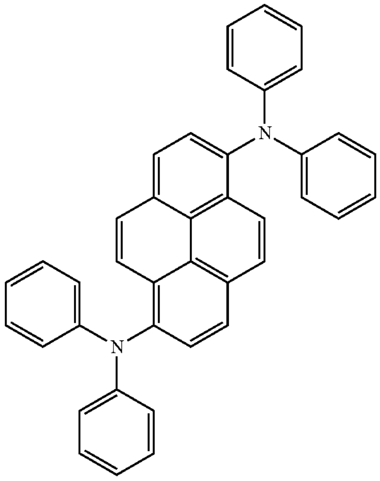

FD2

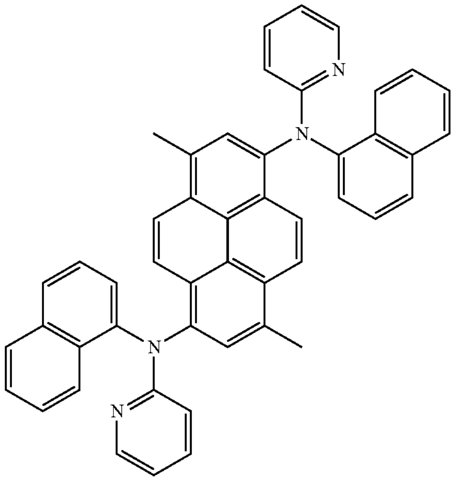

-continued

FD3

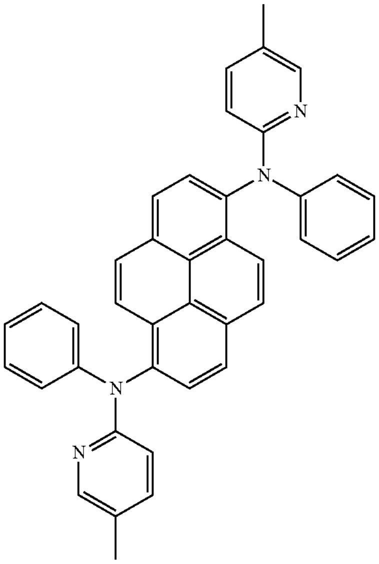

FD4

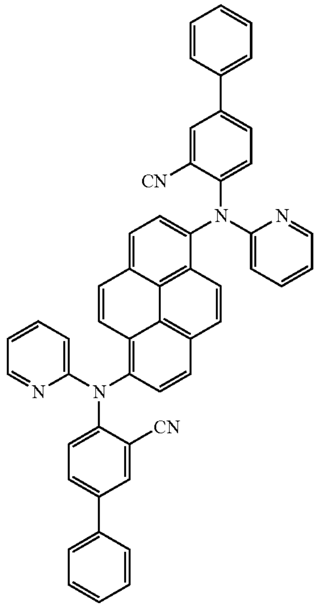

FD5

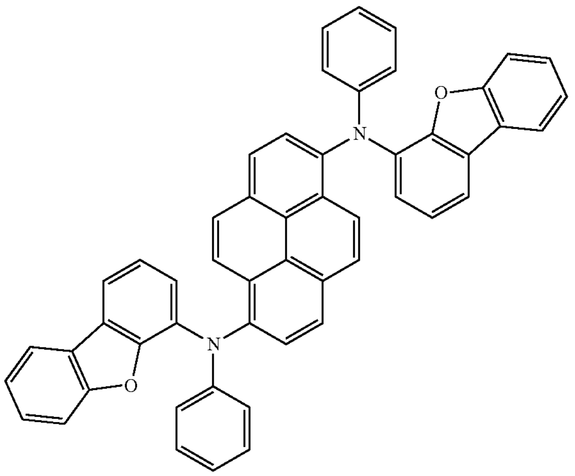

-continued
FD6
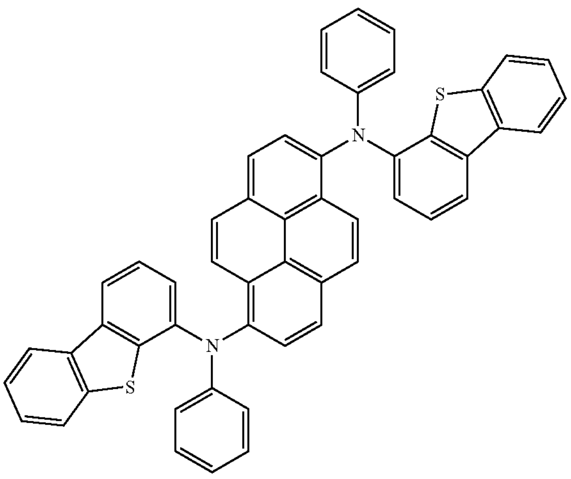
FD7
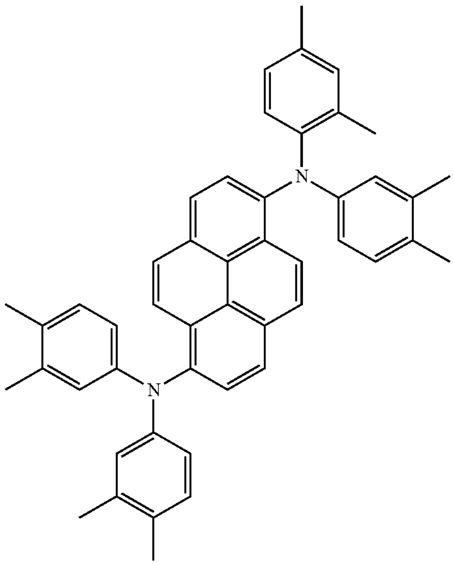
FD8
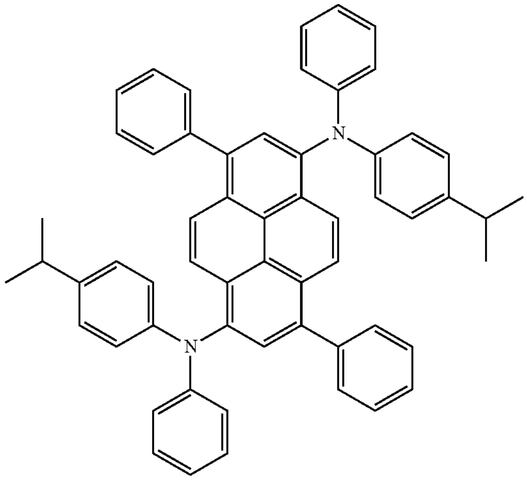
-continued
FD9
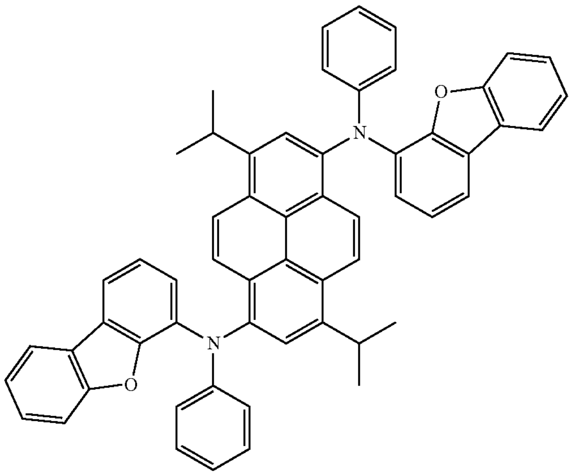
FD10
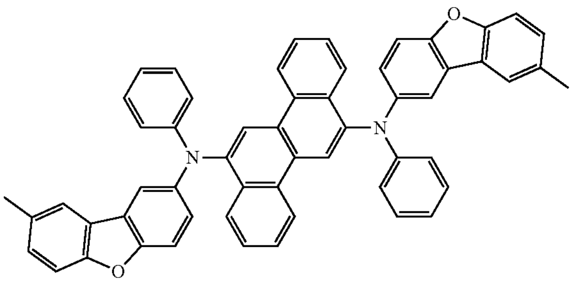
FD11
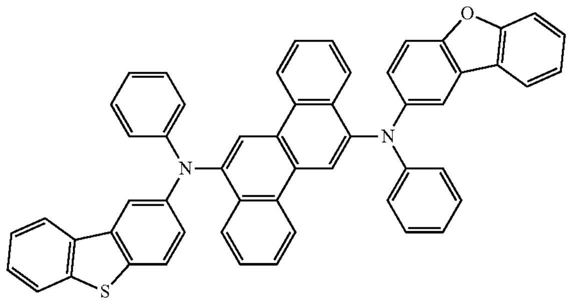
FD12
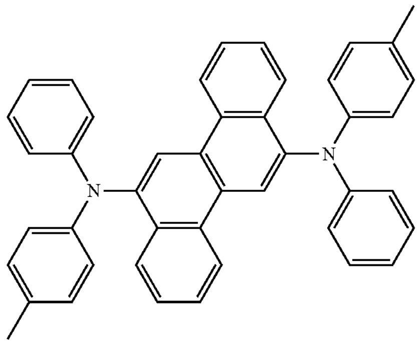

-continued
FD13
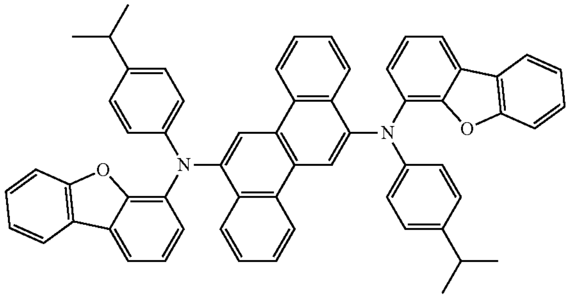
FD14
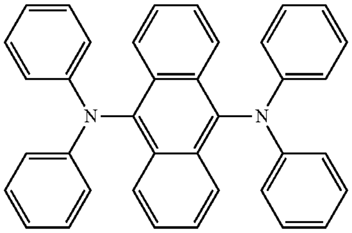
FD15
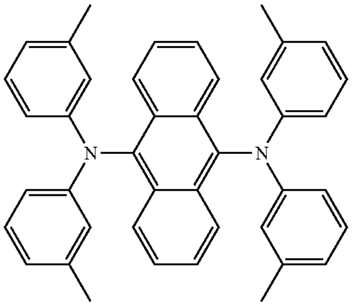
FD16
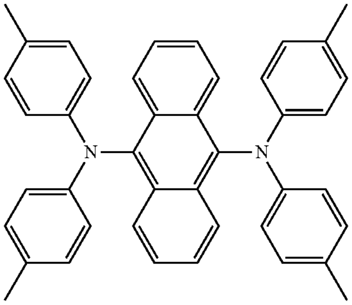
FD17
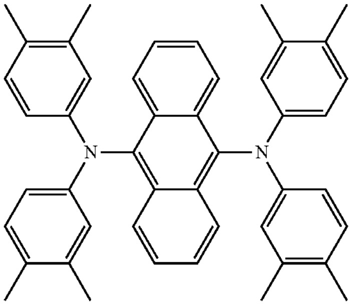
-continued
FD18
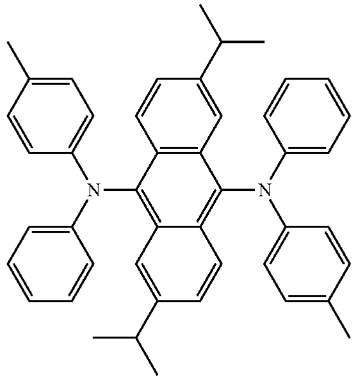
FD19
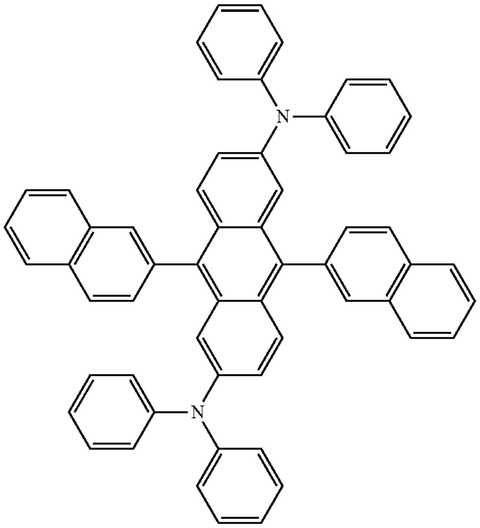
FD20
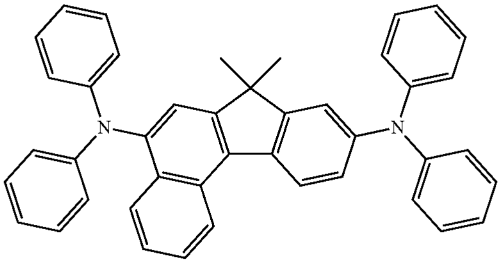
FD21
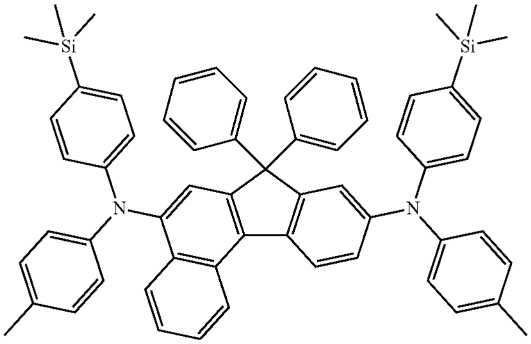

-continued
FD22
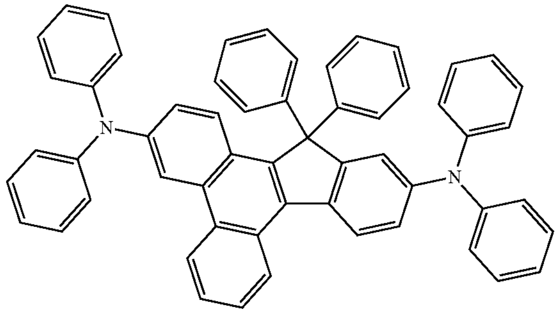
FD23
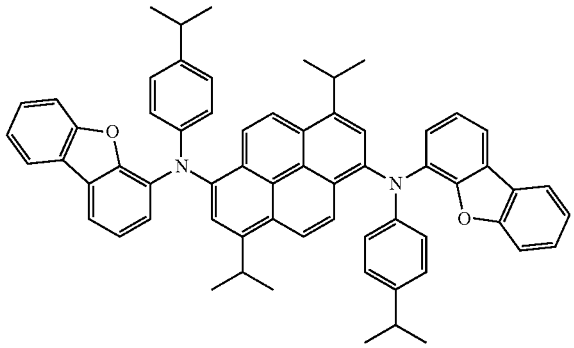
FD24
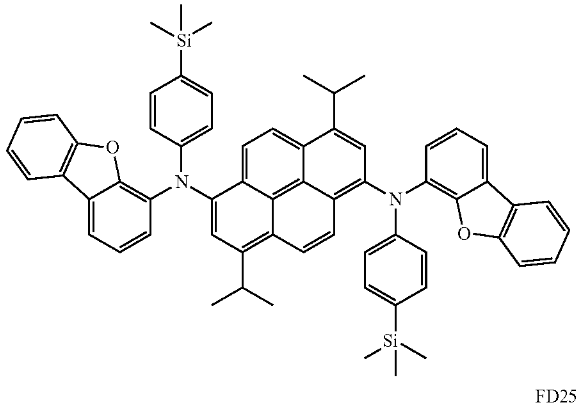
FD25
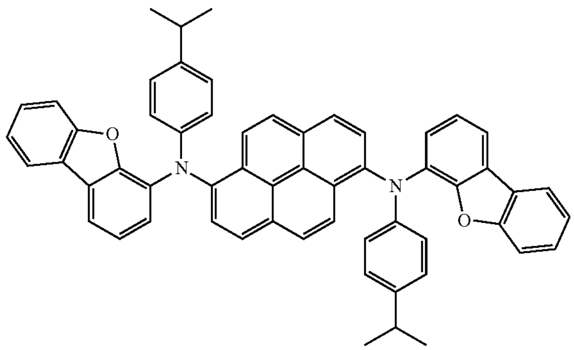
-continued
FD26
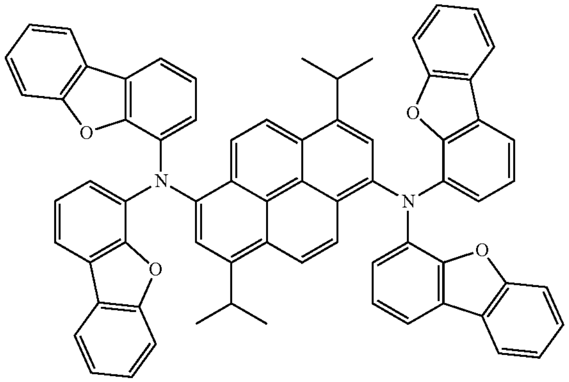
FD27
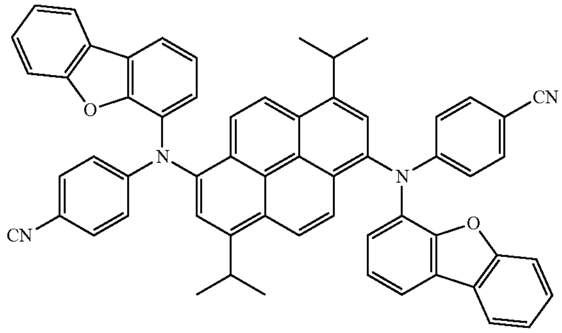
FD28
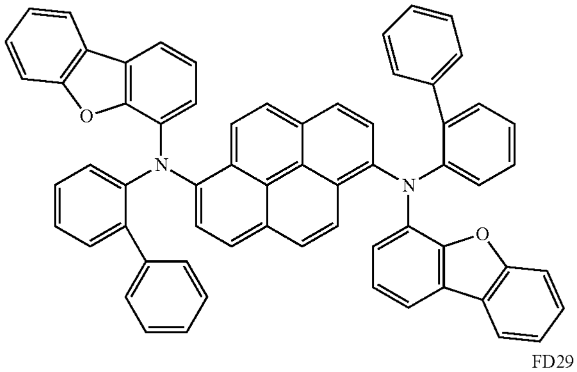
FD29
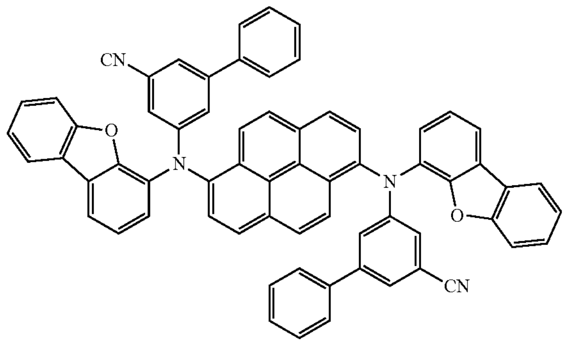

-continued
FD30
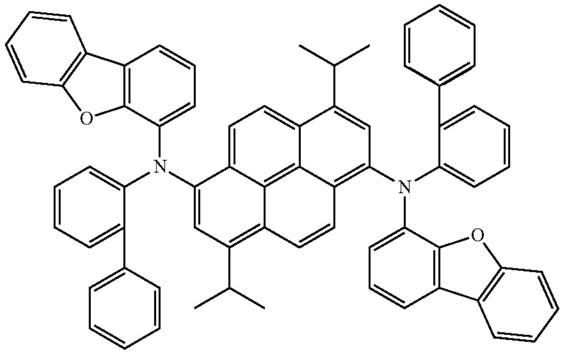
FD31
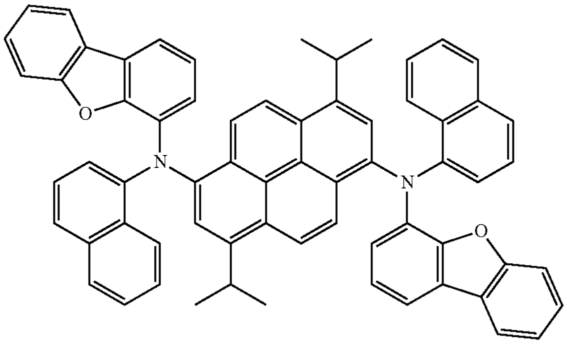
FD32
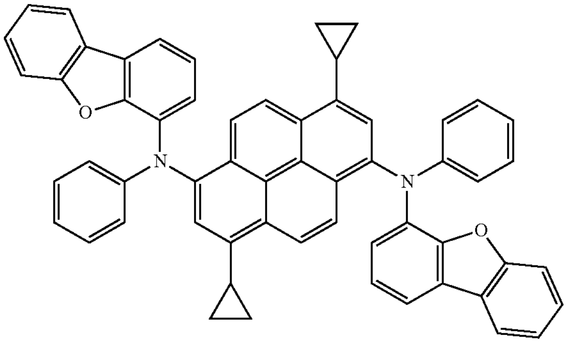
FD33
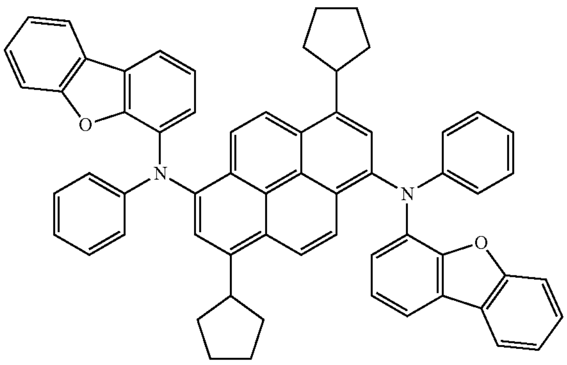
-continued
FD34
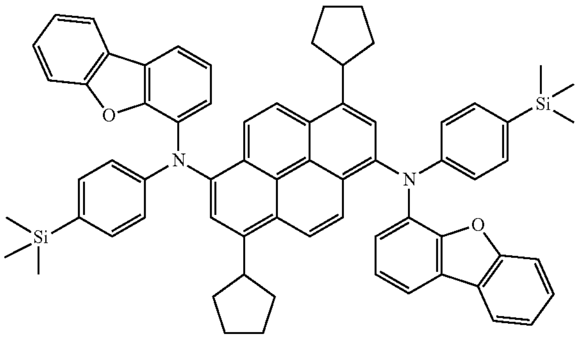
FD35
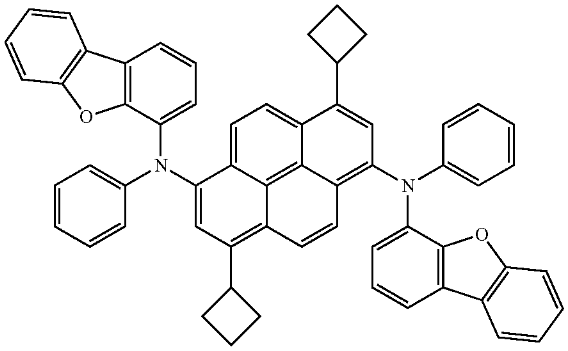
FD36
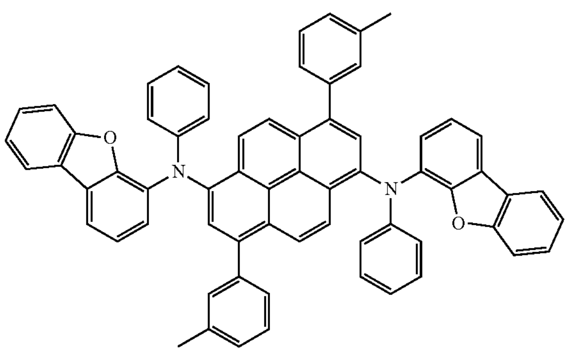
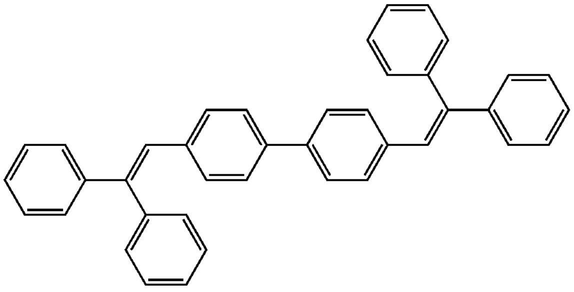
DPVBi -continued

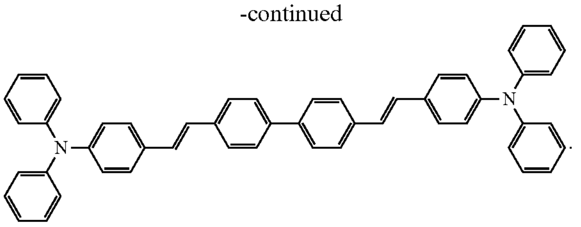

DPAVBi

Quantum Dot

The emission layer may include a quantum dot. The diameter of the quantum dot may be, for example, in a range of about 1 nm to about 10 nm. The quantum dot may be synthesized by a wet chemical process, a metal organic chemical vapor deposition process, a molecular beam epitaxy process, or any process similar thereto.

According to the wet chemical process, a precursor material is mixed with an organic solvent to grow a quantum dot particle crystal. When the crystal grows, the organic solvent naturally acts as a dispersant coordinated on the surface of the quantum dot crystal and controls the growth of the crystal so that the growth of quantum dot particles may be controlled through a process which is more easily performed than vapor deposition methods, such as metal organic chemical vapor deposition (MOCVD) or molecular beam epitaxy (MBE), and which requires low costs.

The quantum dot may include semiconductor compounds of Groups II-VI, semiconductor compounds of Groups III-V, semiconductor compounds of Groups III-VI, semiconductor compounds of Groups I, III, and VI, semiconductor compounds of Groups IV-VI, an element or a compound of Group IV; or any combination thereof.

Examples of the semiconductor compound of Groups II-VI are a binary compound, such as CdSe, CdTe, ZnS, ZnSe, ZnTe, ZnO, HgS, HgSe, HgTe, MgSe, or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, or MgZnS; a quaternary compound, such as CdZnSeS, CdZnSeTe, CdZnSTe, CdHgSeS, CdHgSeTe, CdHgSTe, HgZnSeS, HgZnSeTe, or HgZnSTe; or any combination thereof.

Examples of the semiconductor compound of Groups III-V are a binary compound, such as GaN, GaP, GaAs, GaSb, AlN, AlP, AlAs, AlSb, InN, InP, InAs, InSb, or the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, GaAlNP, or the like; a quaternary compound, such as GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, or the like; or any combination thereof. The semiconductor compound of Groups III-V may further include Group II elements. Examples of the semiconductor compound of Groups III-V further including Group II elements are InZnP, InGaZnP, InAlZnP, etc.

Examples of the semiconductor compound of Groups III-VI are a binary compound, such as GaS, GaSe, $Ga_2Se_3$, GaTe, InS, InSe, $In_2S_3$, $In_2Se_3$, or InTe; a ternary compound, such as $InGaS_3$, or $InGaSe_3$; and any combination thereof. Examples of the semiconductor compound of Groups I, III, and VI are a ternary compound, such as AgInS, $AgInS_2$, CuInS, $CuInS_2$, $CuGaO_2$, $AgGaO_2$, or $AgAlO_2$; or any combination thereof.

Examples of the semiconductor compound of Groups IV-VI are a binary compound, such as SnS, SnSe, SnTe, PbS, PbSe, PbTe, or the like; a ternary compound, such as SnSeS, SnSeTe, SnSTe, PbSeS, PbSeTe, PbSTe, SnPbS, SnPbSe, SnPbTe, or the like; a quaternary compound, such as SnPbSSe, SnPbSeTe, SnPbSTe, or the like; or any combination thereof. The element or compound of Group IV may include a single element compound, such as Si or Ge; a binary compound, such as SiC or SiGe; or any combination thereof.

Each element included in a multi-element compound such as the binary compound, ternary compound and quaternary compound, may be present in a particle with a uniform concentration or non-uniform concentration. The quantum dot may have a single structure or a dual core-shell structure. In the case of the quantum dot having a single structure, the concentration of each element included in the corresponding quantum dot is uniform. In one or more embodiments, the material contained in the core and the material contained in the shell may be different from each other.

The shell of the quantum dot may act as a protective layer to prevent chemical degeneration of the core to maintain semiconductor characteristics and/or as a charging layer to impart electrophoretic characteristics to the quantum dot. The shell may be a single layer or a multi-layer. The interface between the core and the shell may have a concentration gradient that decreases toward the center of the element present in the shell.

Examples of the shell of the quantum dot may be an oxide of a metal, a metalloid, or a non-metal, a semiconductor compound, and any combination thereof. Examples of the oxide of a metal, a metalloid, or a non-metal are a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $CO_3O_4$, or NiO; a ternary compound, such as $MgAl_2O_4$, $CoFe_2O_4$, $NiFe_2O_4$, or $CoMn_2O_4$; and any combination thereof. Examples of the semiconductor compound are, as described herein, semiconductor compounds of Groups II-VI; semiconductor compounds of Groups III-V; semiconductor compounds of Groups III-VI; semiconductor compounds of Groups I, III, and VI; semiconductor compounds of Groups IV-VI; and any combination thereof. In addition, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

The full width at half maximum (FWHM) of an emission wavelength spectrum of the quantum dot may be about 45 nm or less, for example, about 40 nm or less, for example, about 30 nm or less, and within these ranges, color purity or color gamut may be increased. In addition, since the light emitted through the quantum dot is emitted in all directions, the wide viewing angle may be improved.

In addition, the quantum dot may be a generally spherical particle, a generally pyramidal particle, a generally multi-armed particle, a generally cubic nanoparticle, a generally nanotube-shaped particle, a generally nanowire-shaped particle, a generally nanofiber-shaped particle, or a generally nanoplate-shaped particle.

Because the energy band gap may be adjusted by controlling the size of the quantum dot, light having various wavelength bands may be obtained from the quantum dot emission layer. Therefore, by using quantum dots of different sizes, a light-emitting device that emits light of various wavelengths may be implemented. In one or more embodiments, the size of the quantum dot may be selected to emit red, green and/or blue light. In addition, the size of the quantum dot may be configured to emit white light by combining light of various colors.

Electron Transport Region in Interlayer 130

The electron transport region may have: i) a single-layered structure consisting of a single layer consisting of a single material, ii) a single-layered structure consisting of a single layer consisting of a plurality of different materials, or iii) a multi-layered structure including a plurality of layers including different materials.

The electron transport region may include a buffer layer, a hole blocking layer, an electron control layer, an electron transport layer, an electron injection layer, or any combination thereof. In an embodiment, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, for each structure, constituting layers are sequentially stacked from an emission layer.

In an embodiment, the electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group. In an embodiment, the electron transport region may include a compound represented by Formula 601 below:

$$[Ar_{601}]_{xe11}\text{-}[(L_{601})_{xe1}\text{-}R_{601}]_{xe21}$$ Formula 601 wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{601})(Q_{602})(Q_{603})$, —$C(=O)(Q_{601})$, —$S(=O)_2(Q_{601})$, or —$P(=O)(Q_{601})(Q_{602})$, $Q_{601}$ to $Q_{603}$ are the same as described in connection with $Q_1$, xe21 may be 1, 2, 3, 4, or 5, at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

For example, when xe11 in Formula 601 is 2 or more, two or more of $Ar_{601}$(s) may be linked via a single bond. In one or more embodiments, $Ar_{601}$ in Formula 601 may be a substituted or unsubstituted anthracene group. In an embodiment, the electron transport region may include a compound represented by Formula 601-1:

Formula 601-1

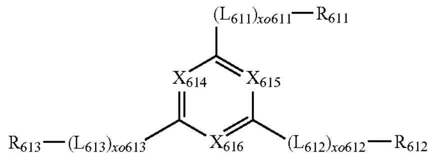

wherein, in Formula 601-1, $X_{614}$ may be N or $C(R_{614})$, $X_{615}$ may be N or $C(R_{615})$, $X_{616}$ may be N or $C(R_{616})$, at least one of $X_{614}$ to $X_{616}$ may be N, $L_{611}$ to $L_{613}$ are the same as described in connection with $L_{601}$, xe611 to xe613 are the same as described in connection with xe1, $R_{611}$ to $R_{613}$ are the same as described in connection with $R_{601}$, $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

For example, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), tris-(8-hydroxyquinoline)aluminum ($Alq_3$), bis(2-methyl-8-quinolinolato-N1,O8)-(1,1'-biphenyl-4-olato)aluminum (BAlq), 3-(biphenyl-4-yl)-5-(4-tert-butylphenyl)-4-phenyl-4H-1,2,4-triazole (TAZ), 4-(naphthalen-1-yl)-3,5-diphenyl-4H-1,2,4-triazole (NTAZ), or any combination thereof.

ET1

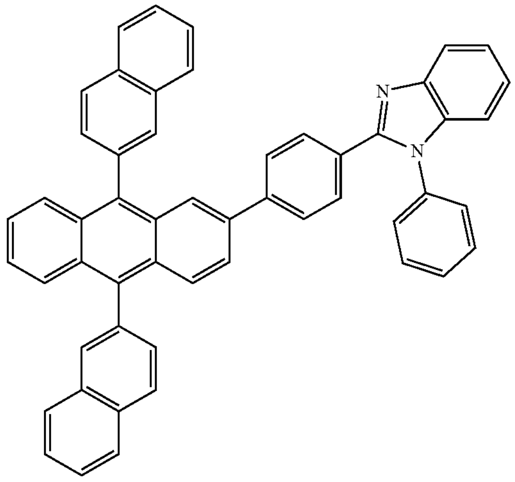

-continued
ET2
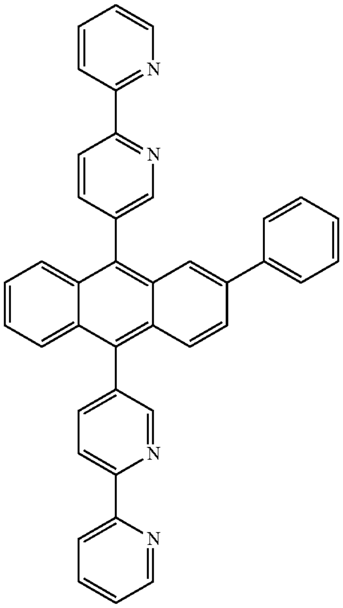
ET3
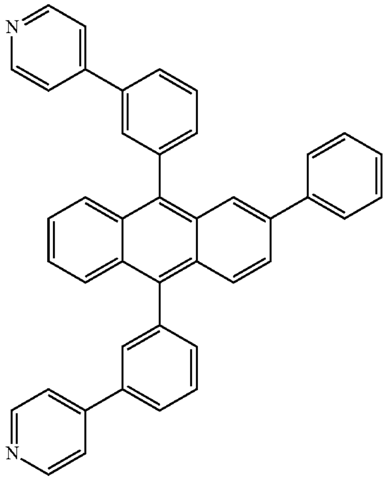
ET4
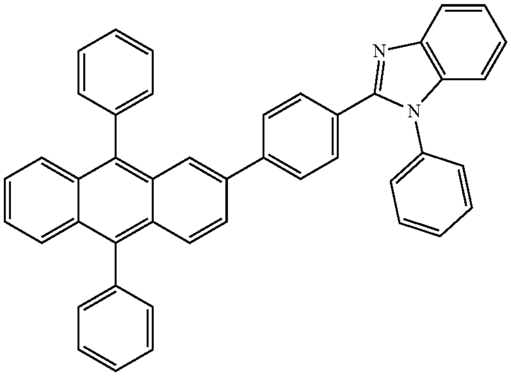
-continued
ET5
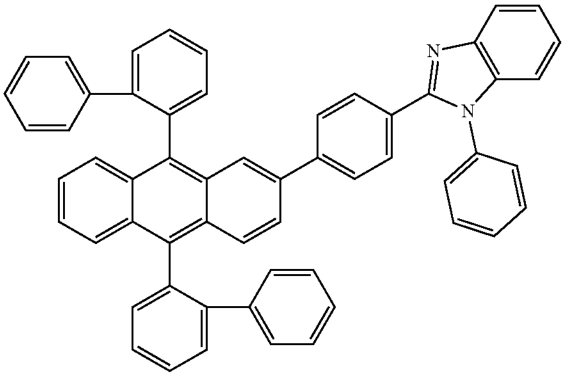
ET6
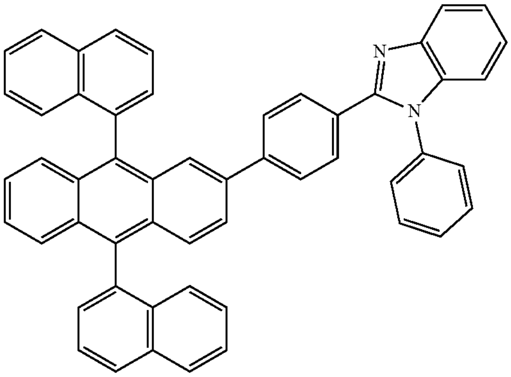
ET7
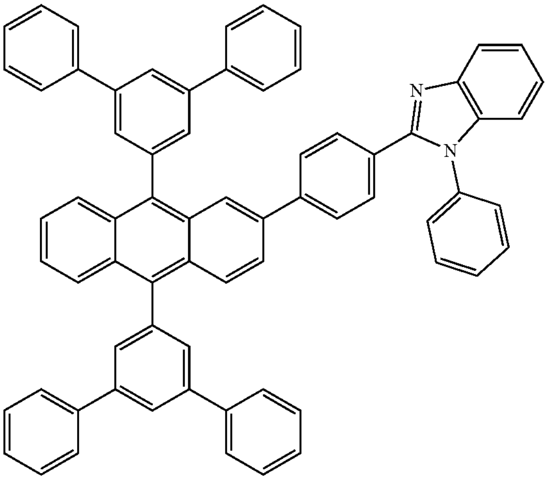

-continued
ET8
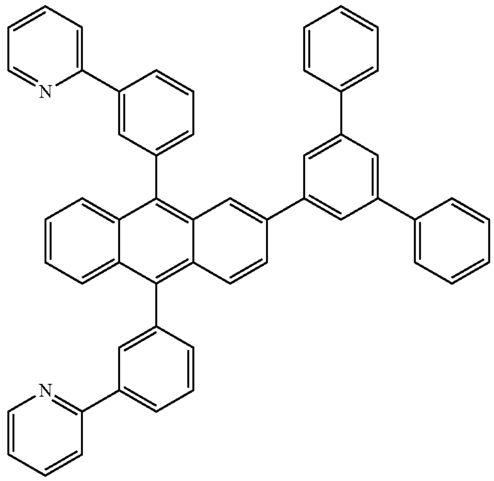
ET9
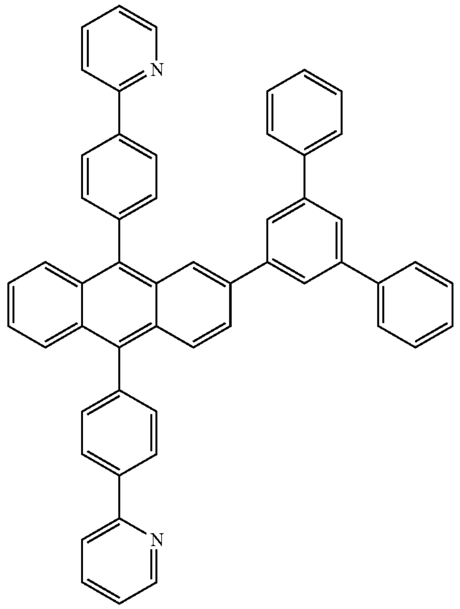
-continued
ET10
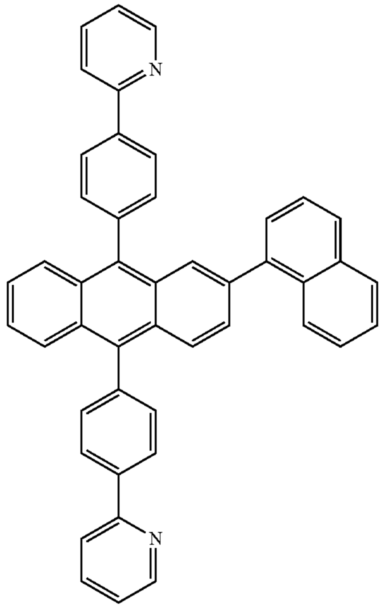
ET11
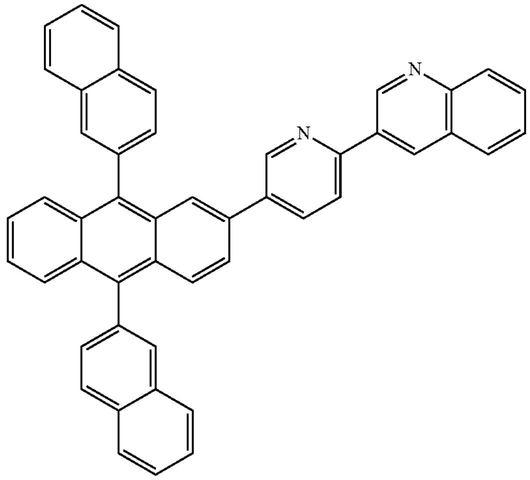
ET12
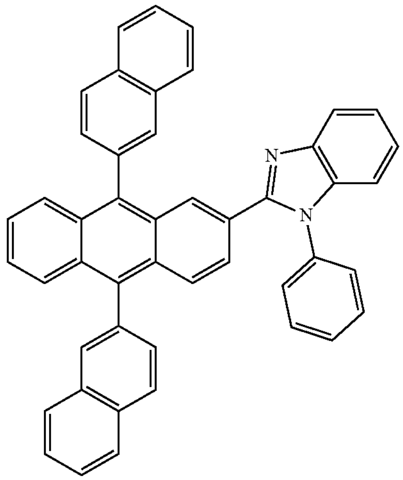

-continued
ET13
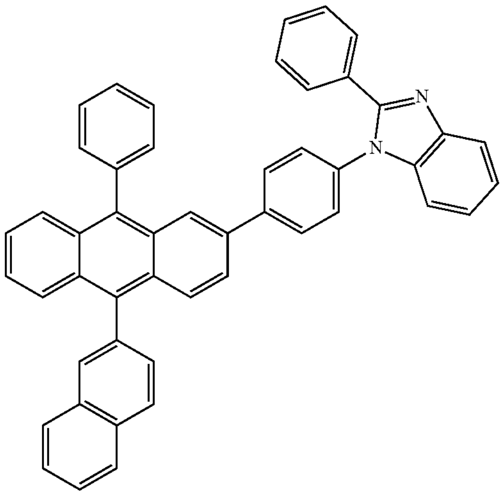
ET14
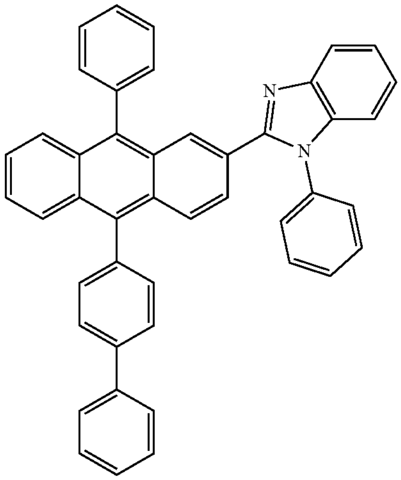
ET15
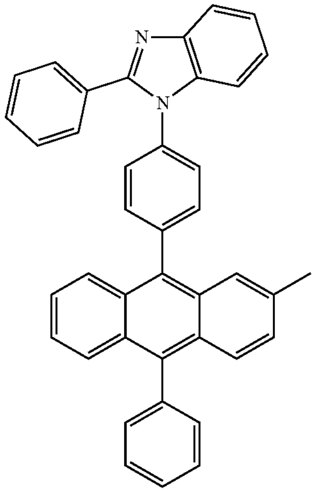
-continued
ET16
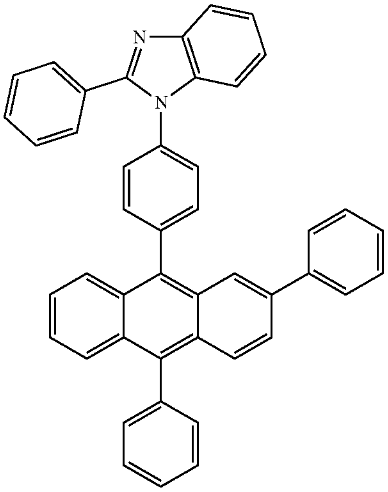
ET17
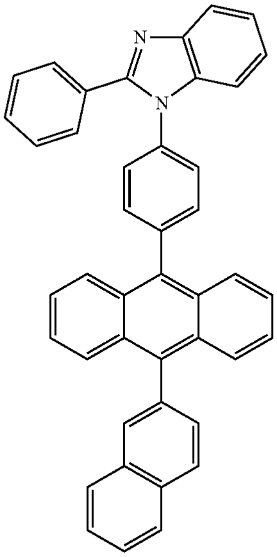
ET18
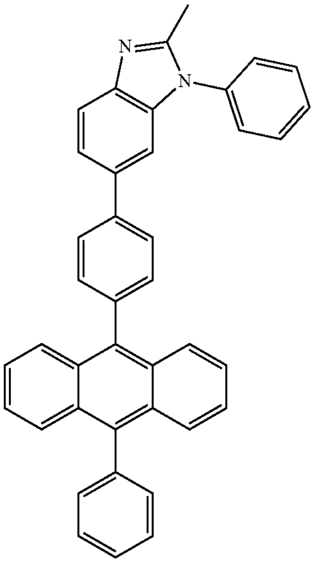

-continued
ET19
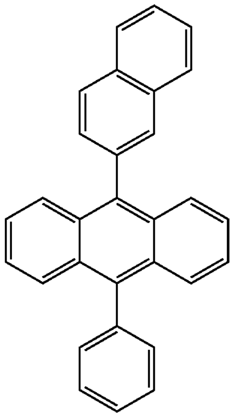
ET20
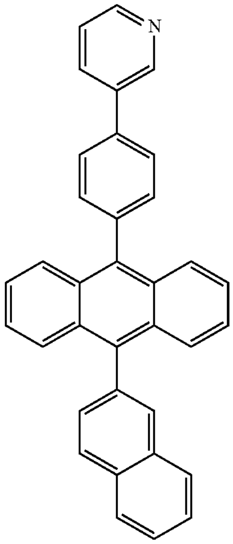
ET21
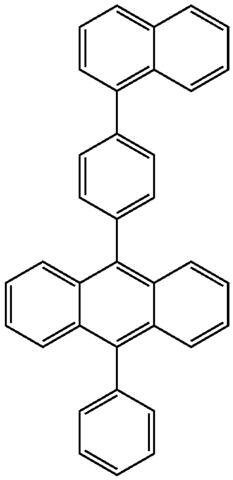
-continued
ET22
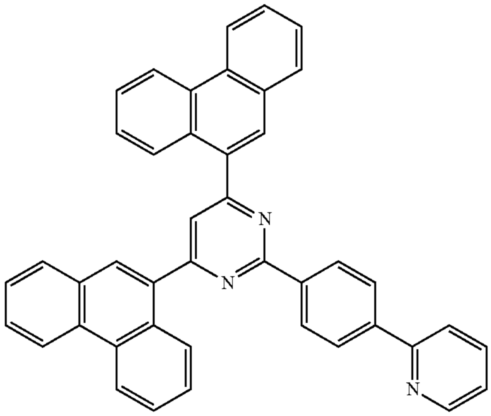
ET23
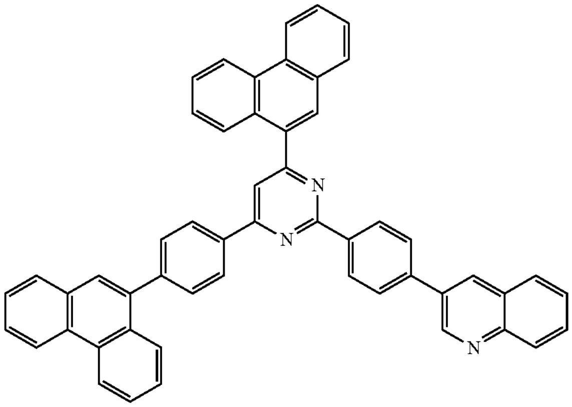
ET24
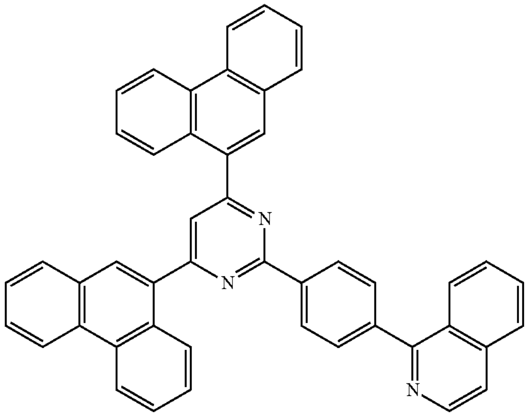

-continued
ET25
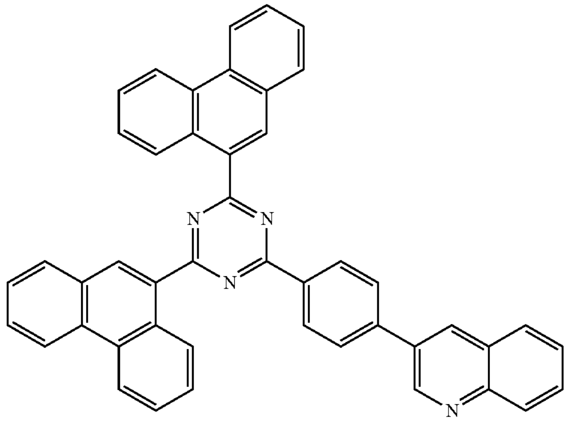
ET26
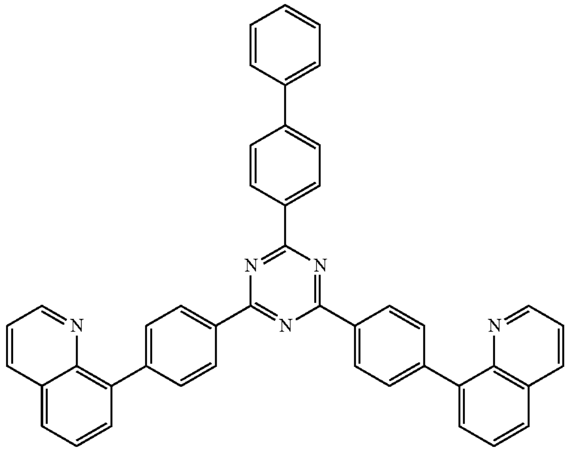
ET27
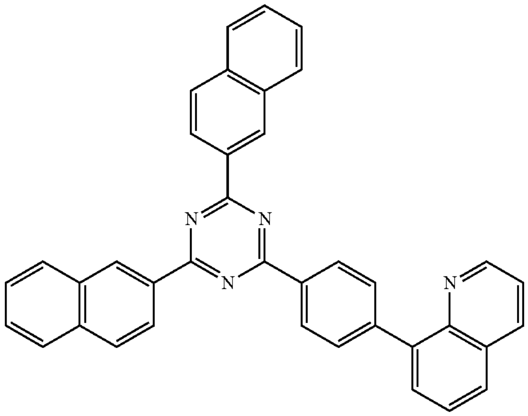
-continued
ET28
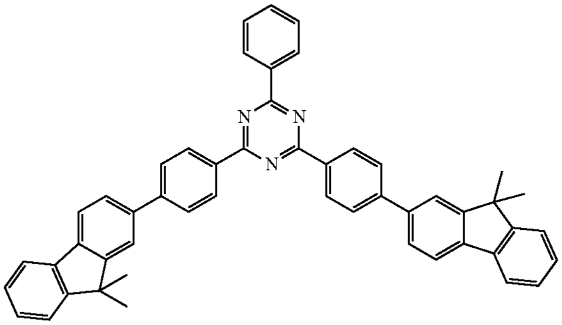
ET29
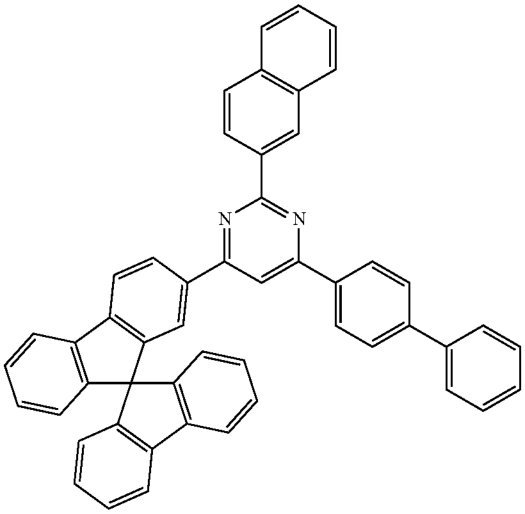
ET30
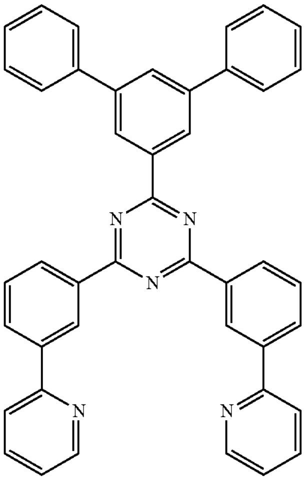

-continued
ET31
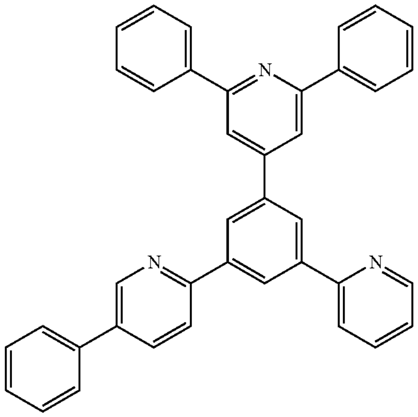
ET32
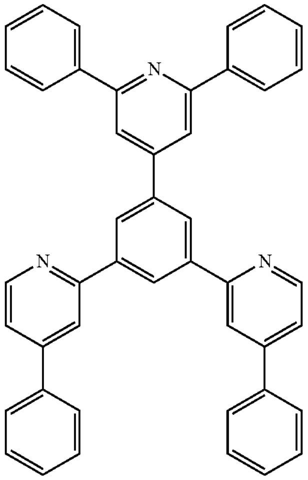
ET33
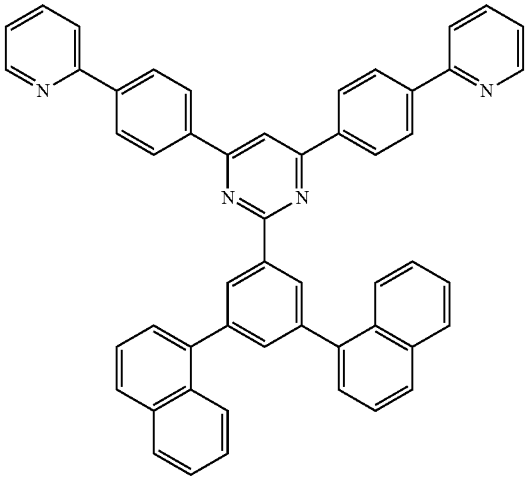
-continued
ET34
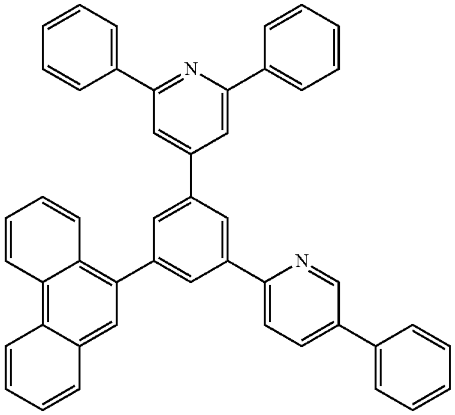
ET35
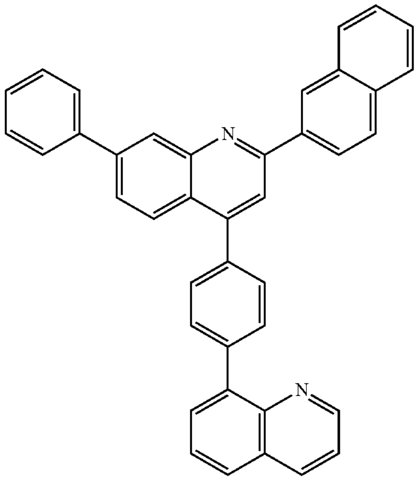
ET36
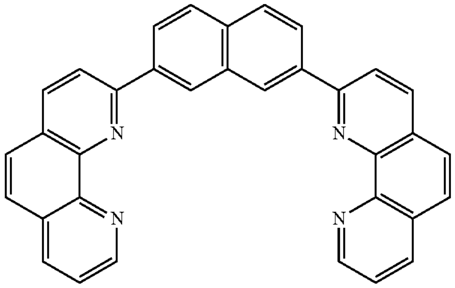
ET37
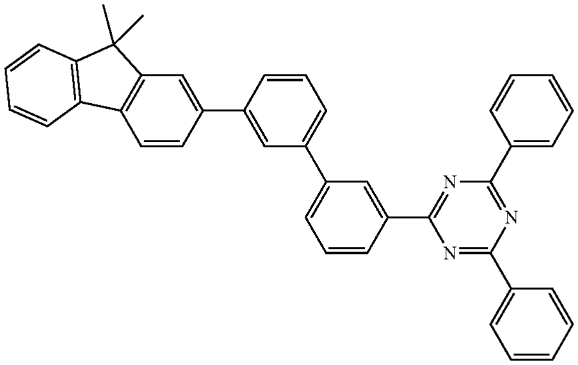

ET38
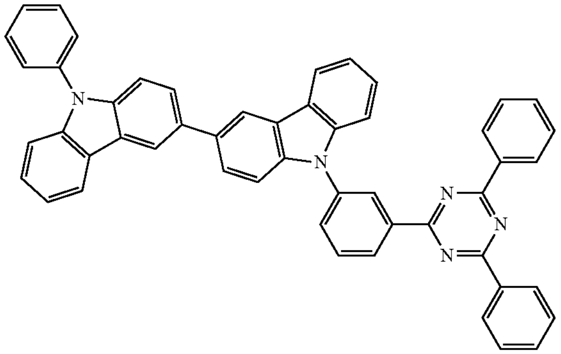
ET39
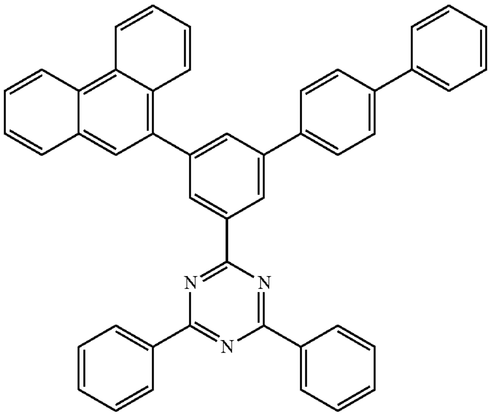
ET40
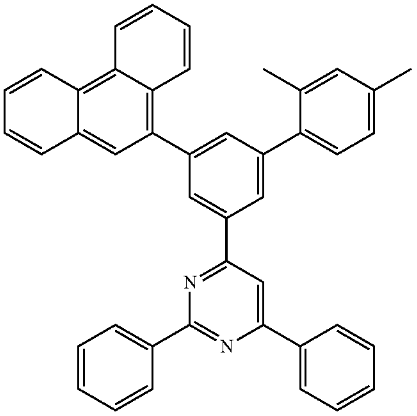
ET41
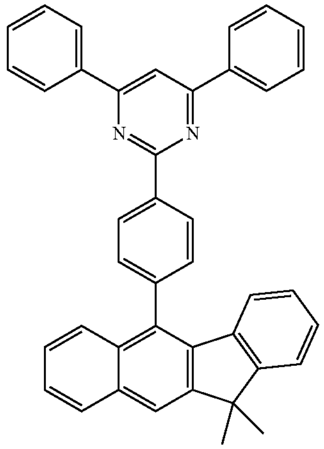
ET42
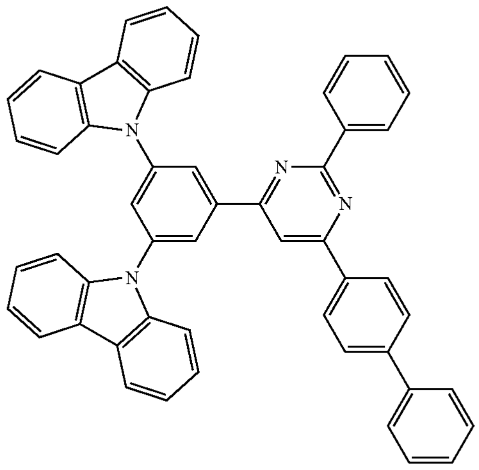
ET43
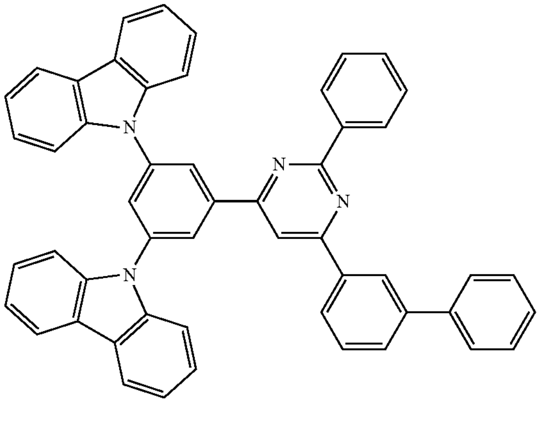

-continued

ET44

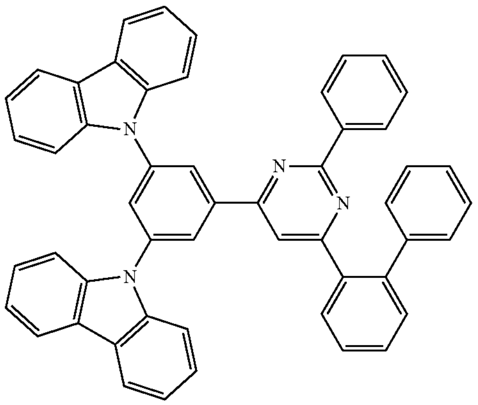

ET45

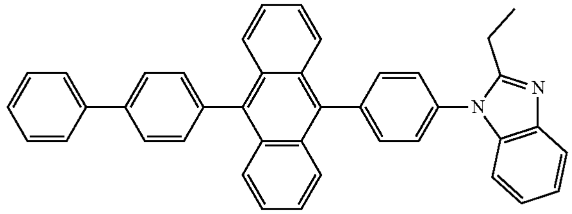

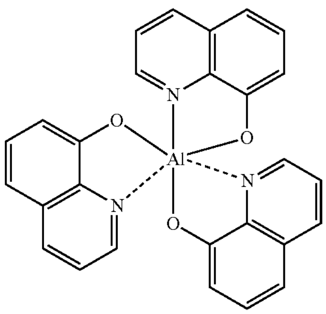

Alq3

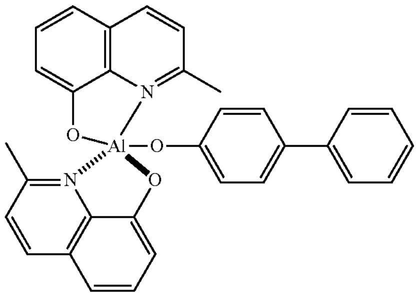

BAlq

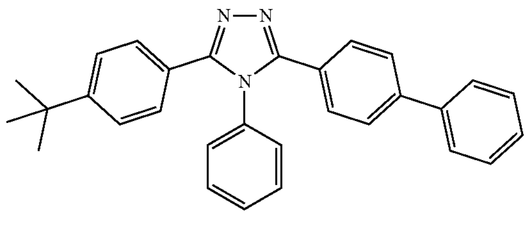

TAZ

-continued

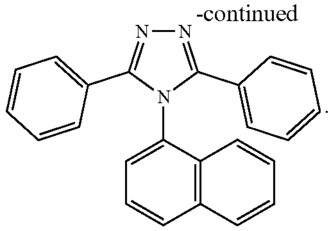

NTAZ

The thickness of the electron transport region may be from about 160 Å to about 5,000 Å, for example, from about 100 Å to about 4,000 Å. When the electron transport region includes a buffer layer, a hole blocking layer, an electron control layer, an electron transport layer, or any combination thereof, the thickness of the buffer layer, the hole blocking layer, or the electron control layer may each independently be from about 20 Å to about 1000 Å, for example, about 30 Å to about 300 Å, and the thickness of the electron transport layer may be from about 100 Å to about 1000 Å, for example, about 150 Å to about 500 Å. When the thicknesses of the buffer layer, hole blocking layer, electron control layer, electron transport layer and/or electron transport layer are within these ranges, satisfactory electron transporting characteristics may be obtained without a substantial increase in driving voltage. The electron transport region (for example, the electron transport layer in the electron transport region) may further include, in addition to the materials described above, a metal-containing material.

The metal-containing material may include an alkali metal complex, alkaline earth metal complex, or any combination thereof. The metal ion of an alkali metal complex may be a Li ion, a Na ion, a K ion, a Rb ion, or a Cs ion, and the metal ion of alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

For example, the metal-containing material may include a Li complex. The Li complex may include, for example, Compound ET-D1 (lithium quinolate, LiQ) or ET-D2:

ET-D1

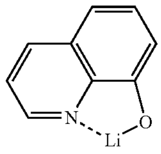

-continued

ET-D2

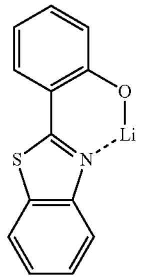

The electron transport region may include an electron injection layer that facilitates the injection of electrons from the second electrode 150. The electron injection layer may directly contact the second electrode 150.

The electron injection layer may have: i) a single-layered structure consisting of a single layer consisting of a single material, ii) a single-layered structure consisting of a single layer consisting of a plurality of different materials, or iii) a multi-layered structure including a plurality of layers including different materials. The electron injection layer may include an alkali metal, alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof. The alkali metal-containing compound, the alkaline earth metal-containing compound, and the rare earth metal-containing compound may be oxides, halides (for example, fluorides, chlorides, bromides, or iodides), or tellurides of the alkali metal, the alkaline earth metal, and the rare earth metal, or any combination thereof.

The alkali metal-containing compound may include alkali metal oxides, such as $Li_2O$, $Cs_2O$, or $K_2O$, alkali metal halides, such as LiF, NaF, CsF, KF, LiI, NaI, CsI, or KI, or any combination thereof. The alkaline earth metal-containing compound may include an alkaline earth metal compound, such as BaO, SrO, CaO, $Ba_xSr_{1-x}O$ (x is a real number satisfying the condition of $0<x<1$), $Ba_xCa_{1-x}O$ (x is a real number satisfying the condition of $0<x<1$), or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In one or more embodiments, the rare earth metal-containing compound may include a lanthanide metal telluride. Examples of the lanthanide metal telluride are LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii), as a ligand bonded to the metal ion, for example, a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenyl benzimidazole, a hydroxyphenylbenzothiazole, a bipyridine, a phenanthroline, a cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In one or more embodiments, the electron injection layer may consist of i) an alkali metal-containing compound (for example, an alkali metal halide), ii) a) an alkali metal-containing compound (for example, an alkali metal halide); and b) an alkali metal, an alkaline earth metal, a rare earth metal, or any combination thereof. In one or more embodiments, the electron injection layer may be a KI:Yb co-deposited layer, an RbI:Yb co-deposited layer, or the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be homogeneously or non-homogeneously dispersed in a matrix including the organic material.

The thickness of the electron injection layer may be in a range of about 1 Å to about 100 Å, and, for example, about 3 Å to about 90 Å. When the thickness of the electron injection layer is within the range described above, the electron injection layer may have satisfactory electron injection characteristics without a substantial increase in driving voltage.

Second Electrode 150

The second electrode 150 may be located on the interlayer 130 having such a structure. The second electrode 150 may be a cathode, which is an electron injection electrode, and as the material for the second electrode 150, a metal, an alloy, an electrically conductive compound, or any combination thereof, each having a low work function, may be used.

In one or more embodiments, the second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), an ITO, an IZO, or any combination thereof. The second electrode 150 may be a transmissive electrode, a semi-transmissive electrode, or a reflective electrode. The second electrode 150 may have a single-layered structure or a multi-layered structure including two or more layers.

Capping Layer

A first capping layer may be located outside the first electrode 110, and/or a second capping layer may be located outside the second electrode 150. In detail, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

Light generated in an emission layer of the interlayer 130 of the light-emitting device 10 may be extracted toward the outside through the first electrode 110, which is a semi-transmissive electrode or a transmissive electrode, and the first capping layer or light generated in an emission layer of the interlayer 130 of the light-emitting device 10 may be extracted toward the outside through the second electrode 150, which is a semi-transmissive electrode or a transmissive electrode, and the second capping layer. Although not wanting to be bound by theory, the first capping layer and the second capping layer may increase external emission efficiency according to the principle of constructive interference. Accordingly, the light extraction efficiency of the light-emitting device 10 is increased, so that the emission efficiency of the light-emitting device 10 may be improved.

Each of the first capping layer and second capping layer may include a material having a refractive index of about 1.6 or more (at 589 nm). The first capping layer and the second capping layer may each independently be an organic capping layer including an organic material, an inorganic capping layer including an inorganic material, or an organic-inorganic composite capping layer including an organic material and an inorganic material.

At least one of the first capping layer and the second capping layer may include carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may be optionally substituted with a substituent containing O, N, S, Se, Si, F, Cl, Br, I, or any combination thereof. In one or more embodiments, at least one of the first capping layer and the second capping layer may each independently include an amine group-containing compound.

In one or more embodiments, at least one of the first capping layer and the second capping layer may each independently include a compound represented by Formula 201, a compound represented by Formula 202, or any combination thereof. In one or more embodiments, at least one of the first capping layer and the second capping layer may each independently include one of Compounds HT28 to HT33, one of Compounds CP1 to CP6, N4,N4'-di(naphthalen-2-yl)-N4,N4'-diphenyl-[1,1'-biphenyl]-4,4'-diamine (β-NPB), or any combination thereof:

CP1

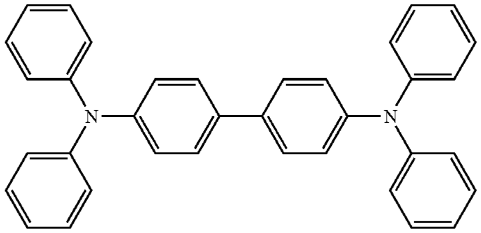

CP2

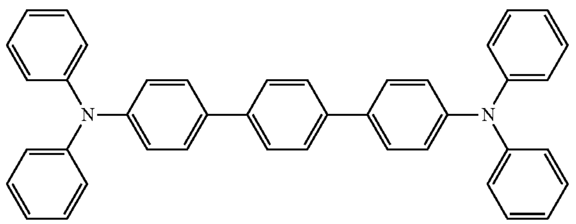

-continued

CP3

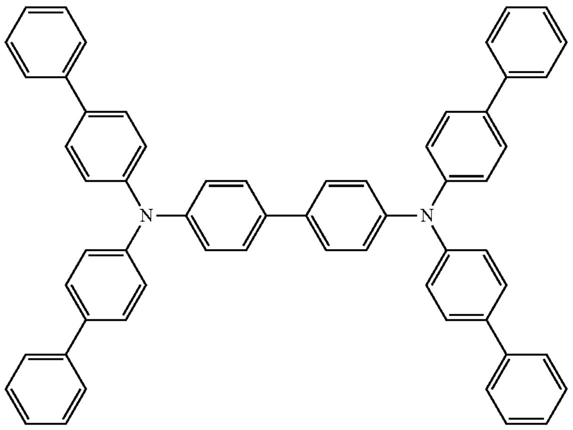

CP4

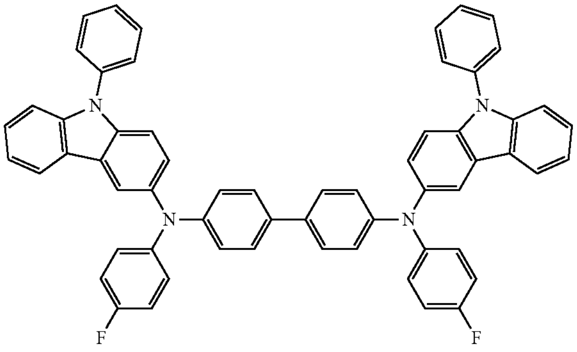

CP5

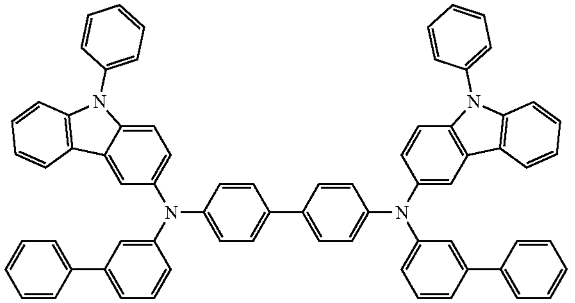

CP6

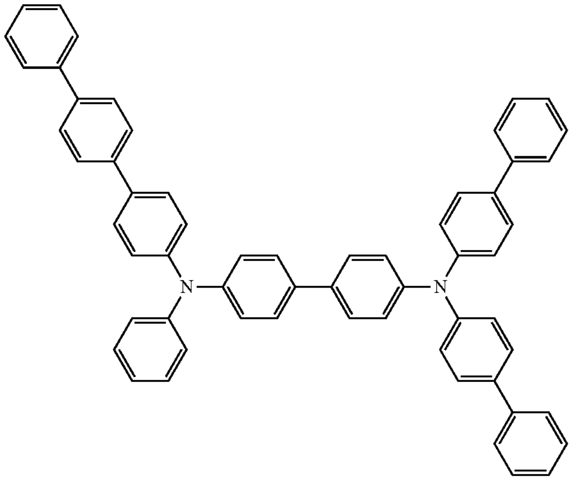

-continued

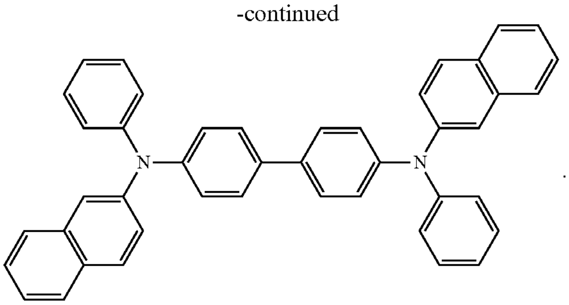

β-NPB

Film

The condensed cyclic compound represented by Formula 1 may be included in various films. Therefore, according to an embodiment, a film including the condensed cyclic compound represented by Formula 1 may be provided. The film may be, for example, an optical member (or light control means) (for example, a color filter, a color conversion member, a capping layer, an optical extraction efficiency improvement layer, an optional light absorbing layer, a polarizing layer, a quantum dot-containing layer, etc.), a light-shielding member (for example, a light reflection layer, a light absorbing layer, etc.), a protective member (for example, an insulating layer, a dielectric layer, etc.), etc.

Electronic Apparatus

The light-emitting device 10 may be included in various electronic apparatuses. In one or more embodiments, the electronic apparatus including the light-emitting device 10 may be a light-emitting apparatus, an authentication apparatus, or the like.

The electronic apparatus (for example, light-emitting apparatus) may further include, in addition to the light-emitting device 10, i) a color filter, ii) a color conversion layer, or iii) a color filter and a color conversion layer. The color filter and/or the color conversion layer may be located in at least one traveling direction of light emitted from the light-emitting device 10. In one or more embodiments, the light emitted from the light-emitting device 10 may be blue light or white light. The light-emitting device 10 may be the same as described above. In one or more embodiments, the color conversion layer may include quantum dots. The quantum dot may be, for example, a quantum dot as described herein.

The electronic apparatus may include a first substrate. The first substrate may include a plurality of subpixel areas, the color filter may include a plurality of color filter areas respectively corresponding to the subpixel areas, and the color conversion layer may include a plurality of color conversion areas respectively corresponding to the subpixel areas. A pixel-defining film may be located among the subpixel areas to define each of the subpixel areas.

The color filter may further include a plurality of color filter areas and light-shielding patterns located among the color filter areas, and the color conversion layer may include a plurality of color conversion areas and light-shielding patterns located among the color conversion areas.

The color filter areas (or the color conversion areas) may include a first area emitting first color light, a second area emitting second color light, and/or a third area emitting third color light, and the first color light, the second color light, and/or the third color light may have different maximum emission wavelengths from one another. In one or more embodiments, the first color light may be red light, the second color light may be green light, and the third color light may be blue light. In one or more embodiments, the color filter areas (or the color conversion areas) may include quantum dots. In detail, the first area may include a red quantum dot, the second area may include a green quantum dot, and the third area may not include a quantum dot. The quantum dot is the same as described herein. The first area, the second area, and/or the third area may each include a scatterer.

In one or more embodiments, the light-emitting device 10 may emit a first light, the first area may absorb the first light to emit a first first-color light, the second area may absorb the first light to emit a second first-color light, and the third area may absorb the first light to emit a third first-color light. In this regard, the first first-color light, the second first-color light, and the third first-color light may have different maximum emission wavelengths. In detail, the first light may be blue light, the first first-color light may be red light, the second first-color light may be green light, and the third first-color light may be blue light.

The electronic apparatus may further include a thin-film transistor in addition to the light-emitting device 10 as described above. The thin-film transistor may include a source electrode, a drain electrode, and an activation layer, wherein any one of the source electrode and the drain electrode may be electrically connected to any one of the first electrode and the second electrode of the light-emitting device 10.

The thin-film transistor may further include a gate electrode, a gate insulating film, etc. The activation layer may include a crystalline silicon, an amorphous silicon, organic semiconductor, an oxide semiconductor, or the like.

The electronic apparatus may further include a sealing portion for sealing the light-emitting device 10. The sealing portion and/or the color conversion layer may be located between the color filter and the light-emitting device. The sealing portion allows light from the light-emitting device 10 to be extracted to the outside, while simultaneously preventing ambient air and moisture from penetrating into the light-emitting device. The sealing portion may be a sealing substrate including a transparent glass substrate or a plastic substrate. The sealing portion may be a thin-film encapsulation layer including at least one layer of an organic layer and/or an inorganic layer. When the sealing portion is a thin-film encapsulation layer, the electronic apparatus may be flexible.

Various functional layers may be additionally located on the sealing portion, in addition to the color filter and/or the color conversion layer, according to the use of the electronic apparatus. The functional layers may include a touch screen layer, a polarizing layer, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, etc.). The authentication apparatus may further include, in addition to the light-emitting device 10, a biometric information collector.

The electronic apparatus may take the form of or be applied to various displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 2:
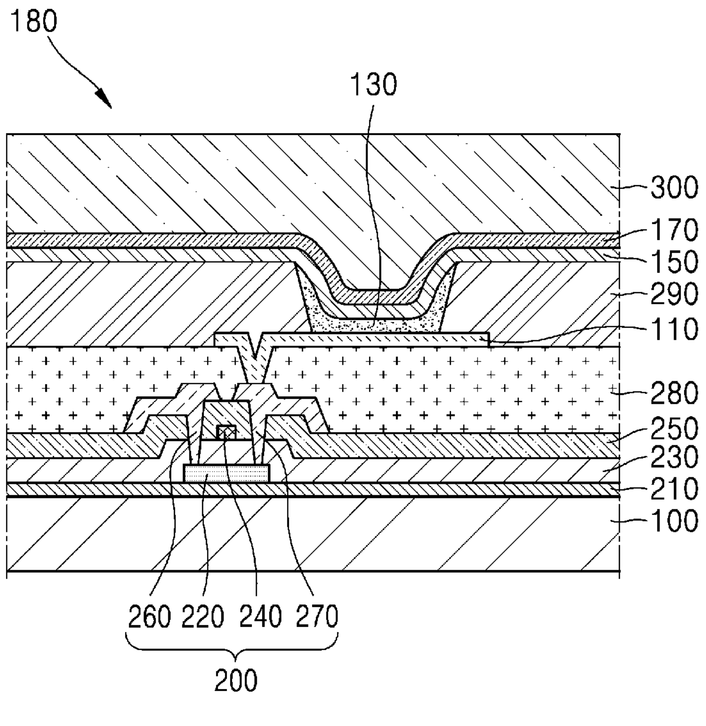
FIG. 2 is a schematic cross-sectional view of an embodiment of a light-emitting apparatus including a light-emitting device constructed according to the principles of the invention.
Figure 3:
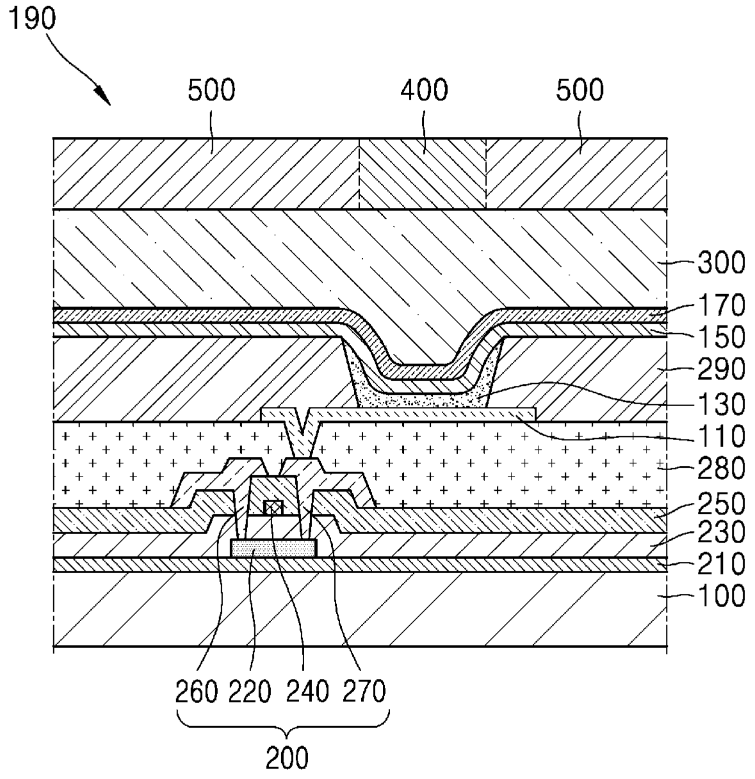
FIG. 3 is a schematic cross-sectional view of another embodiment of a light-emitting apparatus including a light-emitting device constructed according to the principles of the invention.

Description of FIGS. 2 and 3

FIG. 2 is a schematic cross-sectional view of an embodiment of a light-emitting apparatus including a light-emitting device constructed according to the principles of the invention.

The light-emitting apparatus 180 of FIG. 2 includes a substrate 100, a thin-film transistor (TFT) 200, a light-emitting device 10, and an encapsulation portion 300 that seals the light-emitting device 10.

The substrate 100 may be a flexible substrate, a glass substrate, or a metal substrate. A buffer layer 210 may be formed on the substrate 100. The buffer layer 210 may prevent penetration of impurities through the substrate 100 and may provide a substantially flat surface on the substrate 100.

The TFT 200 may be located on the buffer layer 210. The TFT 200 may include an activation layer 220, a gate electrode 240, a source electrode 260, and a drain electrode 270.

The activation layer 220 may include an inorganic semiconductor such as a silicon or a polysilicon, an organic semiconductor, or an oxide semiconductor, and may include a source region, a drain region and a channel region.

A gate insulating film 230 for insulating the activation layer 220 from the gate electrode 240 may be located on the activation layer 220, and the gate electrode 240 may be located on the gate insulating film 230.

An interlayer insulating film 250 is located on the gate electrode 240. The interlayer insulating film 250 may be located between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be located on the interlayer insulating film 250. The interlayer insulating film 250 and the gate insulating film 230 may be formed to expose the source region and the drain region of the activation layer 220, and the source electrode 260 and the drain electrode 270 may be in contact with the exposed portions of the source region and the drain region of the activation layer 220.

The TFT 200 is electrically connected to a light-emitting device 10 to drive the light-emitting device 10, and is covered by a passivation layer 280. The passivation layer 280 may include an inorganic insulating film, an organic insulating film, or any combination thereof. A light-emitting device 10 is provided on the passivation layer 280. The light-emitting device 10 may include a first electrode 110, an interlayer 130, and a second electrode 150.

The first electrode 110 may be formed on the passivation layer 280. The passivation layer 280 does not completely cover the drain electrode 270 and exposes a portion of the drain electrode 270, and the first electrode 110 is connected to the exposed portion of the drain electrode 270.

A pixel defining layer 290 containing an insulating material may be located on the first electrode 110. The pixel defining layer 290 exposes a region of the first electrode 110, and an interlayer 130 may be formed in the exposed region of the first electrode 110. The pixel defining layer 290 may be a polyimide or polyacrylic organic film. At least some layers of the interlayer 130 may extend beyond the upper portion of the pixel defining layer 290 to be located in the form of a common layer.

The second electrode 150 may be located on the interlayer 130, and a capping layer 170 may be additionally formed on the second electrode 150. The capping layer 170 may be formed to cover the second electrode 150.

The encapsulation portion 300 may be located on the capping layer 170. The encapsulation portion 300 may be located on a light-emitting device 10 to protect the light-emitting device 10 from moisture or oxygen. The encapsulation portion 300 may include: an inorganic film including a silicon nitride ($SiN_x$), a silicon oxide ($SiO_x$), an indium tin oxide, an indium zinc oxide, or any combination thereof, an organic film including a polyethylene terephthalate, a polyethylene naphthalate, a polycarbonate, a polyimide, a polyethylene sulfonate, a polyoxymethylene, a polyarylate, a hexamethyldisiloxane, an acrylic resin (for example, a polymethyl methacrylate, a polyacrylic acid, or the like), an epoxy-based resin (for example, an aliphatic glycidyl ether (AGE), or the like), or any combination thereof, or any combination of the inorganic film and the organic film.

FIG. 3 is a schematic cross-sectional view of another embodiment of a light-emitting apparatus including a light-emitting device constructed according to the principles of the invention.

The light-emitting apparatus 190 of FIG. 3 is the same as the light-emitting apparatus 180 of FIG. 2, except that a light-shielding pattern 500 and a functional region 400 are additionally located on the encapsulation portion 300. The functional region 400 may be a combination of i) a color filter area, ii) a color conversion area, or iii) a combination of the color filter area and the color conversion area. In one or more embodiments, the light-emitting device included in the light-emitting apparatus 190 of FIG. 3 may be a tandem light-emitting device 10.

Manufacture Method

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

Definition of Terms

As used herein, a quantum dot refers to a crystal of a semiconductor compound, and may include any material capable of emitting light of various emission wavelengths according to the size of the crystal.

The term "interlayer" as used herein refers to a single layer and/or all layers between a first electrode and a second electrode of a light-emitting device.

As used herein, the abbreviation "eq" means mole equivalent, the abbreviation "wt %" means weight percent, the abbreviation "hr" means hour, and the abbreviation "eV" means energy level.

As used herein, the highest occupied molecular orbital may be abbreviated "HOMO".

As used herein, the term "atom" may mean an element or its corresponding radical bonded to one or more other atoms.

The terms "hydrogen" and "deuterium" refer to their respective atoms and corresponding radicals with the deuterium radical abbreviated "-D", and the terms "—F, —Cl, —Br, and —I" are radicals of, respectively, fluorine, chlorine, bromine, and iodine.

As used herein, a substituent for a monovalent group, e.g., alkyl, may also be, independently, a substituent for a corresponding divalent group, e.g., alkylene.

The term "$C_3$-$C_{60}$ carbocyclic group" as used herein refers to a cyclic group consisting of carbon only as a ring-forming atom and having three to sixty carbon atoms, and the term "$C_1$-$C_{60}$ heterocyclic group" as used herein refers to a cyclic group that has one to sixty carbon atoms and further has, in addition to carbon, a heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are fused with each other. For example, the $C_1$-$C_{60}$ heterocyclic group has 3 to 61 ring-forming atoms.

The "cyclic group" as used herein may include the $C_3$-$C_{60}$ carbocyclic group, and the $C_1$-$C_{60}$ heterocyclic group.

The term "n electron-rich $C_3$-$C_{60}$ cyclic group" as used herein refers to a cyclic group that has three to sixty carbon atoms and does not include *—N═*' as a ring-forming moiety, and the term "n electron-deficient nitrogen-containing $C_1$-$C_{60}$ cyclic group" as used herein refers to a heterocyclic group that has one to sixty carbon atoms and includes *—N═*' as a ring-forming moiety.

For example, the $C_3$-$C_{60}$ carbocyclic group may be i) group TG1 or ii) a fused cyclic group in which two or more groups TG1 are fused with each other for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spirobifluorene group, a benzofluorene group, an indenophenanthrene group, or an indenoanthracene group.

The $C_1$-$C_{60}$ heterocyclic group may be i) group TG2, ii) a fused cyclic group in which two or more groups TG2 are fused with each other, or iii) a fused cyclic group in which at least one group TG2 and at least one group TG1 are fused with each other, for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.

The π electron-rich $C_3$-$C_{60}$ cyclic group may be i) group TG1, ii) a fused cyclic group in which two or more groups TG1 are fused with each other, iii) group TG3, iv) a fused cyclic group in which two or more groups TG3 are fused with each other, or v) a fused cyclic group in which at least one group TG3 and at least one group TG1 are fused with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.

The π electron-deficient nitrogen-containing $C_1$-$C_{60}$ cyclic group may be i) group TG4, ii) a fused cyclic group in which two or more groups TG4 are fused with each other, iii) a fused cyclic group in which at least one group TG4 and at least one group TG1 are fused with each other, iv) a fused cyclic group in which at least one group TG4 and at least one group TG3 are fused with each other, or v) a fused cyclic group in which at least one group TG4, at least one group TG1, and at least one group TG3 are fused with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.

The group TG1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo [2.2.1]heptane) group, a norbornene group, a bicyclo[1.1.1] pentane group, a bicyclo[2.1.1]hexane group, a bicyclo [2.2.2]octane group, or a benzene group.

The group TG2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group.

The group TG3 may be a furan group, a thiophene group, a 1H-pyrrole group, a silole group, or a borole group.

The group TG4 may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group, the $C_3$-$C_{60}$ carbocyclic group, the $C_1$-$C_{60}$ heterocyclic group, the π electron-rich $C_3$-$C_{60}$ cyclic group, or the π electron-deficient nitrogen-containing $C_1$-$C_{60}$ cyclic group" as used herein refer to a group fused with any cyclic group or a polyvalent group (for example, a divalent group, a trivalent group, a tetravalent group, etc.), depending on the structure of a formula in connection with which the terms are used. In an embodiment, "a benzene group" may be a benzo group, a phenyl group, a phenylene group, or the like, which may be easily understand by one of ordinary skill in the art according to the structure of a formula including the "benzene group."

Examples of the monovalent $C_3$-$C_{60}$ carbocyclic group and the monovalent $C_1$-$C_{60}$ heterocyclic group are a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic fused polycyclic group, and a monovalent non-aromatic fused heteropolycyclic group, and examples of the divalent $C_3$-$C_{60}$ carbocyclic group and the monovalent $C_1$-$C_{60}$ heterocyclic group are a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic fused polycyclic group, and a substituted or unsubstituted divalent non-aromatic fused heteropolycyclic group.

The term "$C_1$-$C_{60}$ alkyl group" as used herein refers to a linear or branched aliphatic hydrocarbon monovalent group that has one to sixty carbon atoms, and examples thereof are a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having a structure corresponding to the $C_1$-$C_{60}$ alkyl group.

The term "$C_2$-$C_{60}$ alkenyl group" as used herein refers to a monovalent hydrocarbon group having at least one carbon-carbon double bond in the middle or at the terminus of the $C_2$-$C_{60}$ alkyl group, and examples thereof are an ethenyl group, a propenyl group, and a butenyl group. The term "$C_2$-$C_{60}$ alkenylene group" as used herein refers to a divalent group having a structure corresponding to the $C_2$-$C_{60}$ alkenyl group.

The term "$C_2$-$C_{60}$ alkynyl group" as used herein refers to a monovalent hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group having a structure corresponding to the $C_2$-$C_{60}$ alkynyl group.

The term "$C_1$-$C_{60}$ alkoxy group" as used herein refers to a monovalent group represented by $—OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon cyclic group having 3 to 10 carbon atoms, and examples thereof are a cyclopropyl group, a cyclobutyl group, a cyclopentyl group, a cyclohexyl group, a cycloheptyl group, a cyclooctyl group, an adamantanyl group, a norbornanyl group (or bicyclo [2.2.1]heptyl group), a bicyclo[1.1.1]pentyl group, a bicyclo [2.1.1]hexyl group, and a bicyclo[2.2.2]octyl group. The term "$C_3$-$C_{10}$ cycloalkylene group" as used herein refers to a divalent group having a structure corresponding to the $C_3$-$C_{10}$ cycloalkyl group.

The term "$C_1$-$C_{10}$ heterocycloalkyl group" as used herein refers to a monovalent cyclic group that further includes, in addition to a carbon atom, at least one heteroatom as a ring-forming atom and has 1 to 10 carbon atoms, and examples thereof are a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having a structure corresponding to the $C_1$-$C_{10}$ heterocycloalkyl group.

The term $C_3$-$C_{10}$ cycloalkenyl group used herein refers to a monovalent cyclic group that has three to ten carbon atoms and at least one carbon-carbon double bond in the ring thereof and no aromaticity, and examples thereof are a cyclopentenyl group, a cyclohexenyl group, and a cycloheptenyl group. The term "$C_3$-$C_{10}$ cycloalkenylene group" as used herein refers to a divalent group having a structure corresponding to the $C_3$-$C_{10}$ cycloalkenyl group.

The term "$C_1$-$C_{10}$ heterocycloalkenyl group" as used herein refers to a monovalent cyclic group that has, in addition to a carbon atom, at least one heteroatom as a ring-forming atom, 1 to 10 carbon atoms, and at least one carbon-carbon double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having a structure corresponding to the $C_1$-$C_{10}$ heterocycloalkenyl group.

The term "$C_6$-$C_{60}$ aryl group" as used herein refers to a monovalent group having a carbocyclic aromatic system having six to sixty carbon atoms, and the term "$C_6$-$C_{60}$ arylene group" as used herein refers to a divalent group having a carbocyclic aromatic system having six to sixty carbon atoms. Examples of the $C_6$-$C_{60}$ aryl group are a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the rings may be fused with each other.

The term "$C_1$-$C_{60}$ heteroaryl group" as used herein refers to a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group" as used herein refers to a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be fused with each other.

The term "monovalent non-aromatic fused polycyclic group" as used herein refers to a monovalent group (for example, having 8 to 60 carbon atoms) having two or more rings fused with each other, only carbon atoms as ring-forming atoms, and no aromaticity in its entire molecular structure. Examples of the monovalent non-aromatic fused polycyclic group are an indenyl group, a fluorenyl group, a spiro-bifluorenyl group, a benzofluorenyl group, an indenophenanthrenyl group, and an indeno anthracenyl group. The term "divalent non-aromatic fused polycyclic group" as used herein refers to a divalent group having a structure corresponding to a monovalent non-aromatic fused polycyclic group.

The term "monovalent non-aromatic fused heteropolycyclic group" as used herein refers to a monovalent group (for example, having 1 to 60 carbon atoms) having two or more rings fused with each other, at least one heteroatom other than carbon atoms, as a ring-forming atom, and non-aromaticity in its entire molecular structure. Examples of the monovalent non-aromatic fused heteropolycyclic group are a pyrrolyl group, a thiophenyl group, a furanyl group, an indolyl group, a benzoindolyl group, a naphtho indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic fused heteropolycyclic group" as used herein refers to a divalent group having a structure corresponding to a monovalent non-aromatic fused heteropolycyclic group.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "$C_7$-$C_{60}$ aryl alkyl group" used herein refers to -$A_{104}A_{105}$ (where $A_{104}$ may be a $C_1$-$C_{54}$ alkylene group, and $A_{105}$ may be a $C_6$-$C_{59}$ aryl group), and the term $C_2$-$C_{60}$ heteroaryl alkyl group" used herein refers to -$A_{106}A_{107}$ (where $A_{106}$ may be a $C_1$-$C_{59}$ alkylene group, and $A_{107}$ may be a $C_1$-$C_{59}$ heteroaryl group).

The term "$R_{10a}$" as used herein refers to:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{11})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof, or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

The variables $Q_1$ to $Q_3$, $Q_{11}$ to $Q_{13}$, $Q_{21}$ to $Q_{23}$ and $Q_{31}$ to $Q_{33}$ used herein may each independently be: a group of Formula 2; hydrogen; deuterium; —F; —Cl; —Br; —I; a hydroxyl group; a cyano group; a nitro group; a $C_1$-$C_{60}$ alkyl group, a $C_2$-$C_{60}$ alkenyl group, a $C_2$-$C_{60}$ alkynyl group or a $C_1$-$C_{60}$ alkoxy group each, independently from one another, unsubstituted or substituted with deuterium, —F, a cyano group or any combination thereof, a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, a $C_7$-$C_{60}$ aryl alkyl group; or a $C_2$-$C_{60}$ heteroaryl alkyl group.

The term "heteroatom" as used herein refers to any atom other than a carbon atom. Examples of the heteroatom are O, S, N, P, Si, B, Ge, Se, and any combination thereof.

The term "the third-row transition metal" used herein includes hafnium (Hf), tantalum (Ta), tungsten (W), rhenium (Re), osmium (Os), iridium (Ir), platinum (Pt), gold (Au), etc.

As used herein, the term "Ph" refers to a phenyl group, the term "Me" refers to a methyl group, the term "Et" refers to an ethyl group, the term "t-Bu", "ter-Bu" or "But" refers to a tert-butyl group, and the term "OMe" refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". In other words, the "terphenyl group" is a substituted phenyl group having, as a substituent, a $C_6$-$C_{60}$ aryl group substituted with a $C_6$-$C_{60}$ aryl group.

The symbols * and *' as used herein, unless defined otherwise, each refer to a binding site to a neighboring atom in a corresponding formula or moiety.

Hereinafter, a compound made according to the principles and embodiments of the invention and a light-emitting device including the compound made according to embodiments will be described in detail with reference to Synthesis Examples and Examples. The wording "B was used instead of A" used in describing Synthesis Examples refers to that an identical molar equivalent of B was used in place of A.

EXAMPLES

Synthesis Example 1: Synthesis of Compound 30

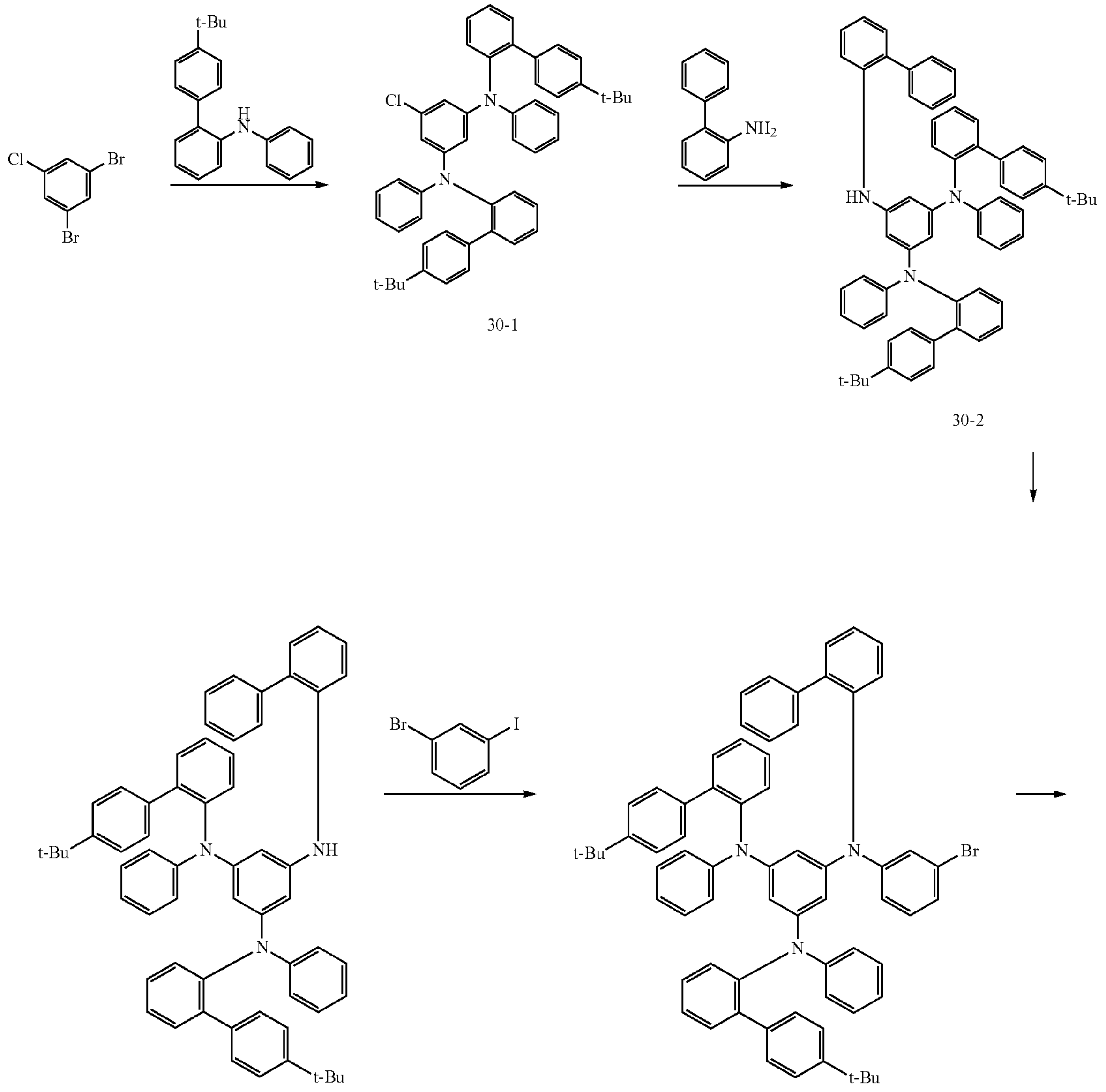

30-1

30-2

30-2

30-3

-continued

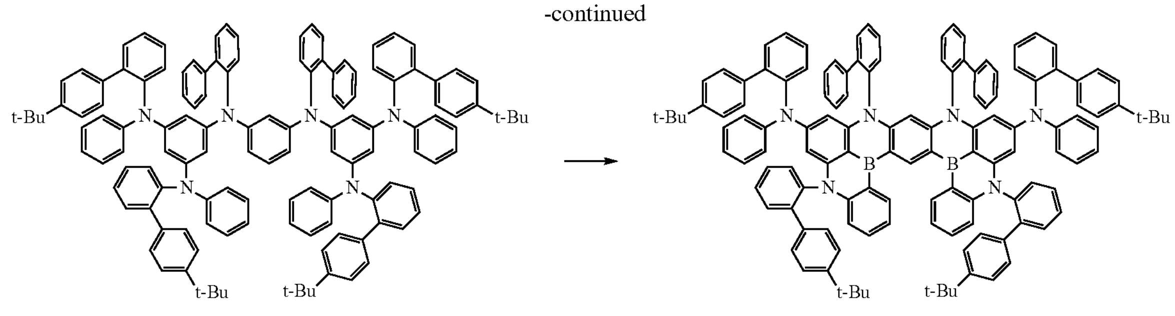

30-4 30

Synthesis of Intermediate 30-1

1,3-dibromo-5-chlorobenzene (1 eq), 4-(tert-butyl)-N-phenyl-(1,1'-biphenyl)-2-amine (2.1 eq), tris(dibenzylideneacetone)dipalladium (0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 30-1. (Yield: 65%).

Synthesis of Intermediate 30-2

Intermediate 30-1 (1 eq), (1,1'-biphenyl)-2-amine (1.5 eq), tris(dibenzylideneacetone)dipalladium (0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 30-2. (Yield: 65%).

Synthesis of Intermediate 30-3

Intermediate 30-2 (1 eq), 1-bromo-3-iodobenzene (2 eq), CuI (0.2 eq), $K_2CO_3$ (3 eq), and picolinic acid (0.4 eq) were dissolved in dimethylformamide (DMF) and stirred at a temperature of 160° C. for 20 hours. After cooling, the reaction mixture was dried under reduced pressure and DMF was removed therefrom. Then, the organic layer obtained by washing with ethyl acetate and water was dried using $MgSO_4$ and dried under reduced pressure. Subsequently, the purification-recrystallization (dichloromethane: n-hexane) process was performed by column chromatography to obtain Intermediate 30-3. (Yield: 60%).

Synthesis of Intermediate 30-4

Intermediate 30-2 (1 eq), Intermediate 30-3 (1 eq), tris (dibenzylideneacetone)dipalladium (0) (0.1 eq), tri-tert-butylphosphine (0.2 eq), and sodium tert-butoxide (3 eq) were dissolved in toluene and stirred in a nitrogen atmosphere at a temperature of 110° C. for 20 hours. After cooling, the reaction mixture was dried under reduced pressure and toluene was removed therefrom. Then, the organic layer obtained by washing three times with ethyl acetate and water was dried using $MgSO_4$ and dried under reduced pressure. Subsequently, the purification (dichloromethane: n-hexane) process was performed by column chromatography to obtain Intermediate 30-4. (Yield: 65%).

Synthesis of Compound 30

Intermediate 30-4 (1 eq) was dissolved in ortho dichlorobenzene, a flask was cooled to 0° C. in a nitrogen atmosphere, and $BBr_3$ (4 eq) was slowly added thereto. After completion of the dropping, the temperature was raised to 19° C. and the reaction mixture was stirred for 24 hours. After cooling to 0° C., triethylamine was slowly added dropwise to the flask to terminate the reaction until the exotherm stopped, and then, a hexane was added thereto to cause precipitation and a solid was obtained therefrom by filtration. The obtained solid was purified by silica-gel filtration, and then, purified using methylene chloride (MC)/hexane (Hex) recrystallization to obtain Compound 30. Subsequently, final purification was performed by sublimation purification. (Yield after sublimation: 3%)

Synthesis Example 2: Synthesis of Compound 34

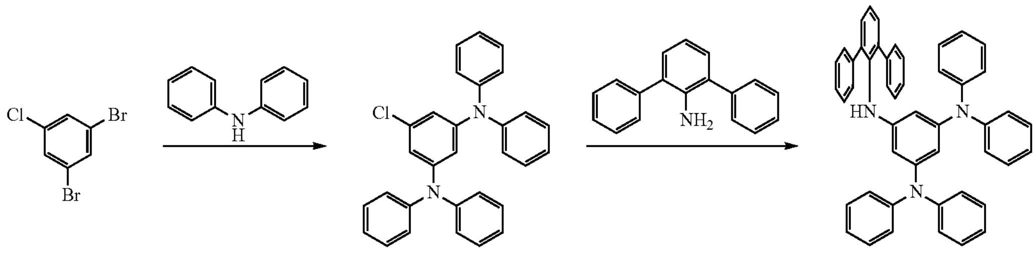

34-1 34-2

-continued

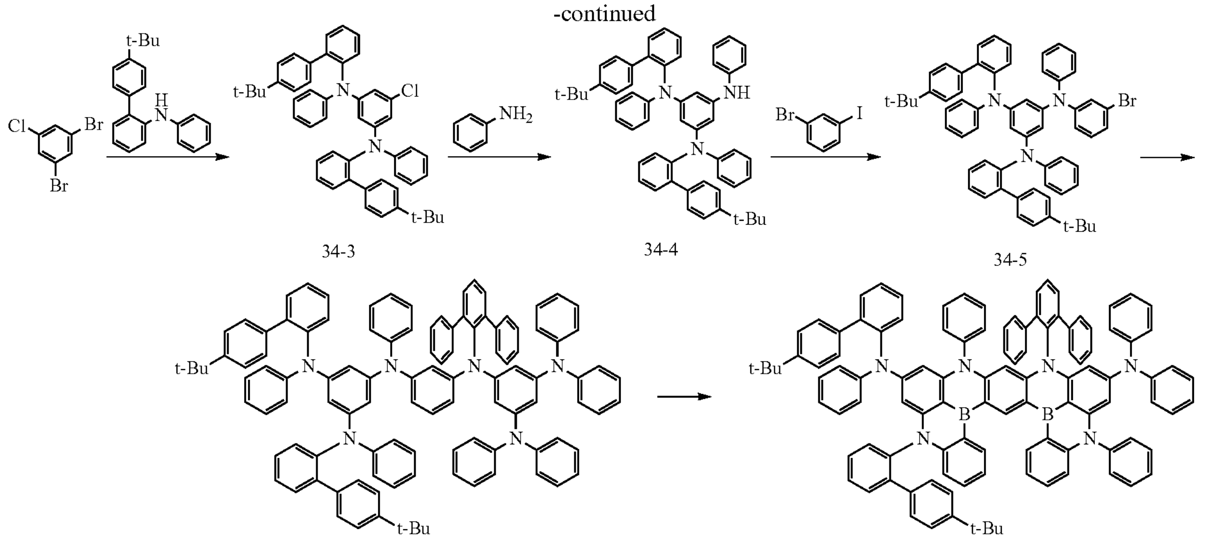

34-3

34-4

34-5

34-6

34

Synthesis of Intermediate 34-1

1,3-dibromo-5-chlorobenzene (1 eq), diphenylamine (2.1 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 34-1. (Yield: 60%).

Synthesis of Intermediate 34-2

Intermediate 34-1 (1 eq), [1,1': 3',1"-terphenyl]-2'-amine (1.5 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 34-2. (Yield: 60%).

Synthesis of Intermediate 34-3

1,3-Dibromo-5-chlorobenzene (1 eq), 4-(tert-Butyl)-N-phenyl-(1,1'-biphenyl)-2-amine (2.1 eq), Tris(dibenzylideneacetone)dipalladium (0) (0.05 eq), Tri-tert-butylphosphine (0.1 eq), and Sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 34-3. (Yield: 65%).

Synthesis of Intermediate 34-4

Intermediate 34-3 (1 eq), aniline (1.5 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 34-4. (Yield: 65%).

Synthesis of Intermediate 34-5

Intermediate 34-4 (1 eq), 1-bromo-3-iodobenzene (2 eq), CuI (0.2 eq), $K_2CO_3$ (3 eq), and picolinic acid (0.4 eq) were dissolved in DMF and stirred at a temperature of 160° C. for hours. After cooling, the reaction mixture was dried under reduced pressure and DMF was removed therefrom. Then, the organic layer obtained by washing with ethyl acetate and water was dried using $MgSO_4$ and dried under reduced pressure. Subsequently, the purification-recrystallization (dichloromethane: n-hexane) process was performed by column chromatography to obtain Intermediate 34-5. (Yield: 60%).

Synthesis of Intermediate 34-6

Intermediate 34-2 (1 eq), Intermediate 34-5 (1 eq), tris (dibenzylideneacetone)dipalladium (0) (0.1 eq), tri-tert-butylphosphine (0.2 eq), and sodium tert-butoxide (3 eq) were dissolved in toluene and stirred in a nitrogen atmosphere at a temperature of 110° C. for 20 hours. After cooling, the reaction mixture was dried under reduced pressure and toluene was removed therefrom. Then, the organic layer obtained by washing three times with ethyl acetate and water was dried using $MgSO_4$ and dried under reduced pressure. Subsequently, the purification (dichloromethane: n-hexane) process was performed by column chromatography to obtain Intermediate 34-6. (Yield: 58%)

Synthesis of Compound 34

Intermediate 34-6 (1 eq) was dissolved in ortho dichlorobenzene, a flask was cooled to 0° C. in a nitrogen atmosphere, and $BBr_3$ (4 eq) was slowly added thereto. After completion of the dropping, the temperature was raised to 19° C. and the reaction mixture was stirred for 24 hours. After cooling to 0° C., triethylamine was slowly added dropwise to the flask to terminate the reaction until the exotherm stopped, and then, a hexane was added thereto to cause precipitation and a solid was obtained therefrom by filtration. The obtained solid was purified by silica-gel filtration, and then, purified using MC/Hex recrystallization to obtain Compound 34. Subsequently, final purification was performed by sublimation purification. (Yield after sublimation: 3%)

Synthesis Example 3: Synthesis of Compound 37

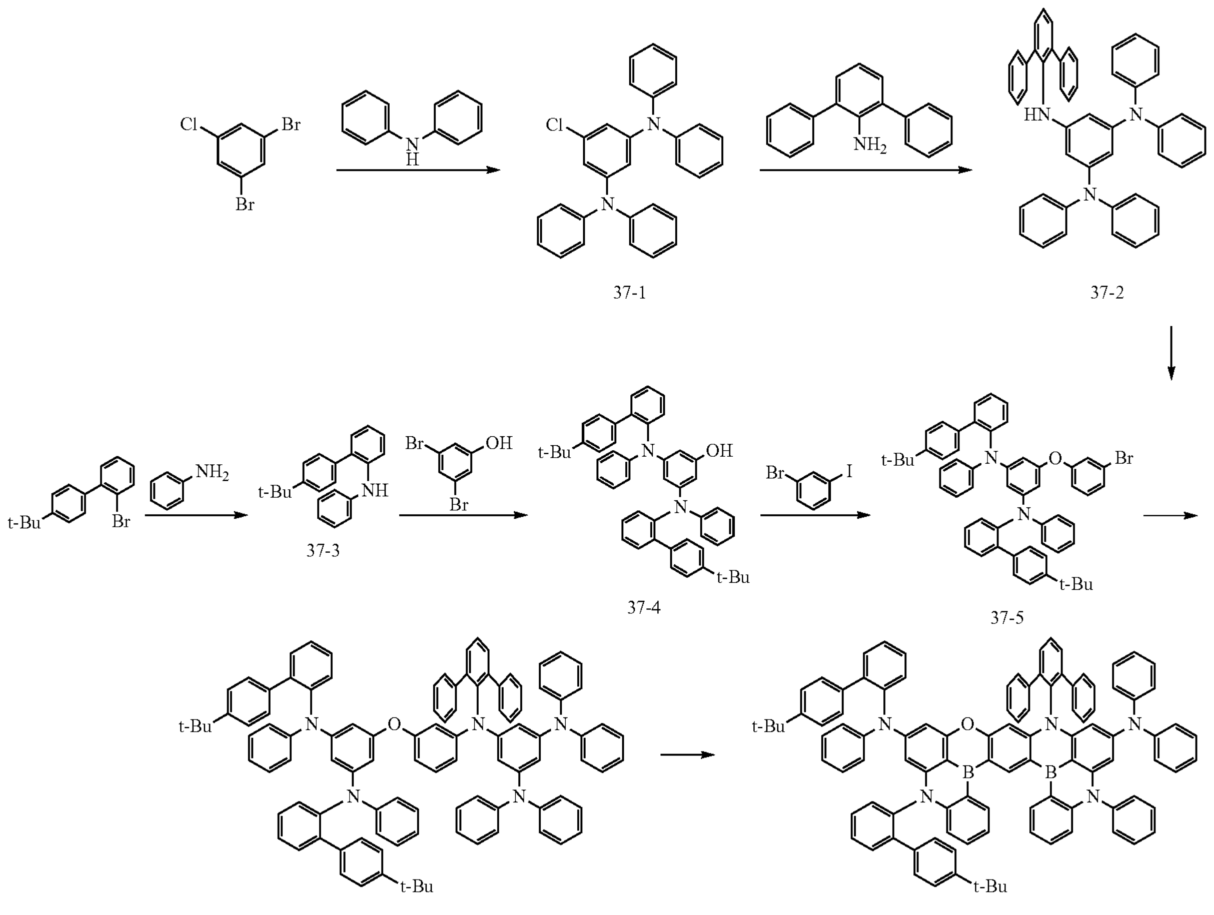

37-1

37-2

37-3

37-4

37-5

37-6

37

Synthesis of Intermediate 37-1

1,3-dibromo-5-chlorobenzene (1 eq), diphenylamine (2.1 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 37-1. (Yield: 60%).

Synthesis of Intermediate 37-2

Intermediate 37-1 (1 eq), [1,1': 3',1''-terphenyl]-2'-amine (1.5 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 37-2. (Yield: 60%).

Synthesis of Intermediate 37-3

2-bromo-4'-(tert-butyl)-1,1'-biphenyl (1 eq), aniline (2.1 eq), tris(dibenzylideneacetone)dipalladium(0) (0.1 eq), tri-tert-butylphosphine (0.2 eq), and sodium tert-butoxide (3 eq) were dissolved in toluene and stirred in a nitrogen atmosphere at a temperature of 110° C. for 8 hours. After cooling, the organic layer obtained by washing three times with ethyl acetate and water was dried using $MgSO_4$ and dried under reduced pressure. Subsequently, the separation-purification process was performed by column chromatography to obtain Intermediate 37-3. (Yield: 60%).

Synthesis of Intermediate 37-4

Intermediate 37-3 (2.1 eq), 3,5-dibromophenol (1 eq), tris(dibenzylideneacetone)dipalladium(0) (0.1 eq), tri-tert-butylphosphine (0.2 eq), and sodium tert-butoxide (4 eq) were dissolved in toluene and stirred in a nitrogen atmosphere at a temperature of 110° C. for 12 hours. After cooling, the reaction mixture was dried under reduced pressure and toluene was removed therefrom. After cooling, the organic layer obtained by washing three times with ethyl acetate and water was dried using $MgSO_4$ and dried under reduced pressure. Subsequently, the separation-purification process was performed by column chromatography to obtain Intermediate 37-4. (Yield: 62%)

Synthesis of Intermediate 37-5

Intermediate 37-4 (1 eq), 1-bromo-3-iodobenzene (2 eq), CuI (0.2 eq), $K_2CO_3$ (3 eq), and picolinic acid (0.4 eq were dissolved in DMF and stirred at a temperature of 160° C. for hours. After cooling, the reaction mixture was dried under reduced pressure and DMF was removed therefrom. Then, the organic layer obtained by washing with ethyl acetate and water was dried using $MgSO_4$ and dried under reduced pressure. Subsequently, the purification-recrystallization (dichloromethane: n-hexane) process was performed by column chromatography to obtain Intermediate 37-5. (Yield: 60%).

Synthesis of Intermediate 37-6

Intermediate 37-2 (1 eq), Intermediate 37-5 (1 eq), tris (dibenzylideneacetone)dipalladium(0) (0.1 eq), tri-tert-butylphosphine (0.2 eq), and sodium tert-butoxide (3 eq) were dissolved in toluene and stirred in a nitrogen atmosphere at a temperature of 110° C. for 20 hours. After cooling, the reaction mixture was dried under reduced pressure and toluene was removed therefrom. Then, the organic layer obtained by washing three times with ethyl acetate and water was dried using $MgSO_4$ and dried under reduced pressure. The purification (dichloromethane: n-hexane) process was performed by column chromatography to obtain Intermediate 37-6. (Yield: 58%)

Synthesis of Compound 37

Intermediate 37-6 (1 eq) was dissolved in ortho dichlorobenzene, a flask was cooled to 0° C. in a nitrogen atmosphere, and $BBr_3$ (4 eq) was slowly added thereto. After completion of the dropping, the temperature was raised to 19° C. and the reaction mixture was stirred for 24 hours. After cooling to 0° C., triethylamine was slowly added dropwise to the flask to terminate the reaction until the exotherm stopped, and then, a hexane was added thereto to cause precipitation and a solid was obtained therefrom by filtration. The obtained solid was purified by silica-gel filtration, and then, purified using MC/Hex recrystallization to obtain Compound 37. Subsequently, final purification was performed by sublimation purification. (Yield after sublimation: 3%)

Synthesis Example 4: Synthesis of Compound 42

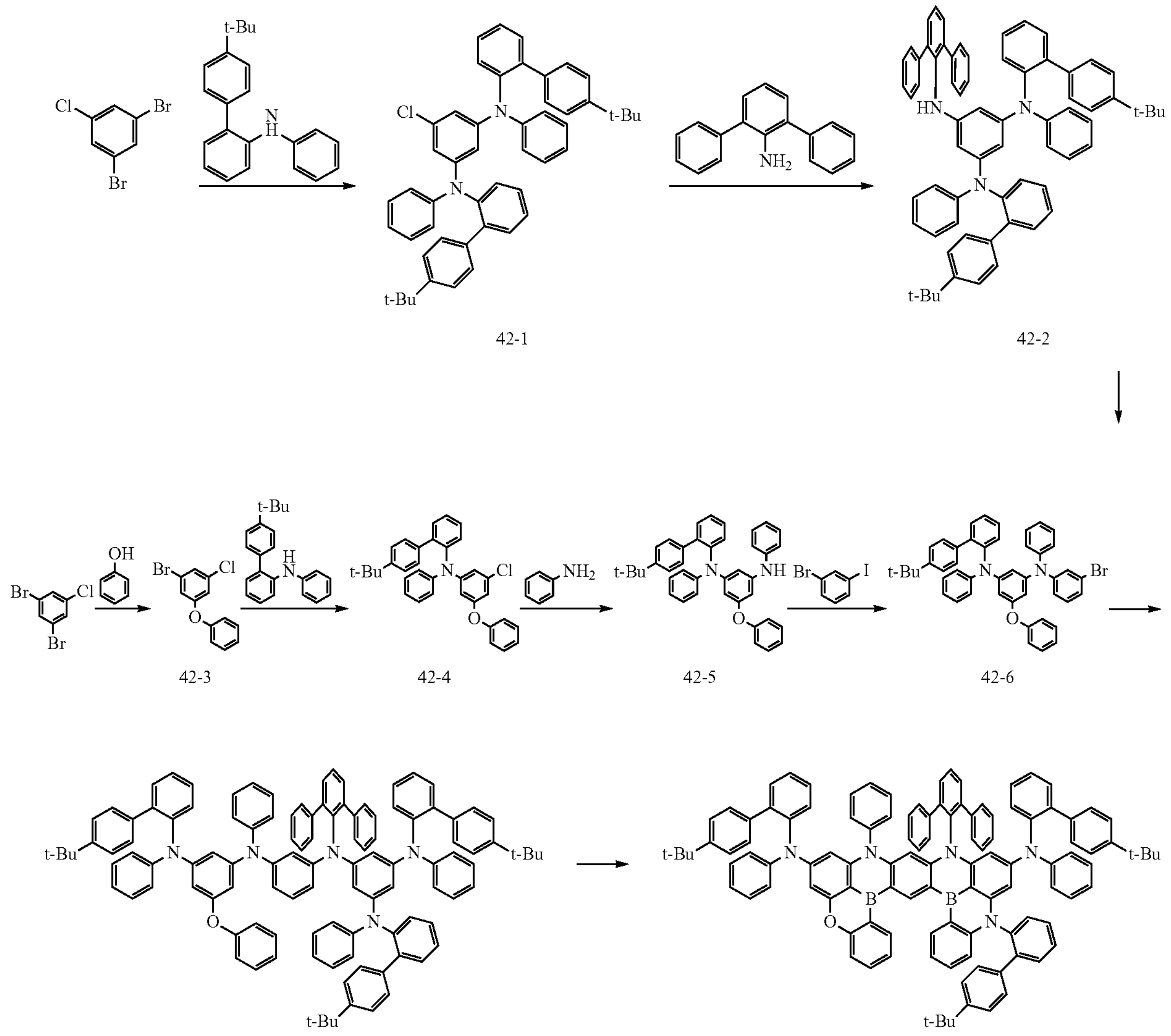

42-1

42-2

42-3

42-4

42-5

42-6

42-7

42

Synthesis of Intermediate 42-1

1,3-dibromo-5-chlorobenzene (1 eq), 4-(tert-butyl)-N-phenyl-(1,1'-biphenyl)-2-amine (2.1 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 42-1. (Yield: 65%).

Synthesis of Intermediate 42-2

Intermediate 42-1 (1 eq), [1,1': 3',1"-terphenyl]-2'-amine (1.5 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 42-2. (Yield: 60%).

Synthesis of Intermediate 42-3

1,3-dibromo-5-chlorobenzene (1 eq), phenol (1 eq), CuI (0.1 eq), and $K_2CO_3$ (3 eq) were dissolved in DMF and stirred at a temperature of 150° C. for 24 hours. After cooling, the reaction product was poured into water, precipitated, and filtrated. The organic layer obtained by washing three times with ethyl acetate and water was dried using $MgSO_4$ and dried under reduced pressure. Subsequently, the separation-purification process was performed by column chromatography to obtain Intermediate 42-3. (Yield: 62%)

Synthesis of Intermediate 42-4

Intermediate 42-3 (1 eq), 4-(tert-butyl)-N-phenyl-(1,1'-biphenyl)-2-amine (2.1 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 42-4. (Yield: 65%).

Synthesis of Intermediate 42-5

Intermediate 42-4 (1 eq), aniline (1.5 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 42-5. (Yield: 65%).

Synthesis of Intermediate 42-6

Intermediate 42-5 (1 eq), 1-bromo-3-iodobenzene (2 eq), CuI (0.2 eq), $K_2CO_3$ (3 eq), and picolinic acid (0.4 eq) were dissolved in DMF and stirred at a temperature of 160° C. for hours. After cooling, the reaction mixture was dried under reduced pressure and DMF was removed therefrom. Then, the organic layer obtained by washing with ethyl acetate and water was dried using $MgSO_4$ and dried under reduced pressure. Subsequently, the purification-recrystallization (dichloromethane: n-hexane) process was performed by column chromatography to obtain Intermediate 42-6. (Yield: 60%).

Synthesis of Intermediate 42-7

Intermediate 42-2 (1 eq), Intermediate 42-6 (1 eq), tris (dibenzylideneacetone)dipalladium (0) (0.1 eq), tri-tert-butylphosphine (0.2 eq), and sodium tert-butoxide (3 eq) were dissolved in toluene and stirred in a nitrogen atmosphere at a temperature of 110° C. for 20 hours. After cooling, the reaction mixture was dried under reduced pressure and toluene was removed therefrom. Then, the organic layer obtained by washing three times with ethyl acetate and water was dried using $MgSO_4$ and dried under reduced pressure. Subsequently, the purification (dichloromethane: n-hexane) process was performed by column chromatography to obtain Intermediate 42-7. (Yield: 58%)

Synthesis of Compound 42

Intermediate 42-7 (1 eq) was dissolved in ortho dichlorobenzene, a flask was cooled to 0° C. in a nitrogen atmosphere, and $BBr_3$ (4 eq) was slowly added thereto. After completion of the dropping, the temperature was raised to 19° C. and the reaction mixture was stirred for 24 hours. After cooling to 0° C., triethylamine was slowly added dropwise to the flask to terminate the reaction until the exotherm stopped, and then, a hexane was added thereto to cause precipitation and a solid was obtained therefrom by filtration. The obtained solid was purified by silica-gel filtration, and then, purified using MC/Hex recrystallization to obtain Compound 42. Subsequently, final purification was performed by sublimation purification. (Yield after sublimation: 3%)

Synthesis Example 5: Synthesis of Compound 67

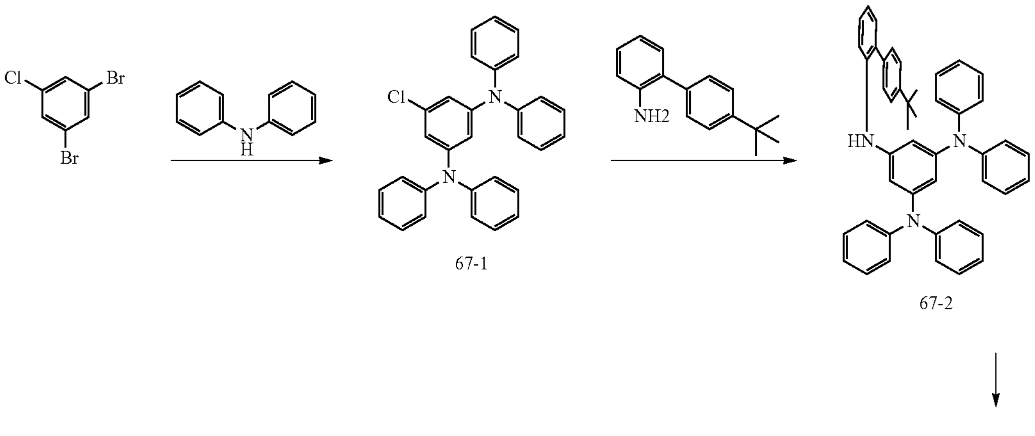

67-1

67-2

-continued

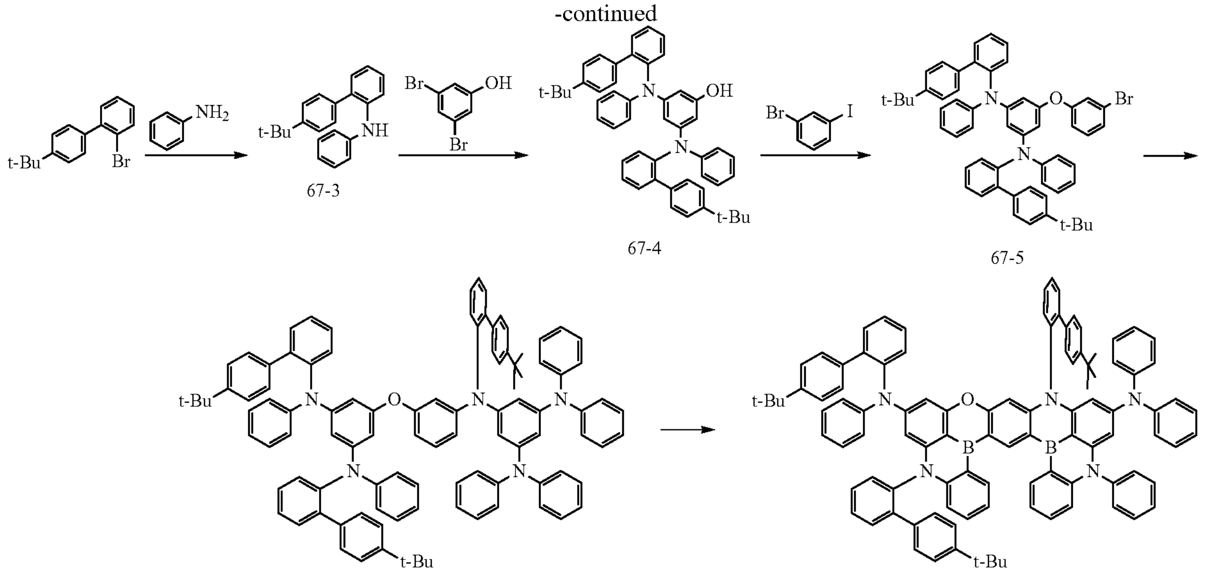

67-3

67-4

67-5

67-6

67

Synthesis of Intermediate 67-1

1,3-dibromo-5-chlorobenzene (1 eq), diphenylamine (2.1 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 67-1. (Yield: 60%).

Synthesis of Intermediate 67-2

Intermediate 67-1 (1 eq), 4'-(tert-butyl)-[1,1'-biphenyl]-2-amine (1.5 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 67-2. (Yield: 60%).

Synthesis of Intermediate 67-3

2-bromo-4'-(tert-butyl)-1,1'-biphenyl (1 eq), aniline (2.1 eq), tris(dibenzylideneacetone)dipalladium(0) (0.1 eq), tri-tert-butylphosphine (0.2 eq), and sodium tert-butoxide (3 eq) were dissolved in toluene and stirred in a nitrogen atmosphere at a temperature of 110° C. for 8 hours. After cooling, the organic layer obtained by washing three times with ethyl acetate and water was dried using $MgSO_4$ and dried under reduced pressure. Subsequently, the separation-purification process was performed by column chromatography to obtain Intermediate 67-3. (Yield: 60%).

Synthesis of Intermediate 67-4

Intermediate 67-3 (2.1 eq), 3,5-dibromophenol (1 eq), tris(dibenzylideneacetone)dipalladium(0) (0.1 eq), tri-tert-butylphosphine (0.2 eq), and sodium tert-butoxide (4 eq) were dissolved in toluene and stirred in a nitrogen atmosphere at a temperature of 110° C. for 12 hours. After cooling, the reaction mixture was dried under reduced pressure and toluene was removed therefrom. After cooling, the organic layer obtained by washing three times with ethyl acetate and water was dried using $MgSO_4$ and dried under reduced pressure. Subsequently, the separation-purification process was performed by column chromatography to obtain Intermediate 67-4. (Yield: 62%)

Synthesis of Intermediate 67-5

Intermediate 67-4 (1 eq), 1-bromo-3-iodobenzene (2 eq), CuI (0.2 eq), $K_2CO_3$ (3 eq), and picolinic acid (0.4 eq) were dissolved in DMF and stirred at a temperature of 160° C. for hours. After cooling, the reaction mixture was dried under reduced pressure and DMF was removed therefrom. Then, the organic layer obtained by washing with ethyl acetate and water was dried using $MgSO_4$ and dried under reduced pressure. Subsequently, the purification-recrystallization (dichloromethane: n-hexane) process was performed by column chromatography to obtain Intermediate 67-5. (Yield: 60%).

Synthesis of Intermediate 67-6

Intermediate 67-2 (1 eq), Intermediate 67-5 (1 eq), tris(dibenzylideneacetone)dipalladium(0) (0.1 eq), tri-tert-butylphosphine (0.2 eq), and sodium tert-butoxide (3 eq) were dissolved in toluene and stirred in a nitrogen atmosphere at a temperature of 110° C. for 20 hours. After cooling, the reaction mixture was dried under reduced pressure and toluene was removed therefrom. Then, the organic layer obtained by washing three times with ethyl acetate and water was dried using $MgSO_4$ and dried under reduced pressure. The purification (dichloromethane: n-hexane) process was performed by column chromatography to obtain Intermediate 67-6. (Yield: 58%)

Synthesis of Compound 67

Intermediate 67-6 (1 eq) was dissolved in ortho dichlorobenzene, a flask was cooled to 0° C. in a nitrogen atmosphere, and $BBr_3$ (4 eq) was slowly added thereto. After completion of the dropping, the temperature was raised to 19° C. and the resultant solution was stirred for 24 hours. After cooling to 0° C., triethylamine was slowly added dropwise to the flask to terminate the reaction until the exotherm stopped, and then, a hexane was added thereto to cause precipitation and a solid was obtained therefrom by filtration. The obtained solid was purified by silica-gel filtration, and then, purified using MC/Hex recrystallization to obtain Compound 67. Subsequently, final purification was performed by sublimation purification. (Yield after sublimation: 3%)

Synthesis Example 6: Synthesis of Compound 82

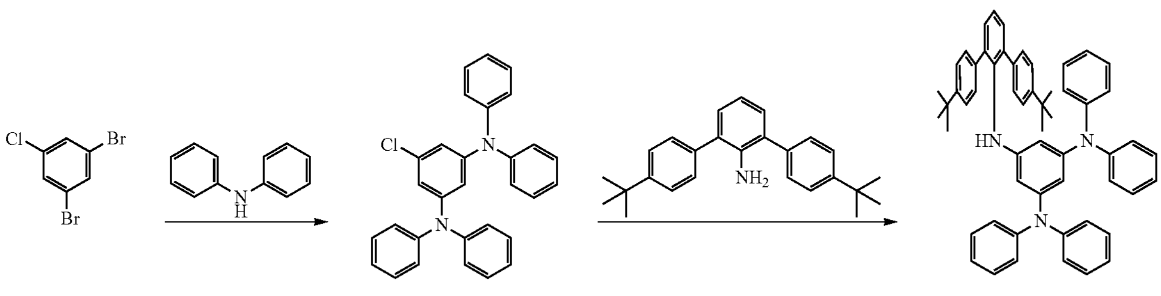

82-1

82-2

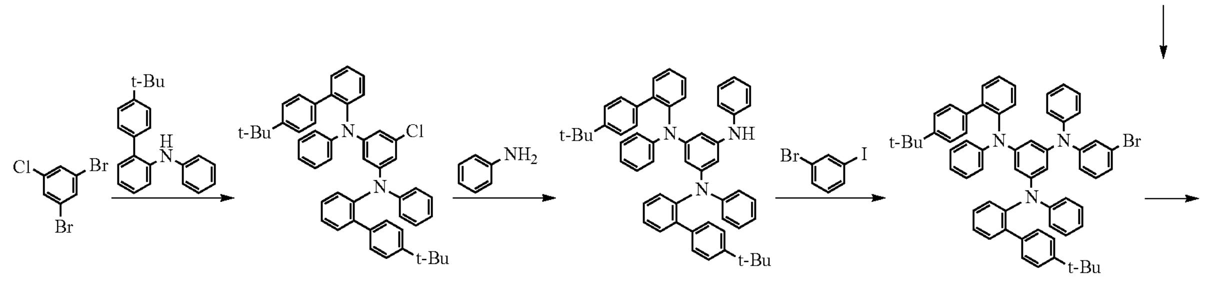

82-3

82-4

82-5

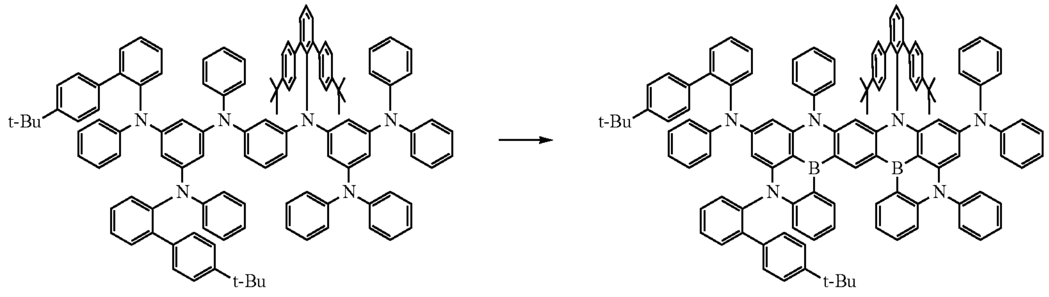

82-6

82

Synthesis of Intermediate 82-1

1,3-dibromo-5-chlorobenzene (1 eq), diphenylamine (2.1 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 82-1. (Yield: 60%).

Synthesis of Intermediate 82-2

Intermediate 82-1 (1 eq), 4,4"-di-tert-butyl-[1,1': 3,1"-terphenyl]-2'-amine (1.5 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 82-2. (Yield: 60%).

Synthesis of Intermediate 82-3

1,3-dibromo-5-chlorobenzene (1 eq), 4-(tert-butyl)-N-phenyl-(1,1'-biphenyl)-2-amine (2.1 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 82-3. (Yield: 65%).

Synthesis of Intermediate 82-4

Intermediate 82-3 (1 eq), aniline (1.5 eq), tris(dibenzylideneacetone)dipalladium(0) (0.05 eq), tri-tert-butylphosphine (0.1 eq), and sodium tert-butoxide (3 eq) were dissolved in toluene and stirred in a nitrogen atmosphere at a temperature of 100° C. for 12 hours. After cooling, the organic layer obtained by washing three times with ethyl acetate and water was dried using $MgSO_4$ and dried under reduced pressure. Subsequently, the separation-purification process was performed by column chromatography to obtain Intermediate 82-4. (Yield: 65%).

Synthesis of Intermediate 82-5

Intermediate 82-4 (1 eq), 1-bromo-3-iodobenzene (2 eq), CuI (0.2 eq), $K_2CO_3$ (3 eq), and picolinic acid (0.4 eq) were dissolved in DMF and stirred at a temperature of 160° C. for hours. After cooling, the reaction mixture was dried under reduced pressure and DMF was removed therefrom. Then, the organic layer obtained by washing with ethyl acetate and water was dried using $MgSO_4$ and dried under reduced pressure. Subsequently, the purification-recrystallization (dichloromethane: n-hexane) process was performed by column chromatography to obtain Intermediate 82-5. (Yield: 60%).

Synthesis of Intermediate 82-6

Intermediate 82-2 (1 eq), Intermediate 82-5 (1 eq), tris (dibenzylideneacetone)dipalladium (0) (0.1 eq), tri-tert-butylphosphine (0.2 eq), and sodium tert-butoxide (3 eq) were dissolved in toluene and stirred in a nitrogen atmosphere at a temperature of 110° C. for 20 hours. After cooling, the reaction mixture was dried under reduced pressure and toluene was removed therefrom. Then, the organic layer obtained by washing three times with ethyl acetate and water was dried using $MgSO_4$ and dried under reduced pressure. Subsequently, the purification (dichloromethane: n-hexane) process was performed by column chromatography to obtain Intermediate 82-6. (Yield: 58%)

Synthesis of Compound 82

Intermediate 82-6 (1 eq) was dissolved in ortho dichlorobenzene, a flask was cooled to 0° C. in a nitrogen atmosphere, and $BBr_3$ (4 eq) was slowly added thereto. After completion of the dropping, the temperature was raised to 19° C. and the reaction mixture was stirred for 24 hours. After cooling to 0° C., triethylamine was slowly added dropwise to the flask to terminate the reaction until the exotherm stopped, and then, a hexane was added thereto to cause precipitation and a solid was obtained therefrom by filtration. The obtained solid was purified by silica-gel filtration, and then, purified using MC/Hex recrystallization to obtain Compound 82. Subsequently, final purification was performed by sublimation purification (Yield after sublimation: 3%).

Proton nuclear magnetic resonance ($^1$H NMR) and mass spectroscopy/fast atom bombardment (MS/FAB) of the compounds synthesized according to Synthesis Examples above are shown in Table 1.

TABLE 1

| Compound | $H^1$ NMR (δ) | MS/FAB Calc | MS/FAB Found |
|---|---|---|---|
| 30 | 8.10 (6H, m), 7.71 (2H, dd), 7.43-7.41 (6H, m), 7.39 (6H, m), 7.38 (8H, m), 7.37 (6H, m), 7.30 (8H, m), 7.29 (2H, m), 7.25 (1H, s), 7.24 (4H, m), 7.18 (2H, m), 7.14 (6H, m), 7.08 (8H, m), 7.01 (2H, m), 7.00 (2H, m), 6.83 (1H, s), 6.49 (4H, s), 1.33 (12H, s) | 1777.97 | 1777.98 |
| 34 | 8.20 (2H, d), 8.10 (2H, m), 7.71 (2H, dd), 7.43-7.41 (6H, m), 7.39 (3H, m), 7.38 (4H, m), 7.37 (2H, m), 7.30 (4H, m), 7.29 (2H, m), 7.25 (1H, s), 7.24 (10H, m), 7.18 (2H, m), 7.14 (2H, m), 7.08 (14H, m), 7.01 (2H, m), 7.00 (5H, m), 6.83 (1H, s), 6.49 (4H, s), 1.33 (6H, s) | 1513.56 | 1513.56 |
| 37 | 8.20 (2H, d), 8.10 (2H, m), 7.71 (2H, dd), 7.43-41 (6H, m), 7.39 (3H, m), 7.38 (4H, m), 7.37 (2H, m), 7.30 (4H, m), 7.29 (2H, m), 7.25 (1H, s), 7.24 (8H, m), 7.18 (2H, m), 7.14 (2H, m), 7.08 (12H, m), 7.01 (2H, m), 7.00 (4H, m), 6.86 (1H, s), 6.55 (1H, d), 6.52 (1H, d), 6.49 (2H, s), 1.33 (6H, s) | 1438.45 | 1438.45 |
| 42 | 8.20 (2H, d), 8.10 (3H, m), 7.71 (2H, dd), 7.43-7.41 (6H, m), 7.39 (4H, m), 7.38 (6H, m), 7.35 (1H, m), 7.30 (6H, m), 7.29 (1H, m), 7.25 (1H, s), 7.24 (6H, m), 7.18 (1H, m), 7.14 (3H, m), 7.08 (10H, m), 7.07 (1H, m), 7.00 (4H, m), 6.83 (1H, s), 6.55 (1H, d), 6.52 (1H, d), 6.49 (2H, s), 1.33 (9H, s) | 1570.65 | 1570.65 |
| 67 | 8.10 (3H, m), 7.71 (2H, dd), 7.39 (3H, m), 7.38 (6H, m), 7.37 (3H, m), 7.30 (6H, m), 7.29 (2H, m), 7.25 (1H, s), 7.24 (8H, m), 7.18 (2H, m), 7.14 (3H, m), 7.08 (8H, m), 7.01 (2H, m), 7.00 (4H, m), 6.86 (1H, s), 6.55 (1H, d), 6.52 (1H, d), 6.49 (2H, s), 1.33 (9H, s) | 1418.46 | 1418.47 |
| 82 | 8.20 (2H, d), 8.10 (2H, m), 7.71 (2H, dd), 7.39 (3H, m), 7.38 (8H, m), 7.37 (2H, m), 7.30 (8H, m), 7.29 (2H, m), 7.25 (1H, s), 7.24 (10H, m), 7.18 (2H, m), 7.14 (2H, m), 7.08 (10H, m), 7.01 (2H, m), 7.00 (5H, m), 6.83 (1H, s), 6.49 (4H, s), 1.33 (12H, s) | 1625.78 | 1625.79 |

Evaluation Example 1

Table 2 shows the physical properties of the synthesized compounds. Particularly, The $T_1$ energy level and Si energy level were calculated using the quantum calculation method (S/W: Gaussian09) sold by Gaussian, Inc., Wallingford CT

TABLE 2

| No. | Compound | HOMO (eV) | LUMO (eV) | $S_1$ (eV) | $T_1$ (eV) | $\Delta E_{S-T}$ (eV) |
|---|---|---|---|---|---|---|
| Example 1 | Compound 30 | −4.77 | −1.38 | 2.88 | 2.57 | 0.31 |
| Example 2 | Compound 34 | −4.81 | −1.42 | 2.88 | 2.58 | 0.30 |
| Example 3 | Compound 37 | −4.94 | −1.53 | 2.91 | 2.60 | 0.31 |
| Example 4 | Compound 42 | −4.96 | −1.58 | 2.89 | 2.59 | 0.30 |
| Example 5 | Compound 67 | −4.93 | −1.54 | 2.89 | 2.58 | 0.31 |
| Example 6 | Compound 82 | −4.80 | −1.43 | 2.88 | 2.57 | 0.31 |
| Comparative Example 1 | DABNA1 | −5.00 | −1.37 | 3.01 | 2.62 | 0.39 |
| Comparative Example 2 | 1-A | −4.83 | −1.46 | 2.87 | 2.55 | 0.32 |
| Comparative Example 3 | 1-2 | −4.77 | −1.39 | 2.88 | 2.56 | 0.32 |

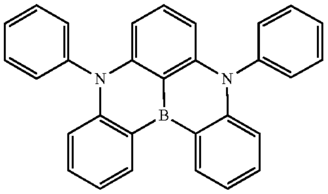

DABNA-1

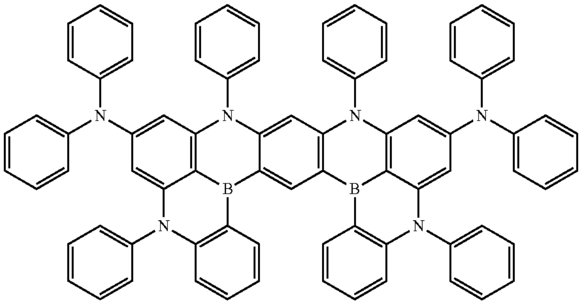

1-A

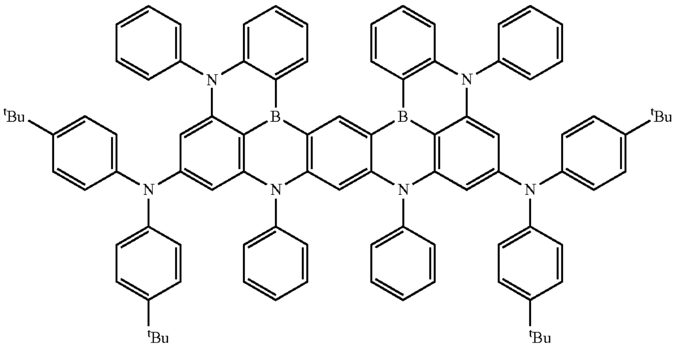

(1-2)

Evaluation Example 2

Using the quantum calculation method (S/W: Gaussian09), vibronic coupling constants between triplet states (VIII), and kRISC values measured using the vibronic coupling constants, Bond Dissociation Energy (BDE) values were calculated, and the results thereof are shown in Table 3.

TABLE 3

| | Compound | Oscillator strength (f) | VIB ($cm^{-1}$) | $k_{RISC}$ ($s^{-1}$) | BDE (eV) |
|---|---|---|---|---|---|
| Example 1 | Compound 30 | 0.71 | 0.32 | 1.96E+06 | 2.20 |
| Example 2 | Compound 34 | 0.63 | 0.27 | 1.23E+06 | 2.25 |
| Example 3 | Compound 37 | 0.71 | 0.31 | 1.48E+06 | 2.35 |
| Example 4 | Compound 42 | 0.66 | 0.26 | 1.17E+06 | 2.20 |

TABLE 3-continued

| | Compound | Oscillator strength (f) | VIB ($cm^{-1}$) | $k_{RISC}$ ($s^{-1}$) | BDE (eV) |
|---|---|---|---|---|---|
| Example 5 | Compound 67 | 0.67 | 0.32 | 1.36E+06 | 2.27 |
| Example 6 | Compound 82 | 0.67 | 0.37 | 1.17E+06 | 2.27 |
| Comparative Example 2 | 1-A | 0.64 | 0.22 | 2.76E+05 | 2.16 |
| Comparative Example 3 | 1-2 | 0.65 | 0.23 | 2.83E+05 | 2.14 |

Example 1

As an anode, a glass substrate (product of Corning Inc., of Corning, New York) with a 15 Ω/$cm^2$ (1,200 Å) ITO electrode formed thereon was cut to a size of 50 mm×50 mm×0.7 mm, sonicated with isopropyl alcohol and pure water each for 5 minutes, and then cleaned by exposure to ultraviolet rays and ozone for 30 minutes. Then, the resultant structure was mounted on a vacuum deposition apparatus.

The compound N,N-di(1-naphthyl)-N,N-diphenylbenzidine (NPD) was vacuum-deposited on the anode to form a hole injection layer having a thickness of 300 Å, the compound TCTA was vacuum-deposited on the hole injection layer to form a hole transport layer having a thickness of 200 Å, and a hole transporting compound 9-(4-tert-Butylphenyl)-3,6-bis(triphenylsilyl)-9H-carbazole (CzSi) was vacuum-deposited on the hole transport layer to form an emission auxiliary layer having a thickness of 100 Å.

The compound mCP (host) and Compound 30 (dopant) were co-deposited to a weight ratio of 99:1 on the buffer layer to form an emission layer having a thickness of 200 Å.

Then, the compound TSPO1 was deposited on the emission layer to form an electron transport layer having a thickness of 200 Å, buffer electron transporting compound 2,2',2"-(1,3,5-Benzinetriyl)-tris(1-phenyl-1-H-benzimidazole) (TPBi) was deposited on the electron transport layer to form a buffer layer having a thickness of 300 Å, LiF, which is a halogenated alkali metal, was deposited on the buffer layer to form an electron injection layer having a thickness of 10 Å, AI was vacuum-deposited thereon to form a cathode having a thickness of 3,000 Å, thereby completing the manufacture of an organic light-emitting device having an ITO (1,200 Å)/NPD (300 Å)/TCTA (200 Å)/CzSi (100 Å)/mCP+Compound 1 (1 wt %) (200 Å)/TSPO1 (200 Å)/TPBi (300 Å)/LiF (10 Å)/AI (3,000 Å) structure.

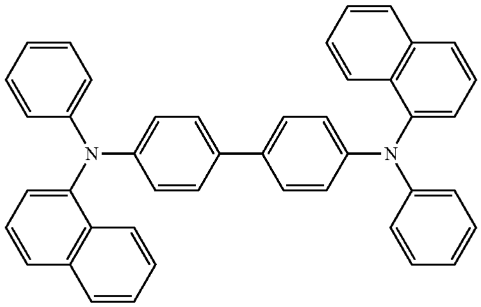

NPD

-continued

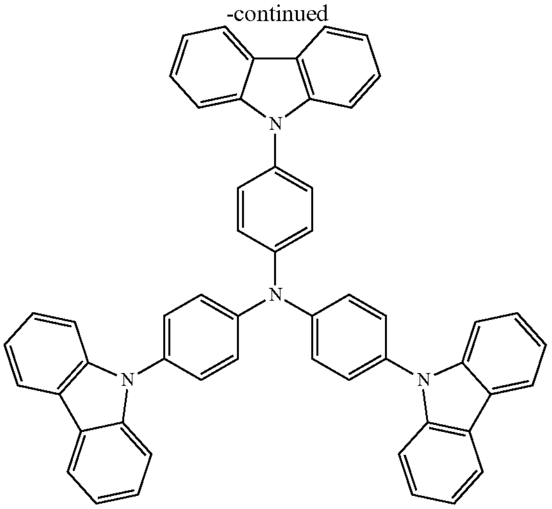

TCTA

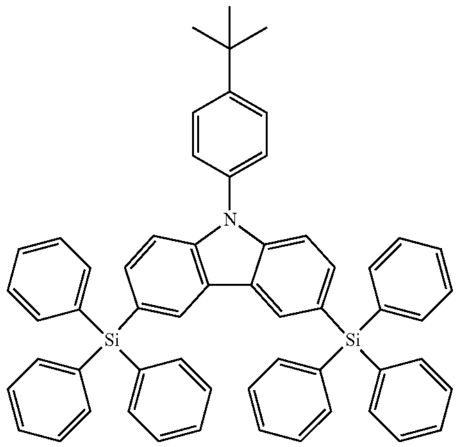

CzSi

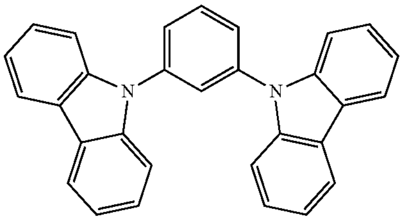

mCP

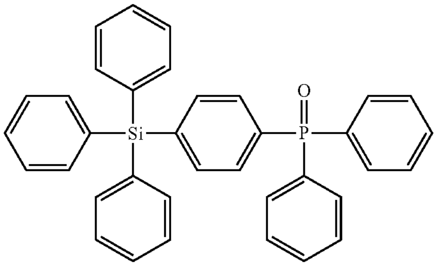

TSPO1

-continued

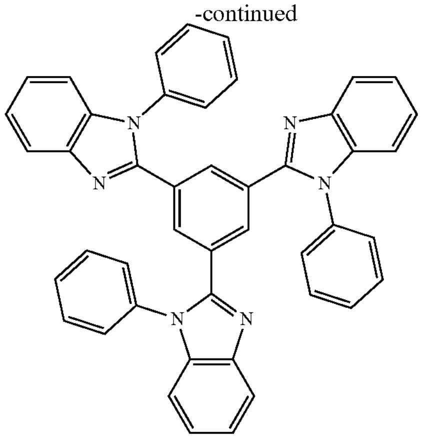

TPBI

Examples 2 to 6 and Comparative Examples 1 to 3

Organic light-emitting devices were manufactured in the same manner as in Example 1, except that, in forming an emission layer, the compounds shown in Table 4 were each used as a dopant instead of Compound 30.

Evaluation Example 3

To evaluate characteristics of the light-emitting devices manufactured according to Examples 1 to 6 and Comparative Examples 1 to 3, the driving voltage in volt (V) at a current density of 10 mA/cm$^2$, emission or luminescence efficiency in candela per meter squared (cd/A), and maximum external quantum efficiency (EQE) in percent (%) thereof were measured. The driving voltage of the light-emitting devices were measured using a source meter (sold under the trade designation Keithley Instrument, 2400 series, by Tektronix, Inc., of Beaverton, Oregon), and the maximum quantum efficiency was measured using the external quantum efficiency measurement device sold under the trade designation $C_{9920}$-2-12 by Hamamatsu Photonics Inc., of Hamamatsu-city, Japan. The $T_{95}$ lifespan is the time it takes to achieve 95% of the initial luminance measured in hour at 100 milliamp per centimeter squared.

Table 4 shows the evaluation results of the characteristics of the light-emitting devices.

TABLE 4

| | Hole transport layer material | Dopant in emission layer | Driving voltage (V) | Luminiscence Efficiency (cd/A) | Maximum external quantum efficiency (%) | Half lifespan (T95) (hr @100 mA/cm$^2$) | Emission color |
|---|---|---|---|---|---|---|---|
| Example 1 | TCTA | Compound 30 | 4.2 | 23.6 | 23.0 | 164 | Blue |
| Example 2 | TCTA | Compound 34 | 4.0 | 23.2 | 22.5 | 170 | Blue |
| Example 3 | TCTA | Compound 37 | 3.8 | 24.2 | 23.8 | 188 | Blue |
| Example 4 | TCTA | Compound 42 | 4.3 | 22.9 | 21.1 | 153 | Blue |
| Example 5 | TCTA | Compound 67 | 4.0 | 24.0 | 23.3 | 180 | Blue |
| Example 6 | TCTA | Compound 82 | 4.1 | 23.3 | 23.2 | 179 | Blue |
| Comparative Example 1 | TCTA | DABNA-1 | 5.7 | 16.0 | 15.7 | 38 | Blue |
| Comparative Example 2 | TCTA | 1-A | 5.0 | 20.0 | 18.2 | 56 | Blue |
| Comparative Example 3 | TCTA | 1-2 | 5.0 | 20.2 | 18.3 | 59 | Blue |

Table 4 shows that the organic light-emitting devices of Examples 1 to 6 each emit blue light and have significant and unexpectedly improved driving voltage, emission efficiency, and maximum quantum efficiency, as compared with the organic light-emitting devices of Comparative Examples 1 to 3.

Light-emitting devices made according to illustrative implementations and/or illustrative methods of the invention have a fused cyclic compound represented by Formula 1 have a particular structure that provides, the light-emitting device with have excellent emission efficiency and a long lifespan, and may be used to manufacture high-quality electronic apparatuses.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A light-emitting device comprising:

a first electrode;

a second electrode facing the first electrode;

a first layer between the first electrode and the second electrode and comprising a second layer; and a fused cyclic compound of Formula 1:

Formula 1

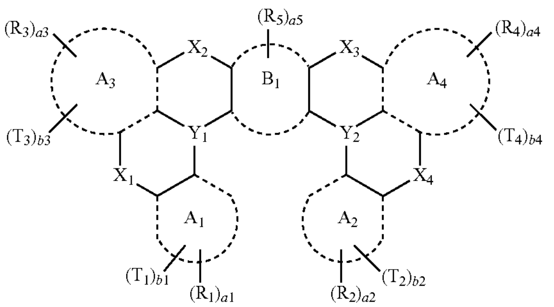

Formula 2

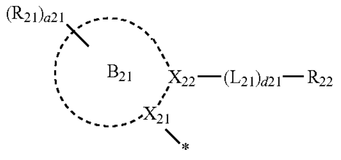

wherein, in Formula 1 and Formula 2, rings $A_1$ to $A_4$, $B_1$, and $B_{21}$ are each, independently from one another, a $C_5$-$C_{60}$ carbocyclic group or a $C_1$-$C_{60}$ heterocyclic group, $Y_1$ and $Y_2$ are each, independently from one another, B, P(=O), or P(=S), $X_1$ is N($Ar_1$), N($Z_1$), O, S, or Se, $X_2$ is N($Ar_2$), N($Z_2$), O, S, or Se, X3 is N(Ar3), N(Z3), O, S, or Se, X4 is N(Ar4), N(Z4), O, S, or Se, Z1 to Z4 are each, independently from one another, a group of Formula 2, $Ar_1$ to $Ar_4$, $R_1$ to $R_5$, and $R_{21}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), $T_1$ to $T_4$ each independently comprise a group of Formula 2, a1 to a5, b1 to b4, and a21 are each, independently from one another, an integer from 0 to 10, $X_{21}$ and $X_{22}$ are each, independently from one another, carbon or a heteroatom, and $X_{21}$ and $X_{22}$ are linked to each other by a chemical bond, $L_{21}$ is a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, d21 is an integer from 1 to 3, $R_{22}$ is a hydroxyl group, a $C_1$-$C_{20}$ alkyl group unsubstituted or substituted with at least one $R_{10a}$, provided that the $C_1$-$C_{20}$ alkyl group unsubstituted or substituted with at least one $R_{10a}$ is not a methyl group, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_1$-$C_{60}$ aryl group unsubstituted or substituted with at least one $R_{10a}$, or —N($Q_1$)($Q_2$),

* indicates a binding site to a neighboring atom, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof, or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each, independently from one another: a group of Formula 2; hydrogen; deuterium; —F; —Cl; —Br; —I; a hydroxyl group; a cyano group; a nitro group; a $C_1$-$C_{60}$ alkyl group, a $C_2$-$C_{60}$ alkenyl group, a $C_2$-$C_{60}$ alkynyl group or a $C_1$-$C_{60}$ alkoxy group each, independently from one another, unsubstituted or substituted with deuterium, —F, a cyano group or any combination thereof; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and the fused cyclic compound satisfies at least one of Conditions 1 to 5:

Condition 1 $X_1$ is $N(Z_1)$,

Condition 2 $X_2$ is $N(Z_2)$,

Condition 3 $X_3$ is $N(Z_3)$,

Condition 4 $X_4$ is $N(Z_4)$,

Condition 5 The sum of b1 to b4 is 1 or more.

2. The light-emitting device of claim 1, wherein the first electrode comprises an anode, the second electrode comprises a cathode, the first layer comprising an interlayer that further includes a hole transport region between the first electrode and the second layer comprising an emission layer, and an electron transport region between the second layer comprising emission layer and the second electrode, the hole transport region includes a hole injection layer, a hole transport layer, an emission auxiliary layer, an electron blocking layer, or any combination thereof, and the electron transport region includes a hole blocking layer, an electron transport layer, an electron injection layer, or any combination thereof.

3. The light-emitting device of claim 1, wherein the second layer comprises an emission layer that includes the fused cyclic compound of Formula 1.

4. The light-emitting device of claim 3, wherein the fused cyclic compound included in the emission layer is a condensed cyclic compound comprising a delayed fluorescence emitter, and the emission layer is configured to emit delayed fluorescence.

5. The light-emitting device of claim 3, wherein the emission layer is configured to emit blue light.

6. The light-emitting device of claim 3, wherein the emission layer further includes a host, and the fused cyclic compound included in the emission layer is a dopant, and the amount of the host included in the emission layer is greater than the amount of the fused cyclic compound included in the emission layer.

7. The light-emitting device of claim 1, further comprising a capping layer located outside the first electrode or outside the second electrode, wherein the capping layer includes the fused cyclic compound of Formula 1.

8. An electronic apparatus comprising the organic light-emitting device of claim 1.

9. The electronic apparatus of claim 8, further comprising a thin-film transistor, wherein the thin-film transistor includes a source electrode and a drain electrode, and the first electrode of the organic light-emitting device is electronically connected to the source electrode or the drain electrode.

10. A fused cyclic compound of Formula 1:

Formula 1

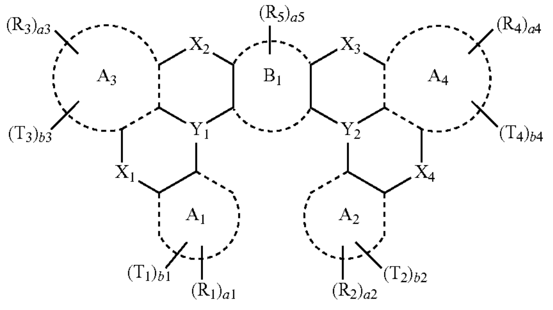

Formula 2

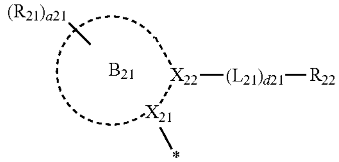

wherein, in Formula 1 and Formula 2, rings $A_1$ to $A_4$, $B_1$, and $B_{21}$ are each, independently from one another, a $C_5$-$C_{60}$ carbocyclic group or a $C_1$-$C_{60}$ heterocyclic group, $Y_1$ and $Y_2$ are each, independently from one another, B, P(=O), or P(=S), $X_1$ is $N(Ar_1)$, $N(Z_1)$, O, S, or Se, $X_2$ is $N(Ar_2)$, $N(Z_2)$, O, S, or Se, $X_3$ is $N(Ar_3)$, $N(Z_3)$, O, S, or Se, $X_4$ is $N(Ar_4)$, $N(Z_4)$, O, S, or Se, $Z_1$ to $Z_4$ are each, independently from one another, a group of Formula 2, $Ar_1$ to $Ar_4$, $R_1$ to $R_5$, and $R_{21}$ are each, independently from one another, hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$, $T_1$ to $T_4$ each independently comprise a group of Formula 2, a1 to a5, b1 to b4, and a21 are each, independently from one another, an integer from 0 to 10, $X_{21}$ and $X_{22}$ are each, independently from one another, carbon or a heteroatom, and $X_{21}$ and $X_{22}$ are linked to each other by a chemical bond, $L_{21}$ is a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, d21 is an integer from 1 to 3, $R_{22}$ is a hydroxyl group, a $C_1$-$C_{20}$ alkyl group unsubstituted or substituted with at least one $R_{10a}$, provided that the $C_1$-$C_{20}$ alkyl group unsubstituted or substituted with at least one $R_{10a}$ is not a methyl group, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_1$-$C_{60}$ aryl group unsubstituted or substituted with at least one $R_{10a}$, or —N($Q_1$)($Q_2$),

* indicates a binding site to a neighboring atom, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each, independently from one another: a group of Formula 2; hydrogen; deuterium; —F; —Cl; —Br; —I; a hydroxyl group; a cyano group; a nitro group; $C_1$-$C_{60}$ alkyl group, $C_2$-$C_{60}$ alkenyl group, $C_2$-$C_{60}$ alkynyl group or $C_1$-$C_{60}$ alkoxy group each, independently from one another, unsubstituted or substituted with deuterium, —F, a cyano group or any combination thereof; a $C_3$-$C_{60}$ carbocyclic group or a $C_1$-$C_{60}$ heterocyclic group, each independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and the fused cyclic compound satisfies at least one of Conditions 1 to 5:

Condition 1 $X_1$ is N($Z_1$),

Condition 2 $X_2$ is N($Z_2$),

Condition 3 $X_3$ is N($Z_3$),

Condition 4 $X_4$ is N($Z_4$),

Condition 5 the sum of b1 to b4 is 1 or more.

11. The fused cyclic compound of claim 10, wherein rings $A_1$ to $A_4$ are each, independently from one another, a benzene group, a naphthalene group, an anthracene group, a fluoranthene group, a triphenylene group, a pyrene group, a chrysene group, or a perylene group, and ring $B_1$ is a benzene group.

12. The fused cyclic compound of claim 10, wherein $Y_1$ and $Y_2$ are identical to each other.

13. The fused cyclic compound of claim 10, wherein a group of *-($L_{21}$)$_{d21}$-$R_{22}$ in Formula 2 is a group of one of Formulae 3-1 to 3-5:

3-1

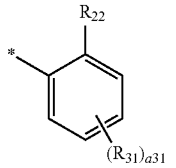

3-2

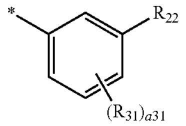

3-3

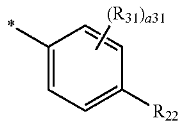

3-4

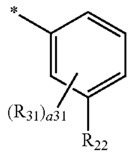

3-5

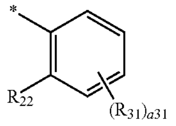

wherein, in Formulae 3-1 to 3-5, $R_{31}$ is hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), a31 is an integer from 0 to 4, $R_{22}$, $R_{10a}$, and $Q_{31}$ to $Q_{33}$ have, independently from one another, the same meaning as in claim 10, and

* indicates a binding site to a neighboring atom.

14. The fused cyclic compound of claim 10, wherein $T_1$ to $T_4$ are each, independently from one another, of —N($Q_{1a}$)($Q_{2a}$), $Q_{1a}$ and $Q_{2a}$ are each, independently from one another: a group of Formula 2; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and at least one of $Q_{1a}$ and $Q_{2a}$ is a group of Formula 2.

15. The fused cyclic compound of claim 10, wherein a group of

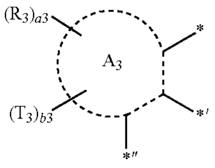

in Formula 1 is a group of one of Formulae 4-1 to 4-3:

4-1

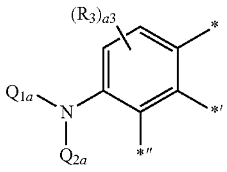

4-2

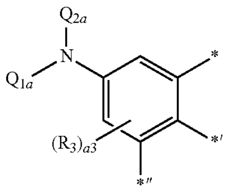

4-3

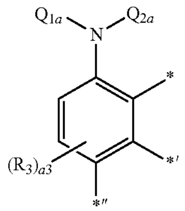

wherein, in Formulae 4-1 to 4-3, $Q_{1a}$ and $Q_{2a}$ are each, independently from one another: a group of Formula 2; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, at least one of $Q_{1a}$ and $Q_{2a}$ is a group of Formula 2, a3 is an integer from 0 to 2, $R_3$ has the same meaning as in claim 10, and

*, *', and *" each indicate a condensation site to a neighboring ring in Formula 1.

16. The fused cyclic compound of claim 10, wherein a group of

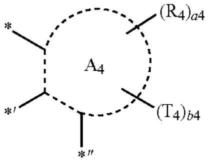

in Formula 1 is a group of one of Formulae 5-1 to 5-3:

5-1

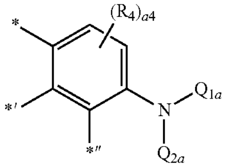

5-2

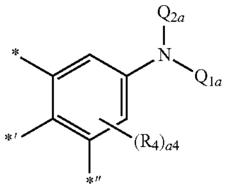

5-3

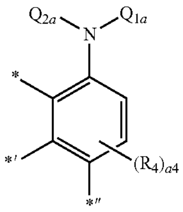

wherein, in Formulae 5-1 to 5-3, $Q_{1a}$ and $Q_{2a}$ are each, independently from one another: a group of Formula 2; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, at least one of $Q_{1a}$ and $Q_{2a}$ is a group of Formula 2, a4 is an integer from 0 to 2, $R_4$ has the same meaning as in claim 10, and

*, *', and *" each indicate a condensation site to a neighboring ring in Formula 1.

17. The fused cyclic device of claim 11, wherein a group of

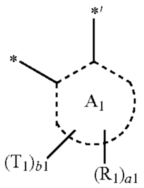

in Formula 1 is a group of one of Formulae 6-1 to 6-4:

6-1

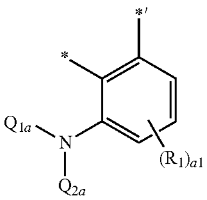

-continued 6-2

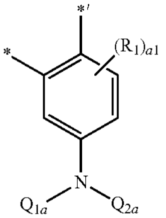

6-3

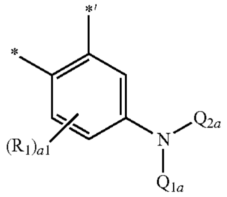

6-4

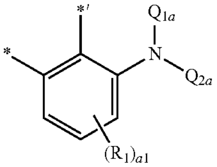

wherein in Formulae 6-1 to 6-4, $Q_{1a}$ and $Q_{2a}$ are each, independently from one another: a group of Formula 2; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, at least one of $Q_{1a}$ and $Q_{2a}$ is a group of Formula 2, a1 is an integer from 0 to 3, $R_1$ has the same meaning as in claim 10, and

* and *' each indicate a fused site to a neighboring ring in Formula 1.

18. The fused cyclic compound of claim 10, wherein a group of

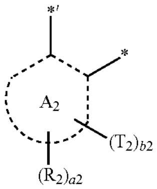

in Formula 1 is a group of one of Formulae 7-1 to 7-4:

7-1

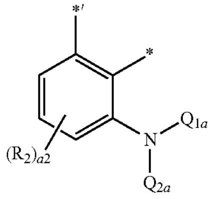

-continued 7-2

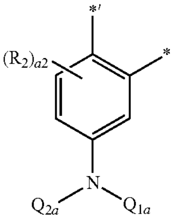

7-3

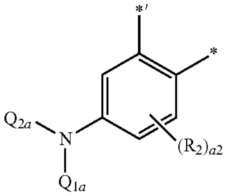

7-4

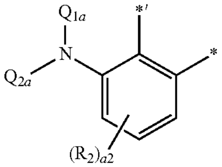

wherein, in Formulae 7-1 to 7-4, $Q_{1a}$ and $Q_{2a}$ are each, independently from one another: a group of Formula 2; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, at least one of $Q_{1a}$ and $Q_{2a}$ is a group of Formula 2, a2 is an integer from 0 to 3, $R_2$ has the same meaning as in claim 10, and

* and *' each indicate a condensation site to a neighboring ring in Formula 1.

19. The fused cyclic compound of claim 10, the fused cyclic compound satisfying i) one of Conditions 1 to 5, ii) Conditions 1 and 5; Conditions 2 and 5; Conditions 3 and 5; or Conditions 4 and 5, iii) Conditions 1, 4, and 5; Conditions 1, 3, and 5; Conditions 2, 4, and 5; or Conditions 3, 4, and 5, iv) Conditions 1 to 3 and 5; Conditions 1 and 3 to 5; or Conditions 2 to 5, or v) Conditions 1 to 5.

* * * * *